United States Patent
Zucherman et al.

(10) Patent No.: US 8,894,686 B2
(45) Date of Patent: Nov. 25, 2014

(54) INTERSPINOUS PROCESS IMPLANTS AND METHODS OF USE

(75) Inventors: James F. Zucherman, San Francisco, CA (US); Ken Y. Hsu, San Francisco, CA (US); Charles J. Winslow, Walnut Creek, CA (US); Scott A. Yerby, Montara, CA (US); John J. Flynn, West Milford, NJ (US); Steven T. Mitchell, Pleasant Hill, CA (US); John A. Markwart, Castro Valley, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 960 days.

(21) Appl. No.: 11/771,087

(22) Filed: Jun. 29, 2007

(65) Prior Publication Data

US 2008/0039947 A1 Feb. 14, 2008

Related U.S. Application Data

(63) Continuation of application No. 11/806,528, filed on May 31, 2007, now abandoned, and a continuation of (Continued)

(51) Int. Cl.
  *A61B 17/70* (2006.01)
  *A61B 17/84* (2006.01)

(52) U.S. Cl.
  CPC .......... *A61B 17/7053* (2013.01); *A61B 17/7062* (2013.01); *A61B 17/7068* (2013.01); *A61B 17/7065* (2013.01); *A61B 17/7047* (2013.01); *A61B 17/842* (2013.01)
  USPC .......................................... 606/249; 606/248

(58) Field of Classification Search
  USPC .............. 606/60, 246–279; 623/17.11–17.16, 623/23.69; 411/16, 321; 52/157, 187, 705; 5/269, 271, 272; 24/115 N; 333/141, 333/148, 218, 267; 73/742; 74/665 GD, 74/458; 83/672; 104/167; 160/316; 174/DIG. 12; 200/500; 241/82.1; 446/430; 403/408.1, 13; 15/179
  See application file for complete search history.

(56) References Cited

U.S. PATENT DOCUMENTS 56,273 A * 7/1866 Rundell ........................... 52/157
624,969 A * 5/1899 Peterson ........................ 411/340

(Continued)

FOREIGN PATENT DOCUMENTS

DE        2821678 A1    11/1979
EP        0322334 B1     2/1992

(Continued)

OTHER PUBLICATIONS

Albee, Fred H. M.D. "Bone surgery with machine tools," Scientific American, Munn & Company, NY, pp. 178-181, Apr. 1936.*

(Continued)

*Primary Examiner* — Christian Sevilla

(57) ABSTRACT

Systems and method in accordance with an embodiment of the present invention can includes an implant comprising a first wing, a spacer extending from the first wing, and a distraction guide. The distraction guide is arranged in a first configuration to pierce and/or distract tissue associated with adjacent spinous processes extending from vertebrae of a targeted motion segment. The implant can be positioned between the adjacent spinous processes and once positioned, the implant can be arranged in a second configuration. When arranged in a second configuration, the distraction guide can act as a second wing. The first wing and the second wing can limit or block movement of the implant along a longitudinal axis of the implant.

32 Claims, 146 Drawing Sheets

Related U.S. Application Data application No. 11/806,526, filed on May 31, 2007, now Pat. No. 8,221,463, said application No. 11/806,528 is a continuation-in-part of application No. 10/694,103, filed on Oct. 27, 2003, now abandoned, said application No. 11/806,528 is a continuation-in-part of application No. 11/234,555, filed on Sep. 23, 2005, now Pat. No. 8,048,117, and a continuation-in-part of application No. 10/850,267, filed on May 20, 2004, now Pat. No. 7,695,513, said application No. 10/806,528 is a continuation-in-part of application No. 11/378,893, filed on Mar. 17, 2006, now Pat. No. 8,070,778, and a continuation-in-part of application No. 10/850,267, filed on May 20, 2004, now Pat. No. 7,695,513, said application No. 11/806,528 is a continuation-in-part of application No. 11/384,055, filed on Mar. 17, 2006, now abandoned, and a continuation-in-part of application No. 10/850,267, filed on May 20, 2004, now Pat. No. 7,695,513, said application No. 11/806,528 is a continuation-in-part of application No. 10/816,173, filed on Apr. 1, 2004, now Pat. No. 7,549,999, said application No. 11/806,528 is a continuation-in-part of application No. 11/095,440, filed on Mar. 31, 2005, now abandoned, said application No. 11/806,528 is a continuation-in-part of application No. 11/095,680, filed on Mar. 31, 2005, now Pat. No. 7,909,853, said application No. 11/806,528 is a continuation-in-part of application No. 11/378,108, filed on Mar. 17, 2006, now Pat. No. 7,749,252, said application No. 11/806,528 is a continuation-in-part of application No. 11/377,971, filed on Mar. 17, 2006, now Pat. No. 7,931,674, said application No. 11/806,528 is a continuation-in-part of application No. 11/378,894, filed on Mar. 17, 2006, now abandoned, said application No. 11/806,528 is a continuation-in-part of application No. 11/389,002, filed on Mar. 24, 2006, now Pat. No. 7,959,652, said application No. 11/806,528 is a continuation-in-part of application No. 11/378,892, filed on Mar. 17, 2006, now Pat. No. 8,147,548, application No. 11/771,087, which is a continuation of application No. 11/806,526, filed on May 31, 2007, now Pat. No. 8,221,463, which is a continuation-in-part of application No. 10/694,103, filed on Oct. 27, 2003, now abandoned, said application No. 11/806,526 is a continuation-in-part of application No. 11/234,555, filed on Sep. 23, 2005, now Pat. No. 8,048,117, and a continuation-in-part of application No. 10/850,267, filed on May 20, 2004, now Pat. No. 7,695,513, said application No. 11/806,526 is a continuation-in-part of application No. 11/378,893, filed on Mar. 17, 2006, now Pat. No. 8,070,778, and a continuation-in-part of application No. 10/850,267, filed on May 20, 2004, now Pat. No. 7,659,513, said application No. 11/806,526 is a continuation-in-part of application No. 11/384,055, filed on Mar. 17, 2006, now abandoned, and a continuation-in-part of application No. 10/850,267, filed on May 20, 2004, now Pat. No. 7,695,513, said application No. 11/806,526 is a continuation-in-part of application No. 10/816,173, filed on Apr. 1, 2004, now Pat. No. 7,549,999, said application No. 11/806,526 is a continuation-in-part of application No. 11/095,440, filed on Mar. 31, 2005, now abandoned, said application No. 11/806,526 is a continuation-in-part of application No. 11/095,680, filed on Mar. 31, 2005, now Pat. No. 7,909,853, said application No. 11/806,526 is a continuation-in-part of application No. 11/378,108, filed on Mar. 17, 2006, now Pat. No. 7,749,252, said application No. 11/806,526 is a continuation-in-part of application No. 11/377,971, filed on Mar. 17, 2006, now Pat. No. 7,931,674, said application No. 11/806,526 is a continuation-in-part of application No. 11/378,894, filed on Mar. 17, 2006, now abandoned, said application No. 11/806,526 is a continuation-in-part of application No. 11/389,002, filed on Mar. 24, 2006, now Pat. No. 7,959,652, said application No. 11/806,526 is a continuation-in-part of application No. 11/378,892, filed on Mar. 17, 2006, now Pat. No. 8,147,548.

(60) Provisional application No. 60/421,915, filed on Oct. 29, 2002, provisional application No. 60/612,582, filed on Sep. 23, 2004, provisional application No. 60/472,817, filed on May 22, 2003, provisional application No. 60/664,311, filed on Mar. 22, 2005, provisional application No. 60/664,049, filed on Mar. 22, 2005, provisional application No. 60/612,465, filed on Sep. 23, 2004, provisional application No. 60/663,918, filed on Mar. 21, 2005, provisional application No. 60/663,885, filed on Mar. 21, 2005, provisional application No. 60/664,076, filed on Mar. 22, 2005, provisional application No. 60/672,402, filed on Apr. 18, 2005, provisional application No. 60/663,922, filed on Mar. 21, 2005.

(56) References Cited

U.S. PATENT DOCUMENTS

| | | | | |
|---|---|---|---|---|
| 1,193,725 | A * | 8/1916 | Smith | 52/157 |
| 1,230,603 | A * | 6/1917 | Richmond | 52/705 |
| 2,077,804 | A * | 4/1937 | Morrison | 606/68 |
| 2,677,369 | A | 5/1954 | Knowles | |
| 3,093,222 | A * | 6/1963 | Christoffersen et al. | 403/408.1 |
| 3,205,626 | A * | 9/1965 | Attenberger | 52/103 |
| 3,302,509 | A * | 2/1967 | Modrey | 411/18 |
| 3,509,670 | A * | 5/1970 | Boll et al. | 52/99 |
| 3,648,691 | A * | 3/1972 | Lumb et al. | 606/279 |
| 3,688,454 | A * | 9/1972 | Wolfcarius et al. | 52/103 |
| 4,011,602 | A | 3/1977 | Rybicki et al. | |
| 4,257,409 | A | 3/1981 | Bacal et al. | |
| 4,291,608 | A * | 9/1981 | Lang et al. | 411/16 |
| 4,401,112 | A * | 8/1983 | Rezaian | 606/279 |
| 4,479,491 | A * | 10/1984 | Martin | 606/279 |
| 4,553,273 | A * | 11/1985 | Wu | 623/23.45 |
| 4,554,914 | A * | 11/1985 | Kapp et al. | 606/86 A |
| 4,573,454 | A | 3/1986 | Hoffman | |
| 4,599,086 | A * | 7/1986 | Doty | 606/86 A |
| 4,604,995 | A | 8/1986 | Stephens et al. | |
| 4,657,550 | A * | 4/1987 | Daher | 623/17.11 |
| 4,686,970 | A | 8/1987 | Dove et al. | |
| 4,721,103 | A * | 1/1988 | Freedland | 606/319 |
| 4,827,918 | A | 5/1989 | Olerud | |
| 4,886,405 | A * | 12/1989 | Blomberg | 411/16 |
| 5,011,484 | A | 4/1991 | Breard | |
| 5,047,055 | A | 9/1991 | Bao et al. | |
| 5,092,866 | A | 3/1992 | Breard et al. | |
| 5,098,433 | A * | 3/1992 | Freedland | 606/63 |
| 5,201,734 | A | 4/1993 | Cozad et al. | |
| 5,306,275 | A | 4/1994 | Bryan | |
| 5,316,422 | A * | 5/1994 | Coffman | 411/107 |
| 5,360,430 | A | 11/1994 | Lin | |
| 5,366,455 | A | 11/1994 | Dove | |
| 5,415,661 | A | 5/1995 | Holmes | |
| 5,437,672 | A | 8/1995 | Alleyne | |
| 5,454,812 | A | 10/1995 | Lin | |
| 5,458,638 | A | 10/1995 | Kuslich et al. | |

(56) References Cited

U.S. PATENT DOCUMENTS

| | | | |
|---|---|---|---|
| 5,458,641 A * | 10/1995 | Ramirez Jimenez | 623/17.11 |
| 5,496,318 A * | 3/1996 | Howland et al. | 606/249 |
| 5,609,634 A | 3/1997 | Voydeville | |
| 5,628,756 A | 5/1997 | Barker, Jr. et al. | |
| 5,645,599 A | 7/1997 | Samani | |
| 5,658,336 A * | 8/1997 | Pisharodi | 623/17.16 |
| 5,674,295 A | 10/1997 | Ray et al. | |
| 5,676,702 A | 10/1997 | Ratron | |
| 5,683,463 A | 11/1997 | Godefroy et al. | |
| 5,690,649 A | 11/1997 | Li | |
| 5,702,452 A | 12/1997 | Argenson et al. | |
| 5,810,815 A | 9/1998 | Morales | |
| 5,836,948 A | 11/1998 | Zucherman et al. | |
| 5,860,977 A | 1/1999 | Zucherman et al. | |
| 5,876,404 A * | 3/1999 | Zucherman et al. | 606/249 |
| 5,976,186 A | 11/1999 | Bao et al. | |
| 6,022,376 A | 2/2000 | Assell et al. | |
| 6,048,342 A | 4/2000 | Zucherman et al. | |
| 6,068,630 A | 5/2000 | Zucherman et al. | |
| 6,093,207 A | 7/2000 | Pisharodi | |
| 6,132,464 A | 10/2000 | Martin | |
| 6,235,030 B1 * | 5/2001 | Zucherman et al. | 606/249 |
| 6,293,949 B1 | 9/2001 | Justis et al. | |
| 6,352,537 B1 | 3/2002 | Strnad | |
| 6,364,883 B1 | 4/2002 | Santilli | |
| 6,402,750 B1 | 6/2002 | Atkinson et al. | |
| 6,440,169 B1 | 8/2002 | Elberg et al. | |
| 6,451,019 B1 | 9/2002 | Zucherman et al. | |
| 6,582,433 B2 | 6/2003 | Yun | |
| 6,626,944 B1 | 9/2003 | Taylor | |
| 6,645,207 B2 | 11/2003 | Dixon et al. | |
| 6,695,842 B2 * | 2/2004 | Zucherman et al. | 606/249 |
| 6,702,239 B2 * | 3/2004 | Boucher | 248/156 |
| 6,709,435 B2 | 3/2004 | Lin | |
| 6,723,126 B1 | 4/2004 | Berry | |
| 6,733,534 B2 | 5/2004 | Sherman | |
| 6,761,720 B1 | 7/2004 | Senegas | |
| 6,835,205 B2 | 12/2004 | Atkinson et al. | |
| 6,905,512 B2 | 6/2005 | Paes et al. | |
| 6,946,000 B2 | 9/2005 | Senegas et al. | |
| 7,041,136 B2 | 5/2006 | Goble et al. | |
| 7,048,736 B2 | 5/2006 | Robinson et al. | |
| 7,087,083 B2 | 8/2006 | Pasquet et al. | |
| 7,163,558 B2 | 1/2007 | Senegas et al. | |
| 7,201,751 B2 | 4/2007 | Zucherman et al. | |
| 7,238,204 B2 | 7/2007 | Le Couedic et al. | |
| 7,306,628 B2 | 12/2007 | Zucherman et al. | |
| 7,377,942 B2 | 5/2008 | Berry | |
| 7,442,208 B2 | 10/2008 | Mathieu et al. | |
| 7,445,637 B2 | 11/2008 | Taylor | |
| 2002/0143331 A1 | 10/2002 | Zucherman et al. | |
| 2003/0153915 A1 | 8/2003 | Nekozuka et al. | |
| 2004/0097931 A1 | 5/2004 | Mitchell | |
| 2005/0010293 A1 | 1/2005 | Zucherman et al. | |
| 2005/0049708 A1 | 3/2005 | Atkinson et al. | |
| 2005/0165398 A1 | 7/2005 | Reiley | |
| 2005/0203512 A1 | 9/2005 | Hawkins et al. | |
| 2005/0203624 A1 | 9/2005 | Serhan et al. | |
| 2005/0228391 A1 | 10/2005 | Levy et al. | |
| 2005/0261768 A1 | 11/2005 | Trieu | |
| 2005/0288672 A1 | 12/2005 | Ferree | |
| 2006/0004447 A1 | 1/2006 | Mastrorio et al. | |
| 2006/0015181 A1 | 1/2006 | Elberg | |
| 2006/0064165 A1 | 3/2006 | Zucherman et al. | |
| 2006/0084983 A1 | 4/2006 | Kim | |
| 2006/0084985 A1 | 4/2006 | Kim | |
| 2006/0084987 A1 | 4/2006 | Kim | |
| 2006/0084988 A1 | 4/2006 | Kim | |
| 2006/0085069 A1 | 4/2006 | Kim | |
| 2006/0085070 A1 | 4/2006 | Kim | |
| 2006/0085074 A1 | 4/2006 | Raiszadeh | |
| 2006/0089654 A1 | 4/2006 | Lins et al. | |
| 2006/0089719 A1 | 4/2006 | Trieu | |
| 2006/0106381 A1 | 5/2006 | Ferree et al. | |
| 2006/0106397 A1 | 5/2006 | Lins | |
| 2006/0111728 A1 | 5/2006 | Abdou | |
| 2006/0122620 A1 | 6/2006 | Kim | |
| 2006/0136060 A1 | 6/2006 | Taylor | |
| 2006/0184247 A1 | 8/2006 | Edidin et al. | |
| 2006/0184248 A1 | 8/2006 | Edidin et al. | |
| 2006/0195102 A1 | 8/2006 | Malandain | |
| 2006/0217726 A1 | 9/2006 | Maxy et al. | |
| 2006/0235387 A1 | 10/2006 | Peterman | |
| 2006/0235532 A1 | 10/2006 | Meunier et al. | |
| 2006/0241613 A1 | 10/2006 | Bruneau et al. | |
| 2006/0247623 A1 | 11/2006 | Anderson et al. | |
| 2006/0247640 A1 | 11/2006 | Blackwell et al. | |
| 2006/0264938 A1 | 11/2006 | Zucherman et al. | |
| 2006/0271044 A1 | 11/2006 | Petrini et al. | |
| 2006/0293662 A1 | 12/2006 | Boyer, II et al. | |
| 2006/0293663 A1 | 12/2006 | Walkenhorst et al. | |
| 2007/0043362 A1 | 2/2007 | Malandain et al. | |
| 2007/0162000 A1 | 7/2007 | Perkins | |
| 2007/0198091 A1 | 8/2007 | Boyer et al. | |
| 2007/0233068 A1 | 10/2007 | Bruneau et al. | |
| 2007/0233081 A1 | 10/2007 | Pasquet et al. | |
| 2007/0233089 A1 | 10/2007 | DiPoto et al. | |
| 2007/0270834 A1 | 11/2007 | Bruneau et al. | |
| 2008/0161818 A1 | 7/2008 | Kloss et al. | |

FOREIGN PATENT DOCUMENTS

| | | |
|---|---|---|
| EP | 1138268 A1 | 10/2001 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2816197 A1 | 5/2002 |
| JP | 02-224660 | 9/1990 |
| JP | 09-075381 | 3/1997 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 98/20939 | 5/1998 |
| WO | WO 2004/047691 A1 | 6/2004 |
| WO | WO 2005/009300 A1 | 2/2005 |
| WO | WO 2005/044118 A1 | 5/2005 |
| WO | WO 2005/110258 A1 | 11/2005 |
| WO | WO 2007/034516 A1 | 3/2007 |

OTHER PUBLICATIONS

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, Dispositif Intervertébral Amortissant, Jun. 1998, pp. 1-4.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE 1992, pp. S44-S50, vol. 17, No. 3S.

(56) References Cited

OTHER PUBLICATIONS

Fassio et al., "Treatment of Degenerative Lumbar Spinal Instability L4-L5 by Interspinous Ligamentoplasty," Rachis, Dec. 1991, pp. 465-474, vol. 3, No. 6.
Fassio, "Mise au Point Sur la Ligamentoplastie Inter-Epineuse Lombaire Dans les Instabilites," Maîtrise Orthopédique, Jul. 1993, pp. 18, No. 25.
Garner et al., "Development and Preclinical Testing of a New Tension-Band Device for the Spine: the Loop System," Eur. Spine J., Aug. 7, 2002, pp. S186-S191, vol. 11, Suppl. 2.
Guang et al., "Interspinous Process Segmental Instrumentation with Bone-Button-Wire for Correction of Scoliosis," Chinese Medical J., 1990, pp. 721-725, vol. 103.
Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.
Hambly et al., "Tension Band Wiring-Bone Grafting for Spondylolysis and Spondylolisthesis," SPINE, 1989, pp. 455-460, vol. 14, No. 4.
Kiwerski, "Rehabilitation of Patients with Thoracic Spine Injury Treated by Spring Alloplasty," Int. J. Rehab. Research, 1983, pp. 469-474, vol. 6, No. 4.
Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.
Mah et al., "Threaded K-Wire Spinous Process Fixation of the Axis for Modified Gallie Fusion in Children and Adolescents," J. Pediatric Othopaedics, 1989, pp. 675-679, vol. 9.
Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.
McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.
Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.
Müller, "Restauration Dynamique de la Stabilité Rachidienne," Tiré de la Sulzer Technical Review, Jan. 1999, Sulzer Management Ltd, Winterthur, Switzerland.
Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.
Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.
Petrini et al., "Stabilizzazione Elastica," Patologia Degenerativa del Rachide Lombare, Oct. 5-6, 2001, Rimini.
Porter, "Spinal Stenosis and Neurogenic Claudication," SPINE, Sep. 1, 1996, pp. 2046-2052, vol. 21, No. 17.
Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.
Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.
Richards et al., "The Treatment Mechanism of an Interspinous Process Implant for Lumbar Neurogenic Intermittent Claudication," SPINE, 2005, pp. 744-749, vol. 30, No. 7.
Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.
Schlegel et al., "The Role of Distraction in Improving the Space Available in the Lumbar Stenotic Canal and Foramen," SPINE, 1994, pp. 2041-2047, vol. 19, No. 18.
Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.
Senegas et al., "Stabilisation Lombaire Souple," Instabilité Vertébrales Lombaires, Gastambide, ed., 1995, pp. 122-132, Expansion Scientifique Française, Paris, France.
Senegas, "La Ligamentoplastie Inter Vertébrale Lombaire, Alternative a L'Arthrèdese," La Revue de Medécine Orthopédique, Jun. 1990, pp. 33-35, No. 20.
Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.
Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.
Senegas, "Rencontre," Maîtrise Orthopédique, May 1995, pp. 1-3, No. 44.
Serhan, "Spinal Implants: Past, Present, and Future," 19th International IEEE/EMBS Conference, Oct. 30-Nov. 2, 1997, pp. 2636-2639, Chicago, Illinois.
Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.
Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.
Taylor et al., "Technical and Anatomical Considerations for the Placement of a Posterior Interspinous Stabilizer," 2004, pp. 1-10, Medtronic Sofamor Danek USA, Inc., Memphis, Tennessee.
Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.
Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.
Taylor, "Présentation à un an d'un dispositif amortissant d'assistance discale," 5èmes journées Avances & Controverses en pathologie rachidienne, Oct. 1-2, 1998, Faculté Libre de Médecine de Lille.
Tsuji et al., "Ceramic Interspinous Block (CISB) Assisted Anterior Interbody Fusion," J. Spinal Disorders, 1990, pp. 77-86, vol. 3, No. 1.
Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.
Voydeville et al., "Experimental Lumbar Instability and Artificial Ligament," Eur. J. Orthop. Surg. Traumatol., Jul. 15, 2000, pp. 167-176, vol. 10.
Voydeville et al., "Lumbar Instability Treated by Intervertebral Ligamentoplasty with Smooth Wedges," Orthopédie Traumatologie, 1992, pp. 259-264, vol. 2, No. 4.
Waldemar Link, "Spinal Surgery: Instrumentation and Implants for Spinal Surgery," 1981, Link America Inc., New Jersey.
Wiltse et al., "The Treatment of Spinal Stenosis," Clinical Orthopaedics and Related Research, Urist, ed., Mar.-Apr. 1976, pp. 83-91, No. 115.
Wisneski et al., "Decompressive Surgery for Lumbar Spinal Stenosis," Seminars in Spine Surgery, Wiesel, ed., Jun. 1994, pp. 116-123, vol. 6, No. 2.
Zucherman et al., "Clinical Efficacy of Spinal Instrumentation in Lumbar Degenerative Disc Disease," SPINE, Jul. 1992, pp. 834-837, vol. 17, No. 7.
Kramer et al., "Intervetertebral Disk Diseases: Causes, Diagnosis, Treatment and Prophylaxis," pp. 244-249, Medical, 1990.
Zdeblick et al., "Two-Point Fixation of the Lumbar Spine Differential Stability in Rotation," SPINE, 1991, pp. S298-S301, vol. 16, No. 6, Supplement.

* cited by examiner

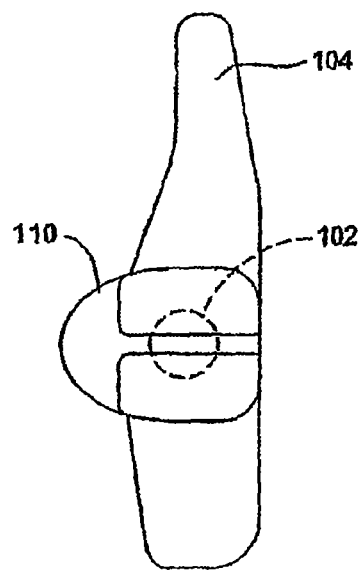
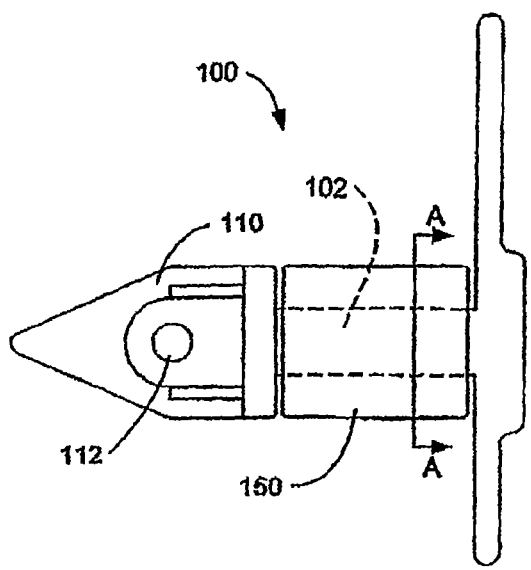
FIG. - 1B  FIG. - 1C
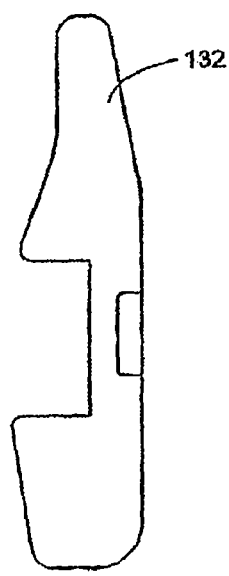
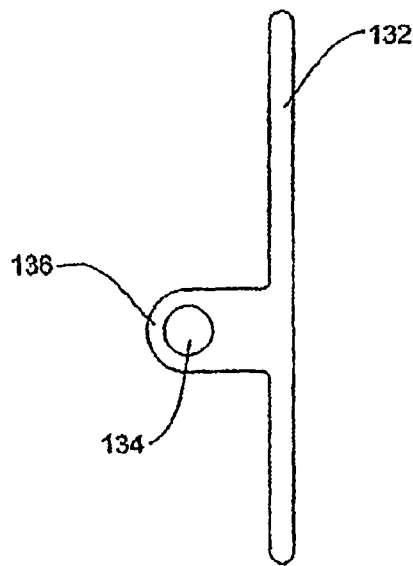
FIG. – 1D  FIG. – 1E

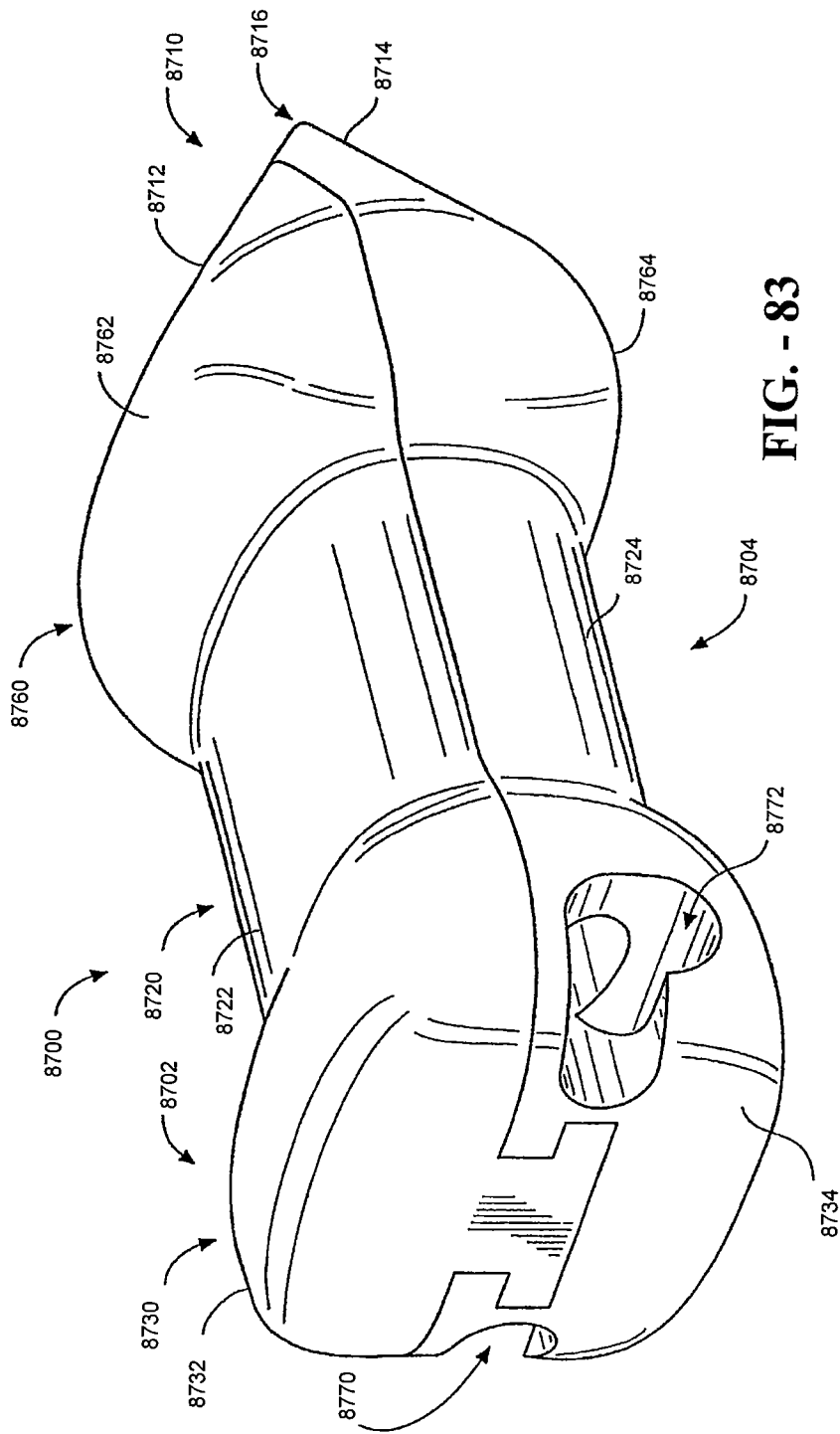

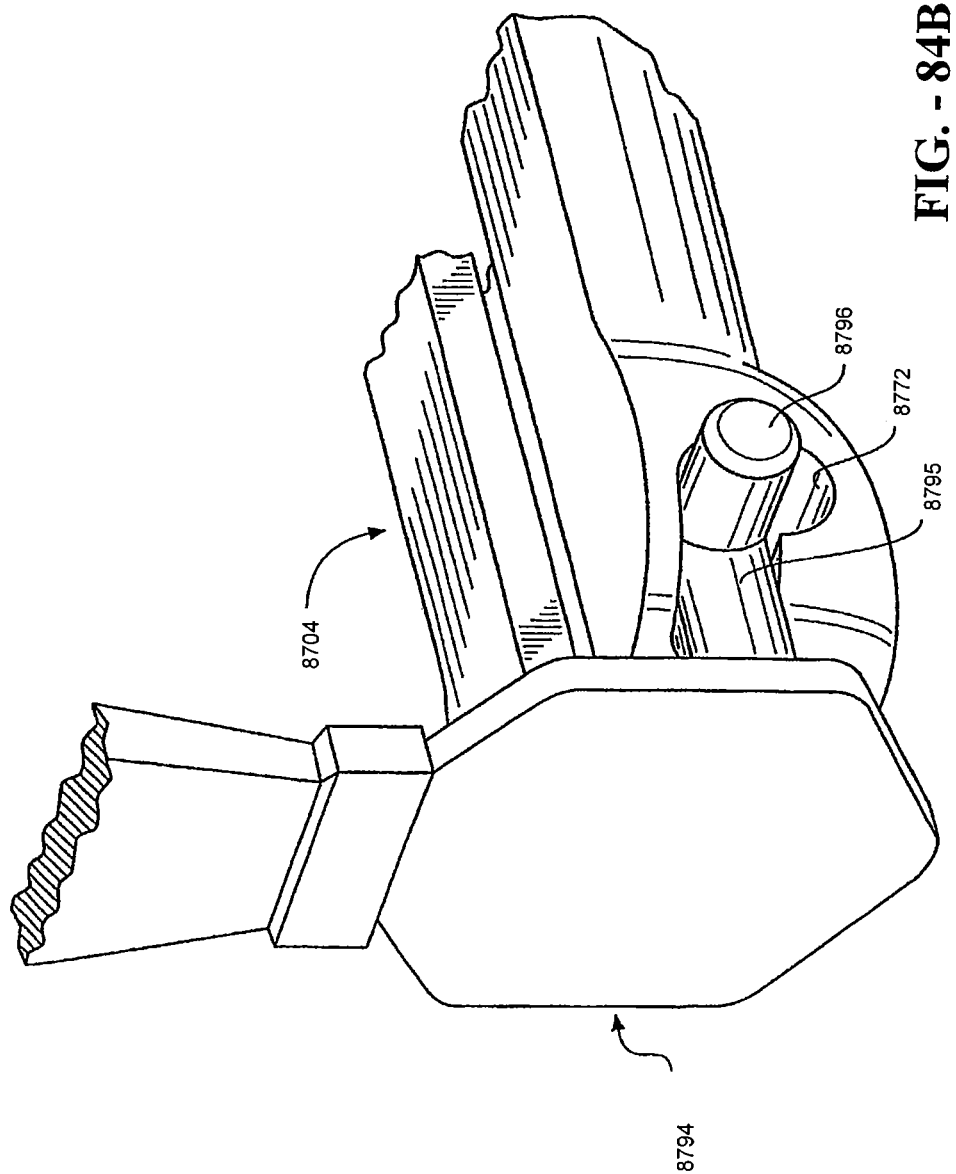

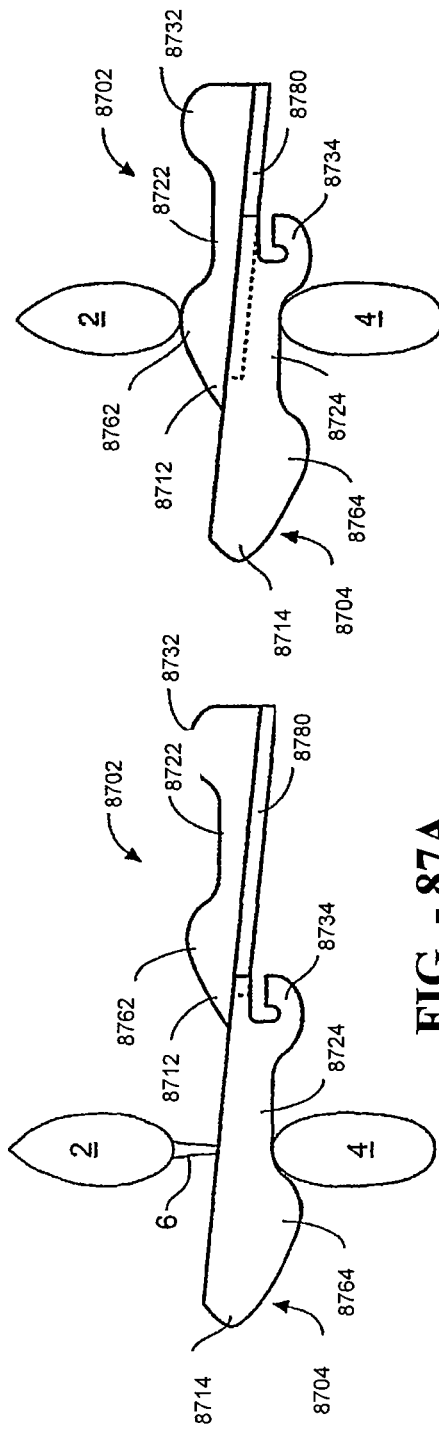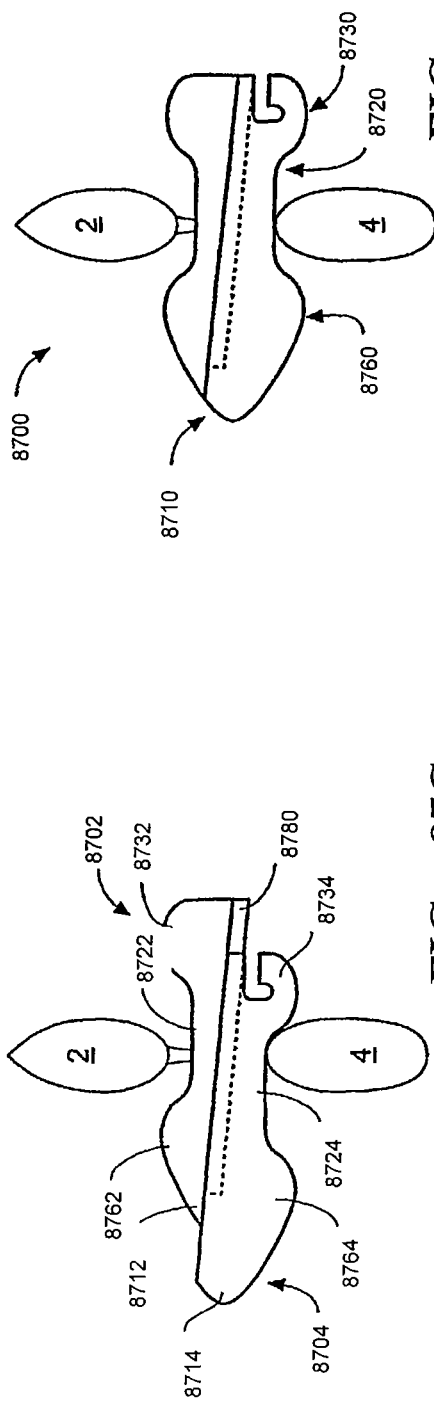

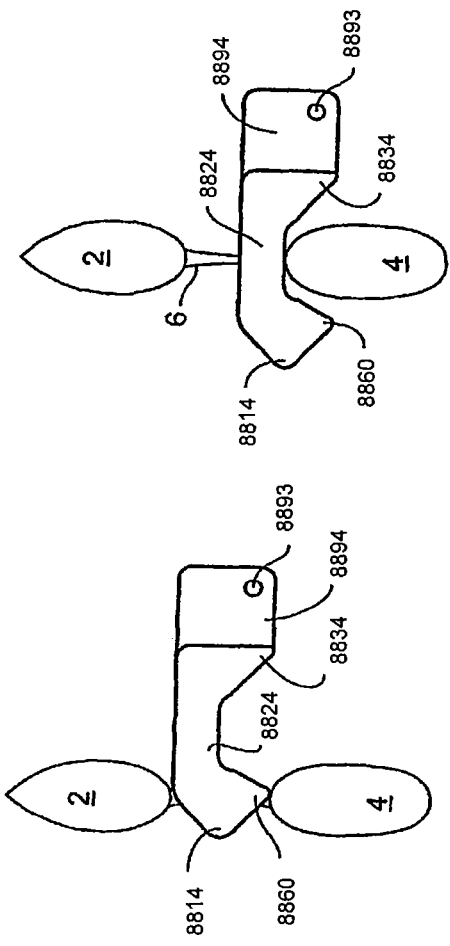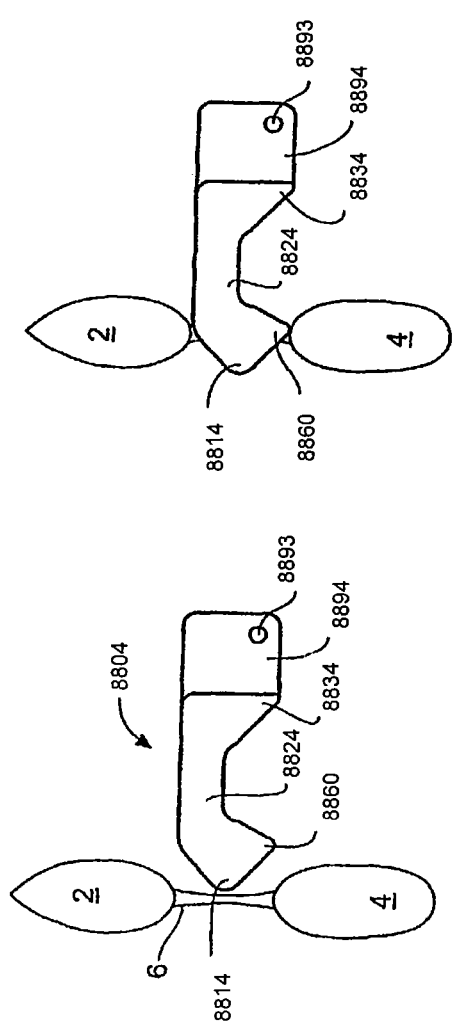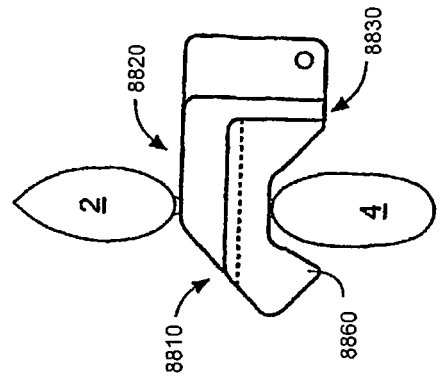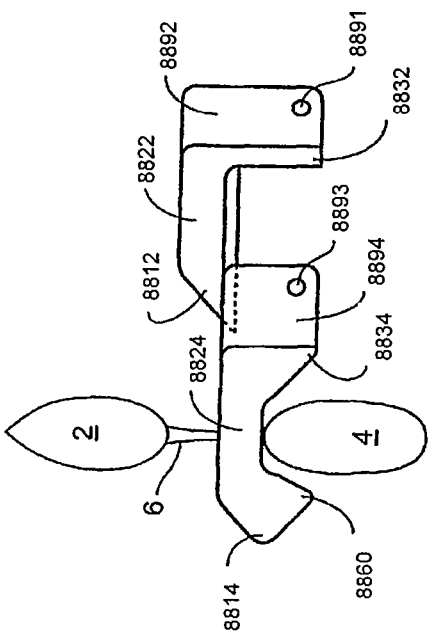
FIG. - 89C
FIG. - 89E
FIG. - 89B
FIG. - 89A
FIG. - 89D

INTERSPINOUS PROCESS IMPLANTS AND METHODS OF USE

CROSS-REFERENCE TO RELATED APPLICATIONS

This application is a continuation of each of U.S. patent application Ser. Nos. 11/806,528 and 11/806,526, each entitled "Interspinous Process Implants and Methods of Use," and filed May 31, 2007; each of which is incorporated herein by reference in its entirety.

Each of U.S. patent application Ser. Nos. 11/806,528 and 11/806,526 is a continuation-in-part of U.S. patent application Ser. No. 10/694,103, entitled "Interspinous Process Implant with Radiolucent Spacer and Lead-in Tissue Expander," filed Oct. 27, 2003, which claims priority to U.S. Provisional Application Ser. No. 60/421,915, entitled "Interspinous Process Implant with Radiolucent Spacer and Lead-in Tissue Expander," filed Oct. 29, 2002; each of which is incorporated herein by reference in its entirety.

Each of U.S. patent application Ser. Nos. 11/806,528 and 11/806,526 is a continuation-in-part of U.S. patent application Ser. No. 11/234,555, entitled "Interspinous Process Implant and Method of Implantation," filed Sep. 23, 2005, which claims priority to U.S. Provisional Application Ser. No. 60/612,582, entitled "Interspinous Process Implant and Method of Implantation," filed Sep. 23, 2004 and which is a continuation-in-part of U.S. patent application Ser. No. 10/850,267, entitled "Distractible Interspinous Process Implant and Method of Implantation," filed May 20, 2004, which claims priority to U.S. Provisional Application Ser. No. 60/472,817, entitled "Cervical Interspinous Process Implant and Method of Implantation," filed May 22, 2003; each of which is incorporated herein by reference in its entirety.

Each of U.S. patent application Ser. Nos. 11/806,528 and 11/806,526 is a continuation-in-part of U.S. patent application Ser. No. 11/378,893, entitled "Interspinous Process Implant with Slide-in Distraction Piece and Method of Implantation," filed Mar. 17, 2006, which claims priority to U.S. Provisional Application Ser. No. 60/664,311, entitled "Interspinous Process Implant with Slide-in Distraction Piece and Method of Implantation," filed Mar. 22, 2005 and which is a continuation-in-part of U.S. patent application Ser. No. 10/850,267, entitled "Distractible Interspinous Process Implant and Method of Implantation," filed May 20, 2004, which claims priority to U.S. Provisional Application Ser. No. 60/472,817, entitled "Cervical Interspinous Process Implant and Method of Implantation," filed May 22, 2003; each of which is incorporated herein by reference in its entirety.

Each of U.S. patent application Ser. Nos. 11/806,528 and 11/806,526 is a continuation-in-part of U.S. patent application Ser. No. 11/384,055, entitled "Interspinous Process Implant with Slide-in Distraction Piece and Method of Implantation," filed Mar. 17, 2006, which claims priority to U.S. Provisional Application Ser. No. 60/664,049, entitled "Interspinous Process Implant with Slide-in Distraction Piece and Method of Implantation," filed Mar. 22, 2005 and which is a continuation-in-part of U.S. patent application Ser. No. 10/850,267, entitled "Distractible Interspinous Process Implant and Method of Implantation," filed May 20, 2004, which claims priority to U.S. Provisional Application Ser. No. 60/472,817, entitled "Cervical Interspinous Process Implant and Method of Implantation," filed May 22, 2003; each of which is incorporated herein by reference in its entirety.

Each of U.S. patent application Ser. Nos. 11/806,528 and 11/806,526 is a continuation-in-part of U.S. patent application Ser. No. 10/816,173, entitled "Cervical Interspinous Process Implant and Method of Implantation," filed Apr. 1, 2004, which claims priority to U.S. Provisional Application Ser. No. 60/472,817, entitled "Cervical Interspinous Process Implant and Method of Implantation," filed May 22, 2003; each of which is incorporated herein by reference in its entirety.

Each of U.S. patent application Ser. Nos. 11/806,528 and 11/806,526 is a continuation-in-part of U.S. patent application Ser. No. 11/095,440, entitled "Interspinous Process Implant Including a Binder and Method of Implantation," filed Mar. 31, 2005, which claims priority to U.S. Provisional Application Ser. No. 60/612,465, entitled "Interspinous Process Implant Including a Binder and Method of Implantation," filed Sep. 23, 2004; each of which is incorporated herein by reference in its entirety.

Each of U.S. patent application Ser. Nos. 11/806,528 and 11/806,526 is a continuation-in-part of U.S. patent application Ser. No. 11/095,680, entitled "Interspinous Process Implant Including a Binder and Method of Implantation," filed Mar. 31, 2005, which claims priority to U.S. Provisional Application Ser. No. 60/612,465, entitled "Interspinous Process Implant Including a Binder and Method of Implantation," filed Sep. 23, 2004; each of which is incorporated herein by reference in its entirety.

Each of U.S. patent application Ser. Nos. 11/806,528 and 11/806,526 is a continuation-in-part of U.S. patent application Ser. No. 11/378,108, entitled "Interspinous Process Implant Having Deployable Wing and Method of Implantation," filed Mar. 17, 2006, which claims priority to U.S. Provisional Application Ser. No. 60/663,918, entitled "Interspinous Process Implant Having Deployable Wing and Method of Implantation," filed Mar. 21, 2005; each of which is incorporated herein by reference in its entirety.

Each of U.S. patent application Ser. Nos. 11/806,528 and 11/806,526 is a continuation-in-part of U.S. patent application Ser. No. 11/377,971, entitled "Interspinous Process Implant Having Deployable Wing and Method of Implantation," filed Mar. 17, 2006, which claims priority to U.S. Provisional Application Ser. No. 60/663,885, entitled "Interspinous Process Implant Having Deployable Wing and Method of Implantation," filed Mar. 21, 2005; each of which is incorporated herein by reference in its entirety.

Each of U.S. patent application Ser. No. 11/806,528 and 11/806,526 is a continuation-in-part of U.S. patent application Ser. No. 11/378,894, entitled "Interspinous Process Implant Having Deployable Wing and Method of Implantation," filed Mar. 17, 2006, which claims priority to U.S. Provisional Application Ser. No. 60/664,076, entitled "Interspinous Process Implant Having Deployable Wing and Method of Implantation," filed Mar. 22, 2005; each of which is incorporated herein by reference in its entirety.

Each of U.S. patent application Ser. Nos. 11/806,528 and 11/806,526 is a continuation-in-part of U.S. patent application Ser. No. 11/389,002, entitled "Interspinous Process Implant Having Deployable Wings and Method of Implantation," filed Mar. 24, 2006, which claims priority to U.S. Provisional Application Ser. No. 60/672,402, entitled "Interspinous Process Implant Having Deployable Wings and Method of Implantation," filed Apr. 18, 2005; each of which is incorporated herein by reference in its entirety.

Each of U.S. patent application Ser. Nos. 11/806,528 and 11/806,526 is a continuation-in-part of U.S. patent application Ser. No. 11/378,892, entitled "Interspinous Process Implant Having A Thread-Shaped Wing and Method of Implantation," filed Mar. 17, 2006, which claims priority to U.S. Provisional Application Ser. No. 60/663,922, entitled "Interspinous Process Implant Having Deployable Wings and Method of Implantation," filed Mar. 21, 2005; each of which is incorporated herein by reference in its entirety.

BACKGROUND

The spinal column is a bio-mechanical structure composed primarily of ligaments, muscles, vertebrae and intervertebral disks. The bio-mechanical functions of the spine include: (1) support of the body, which involves the transfer of the weight and the bending movements of the head, trunk and arms to the pelvis and legs, (2) complex physiological motion between these parts, and (3) protection of the spinal cord and the nerve roots.

As the present society ages, it is anticipated that there will be an increase in adverse spinal conditions which are characteristic of older people. By way of example only, with aging comes an increase in spinal stenosis (including, but not limited to, central canal and lateral stenosis), and facet arthropathy. Spinal stenosis results in a reduction foraminal area {i.e., the available space for the passage of nerves and blood vessels) which compresses the cervical nerve roots and causes radicular pain. Humpreys, S. C. et al, Flexion and traction effect on C5-C6 foraminal space, Arch. Phys. Med. Rehabil., vol. 79 at 1105 (September 1998). Another symptom of spinal stenosis is myelopathy, which results in neck pain and muscle weakness. Id. Extension and ipsilateral rotation of the neck further reduces the foraminal area and contributes to pain, nerve root compression and neural injury. Id.; Yoo, J. U. et al., Effect of cervical spine motion on the neuroforaminal dimensions of human cervical spine, Spine, vol. 17 at 1131 (Nov. 10, 1992). In contrast, neck flexion increases the foraminal area. Humpreys, S. C. et al, at 1105.

Pain associated with stenosis can be relieved by medication and/or surgery. It is desirable to eliminate the need for major surgery for all individuals, and in particular, for the elderly.

Accordingly, a need exists to develop spine implants that alleviate pain caused by spinal stenosis and other such conditions caused by damage to, or degeneration of, the spine. Such implants would distract, or increase the space between, the vertebrae to increase the foraminal area and reduce pressure on the nerves and blood vessels of the spine. A further need exists for development of a minimally invasive surgical implantation method for spine implants that preserves the physiology of the spine.

Further, a need exists for an implant that accommodates the distinct anatomical structures of the spine, minimizes further trauma to the spine, and obviates the need for invasive methods of surgical implantation. Additionally, a need exists to address adverse spinal conditions that are exacerbated by spinal extension and/or flexion.

SUMMARY

Systems and method in accordance with an embodiment of the present invention can includes an implant comprising a first wing, a spacer extending from the first wing, and a distraction guide. The distraction guide is arranged in a first configuration to pierce and/or distract tissue associated with adjacent spinous processes extending from vertebrae of a targeted motion segment. The implant can be positioned between the adjacent spinous processes and once positioned, the implant can be arranged in a second configuration. When arranged in a second configuration, the distraction guide can act as a second wing. The first wing and the second wing can limit or block movement of the implant along a longitudinal axis of the implant.

BRIEF DESCRIPTION OF THE DRAWINGS

FIGS. 1*a*-1*f*. FIG. 1*a* is a front plan view of an embodiment of an assembled implant of the invention; FIG. 1*b* is a left side view of the embodiment of the invention of FIG. 1*a*; FIG. 1*e* is a front plan view of the embodiment of the invention of FIG. 1*a* including a spacer, a main body and a first wing; FIG. 1*d* is a left side view of the second wing of the embodiment of the invention of FIG. 1*a*; FIG. 1*e* is a front plan view of the second wing of the embodiment of the invention of FIG. 1*a*; FIG. 1*f* is an end view of the spacer of the embodiment of the invention of FIG. 1*a*.

FIG. 69A is a perspective view of the implant of FIG. 68A including a cannula within which the implant is disposed for insertion into desired location between adjacent spinous processes.

FIG. 69B is a perspective view of the implant of FIG. 69A in a partially deployed configuration.

FIG. 69C is a perspective close-up view of the implant of FIG. 69A showing hinged structures connected by cords.

FIG. 70 illustrates an embodiment of a method for implanting an interspinous implant as shown in FIGS. 7-23 in accordance with the present invention.

FIG. 71 illustrates an embodiment of a method for implanting an interspinous implant as shown in FIGS. 64A-67 having deployable first and second wings in accordance with the present invention.

FIG. 72 illustrates an alternative embodiment of a method for implanting an interspinous implant as shown in FIGS. 68A-69B having deployable first and second wings by way of a cannula inserted between adjacent spinous processes in accordance with the present invention.

FIG. 73A is a perspective view of an implant including a spacer having a tear-drop shaped cross-section, a distraction guide, a first wing, and a second wing connectable with the distraction guide.

FIG. 73B is a perspective view of an implant including a rotatable spacer having an elliptical cross-section, a distraction guide, a first wing, and a second wing connectable with the distraction guide.

FIG. 74A is a perspective view of a frame of an implant in accordance with an embodiment of the present invention.

FIG. 74B is a perspective view of a spacer for use with the frame of FIG. 74A.

FIG. 74C is a perspective view of the spacer of FIG. 74B seated within the frame of FIG. 74A.

FIG. 75A is a partial cross-sectional posterior view of the frame of the implant of FIGS. 74A-74C positioned adjacent to an interspinous ligament disposed between adjacent spinous processes.

Figure 74A:
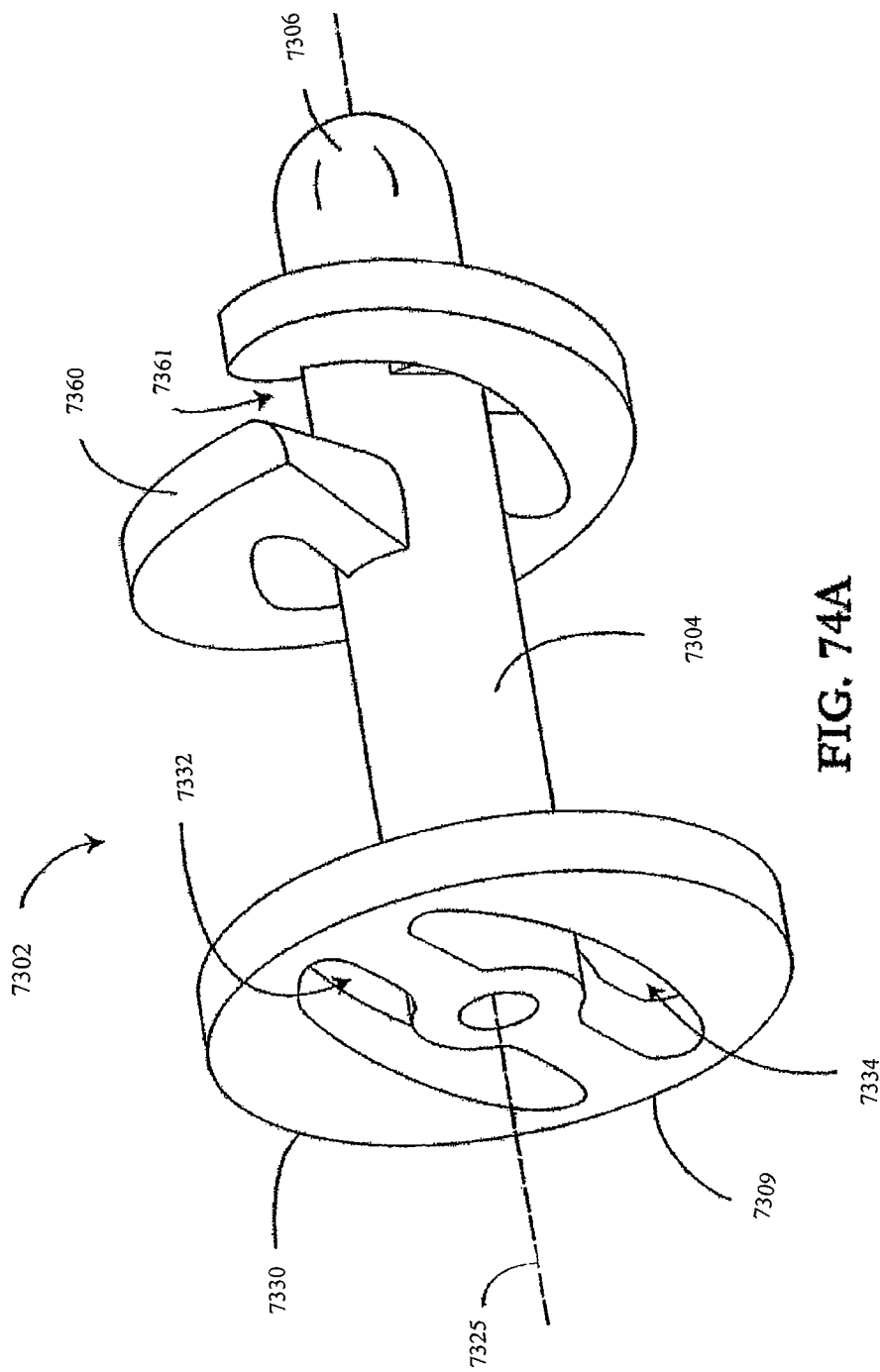
Figure 74B:
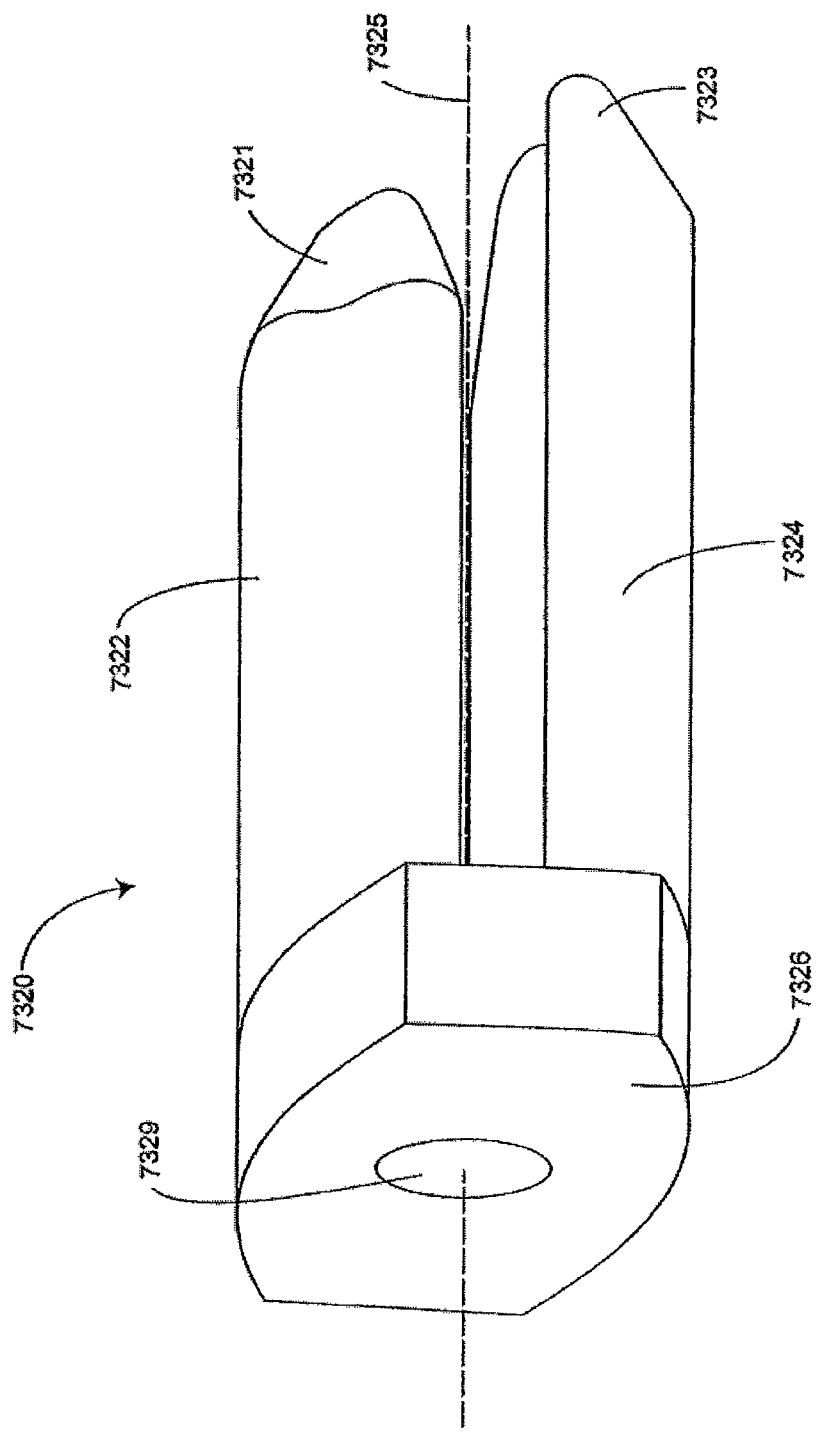
Figure 74C:
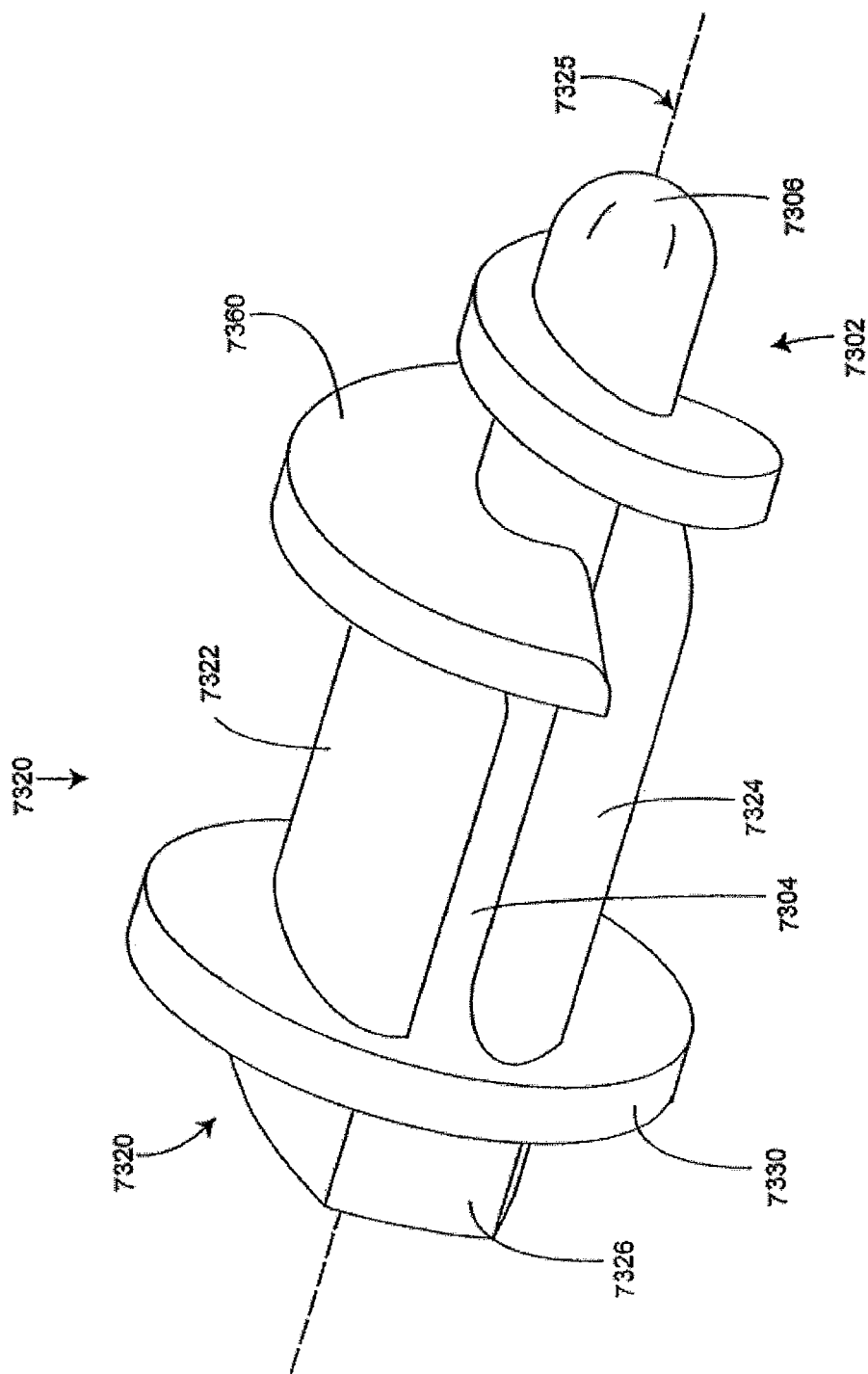
Figure 75A:
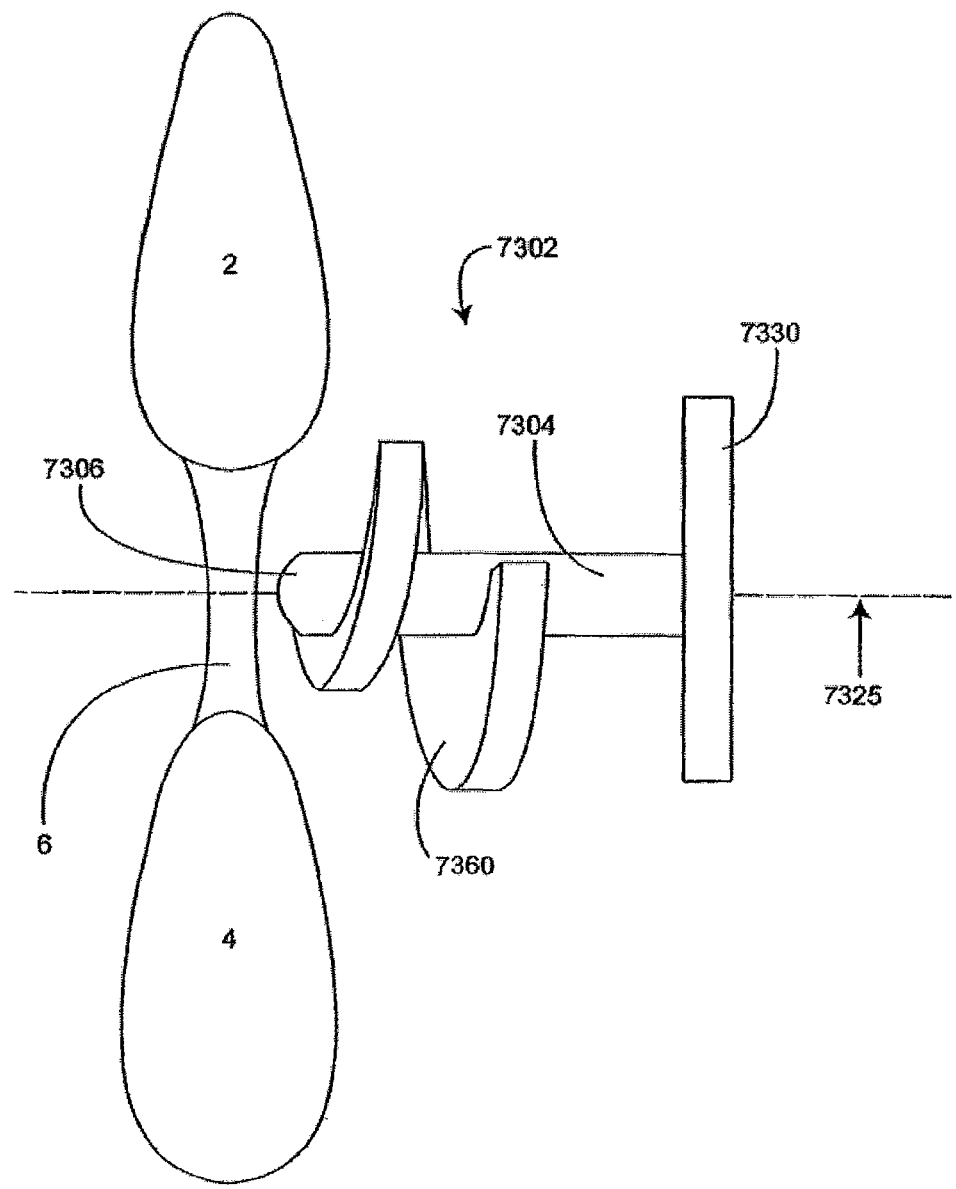
Figure 75B:
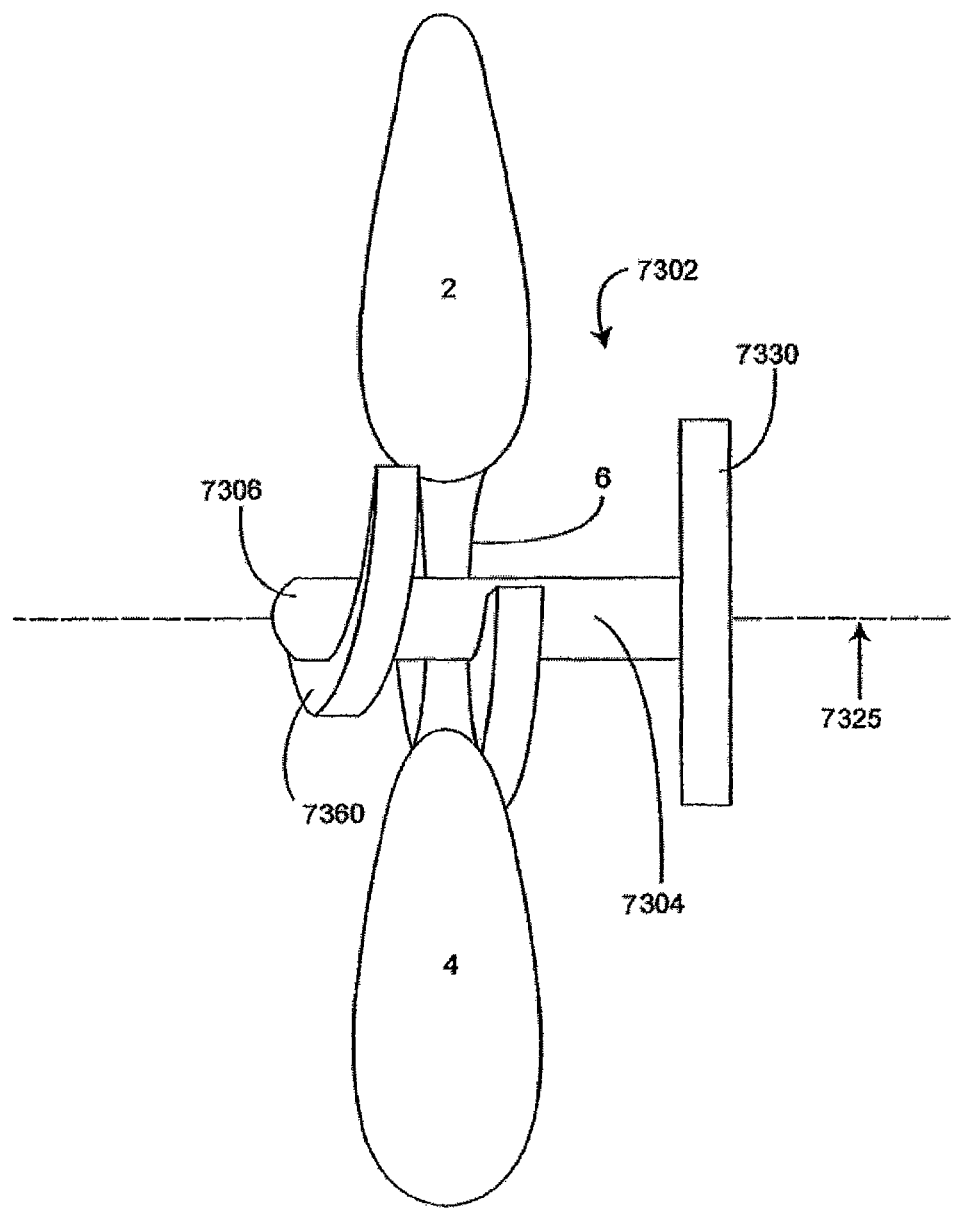

FIG. 75B partial cross-sectional posterior view of the frame of the implant of FIGS. 74A-74C rotated so that the interspinous ligament is disposed between a portion of the helical shaped second wing and the first wing along a longitudinal axis of the implant.

Figure 75C:
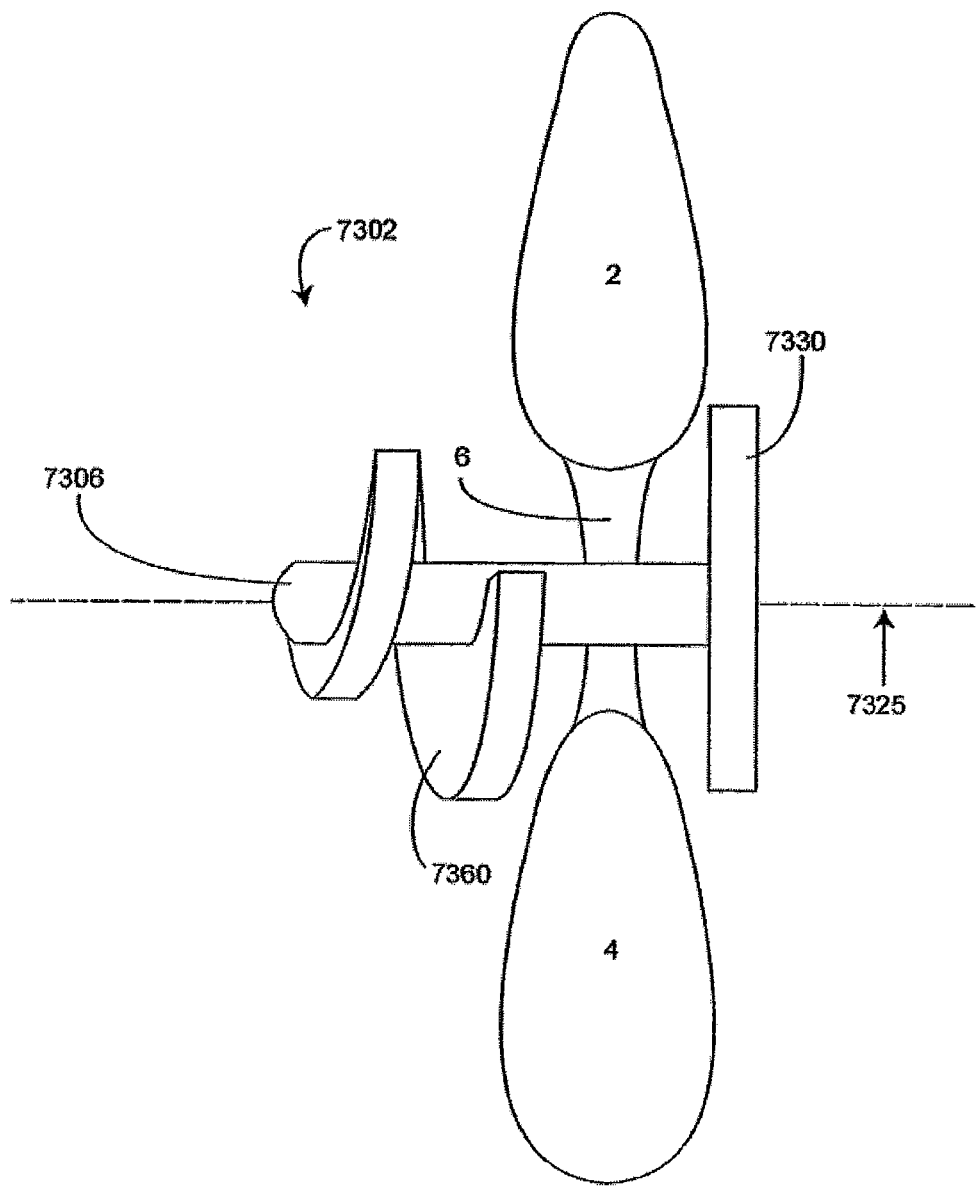

FIG. 75C partial cross-sectional posterior view of the frame of the implant of FIGS. 74A-74C rotated so that the interspinous ligament is disposed between the entire helical shaped second wing and the first wing along the longitudinal axis.

Figure 75D:
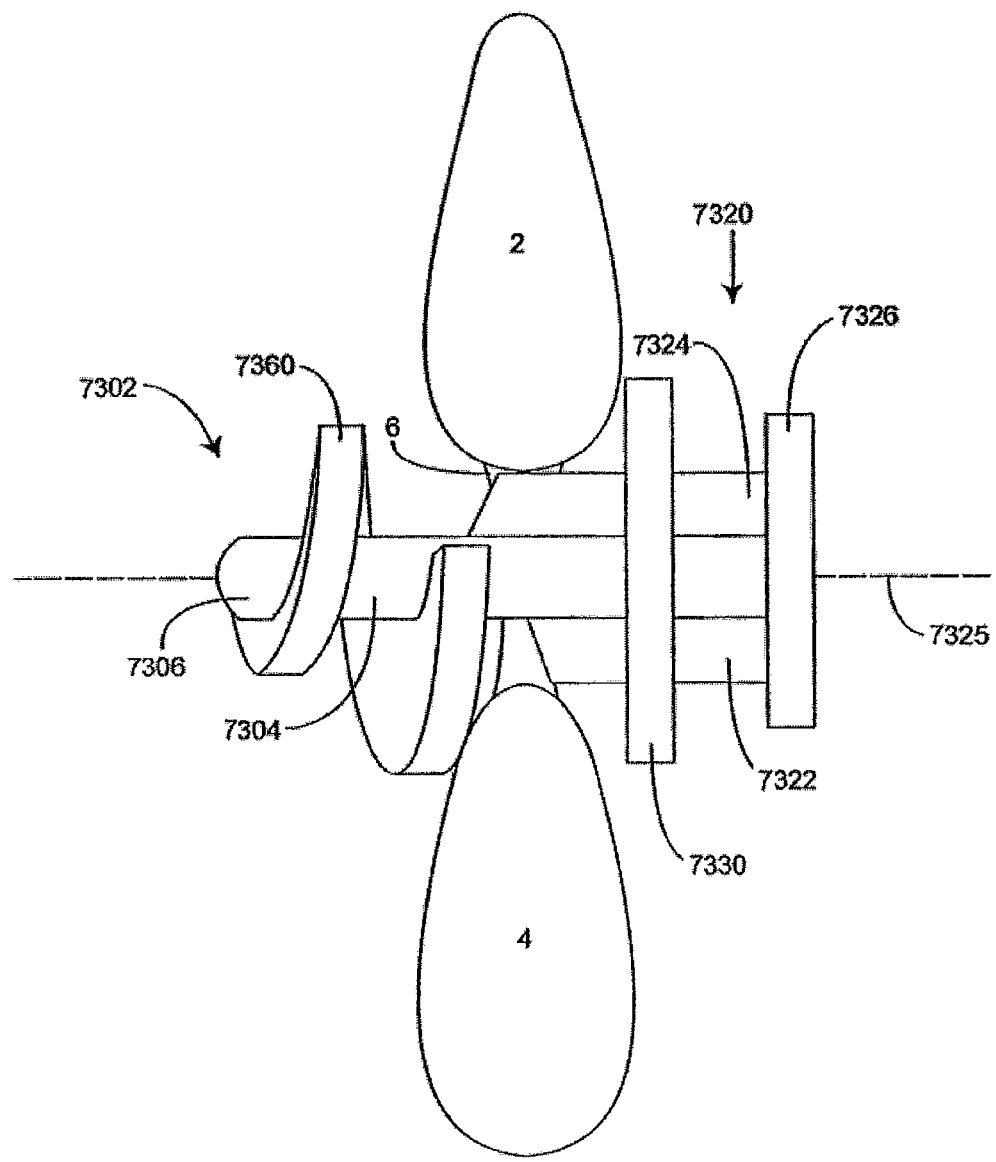

FIG. 75D partial cross-sectional posterior view of the frame of the implant of FIGS. 74A-74C wherein a spacer is partially arranged over a central body of the frame so that a portion of the spacer partially distracts the interspinous ligament.

Figure 75E:
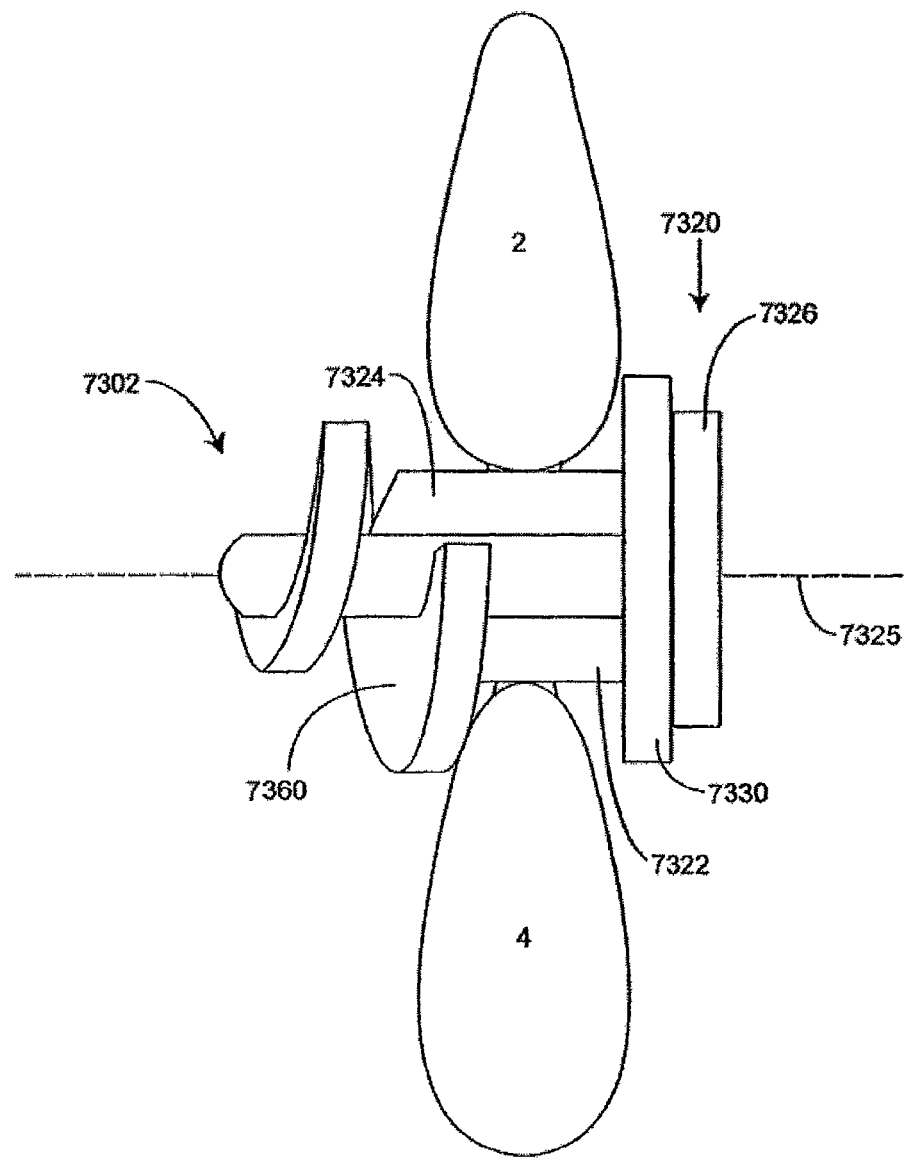

FIG. 75E partial cross-sectional posterior view of the frame of the implant of FIGS. 74A-74C wherein the spacer is seated over the central body of the frame so that a portion of the spacer partially distracts the interspinous ligament.

Figure 76A:
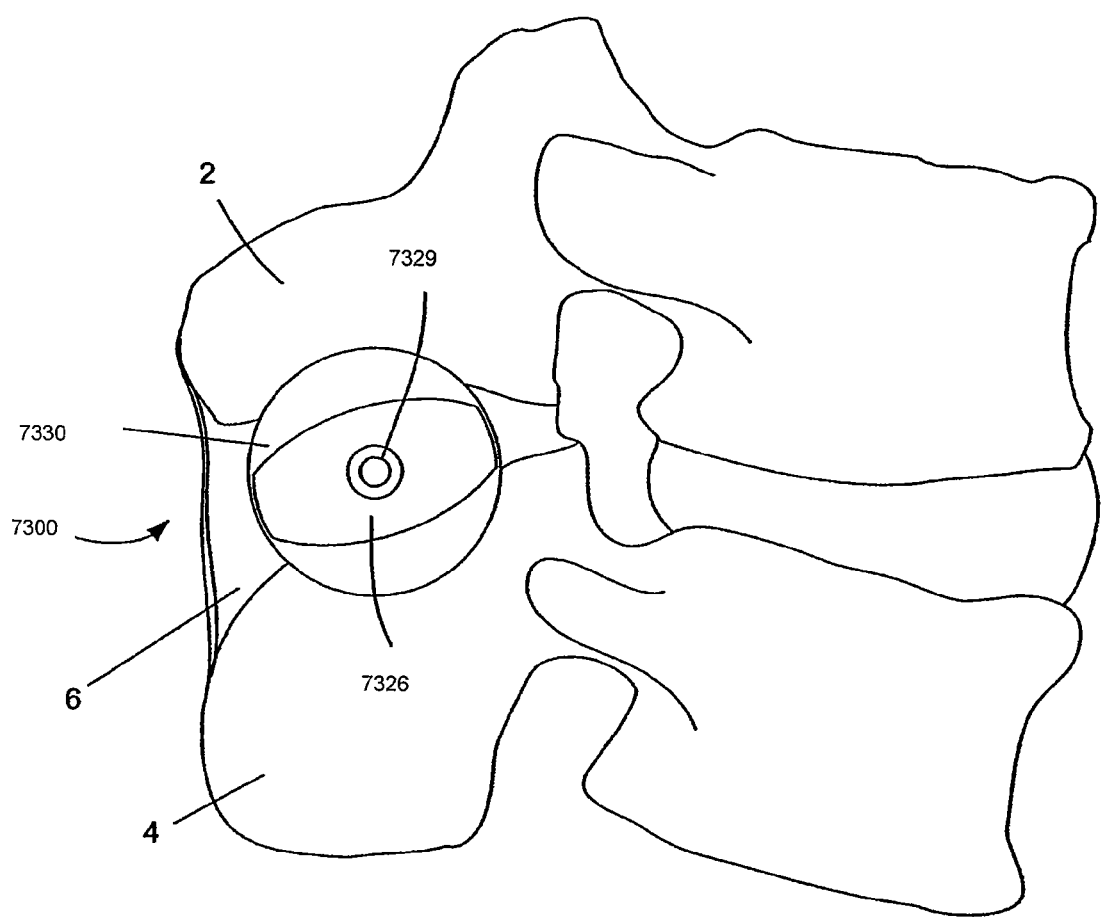

FIG. 76A is an end view of the implant of FIG. 75E positioned between adjacent spinous processes.

Figure 76B:
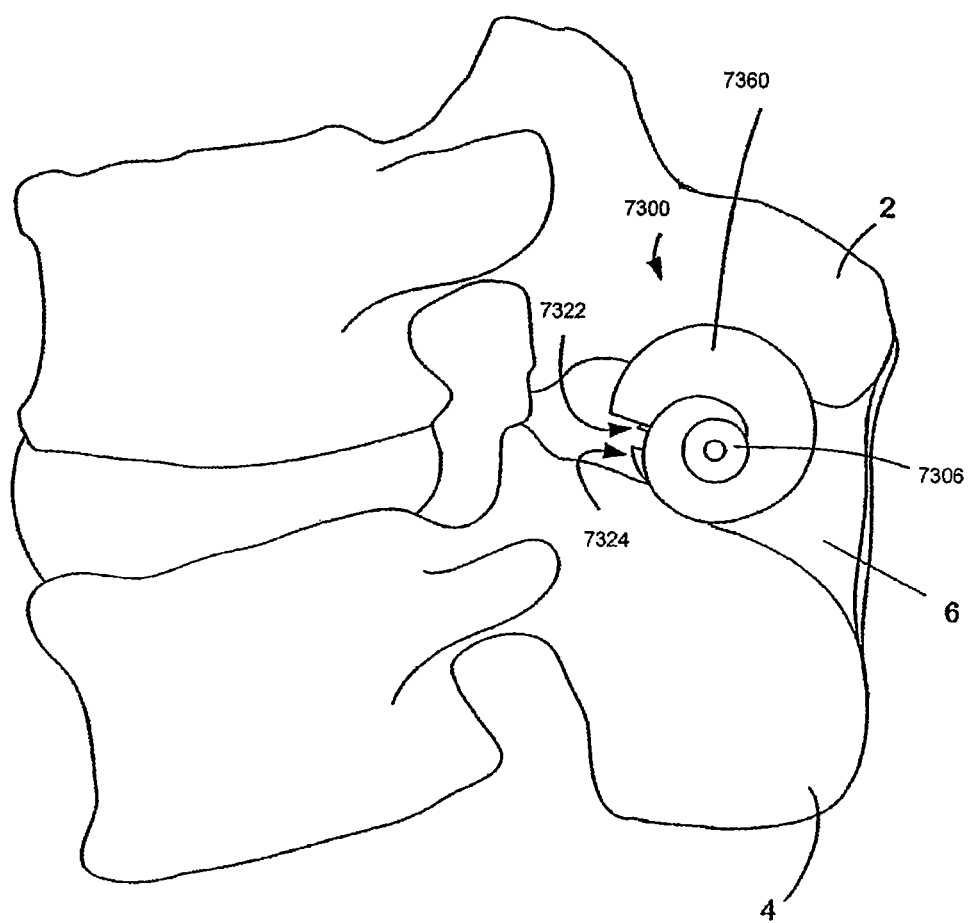

FIG. 76B is an front view of the implant of FIG. 75E positioned between adjacent spinous processes.

Figure 77A:
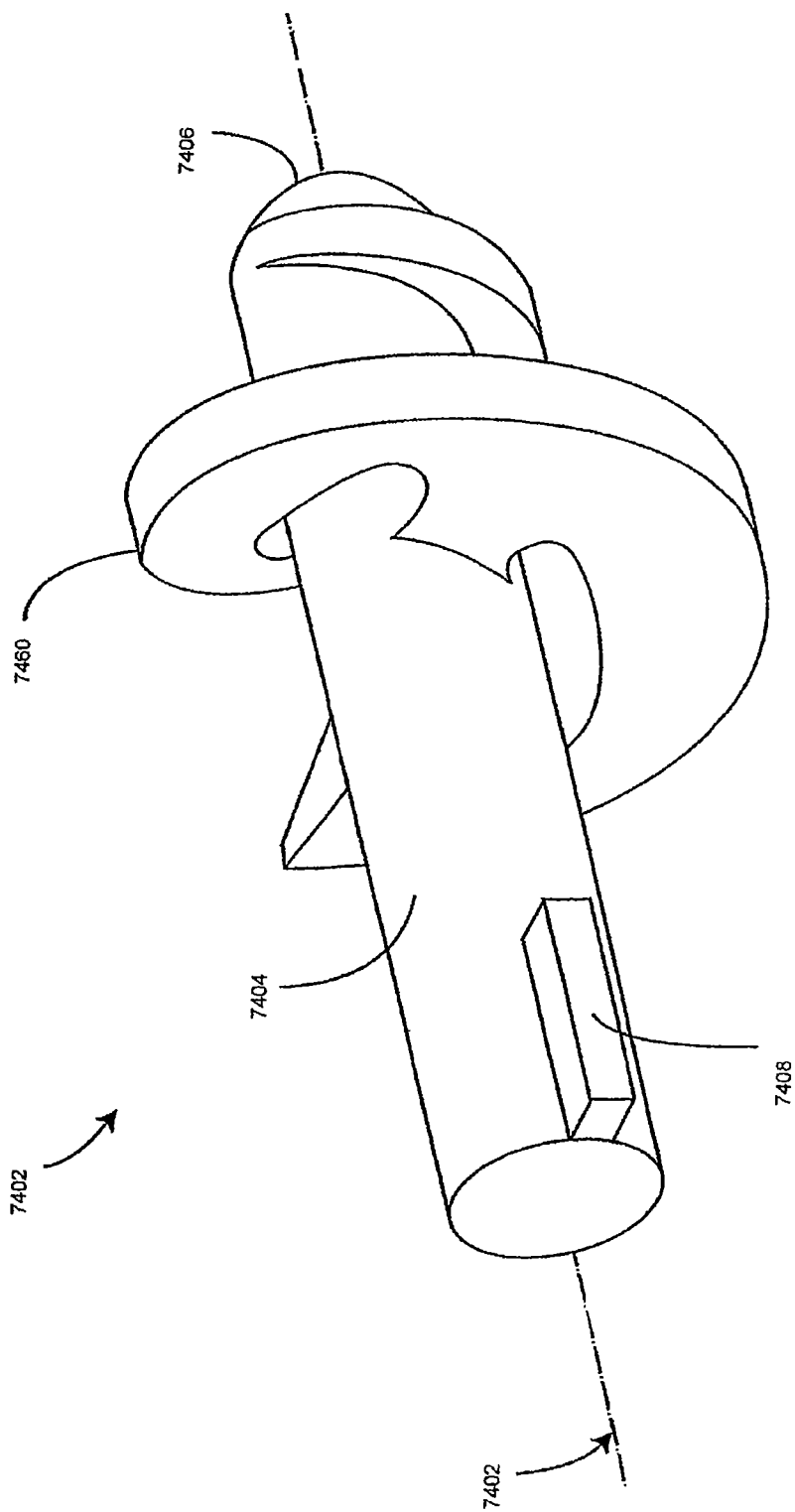

FIG. 77A is a perspective view of a frame from an alternative embodiment of an implant in accordance the present invention.

Figure 77B:
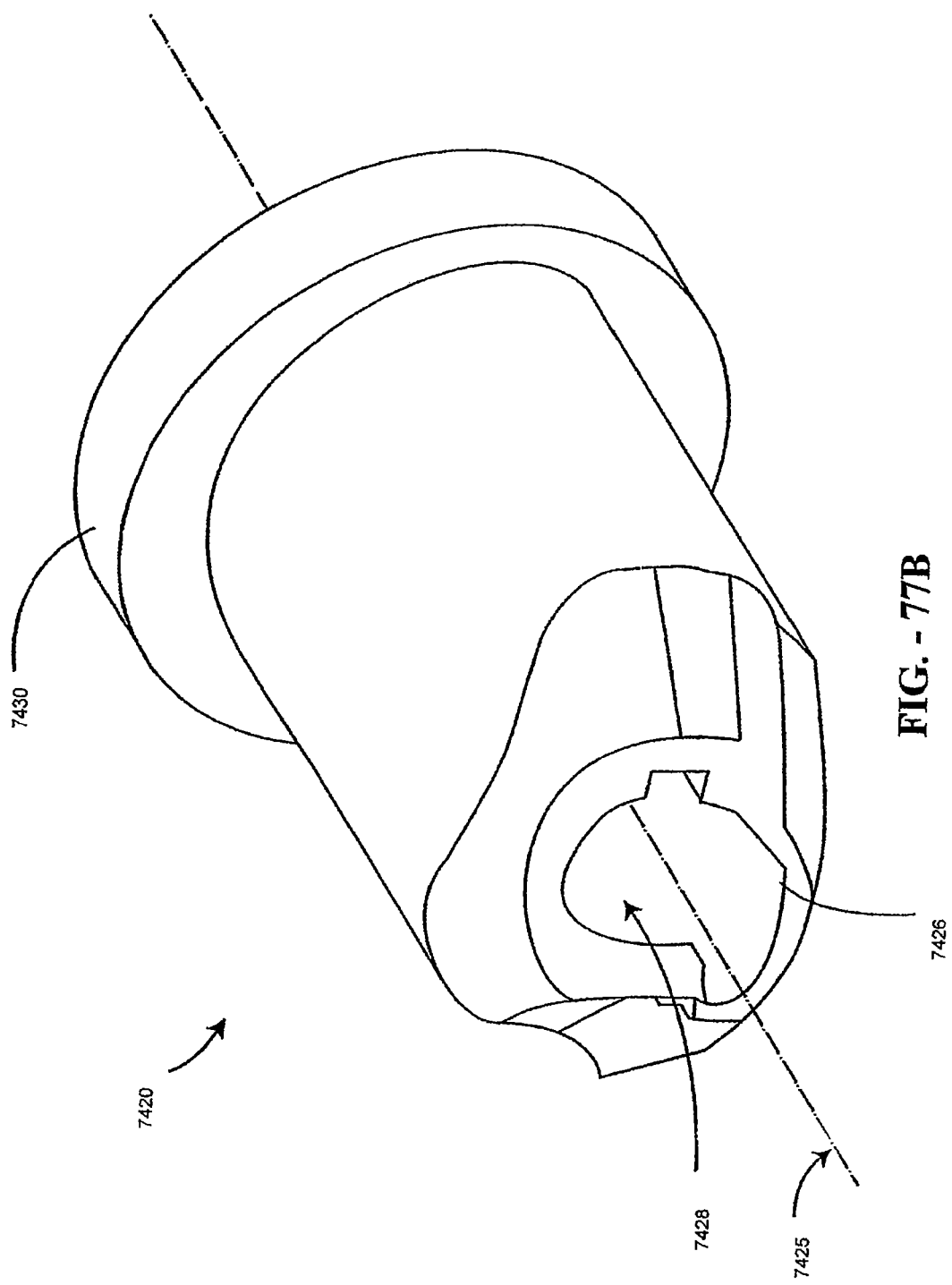

FIG. 77B is a perspective view of a spacer for use with the frame of FIG. 77A.

Figure 77C:
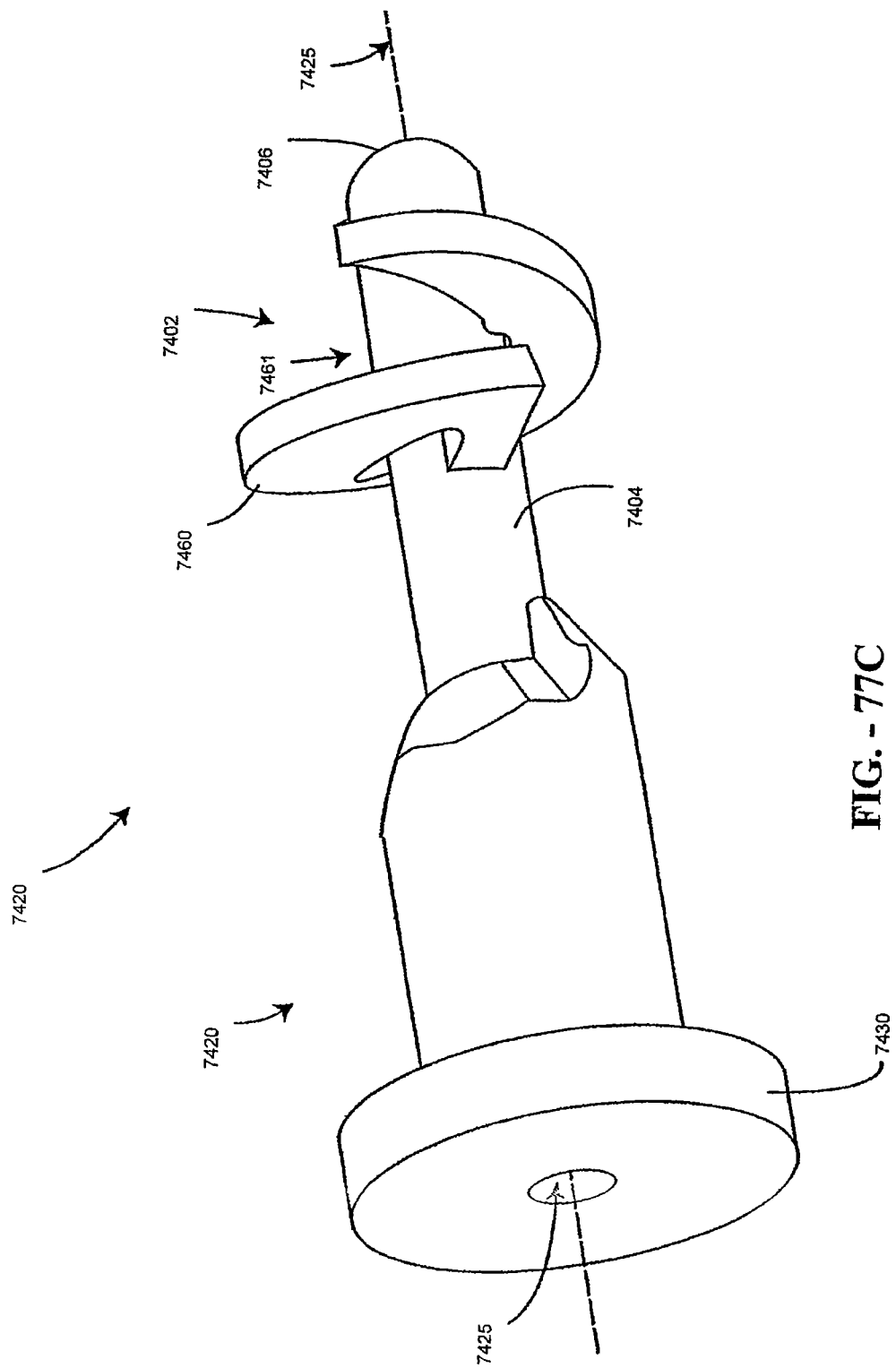

FIG. 77C is a perspective view of the spacer of FIG. 77B seated within the frame of FIG. 77A.

Figure 78:
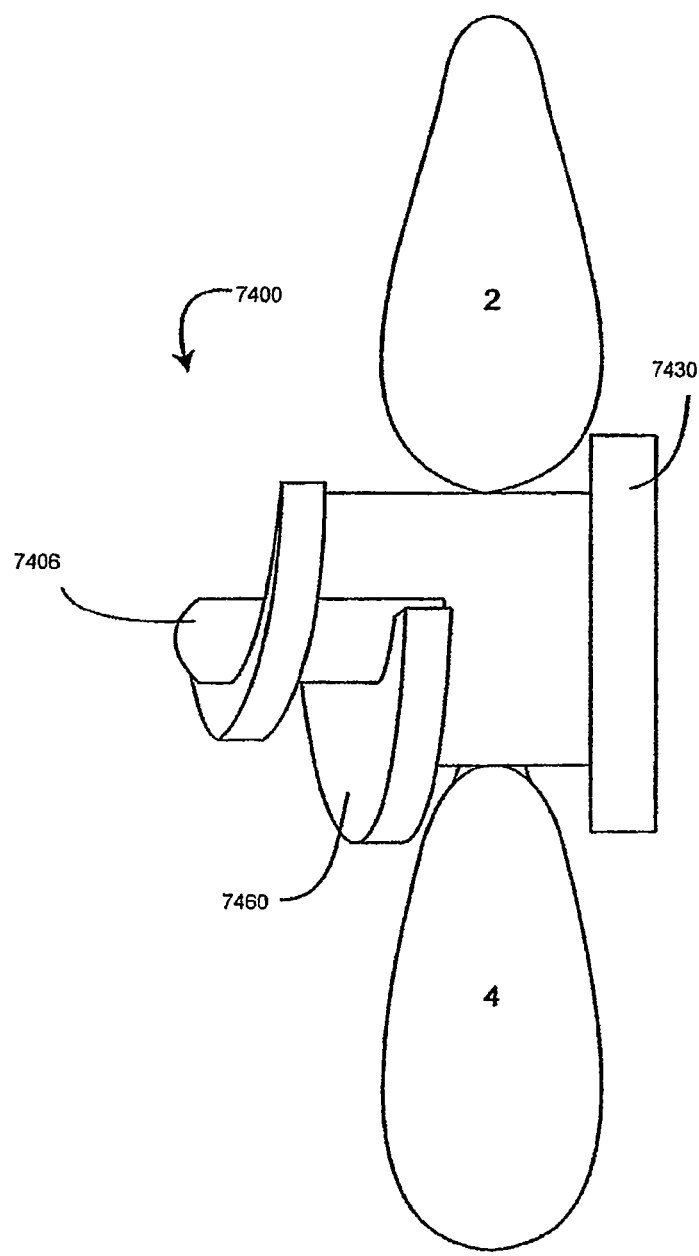

FIG. 78 is a side view of the implant of FIGS. 77A-77C positioned between adjacent spinous processes.

Figure 79A:
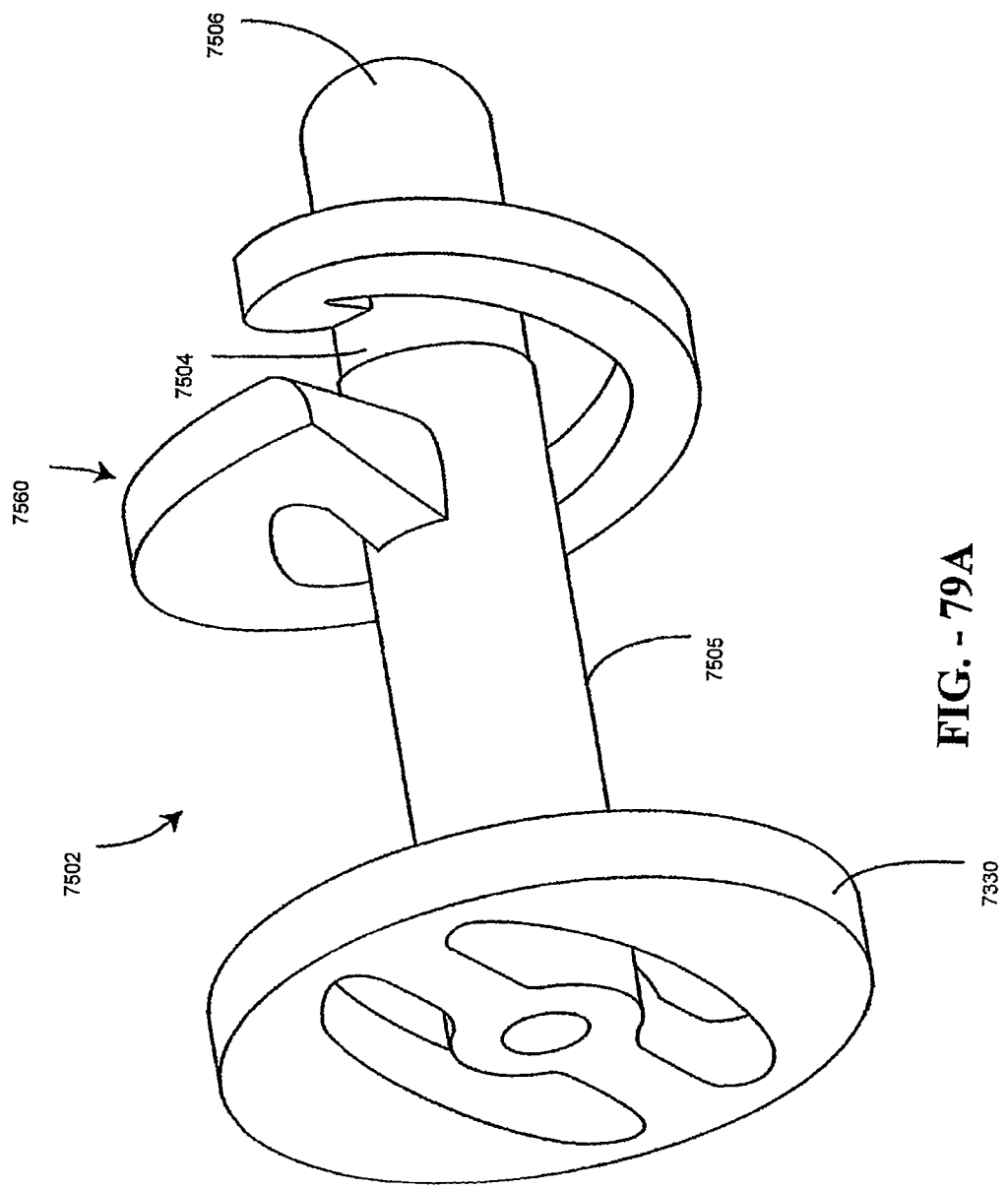

FIG. 79A is a perspective view of a frame from a still further embodiment of an implant in accordance with the present invention.

Figure 79B:
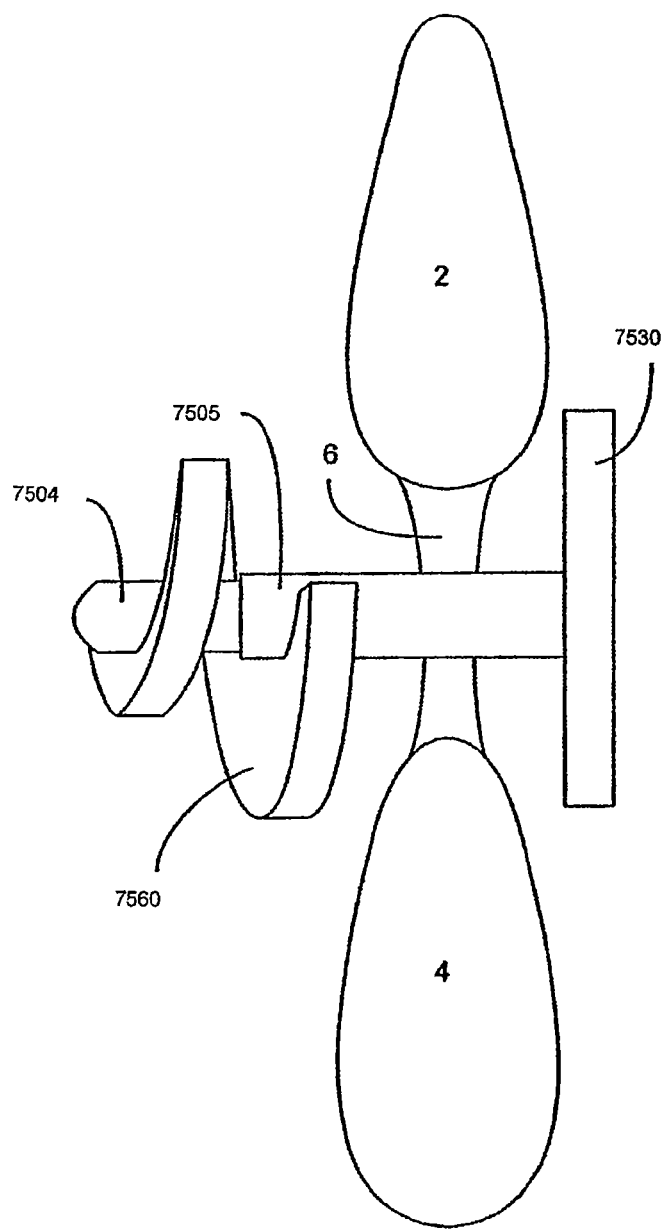

FIG. 79B is a side view of the frame of FIG. 79A positioned between adjacent spinous processes.

Figure 79C:
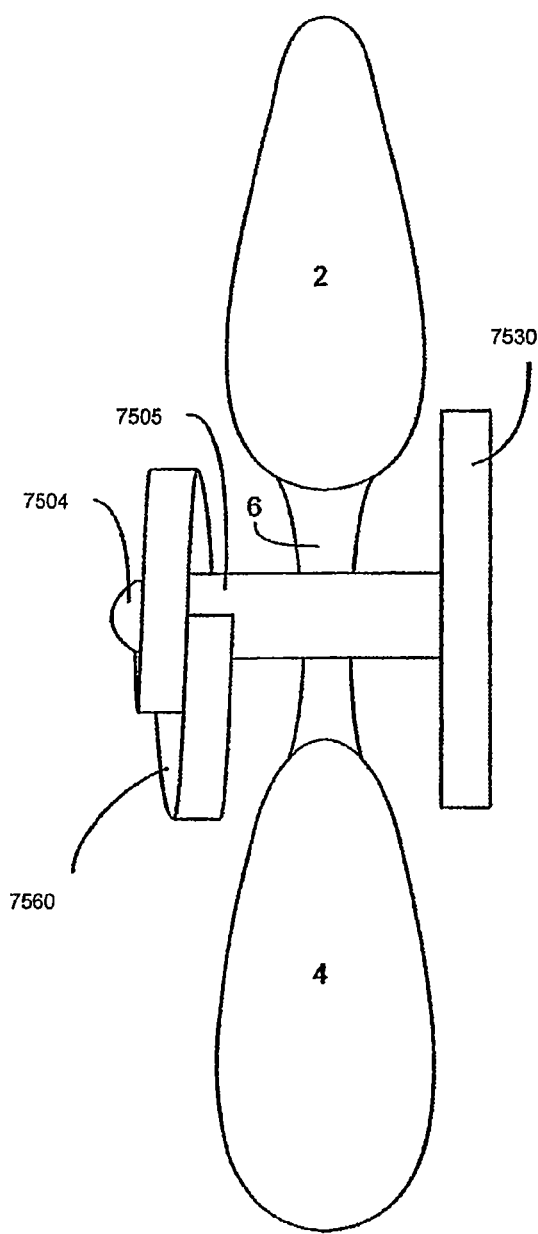

FIG. 79C is a side view of the frame of FIG. 79A positioned between adjacent spinous processes and retracted to collapse the second wing.

Figure 80:
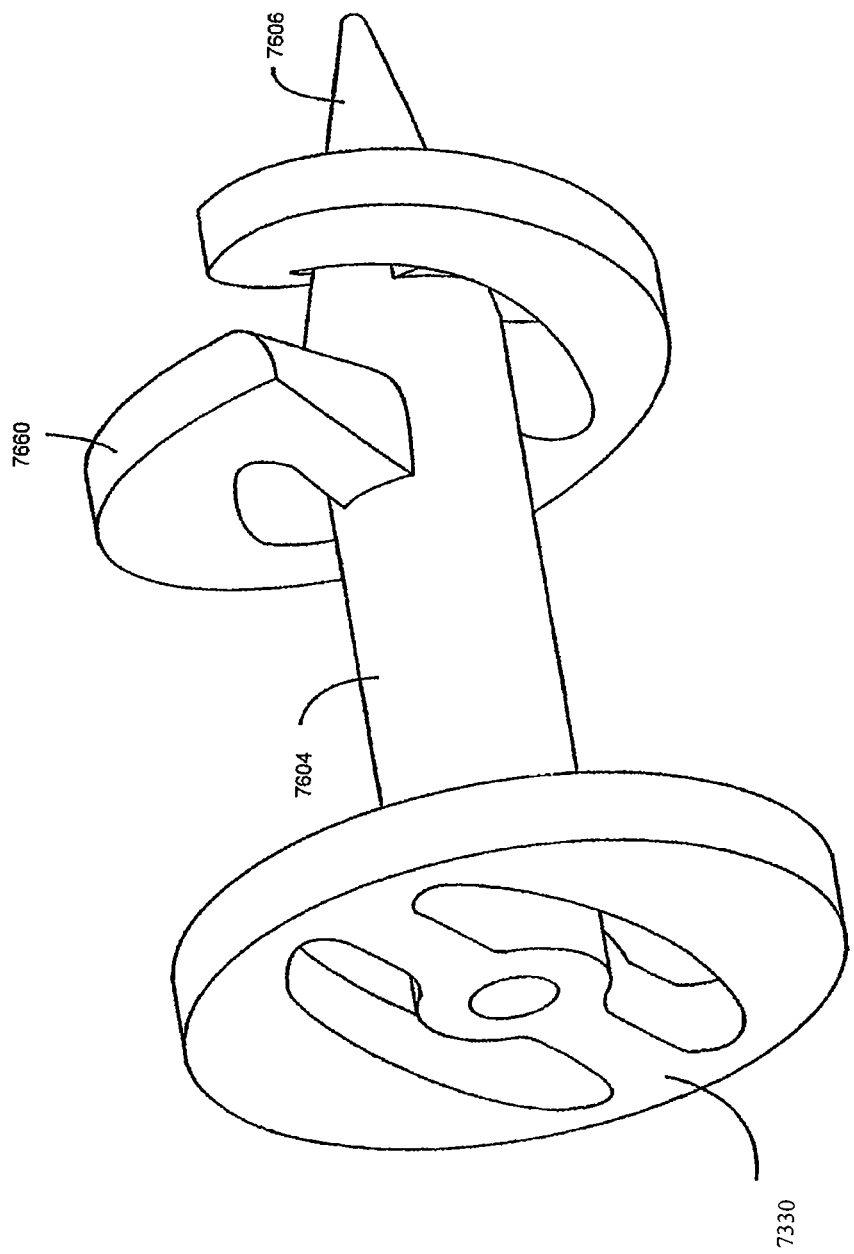

FIG. 80 is a perspective view of a frame from a still further embodiment of an implant in accordance with the present invention.

Figure 81:
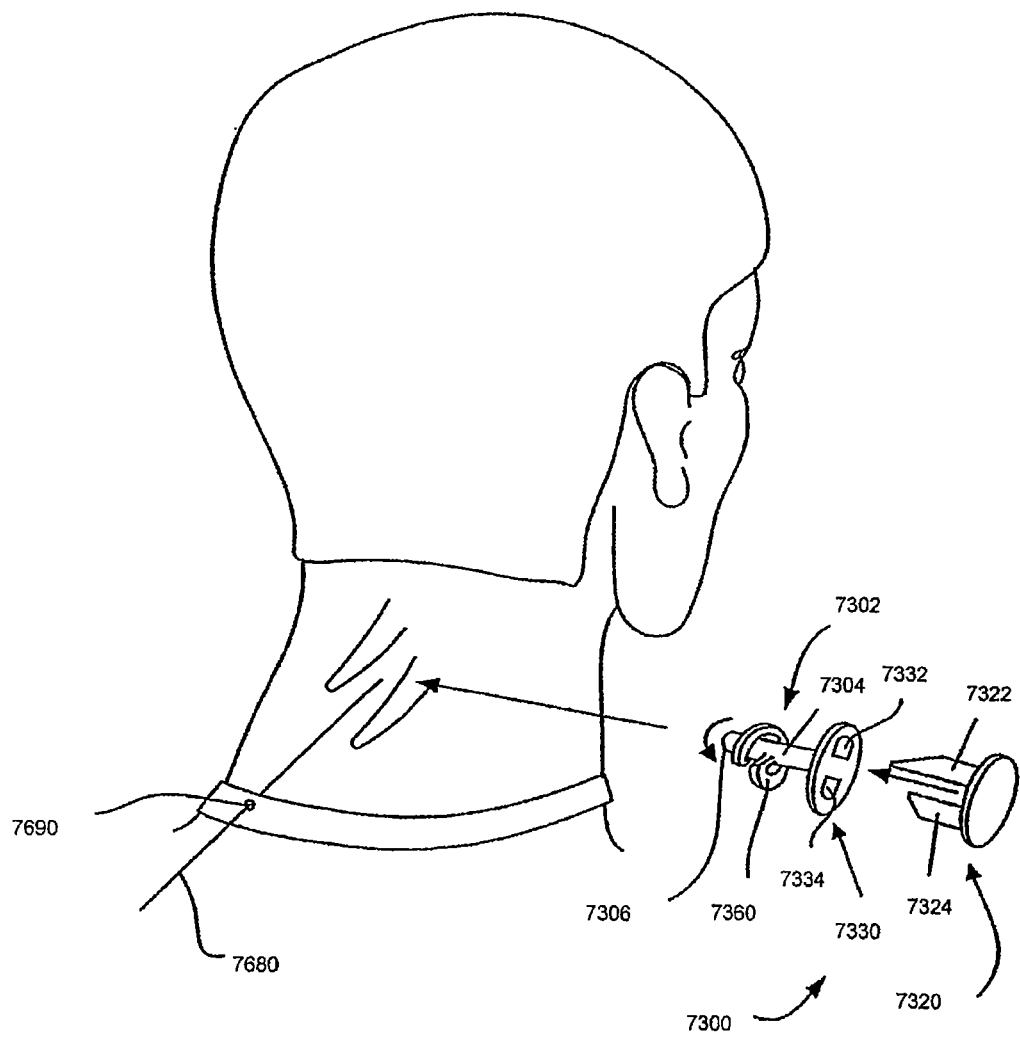

FIG. 81 illustrates an embodiment of a method for implanting an interspinous implant between adjacent spinous processes of the cervical region in accordance with the present invention.

Figure 82:
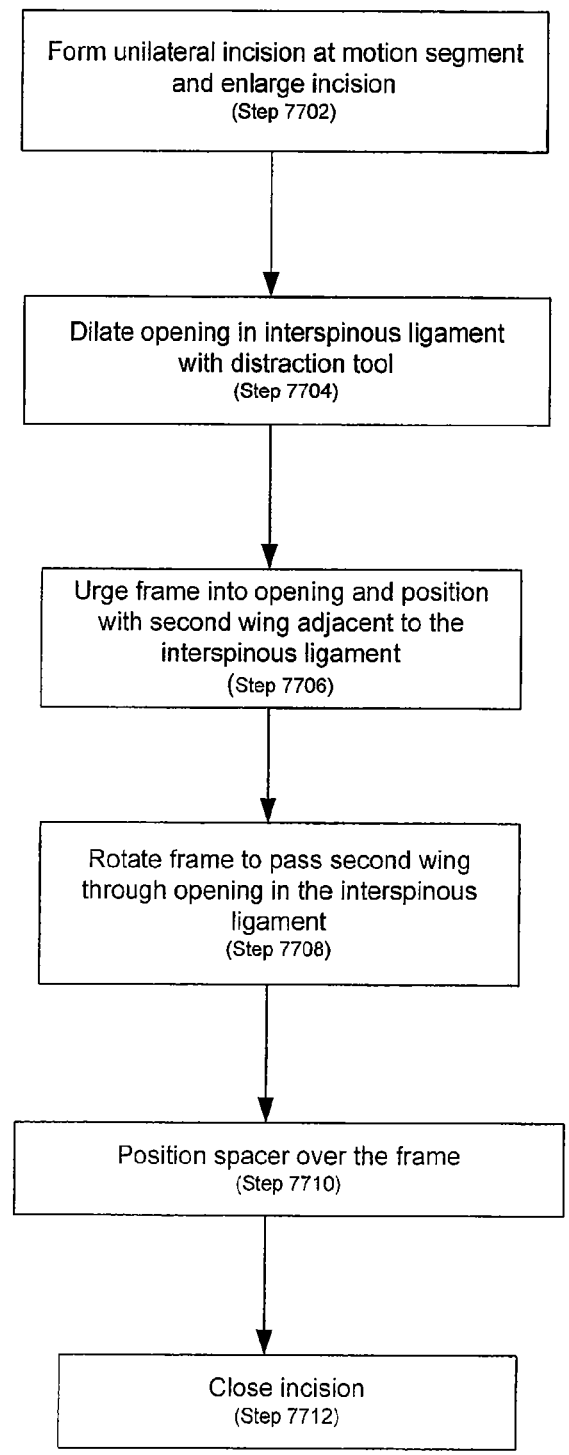

FIG. 82 is a flowchart of a method for implanting an interspinous implant between adjacent spinous processes of the lumbar region in accordance with the present invention.

FIG. 83 is a perspective view of an alternative embodiment of an implant for use with systems and methods of the present invention, the implant including an distraction piece mated with a initiating piece.

Figure 84A:
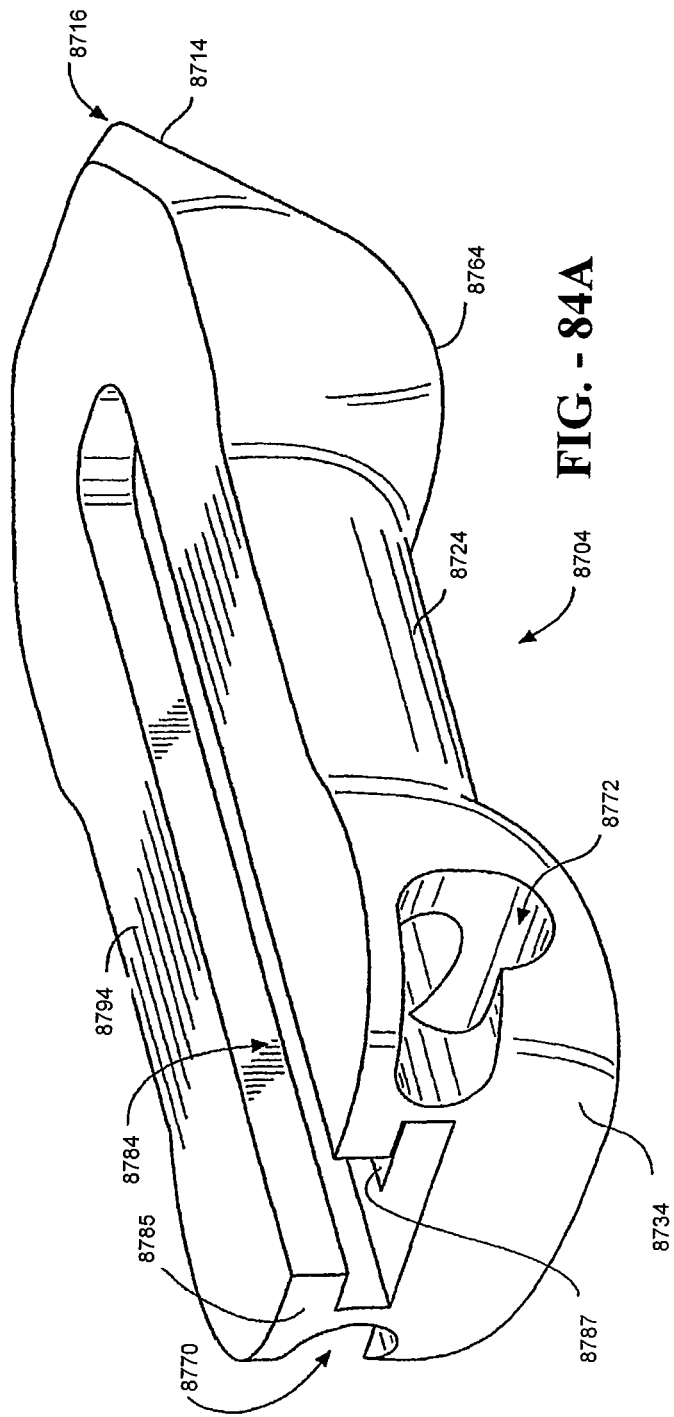

FIG. 84A is a perspective view of the initiating piece of the implant of FIG. 83.

FIG. 84B is a perspective view of a proximal end of an insertion tool having prongs positioned within cavities of the initiating piece.

Figure 84C:
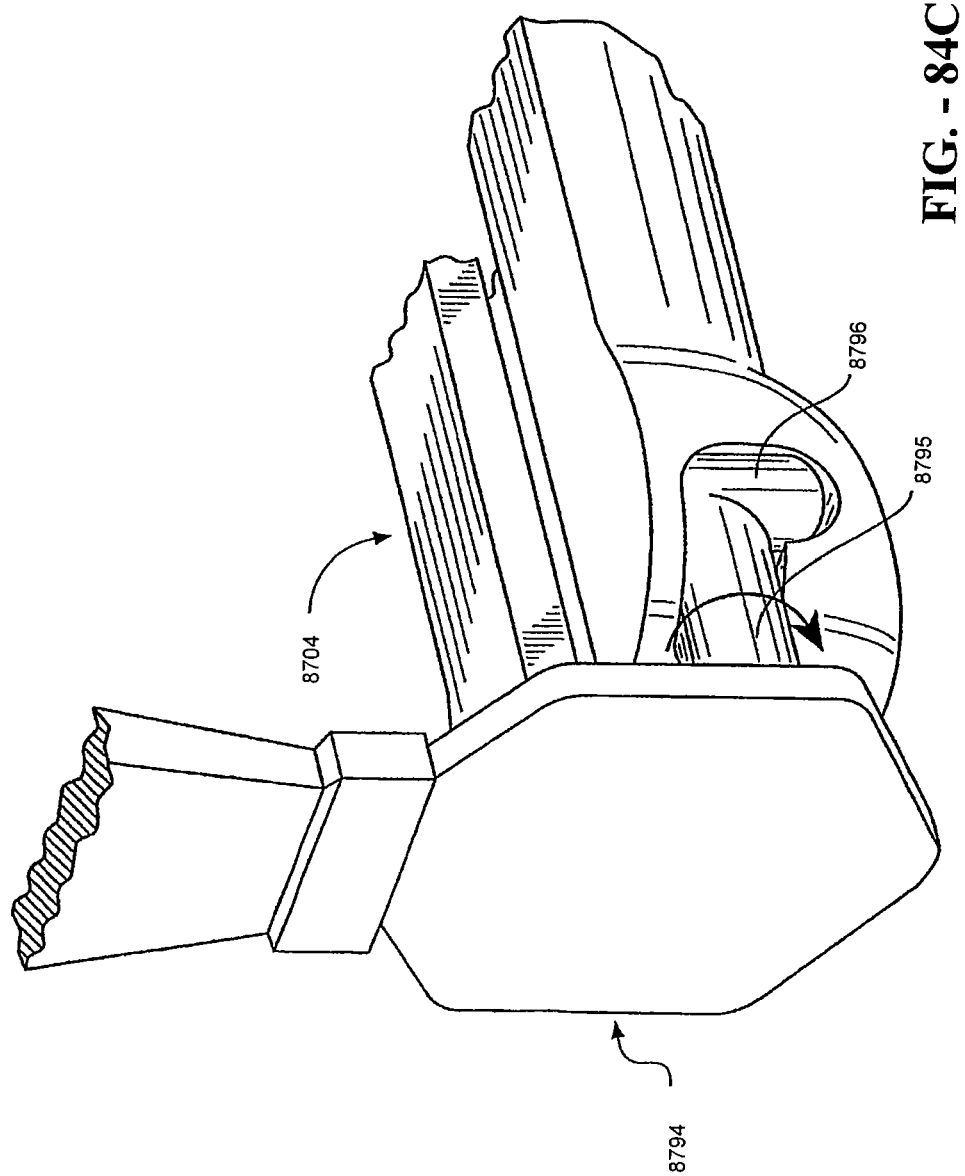

FIG. 84C is a perspective view of the prongs arranged in a locked position within the cavities of the initiating piece.

FIGS. 85A-85D are posterior views of the initiating piece of FIG. 84A as the initiating piece is urged into position with the interspinous ligament disposed between a lower portion of first wing and a lower portion of the second wing.

Figure 86:
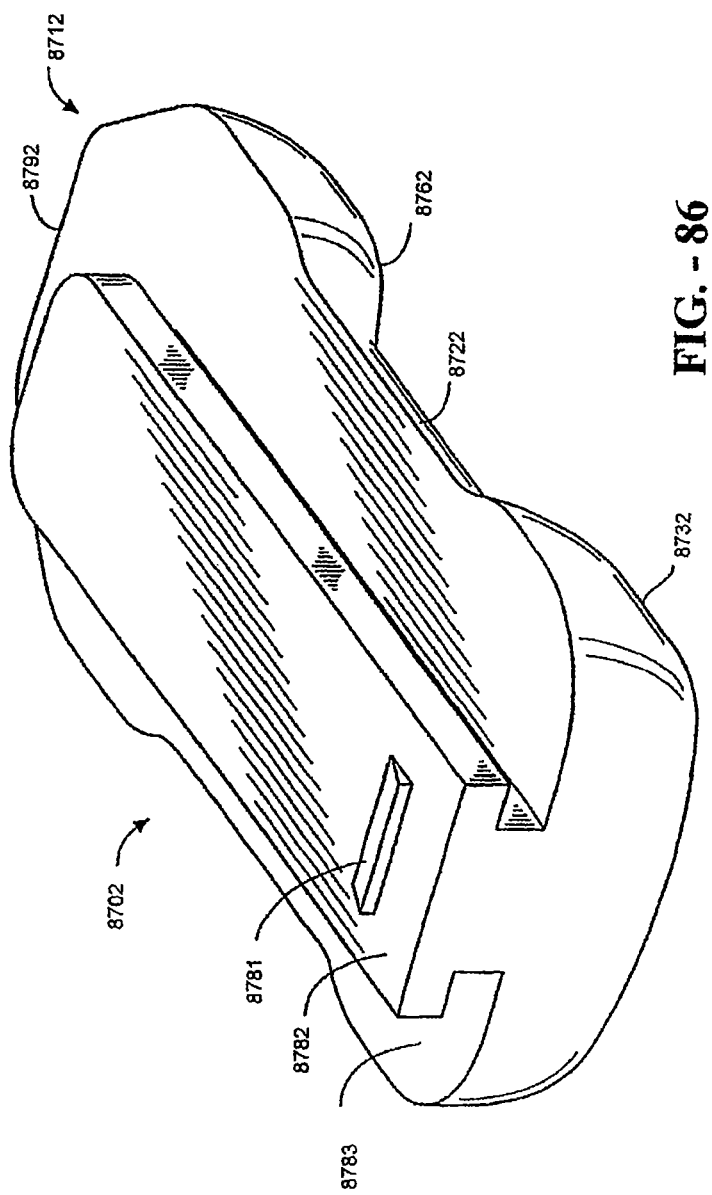

FIG. 86 is a perspective view of the slide-in distraction piece of the implant of FIG. 83.

Figure 85B:
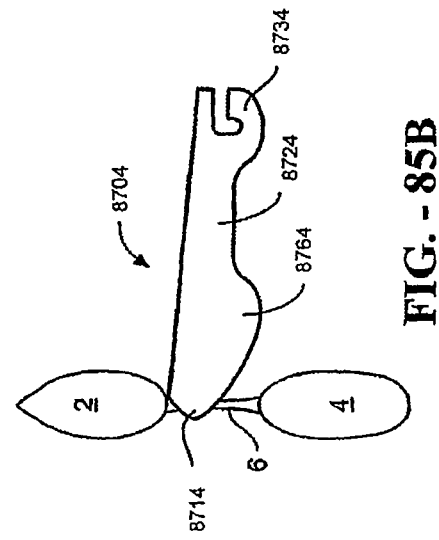
Figure 85A:
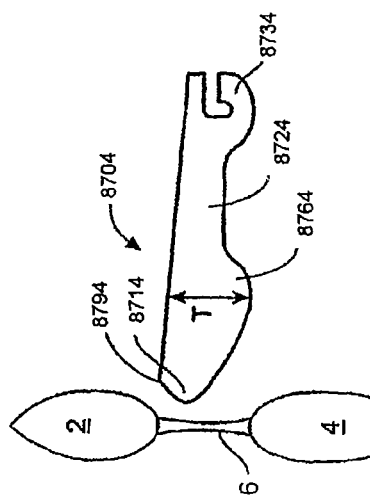
Figure 85D:
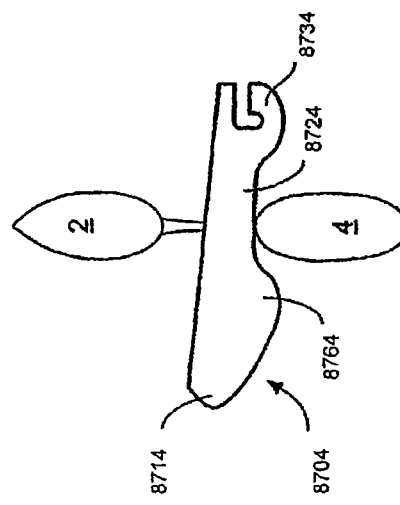

FIGS. 87A-87D are posterior views showing the slide-in distraction piece of FIG. 86 mating with the initiating piece positioned as shown in FIG. 85D so that an implant as shown in FIG. 83 is disposed between the adjacent spinous processes.

Figure 88A:
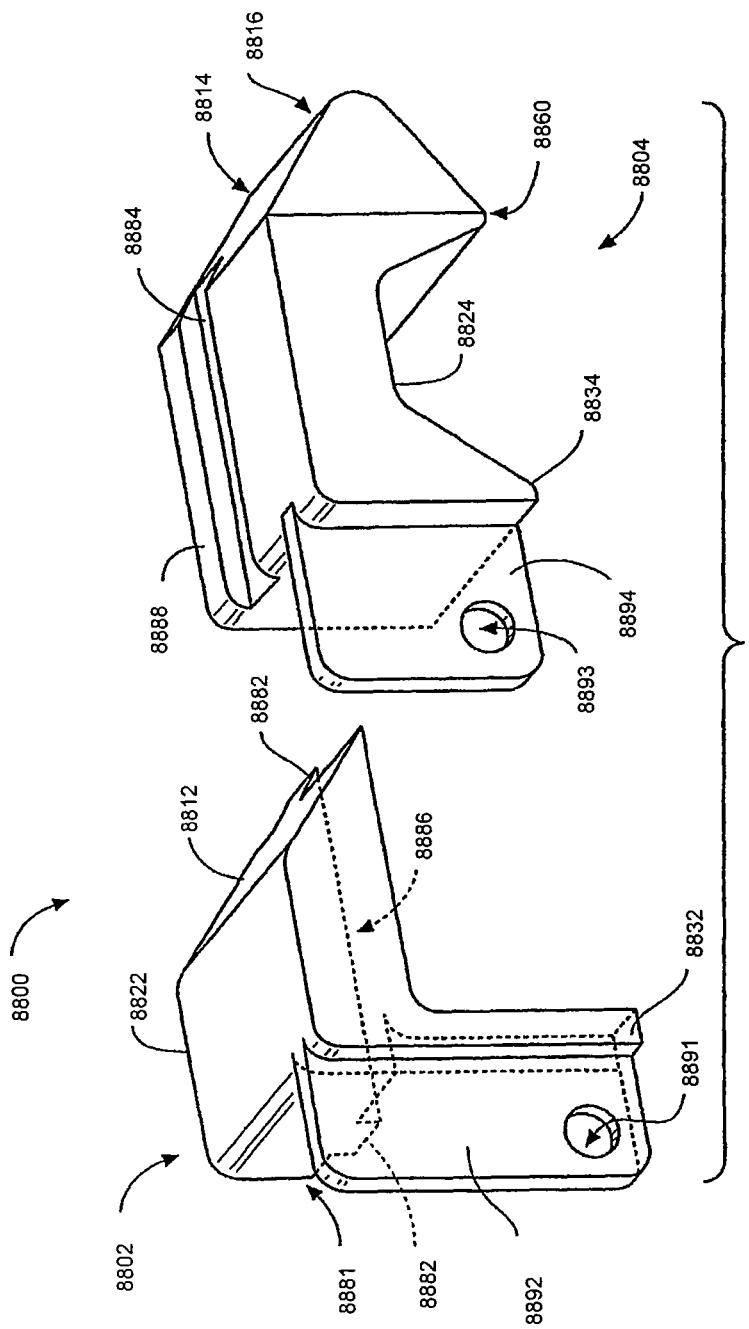

FIG. 88A is a perspective view of an alternative embodiment of an implant for use with systems and methods of the present invention, the implant including an distraction piece mated with a initiating piece.

Figure 88B:
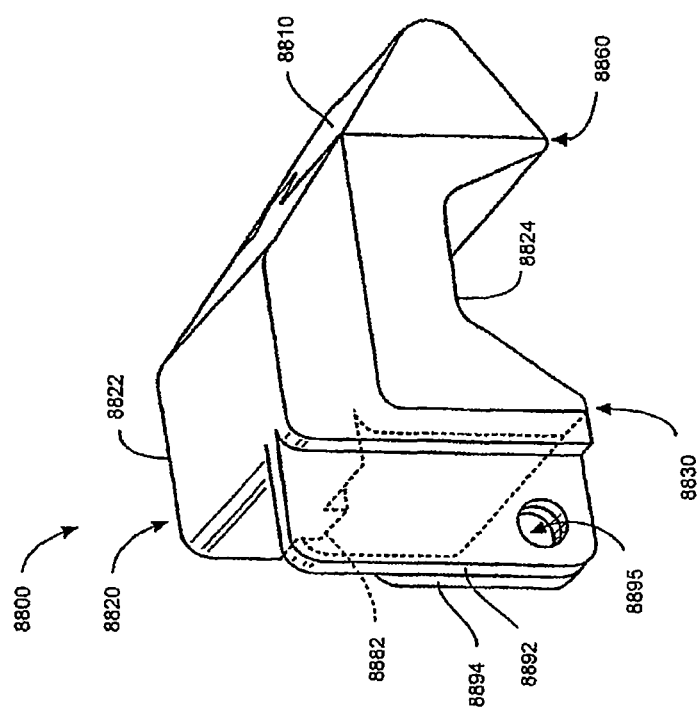

FIG. 88B is a perspective view of the implant of FIG. 88A, the implant including an distraction piece mated with a initiating piece.

FIGS. 89A-89C are posterior views of the initiating piece of FIG. 88A as the initiating piece is urged in position with the interspinous ligament disposed between the first wing and the second wing.

FIGS. 89D and 89E are posterior views showing the distraction piece of FIG. 88A urged so that the distraction piece is mated with the initiating piece.

Figure 90:
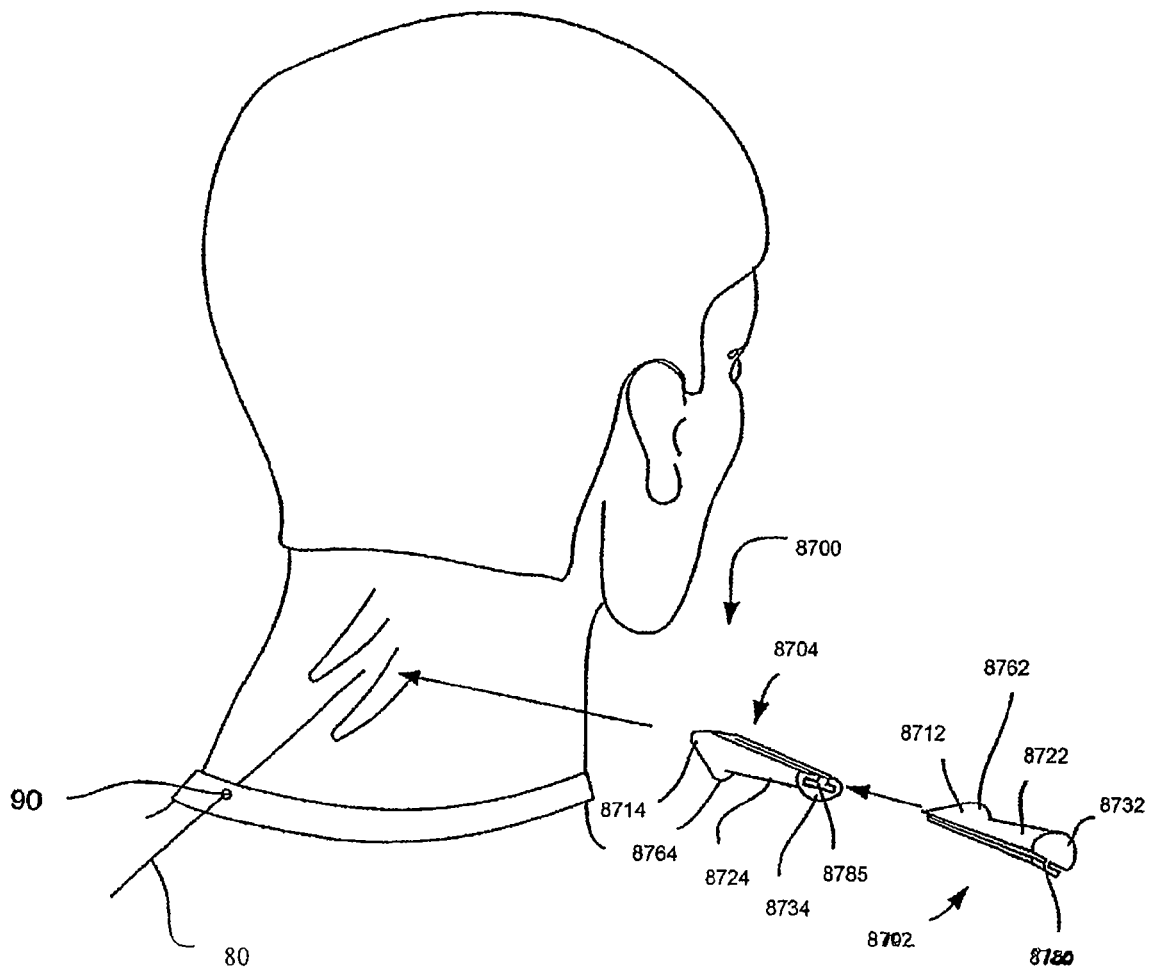

FIG. 90 illustrates an embodiment of a method in accordance with the present invention for implanting the interspinous implant of FIG. 83.

Figure 91:
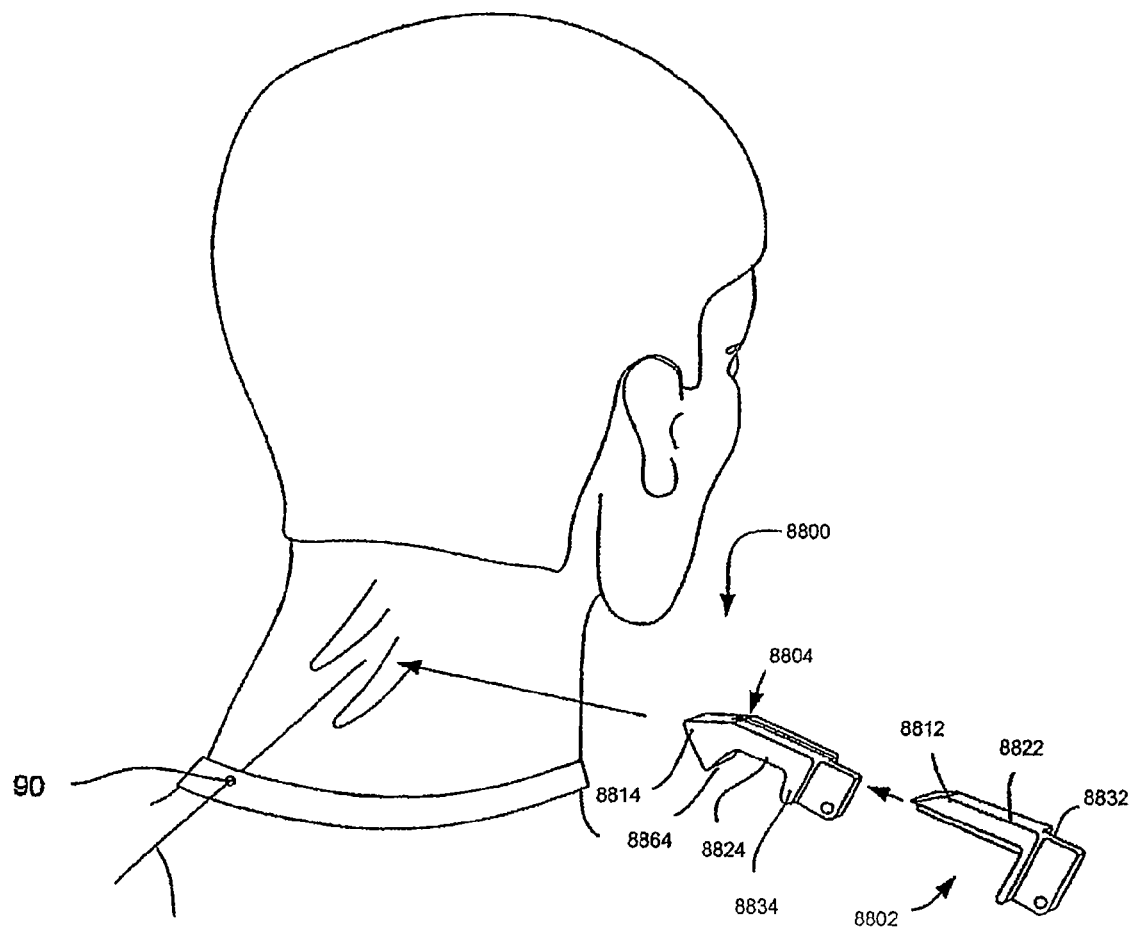

FIG. 91 illustrates an embodiment of a method in accordance with the present invention for implanting the interspinous implant of FIG. 88A.

DETAILED DESCRIPTION

The following description is presented to enable any person skilled in the art to make and use the invention. Various modifications to the embodiments described will be readily apparent to those skilled in the art, and the principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all patents and patent applications cited in this application are incorporated herein by reference.

Figure 1A:
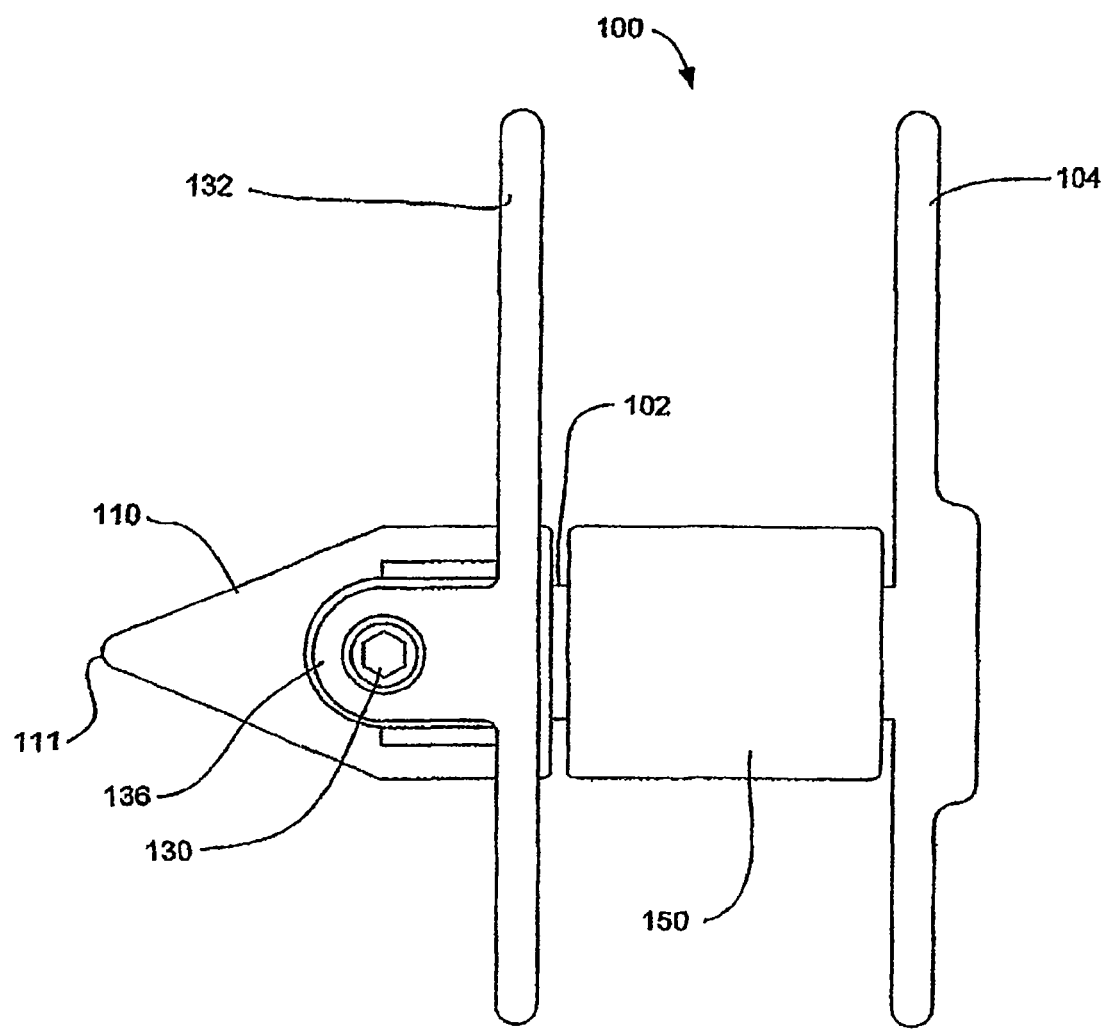

An embodiment of an implant 100 of the invention is depicted in FIG. 1a.

This implant 100 includes a first wing 104 and a spacer 150 and a lead-in tissue expander or distraction guide 110. This embodiment further can include, as required, a second wing 132. As can be seen in FIG. 1a, a shaft 102 extends from the first wing 104 and is the body that connects the first wing 104 to the tissue expander or distraction guide 110. Also, as can be seen in FIGS. 1a and 1b, the distraction guide 110 in this particular embodiment acts to distract the soft tissue and the spinous processes when the implant 100 is inserted between adjacent spinous processes. In this particular embodiment, the guide 110 has an expanding cross-section from the distal end 111 to the area where the second wing 132 is secured to the guide 110. In this embodiment the guide 110 is wedge-shaped.

Figure 1F:
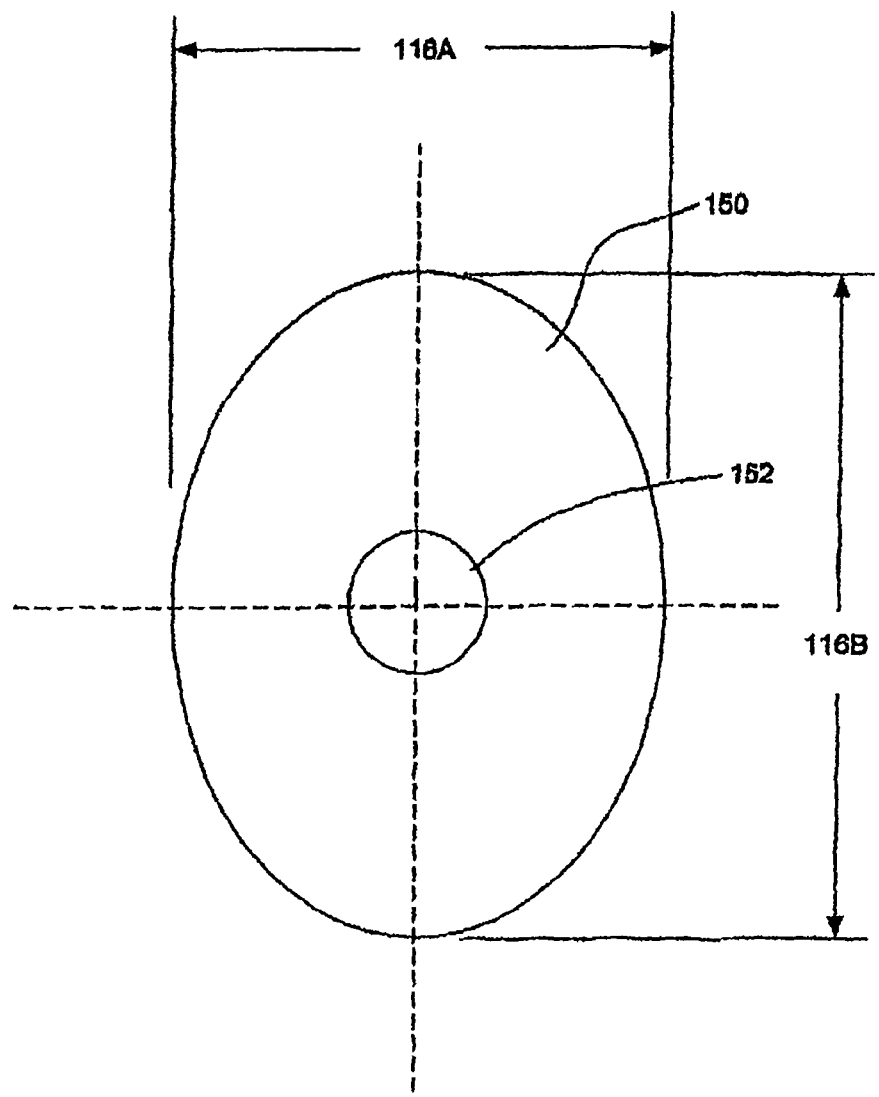

Additionally, as can be seen in FIGS. 1a and 1f, the spacer 150 is elliptical-shaped in cross-section. The spacer 150 can have other shapes such as circular, oval, ovoid, football-shaped, and rectangular-shaped with rounded corners and other shapes, and be within the spirit and scope of the invention. In this preferred embodiment, the spacer 150 includes a bore 152 which extends the length of the spacer 150. The spacer 150 is received over the shaft 102 of the implant 100 and can rotate thereon about the shaft 102. In these embodiments, the spacer 150 can have minor and major dimensions as follows:

| Minor Dimension (116a) | Major Dimension (116b) |
|---|---|
| 6 mm | 13.7 mm |
| 8 mm | 14.2 mm |
| 10 mm | 15.2 mm |
| 12 mm | 16.3 mm |
| 14 mm | 17.8 mm |

The advantage of the use of the spacer 150 as depicted in the embodiment of FIG. 1a, is that the spacer 150 can be rotated and repositioned with respect to the first wing 104, in order to more optimally position the implant 100 between spinous processes. It is to be understood that the cortical bone or the outer bone of the spinous processes is stronger at an anterior position adjacent to the vertebral bodies of the vertebra than at a posterior position distally located from the vertebral bodies. Also, biomechanically for load bearing, it is advantageous for the spacer 150 to be close to the vertebral bodies. In order to facilitate this and to accommodate the anatomical form of the bone structures, as the implant is inserted between the spinous processes and/or urged toward the vertebral bodies, the spacer 150 rotates relative to the wings, such as wing 104, so that the spacer 150 is optimally positioned between the spinous processes, and the wing 104 is optimally positioned relative to the spinous processes. Further, the broad upper and lower surfaces of the spacer 150 helps spread the load that the spinous processes place on the spacer 150.

As may be required for positioning the implant 100 between the spinous processes, the implant 100 can also include a second wing 132 which fits over the guide 110 and is secured by a bolt 130 placed through an aperture 134 provided in a tongue 136 of second wing 132. The bolt 130 is received and secured in the threaded bore 112 located in the guide 110. As implanted, the first wing 104 is located adjacent to first sides of the spinous processes and the second wing 132 is located adjacent to second sides of the same spinous processes.

In another embodiment, the spacer 150 has a cross-section with a major dimension and a minor dimension, wherein the major dimension is greater than the minor dimension, and, for example, less than about two times the minor dimension.

It is to be understood that the spacer 150 can be fabricated from somewhat flexible and/or deflectable material.

In this embodiment the spacer is made out of a polymer, more specifically, the polymer is a thermoplastic. Still more specifically, the polymer is a polyketone known as polyetheretherketone (PEEK). Still more specifically, the material is PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com). The spacer 150 can be formed by extrusion, injection, compression molding and/or machining techniques. This material has appropriate physical and mechanical properties and is suitable for carrying and spreading the physical load between the spinous process. Further in this embodiment, the PEEK has the following additional approximate properties:

| Property | Value |
|---|---|
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

In a preferred embodiment, the implant 100 is comprised in part of titanium or other suitable implant material which may be radiopaque and in part of a radiolucent material that does not show up under x-ray or other type of imaging. In a preferred embodiment, the first and second wings and the shaft are comprised of such a radiopaque material such as titanium and the spacer and the distraction guide or tissue expander are comprised of a radiolucent material such as, for example, PEEK or PEKK or other radiolucent materials described herein. In an embodiment which includes the first wing, the spacer and the tissue expander, under imaging, the implant looks like an "T". In an embodiment which includes both a first and a second wing, the spacer and the tissue expander, under imaging, the implant looks like a "H". This embodiment allows the doctor to have a clearer view of the spine under imaging without the implant interfering as much with the view of the bone structure.

It should be noted that the material selected may also be filled. For example, other grades of PEEK are also available and contemplated, such as 30% glass-filled or 30% carbon-filled, provided such materials are cleared for use in implantable devices by the FDA, or other regulatory body. Glass-filled PEEK reduces the expansion rate and increases the flexural modulus of PEEK relative to that which is unfilled. The resulting product is known to be ideal for improved strength, stiffness, or stability. Carbon-filled PEEK is known to enhance the compressive strength and stiffness of PEEK and lower its expansion rate. Carbon-filled PEEK offers wear resistance and load carrying capability.

In this embodiment, as described above, the spacer 150 is manufactured from polyetheretherketone (PEEK), available from Victrex. As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. The spacer can also be comprised of polyetherketoneketone (PEKK).

Other material that can be used include polyetherketone (PEK), polyetherketoneetherketoneketone (PEKEKK), and polyetheretherketoneketone (PEEKK), and generally a polyaryletheretherketone. Further, other polyketones can be used as well as other thermoplastics. The spacer can also be made of titanium.

Reference to appropriate polymers that can be used in the spacer can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials."

Other materials such as Bionateg, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

Figure 2A:
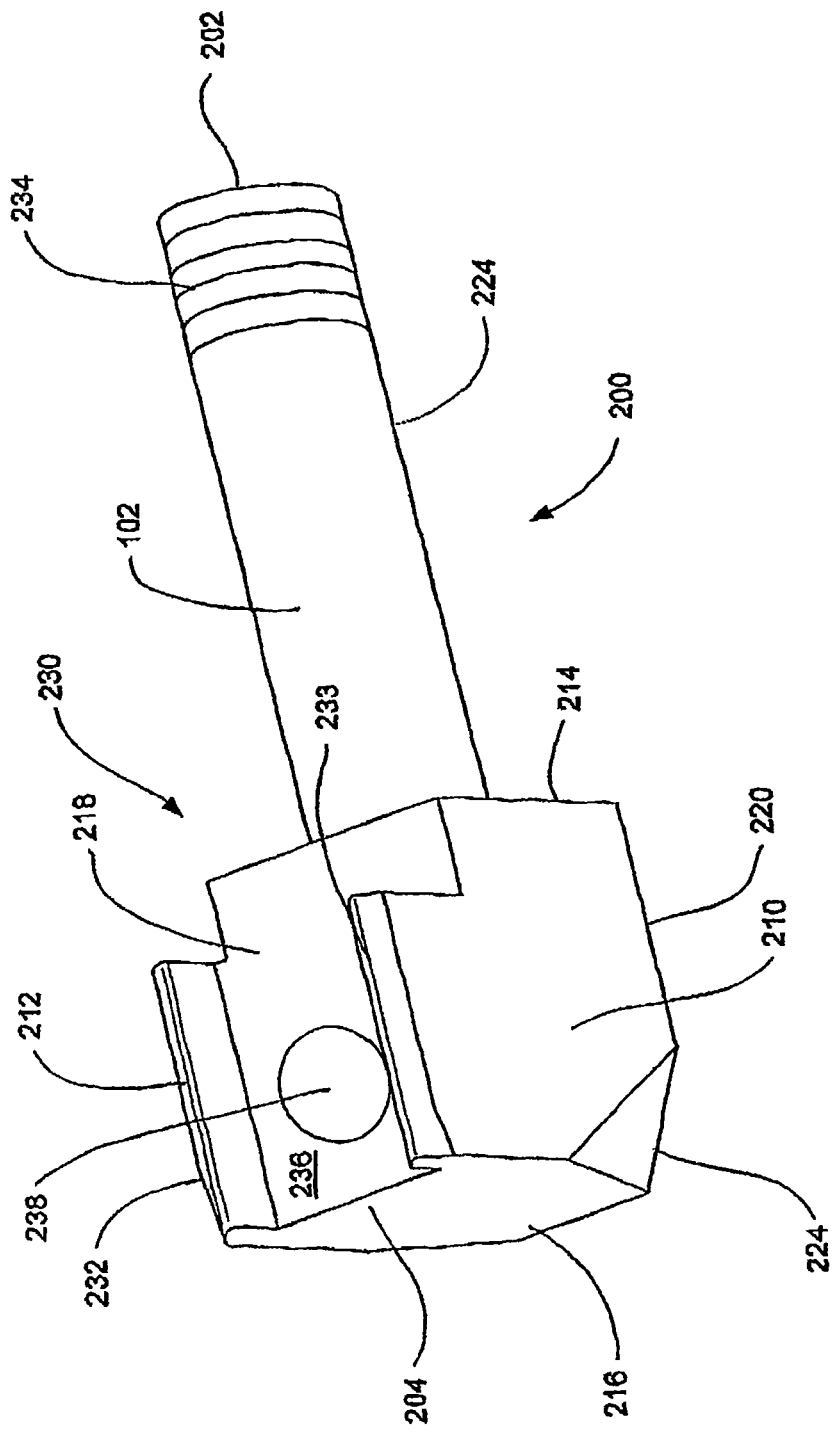
FIG. 2*a* is a perspective view of an embodiment of the frame of the tissue expander or distraction guide of the invention.
Figure 2B:
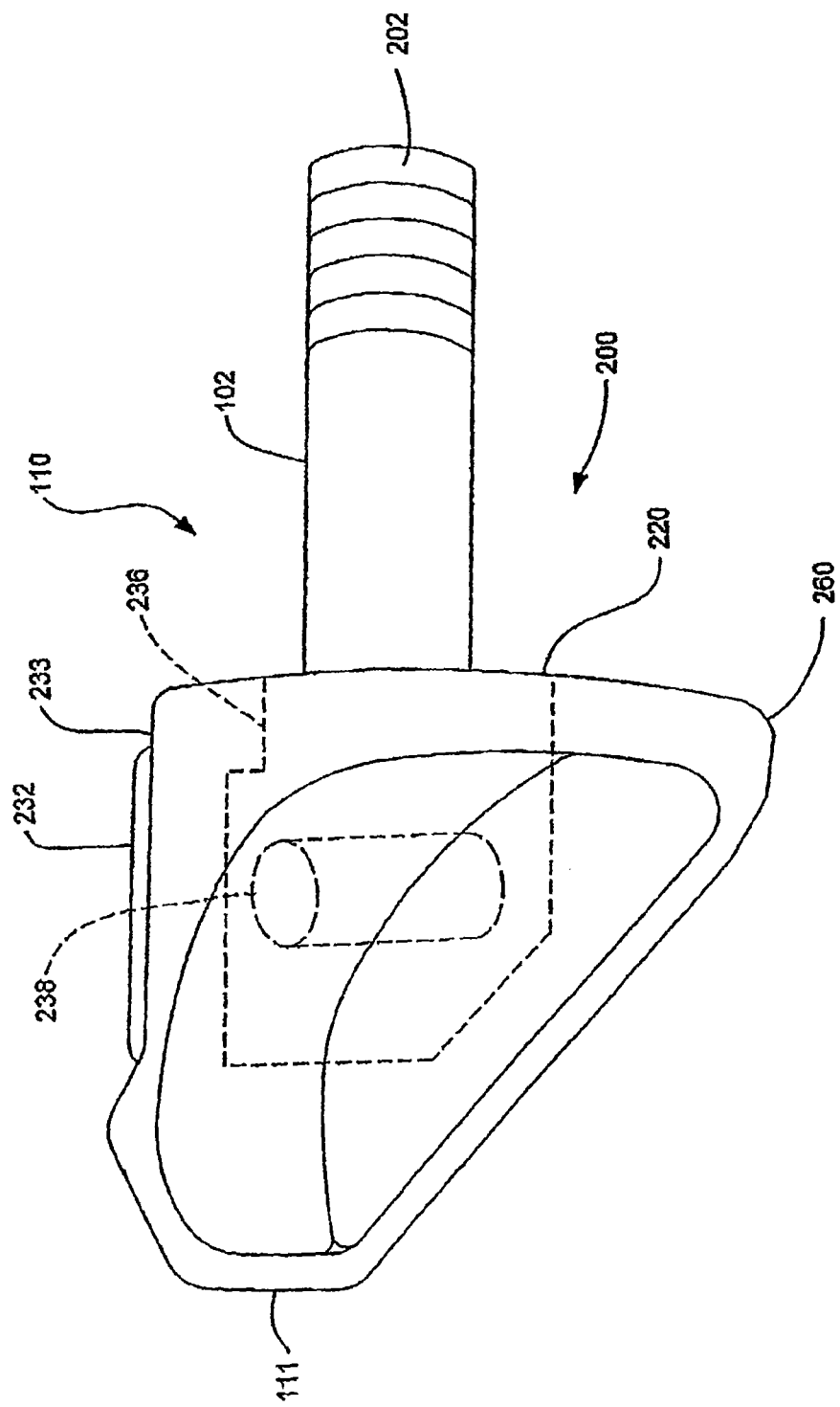
FIG. 2*b* is a perspective view of an embodiment of the lead-in tissue expander or distraction guide of the invention.

FIG. 2a and FIG. 2b shown an embodiment of the distraction guide or tissue expander 110. FIG. 2a shows a frame 200 for a distraction guide 110. The frame 200 is typically manufactured from radiopaque material such as titanium. The frame 200 has a first end 202 and a second end 204. The first end 202 has a shaft 102 which can be threaded with threads 234 at one end to facilitate connection to, for example, a first wing 104. The remaining end of the shaft connects to a distraction head frame 230 for the distraction guide 110. Alternatively, the shaft 102 and the distraction head frame 230 can be formed integral to each other.

Further, the distraction head frame 230, the shaft 102 and the first wing 104 can be formed as one unit. Still further in an embodiment with a screw thread 234 formed at one end of the shaft 102, which thread 234 is received in a threaded bore of the first wing 102, the thread 234 can be laser welded into the threaded bore of the first wing 102, if desired.

The distraction head frame 230 is formed to take on a relatively low profile because, as described above, it is typically formed of radiopaque material. As shown in FIG. 2a, distraction head frame 230 has two pairs of parallel sides. The first pair of parallel sides 210,212 extends into a pair of flanges 232,233 that define a recess 236. The second pair of parallel sides 214,216 are perpendicular to the first pair of parallel sides. One of the second pair of parallel sides 214 abuts the shaft 102. As will be appreciated by those of skill in the art, neither the first or second pair of parallel sides need be parallel to each other, nor do the first pair of parallel sides need to be perpendicular to the second pair of parallel sides in order to practice the invention.

With respect to the frame 200 in FIG. 2a, the distraction head frame 230 has an upper surface 218 within the recess 236 with a threaded bore 112 therein. The threaded bore 112 receives, for example, a bolt 130 to secure the second wing 132 to the distraction guide 110 via the tongue 136 on the second wing 132 (shown in more detail with respect to FIG. 1a). The profile of the bolt 130 is such that the height of the bolt 130 and the tongue 136 fits within the recess 236.

The lower surface 220 opposing the upper surface 218 can have a first portion 222 that is parallel, or substantially parallel, to the upper surface 218.

Additionally, a second portion 224 can be angled from the first portion 222 toward one of the second parallel sides 216. The angled configuration of the lower surface 220 is designed to facilitate the angled profile of the distraction guide.

FIG. 2b shows a perspective view of the distraction guide 110. The frame 200, as described above, is manufactured from radiopaque material. A cap 260 is formed of radiolucent material, such as a suitable polymer, around the frame 200.

Suitable polymers include, but are not limited to the polyketones discussed above with respect to the spacer configurations. Accordingly, for example, PEEK, PEKK, PEK, PEKEKK and PEEKK can be used as well as the other materials that are suitable for the spacer 150. As will be appreciated by those of skill in the art, the cap 260 can be associated with the frame 200 by a variety of techniques such that the cap 260 is formed to the frame 200 or is adhered to the frame 200 using a suitable method. As illustrated in FIG. 2b, the cap 260 has a higher profile than the frame 200 and is shaped to facilitate the second end 204 of the distraction guide 110 acting to expand tissue when the distraction guide is implanted between spinous processes or used to distract adjacent spinous processes.

Referring now to FIGS. 3a-6b, various embodiments of spacers are depicted.

Figure 3A:
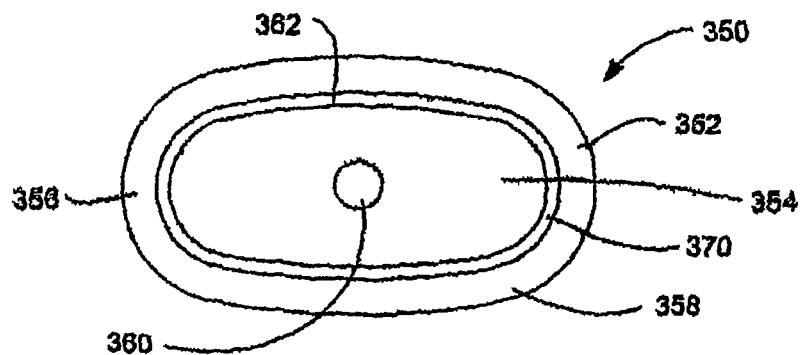
FIGS. 3*a* and 3*b* are an end and a perspective view of still another embodiment of the spacer of the invention.
Figure 3B:
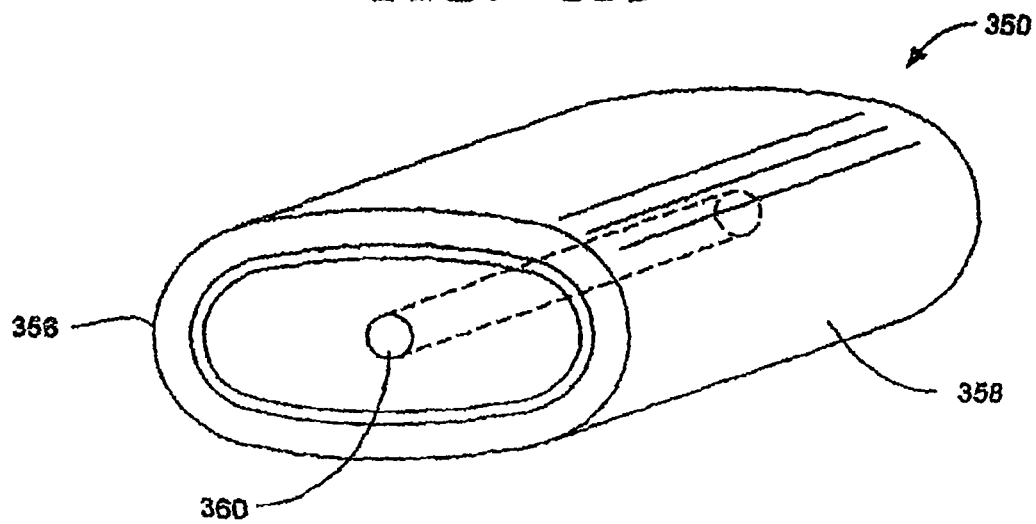
Figure 3C:
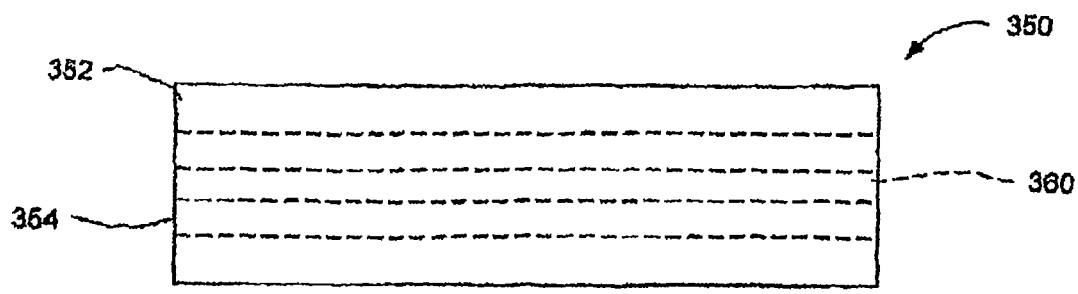
FIG. 3*c* is a front view of the spacer of FIG. 3*a*.

In FIGS. 3a, 3b and 3c, the spacer 350 includes an outer spacer 352 and an inner spacer 354. Inner spacer 354 has a bore 360 therethrough that enables the spacer 350 to rotate about the shaft 102 of implant 100 shown in FIG. 1a.

Each of the inner and outer spacers of the spacer 350 can have a cross-section that is elliptical, oval, ovoid, football-shaped, circular-shaped, rectangular with rounded ends (where the cross-section has two somewhat flattened surfaces and two rounded surfaces similar to the effect of a flattened ellipse). Further, the inner spacer and outer spacer can have different cross-sectional shapes relative to each other. At least the minor outer diameter of the outer spacer is between 6 mm and 14 mm. Typically, the minor outer dimension is one of 6 mm, 8 mm, 10 mm, 12 mm, and 14 mm. The different sizes enable the spacer to accommodate different sized patients.

As depicted in FIG. 3a, the spacer 350 is a rectangle with rounded ends or a flattened ellipse, as it has two sides that are almost parallel to each other, and the ends connecting the parallel sides are curved, similar to a "race-track." Thus, in this and other embodiments, the two sides or surfaces of the spacer, including the upper and the lower spacer, can also be flattened or slightly radiused. The bore 360 is located in the center of the inner spacer 354 and there is a gap 362 between the upper and lower portions of the outer spacer 352 and the inner spacer 354. A gap 370 is provided between the inner and outer spacers at the rounded ends 356,358. In a preferred embodiment, for about an 8 millimeter spacer 350, the upper and lower gaps 362 are about 0.012 of an inch or about a quarter of a millimeter each for a total combined gap of about one half of a millimeter. The gaps 370 at the curved ends 356,358 are about 0.002 of an inch or slightly less than a tenth of a millimeter each in a preferred embodiment. The gap 370 for all of the other spacers is preferably, as specified above, for the 8 mm spacer. For the 6 millimeter spacer, generally this is made of one piece such as seen in FIG. 1f.

However, for the other spacers, these spacers are preferably made of two pieces as seen for example in FIG. 3a. The table below sets our preferred dimensions for the combined upper and lower gap dimension for the spacers.

| Spacer Minor Dimension | Total Combined Gap Dimension |
|---|---|
| 6 mm | n/a |
| 8 mm | 0.020 in (0.51 mm) |
| 10 mm | 0.025 in (0.64 mm) |
| 12 mm | 0.030 in (0.76 mm) |
| 14 mm | 0.035 in (0.89 mm) |

The gap 362 closed and the inner and outer spacers touch each other when the spacer is loaded with 800 Newtons of force. The design is made to take repeated loading at 1200 Newtons of force.

In the above embodiment, the outer spacer 352 is movably or slidably mounted on the inner spacer 354, and the inner spacer 354 is rotatably mounted on the shaft 102 of the implant 100.

As discussed above, the spacer, including either the inner spacer or outer spacer, or both, can be made of deflectable and flexible material. As discussed above, suitable material is a polymer such as for example polyetheretherketone (PEEK). Other suitable materials can include those described above. Further, titanium can be used.

Further, the deflectable or flexible material can have a graduated stiffness to help gradually distribute the load when the spinous processes place a force upon the exterior surface of the outer spacer 352. This can be accomplished by forming multiple layers of the deflectable or flexible material with decreasing stiffness or hardness from the center of the spacer 350 outwardly. Alternatively, the material can have a higher stiffness or hardness in the center of the inner spacer.

Persons of skill in the art will appreciate that the embodiments shown in FIGS. 4a-6b, can be made of the materials similar to those emphasized in the embodiment shown in FIGS. 1a and 3a.

Figure 4A:
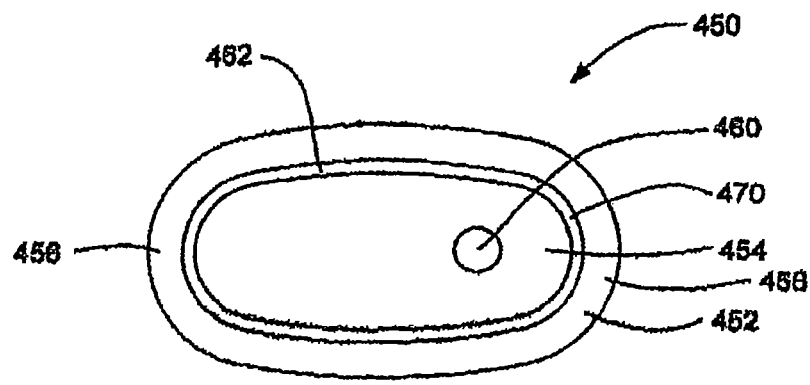
FIGS. 4*a* and 4*b* are an end and a perspective view of yet another embodiment of the spacer of the invention.
Figure 4B:
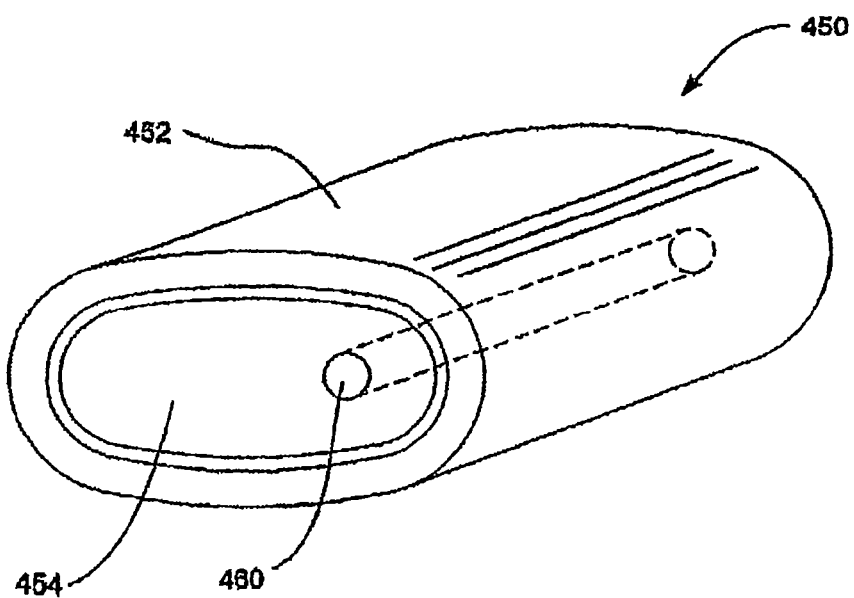

Now referring to FIGS. 4a and 4b, again the spacer 450 is depicted as a somewhat flattened ellipse with rounded ends 456,458, where two sides are somewhat parallel to each other and the ends connecting the parallel sides are curved, similar to a "race-track." The bore 460 is located off-center within the inner spacer 454. Further, there are gaps 462,470 between the outer spacer 452 and the inner spacer 454. Except for the location of the bore 460, the dimensions and materials of the embodiment of FIGS. 4a and 4b are similar to that of FIG. 3a and FIG. 3b.

The off-center bore 460 allows a greater portion of the spacer 450 to be positioned close to the vertebral bodies. With an ovoid ("egg-shaped") spacer, off-set the bore 460 is preferably close to the bulbous end of the spacer with the more pointed end directed toward the vertebral bodies in order to attain the advantages of the spacer being closer to the vertebral bodies and enhanced distributed load bearing.

Figure 5A:
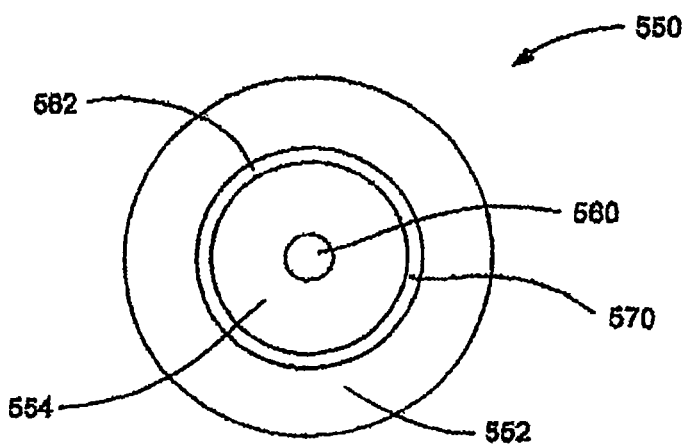
FIGS. 5*a* and 5*b* are an end and a perspective view of still another embodiment of the spacer of the invention.
Figure 5B:
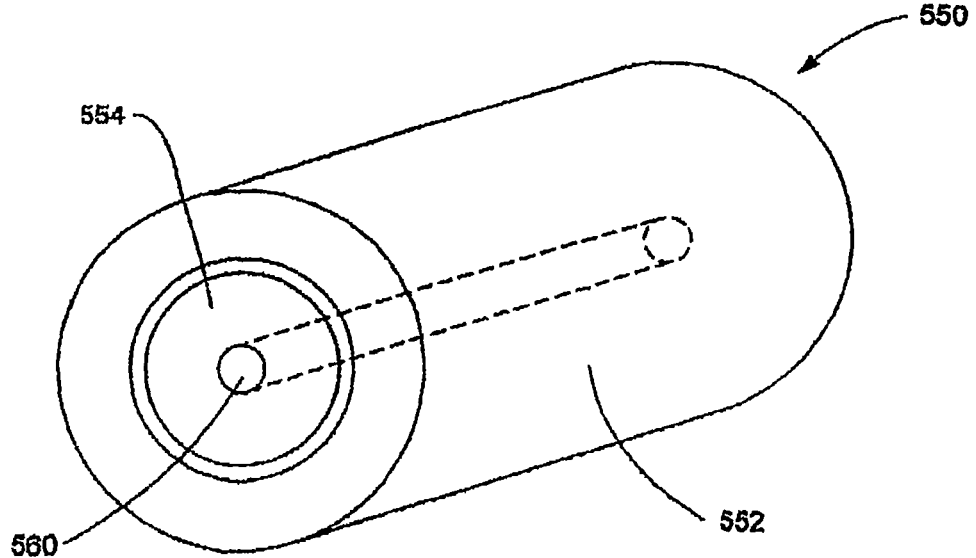

Turning now to FIG. 5, the spacer 550 is depicted as having a circular cross-section. The bore 560 is located within the inner spacer 554. Further, there are gaps 562,570 between the outer spacer 552 and the inner spacer 554. The dimensions of the gap would be the same as those discussed with respect to the embodiment shown in FIG. 3a. The embodiment of FIG. 3a can have a diameter that is the minor diameter of the embodiments shown in FIGS. 1a, 3a, and 4a.

Also, as will be appreciated by those in skill in the art, the outer spacer 552 can be movably mounted on the inner spacer 554 and the inner spacer 554 can be rotatably mounted on the shaft 102 of the implant 100 or any other suitable implant.

Figure 6A:
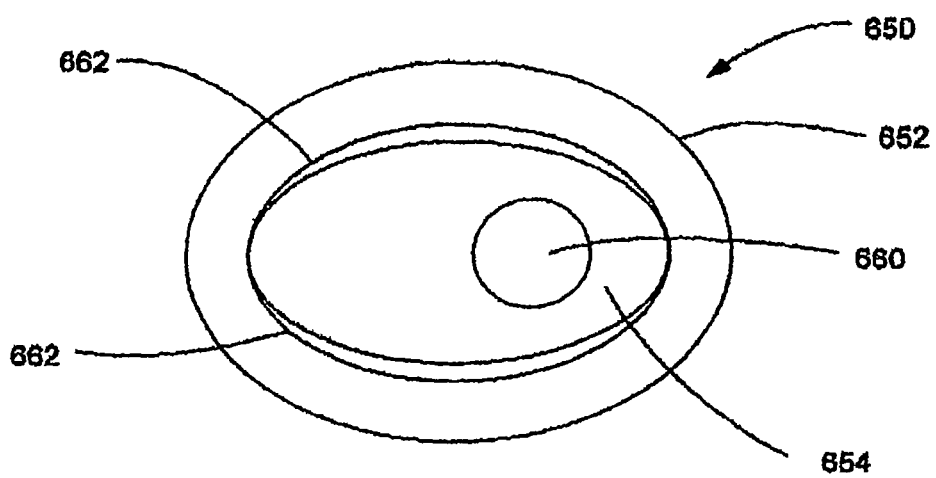
FIGS. 6*a* and 6*b* are an end and a perspective view of a further embodiment of the spacer of the invention.
Figure 6B:
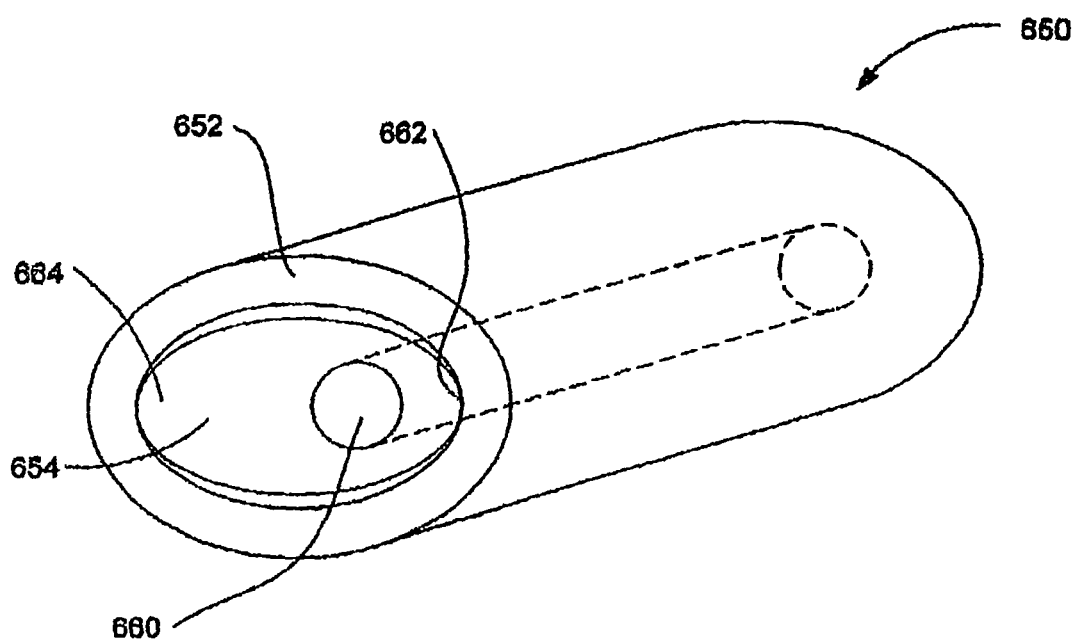

In FIGS. 6a and 6b, the spacer 650 is depicted as having an outer spacer 652 and an inner spacer 654 of two different cross-sectional shapes. In this embodiment, the outer spacer 652 is elliptical and the inner spacer is football-shaped in cross-sections. The bore 660 is located off-center within the inner spacer 654. However, as will be appreciated by those of skill in the art, the bore 660 can be located centrally within the inner spacer without departing from the scope of the invention.

The gaps 662 between the outer spacer 652 and the inner spacer 654 are crescent-shaped as a result of the inner and outer spacers having different cross-sectional shapes. Thus, the gap can have a width ranging from approximately between 0.25 mm at the minor diameter (greatest vertical height) to just enough space at the apexes 662,664 of the inner spacer 654 so that the outer spacer can slide over the inner spacer. The inner spacer 654 can be rotatably mounted on the shaft 102 of the implant 100.

The embodiment of this implant as well as the several other implants described herein act to limit extension (backward bending) of the spine. These implants, however, do not inhibit the flexion (forward bending) of the spinal column.

The foregoing description of embodiments of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims and its equivalence.

Interspinous Implants

Figure 7:
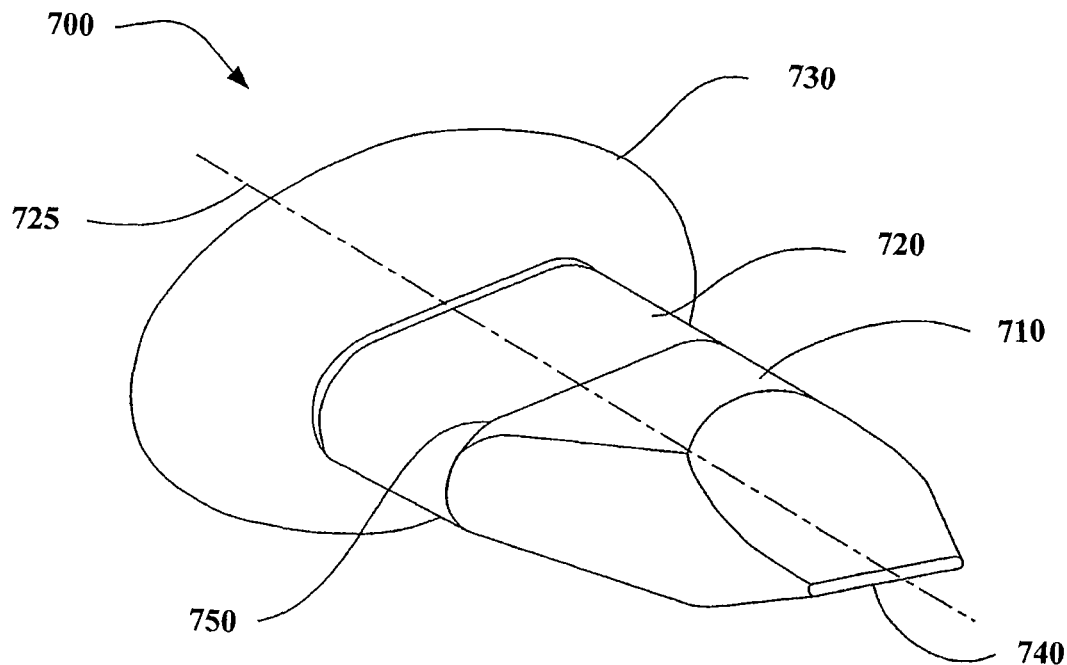
FIG. 7 is a perspective view of an embodiment of an implant in accordance with the present invention having a spacer, a distraction guide, and a wing with an elliptical cross-section.
Figure 8:
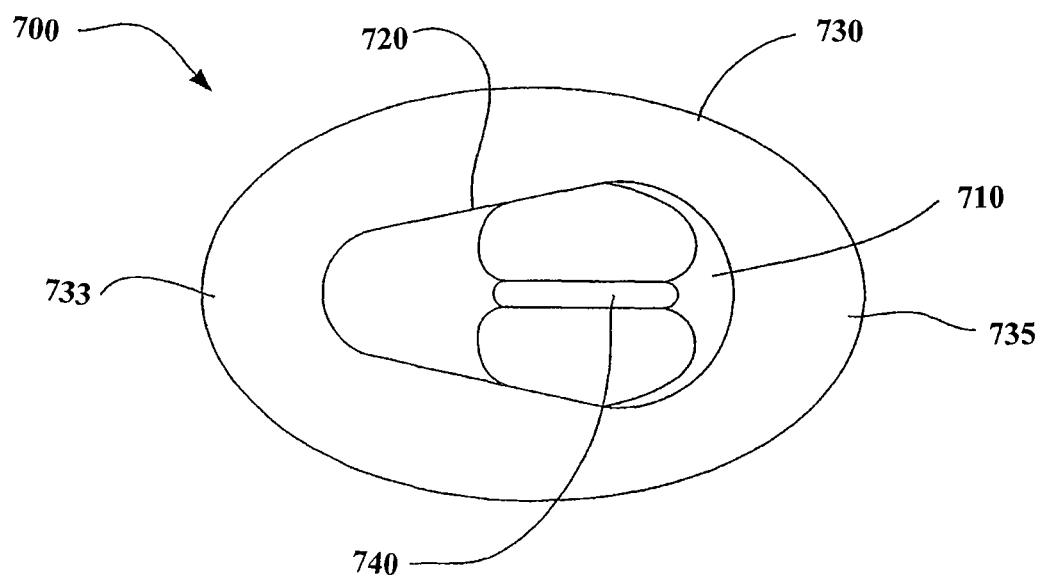
FIG. 8 is an end view of the implant of FIG. 7.

FIGS. 7 and 8 illustrate an implant 700 in accordance with an embodiment of the present invention. The implant 700 comprises a wing 730, a spacer 720, and a lead-in tissue expander (also referred to herein as a distraction guide) 710. The distraction guide 710 in this particular embodiment is wedge-shaped, i.e., the implant has an expanding cross-section from a proximal end of the implant 740 to a region 750 where the guide 710 joins with the spacer 720 (referencing for the figures is based on the point of insertion of the implant between spinous processes). As such, the distraction guide functions to initiate distraction of the soft tissue and the spinous processes when the implant 700 is surgically inserted between the spinous processes. It is to be understood that the distraction guide can be pointed and the like, in order to facilitate insertion of the implant between the spinous processes of adjacent cervical vertebrae. It is advantageous that the insertion technique disturb as little of the bone and surrounding tissue or ligaments as possible in order to reduce trauma to the site and promote early healing, and prevent destabilization of the normal anatomy. In the embodiment of FIGS. 7 and 8, there is no requirement to remove any of the bone of the spinous processes and no requirement to sever, or remove from the body, ligaments and tissues immediately associated with the spinous processes. For example, it is unnecessary to sever the ligamentum nuchae, (supraspinous ligament) which partially cushions the spinous processes of the upper cervical vertebrae.

Figure 9:
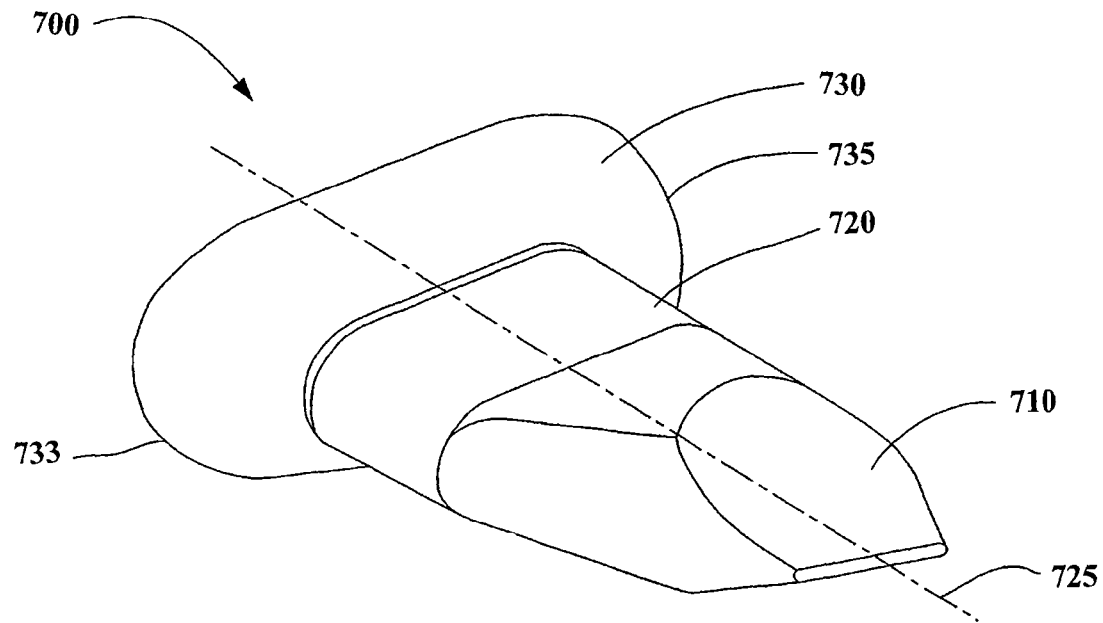
FIG. 9 is a perspective view of another embodiment of an implant in accordance with the present invention having a wing with a teardrop-shaped cross-section.

As can be seen in FIGS. 7-9, the spacer 720 can be teardrop-shaped in cross-section perpendicular to a longitudinal axis 725 of the implant. In this way, the shape of the spacer 720 can roughly conform to a wedge-shaped space, or a portion of the space, between adjacent spinous processes within which the implant 700 is to be positioned. In other embodiments, the spacer 720, can have alternative shapes such as circular, wedge, oval, ovoid, football-shaped, and rectangular-shaped with rounded corners and other shapes, and be within the spirit and scope of the invention. The shape of the spacer can be selected for a particular patient so that the physician can position the implant as close as possible to the anterior portion of the surface of the spinous process. The shape selected for the spacer 720 can effect the contact surface area of the implant 700 and the spinous processes that are to be subject to distraction. Increasing the contact surface area between the implant and the spinous processes can distribute the force and load between the spinous frame and the implant.

As can be seen in FIGS. 7 and 8, the wing 730 in this embodiment 700 is elliptically-shaped in cross-section perpendicular to a longitudinal axis 725 of the spacer 720 and distraction guide 710. The dimensions of the wing 730 can be larger than that of the spacer 720, particularly along the axis of the spine, and can limit or block lateral displacement of the implant in the direction of insertion along the longitudinal axis 725. As illustrated in the embodiment of FIG. 9, the wing 730 can have other cross-sectional shapes, such as teardrop, wedge, circular, oval, ovoid, football-shaped, and rectangular-shaped with rounded corners and other shapes, and be within the spirit and scope of the invention. The wing 730 has an anterior portion 733 and a posterior portion 735.

In other embodiments, the implant 700 can have two wings, with a second wing 760 (shown in FIG. 10) separate from the distraction guide 710, spacer 720 and first wing 730. The second wing can be connected to the proximal end of the spacer 720. The second wing 760, similar to the first wing 730, can limit or block lateral displacement of the implant 700, however displacement is limited or blocked in the direction along the longitudinal axis 725 opposite insertion. When both the first wing 730 and second wing 760 are connected with the implant and the implant is positioned between adjacent spinous processes, a portion of the spinous processes can be sandwiched between the first and second wing, limiting any displacement along the longitudinal axis 725.

Figure 10:
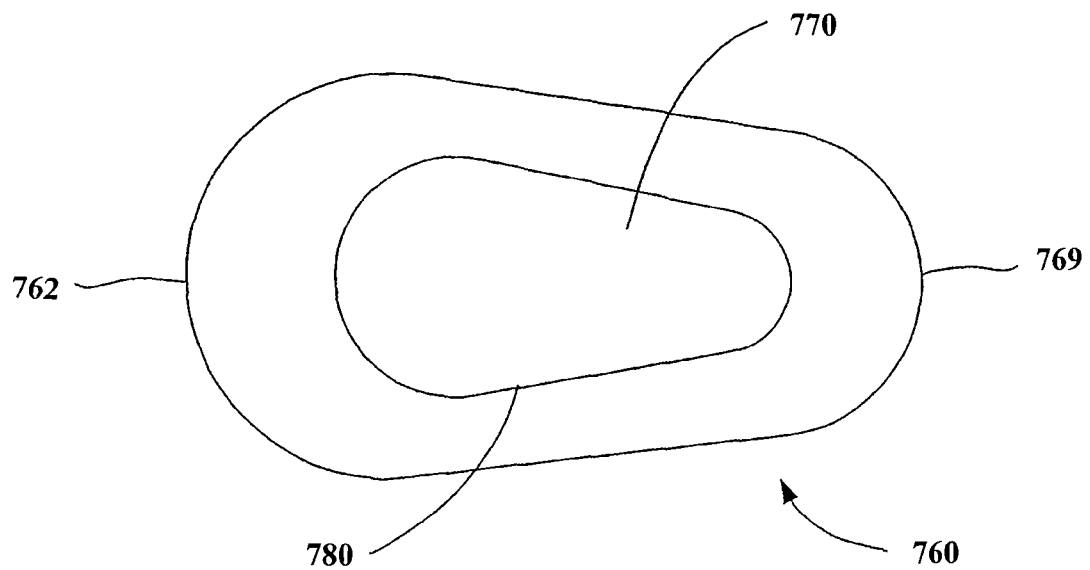
FIG. 10 is an end view of a second wing for use with the implant of FIG. 9.

As can be seen in FIG. 10, the second wing 760 can be teardrop-shaped in cross-section. The wider section or end 762 of the teardrop shape is the posterior end of the second wing 760 and the narrower section or end 769 is the anterior end of the second wing 760. Unlike the first wing 730, however, the sides of the second wing 760 define a space 770 with a lip 780 that allows the second wing 760 to pass over the distraction guide 710 to meet and connect with the spacer 720. The second wing 760 is then secured to the spacer 720 toward the end of the spacer located distally from the first wing 740. The second wing 760 is connected with the implant after the implant 700 is positioned between the spinous processes.

It is to be understood that the implant can be made in two pieces. The first piece can include the first wing 730, the spacer 720, and the distraction guide 710. The second piece can include the second wing 760. Each piece can be manufactured using technique known in the art (e.g., machining, molding, extrusion). Each piece, as will be more fully discussed below, can be made of a material that is bio-compatible with the body of the patient. For example the implants can be made of stainless steel and titanium. Additionally, a shape memory metal such as Nitinol, which is a combination of titanium and nickel, can also be used. Further polymers can also be used. The implant can be formed with multiple pieces and with the pieces appropriately joined together, or alternatively, the implant can be formed as one piece or joined together as one piece.

Figure 11:
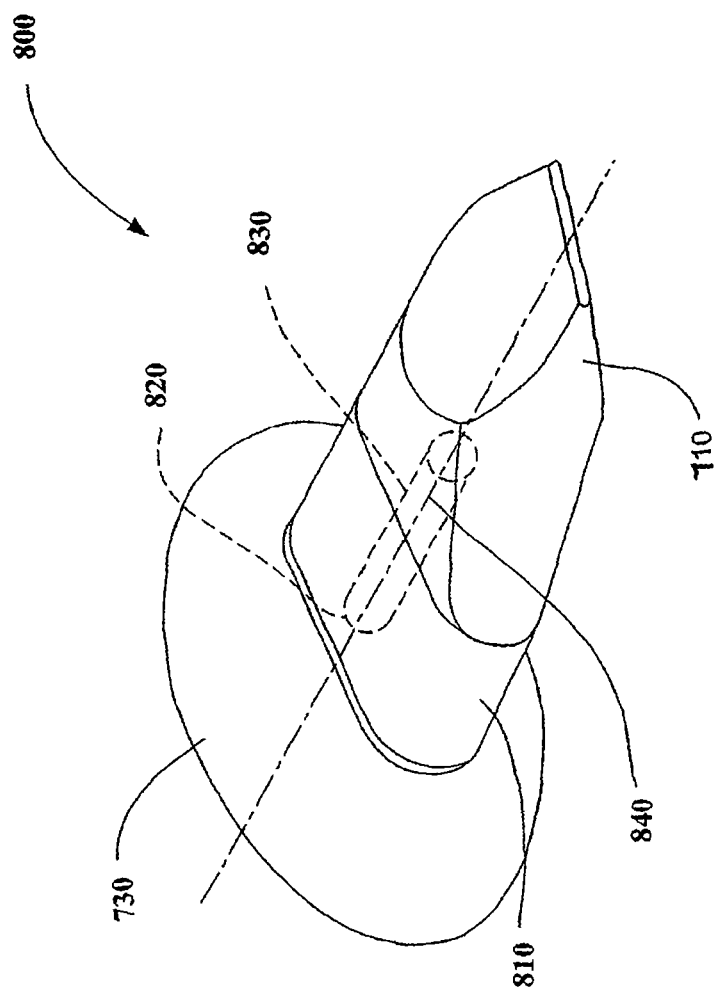
FIG. 11 is a perspective view of an embodiment of an implant in accordance with the present invention having a rotatable spacer and a wing with an elliptical cross-section.
Figure 12:
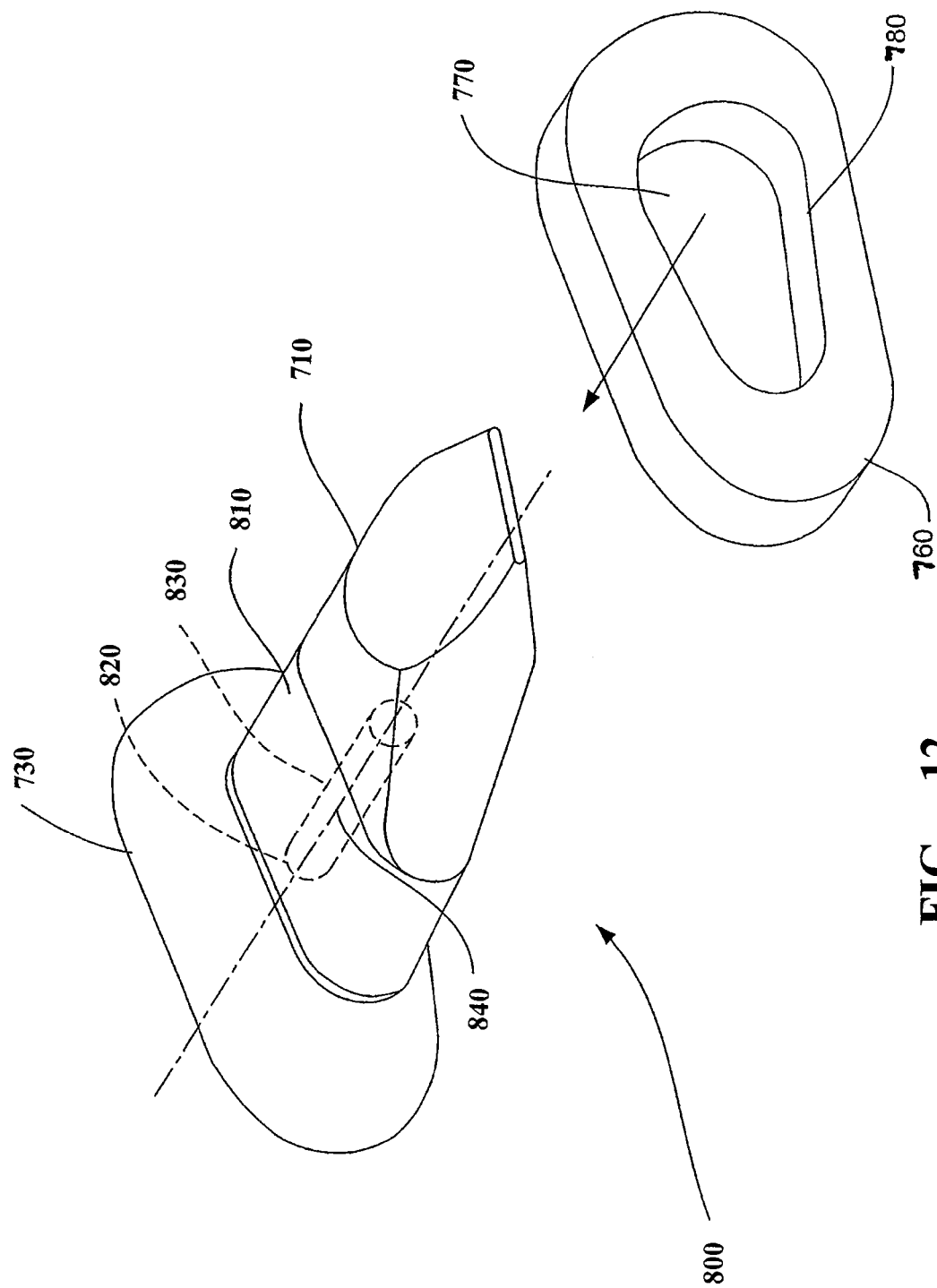
FIG. 12 is a perspective view of an embodiment of an implant in accordance with the present invention having a rotatable spacer with two wings that are teardrop-shaped in cross-section.
Figure 13:
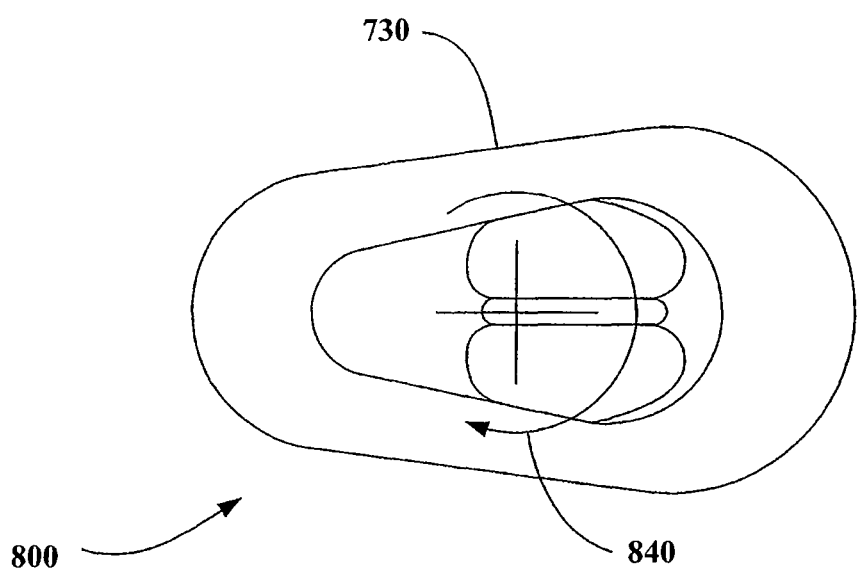
FIG. 13 depicts the axis of rotation of the implant of FIG. 6 as seen from an end view.

Further embodiments of implants in accordance with the present invention are depicted in FIGS. 11-13. In such embodiments, the spacer 810 can be rotatable about the longitudinal axis 840 relative to the first wing 730, or relative to a first and second wing 730,760 where two wings are used. The spacer 810 can be rotatable or fixed relative to the distraction guide 710. Where the spacer 810 is rotatable, the spacer 810 can include a bore 820 running the length of the longitudinal axis 840, and a shaft 830 inserted through the bore 820 and connecting the distraction guide 710 with the first wing 730. It can be advantageous to position any of the implants taught herein as close as possible to the vertebral bodies. The rotatable spacer 810 can rotate to conform to or settle between the bone structures of the cervical spine as the implant is inserted between the spinous processes, so that on average the contact surface area between the spacer 810 and both of the spinous processes can be increased over the contact surface area between a fixed spacer 810 and the spinous processes. Thus, the rotatable spacer 810 improves the positioning of the spacer independent of the wings relative to the spinous processes. The embodiment of FIG. 12 has a first wing 730 and if desired, a second wing 760 similar to the wing depicted in the embodiment of FIG. 9. As discussed below, the shape of the wings in FIGS. 9 and 12 is such that the implants accommodate the twisting of the cervical spine along its axis as, for example, the head of a patient turning from side to side.

Figure 14:
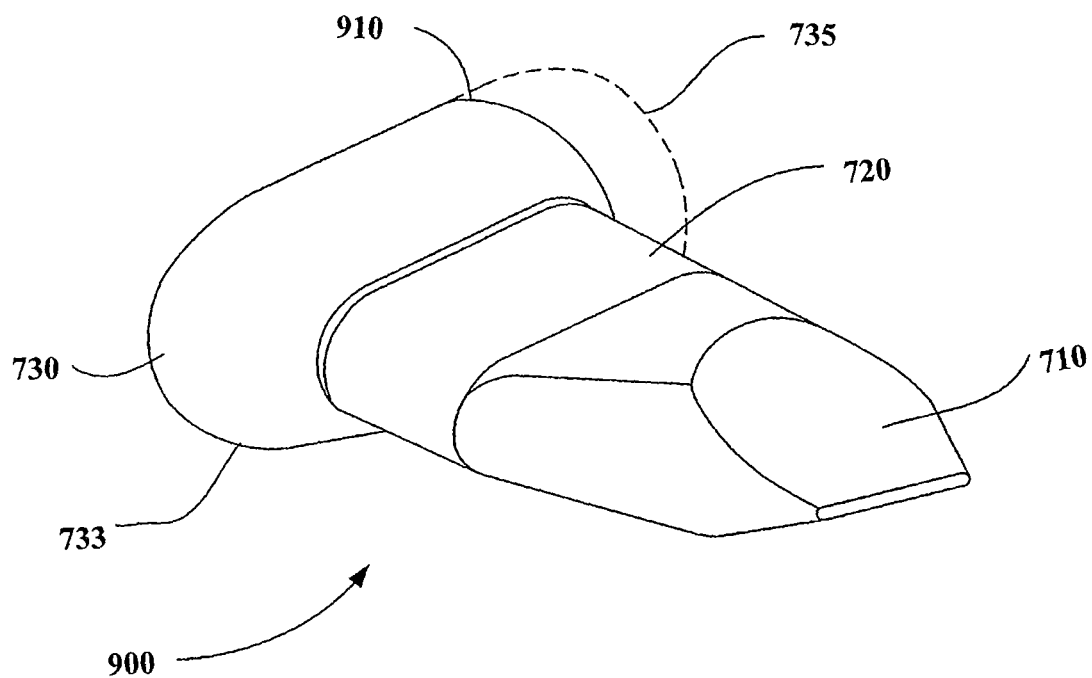
FIG. 14 is a perspective view of an embodiment of an implant in accordance with the present invention having a wing that is truncated at a posterior end.
Figure 15A:
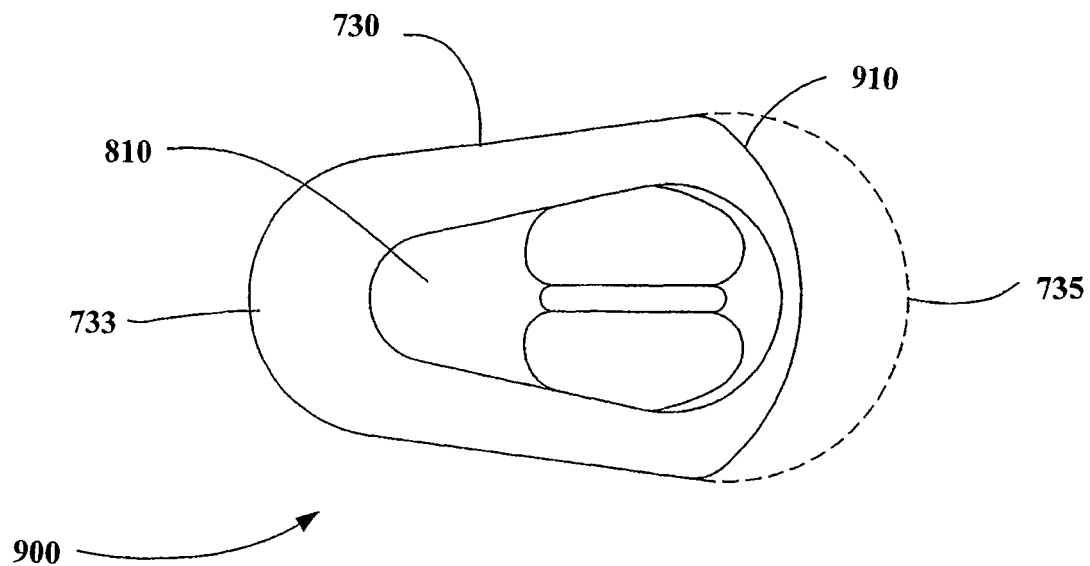
FIG. 15A is an end view of an embodiment of an implant in accordance the present invention having a wing truncated at a posterior end and a rotatable spacer.
Figure 15B:
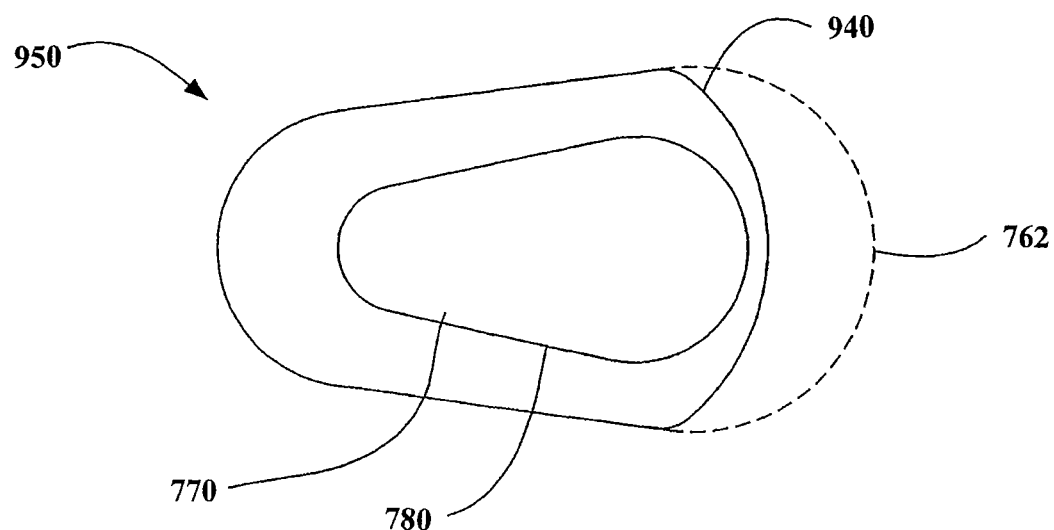
FIG. 15B is a truncated second wing for use with the implant of FIG. 15A.

FIG. 14 is a perspective view and FIG. 15A is an end view of still another embodiment of an implant in accordance with the present invention, wherein the posterior portion 735 of the teardrop-shaped first wing 730 is truncated 910, making the first wing 730 more ovoid in shape. In this configuration, the anterior portion 733 of the first wing 730 can be longer than the truncated posterior end 910 of the first wing 730. As in previous embodiments, the spacer 810 of such implants 900 can be a rotatable spacer rather than a fixed spacer. FIG. 15B illustrates a second wing for use with such implant 900 having a truncated posterior end 940. Truncation of the posterior ends 910,940 of the first and second wings 730,760 can reduce the possibility of interference of implants 900 having such first and second wings 730,760 positioned between spinous processes of adjacent pairs of cervical vertebrae, e.g., implants between cervical vertebrae five and six, and between six and seven.

During rotation of the neck, the spinous process move past each other in a scissor-like motion. Each cervical vertebra can rotate relative to the next adjacent cervical vertebra in the general range of about 6°-12°. In addition, about 50 percent of the rotational movement of the neck is accomplished by the top two neck vertebrae. Thus, such embodiments can accommodate neck rotation without adjacent embodiments interfering with each other.

With respect to the prior embodiments which have first and second wings, the second wing 760, can be designed to be interference-fit onto the spacer 720 (where the spacer is fixed) or a portion of the distraction guide 710 adjacent to the spacer 720 (where the spacer is rotatable). Where the second wing 760 is interference-fit, there is no additional attachment device to fasten the second wing 760 relative to the remainder of the implant.

Figure 16:
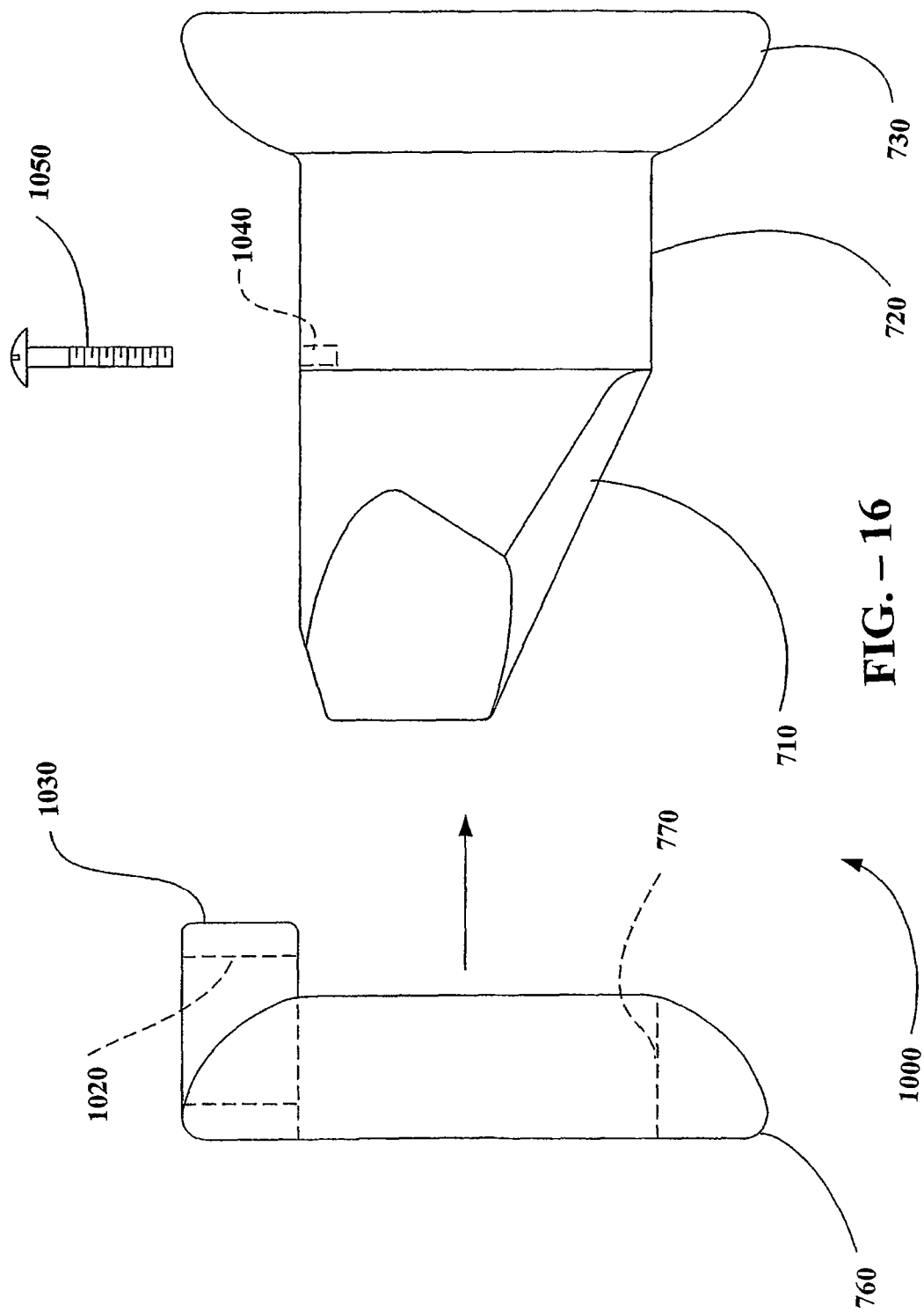
FIG. 16 is a plan view of an embodiment of an implant in accordance with the present invention wherein a screw is used to secure a second wing to the spacer.
Figure 17:
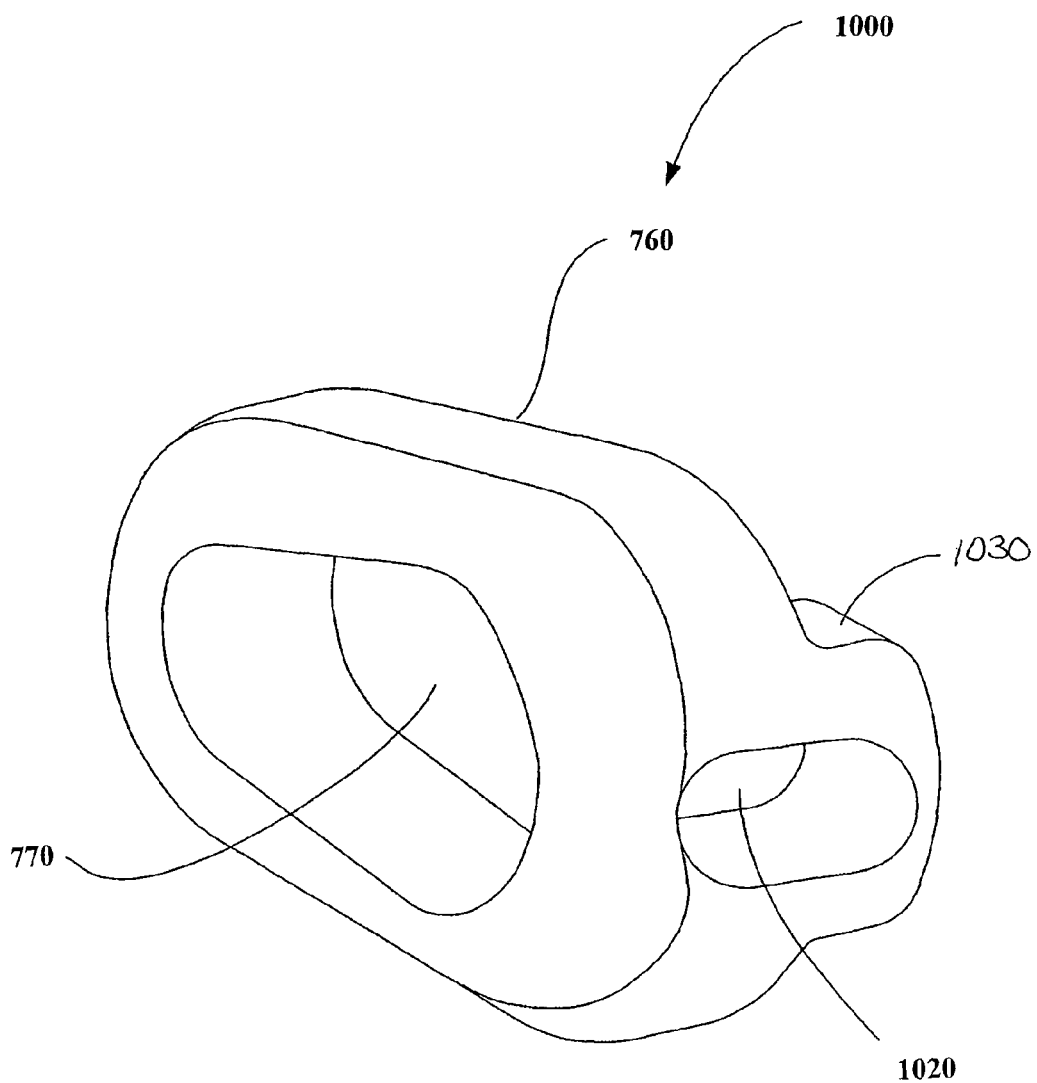
FIG. 17 is a perspective view of the second wing of FIG. 16.
Figure 18:
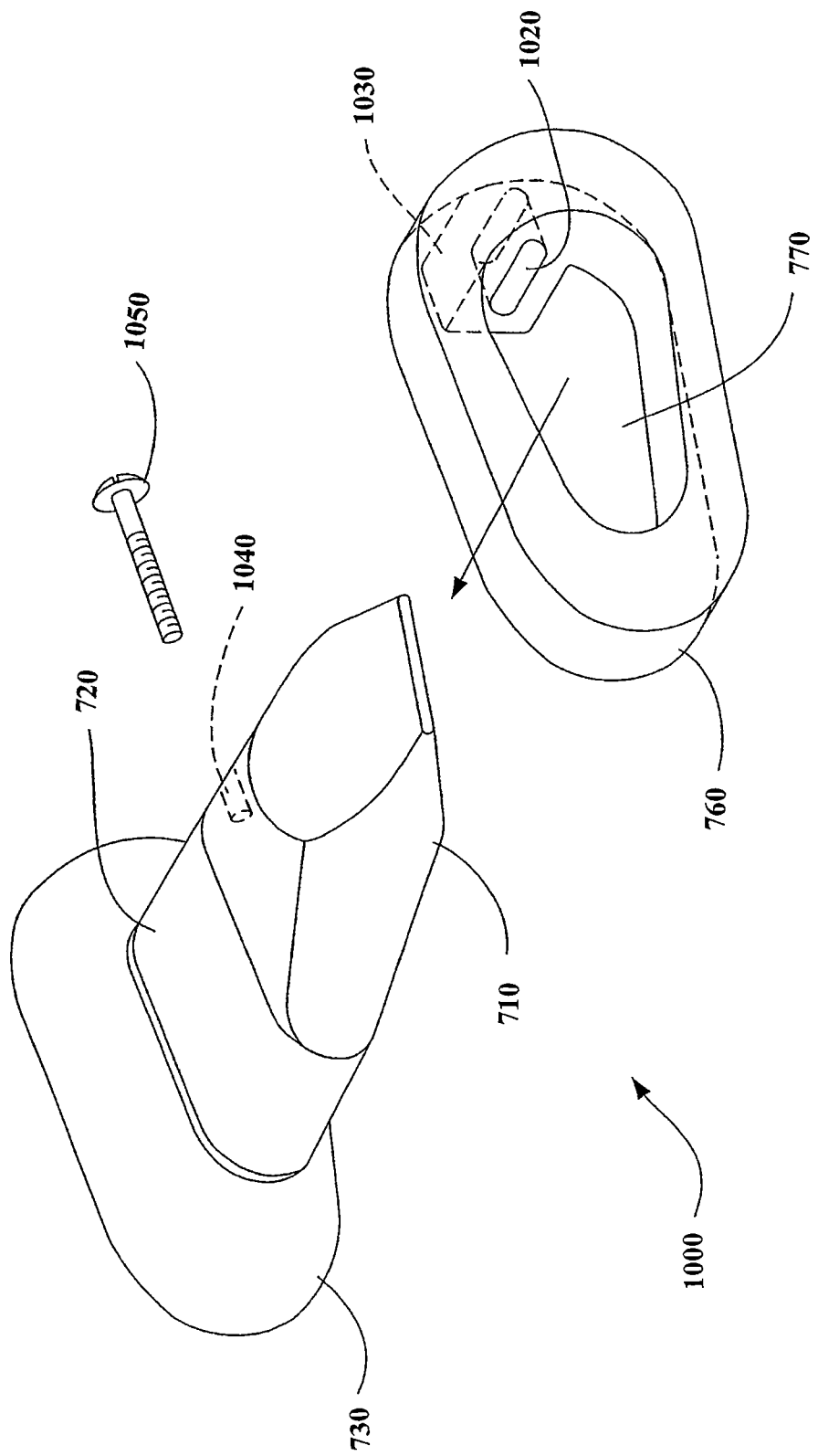
FIG. 18 is a perspective view of the implant of FIG. 16.
Figure 19A:
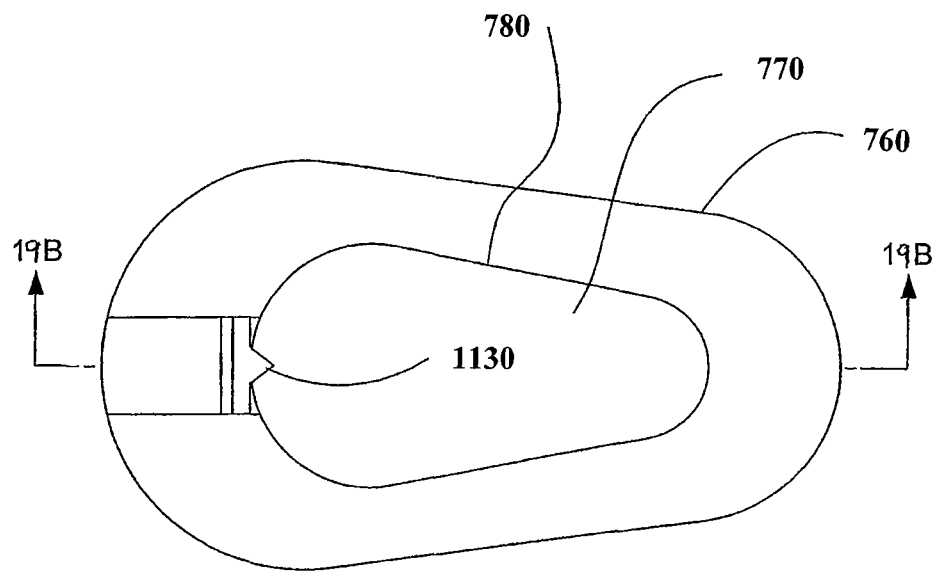
FIG. 19A is a front view of a second wing for use with some embodiments of implants of the present invention having a flexible hinge mechanism for securing the second wing to an implant.
Figure 19B:
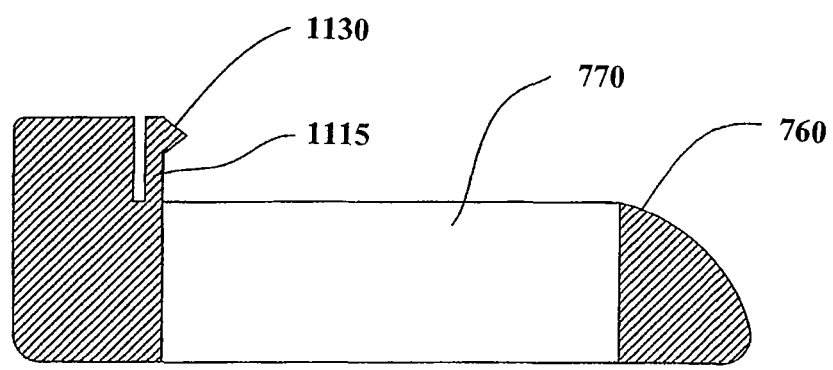
FIG. 19B is a side-sectional view of the second wing of FIG. 19A.
Figure 20A:
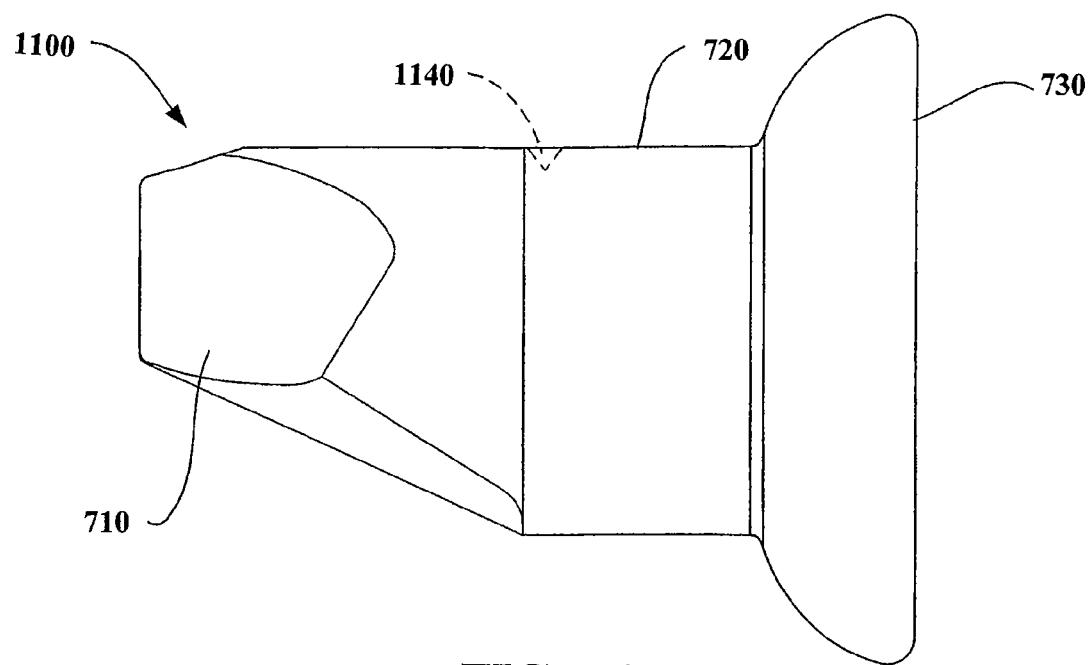
FIG. 20A is a plan view of an embodiment of an implant for use with the second wing of FIGS. 19A and 19B.
Figure 20B:
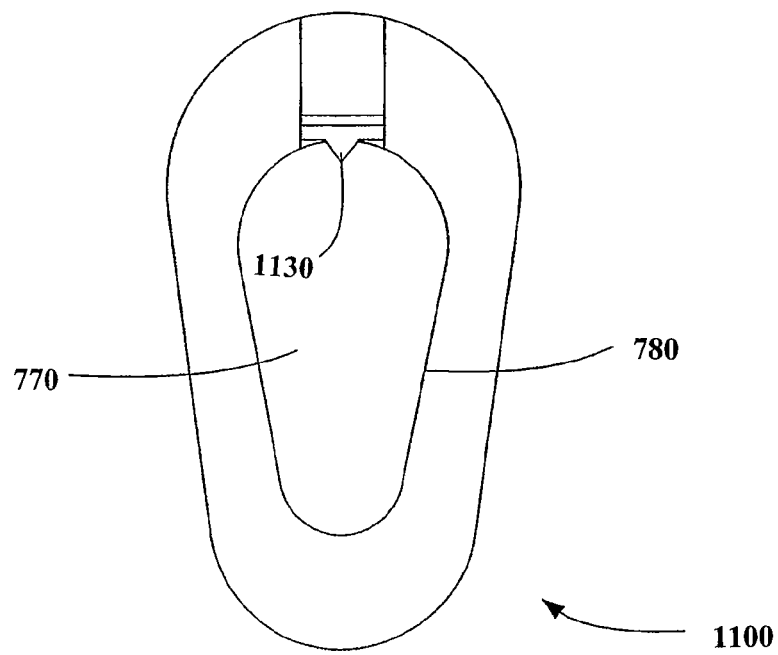
FIG. 20B is a front view of the second wing of FIGS. 19A and 19B.

Alternatively, various fasteners can be used to secure the second wing 760 relative to the remainder of the implant. For example, FIGS. 16-17 illustrate an embodiment of an implant 1000 including a teardrop-shaped second wing 1010 having a bore 1020 through a tongue 1030 at the posterior end of the second wing 760. The bore on the second wing 1020 is brought into alignment with a corresponding bore 1040 on the spacer 720 when the second wing 760 is brought into position by surgical insertion relative to the rest of the implant. A threaded screw 1050 can be inserted through the aligned bores in a posterior-anterior direction to secure the second wing 760 to the spacer 720. The direction of insertion from a posterior to an anterior direction has the screw engaging the bores and the rest of the implant along a direction that is generally perpendicular to the longitudinal axis 725. This orientation is most convenient when the surgeon is required to use a screw 1050 to secure the second wing 760 to the rest of the implant. Other securing mechanisms using a member inserted into corresponding bores 1020,1040 on the spacer 720 and second wing 760 are within the spirit of the invention.

It should be understood that a rotatable spacer 810 also can be accommodated by this embodiment. With a rotatable spacer 810, the second wing 760 would be attached to a portion of the distraction guide 710 that is located adjacent to the rotatable spacer 810.

FIGS. 19A-20B depict a further embodiment 1100 wherein the second wing 760 is secured to the spacer 720 by a mechanism including a flexible hinge 1115, with a protrusion 1130 on the end of the hinge 1110 adjacent to the lip 780 of the hole 770 defined by portions of the second wing 760. The securing mechanism also encompasses an indentation 1140 on the spacer 720, wherein the indentation accommodates the protrusion 1130 on the end of the flexible hinge 1115. During surgery, after insertion of the distraction guide 710, spacer 720, and first wing 730, the second wing 760 is received over the distraction guide 710 and the spacer 720. As the second wing 760 is received by the spacer 720, the flexible hinge 1115 and its protrusion 1130 deflect until the protrusion 1130 meets and joins with the indentation 1140 in the spacer 720, securing the second wing 760 to the spacer 720. Again in embodiments where the spacer can rotate, the indentation 1140 is located on an end of the distraction guide 710 that is adjacent to 750 the rotatable spacer 810. With respect to the flexible hinge 1115, this hinge is in a preferred embodiment formed with the second wing 760 and designed in such a way that it can flex as the hinge 1115 is urged over the distraction guide 710 and the spacer 720 and then allow the protrusion 1130 to be deposited into the indentation 1140.

Alternatively, it can be appreciated that the indentation 1140 can exist in the second wing 760 and the flexible hinge 1115 and the protrusion 1130 can exist on the spacer 720 in order to mate the second wing 760 to the spacer 720. Still alternatively, the flexible hinge 1115 can be replaced with a flexible protrusion that can be flexed into engagement with the indentation 1140 in the embodiment with the indentation 1140 in the spacer 720 or in the embodiment with the indentation 1140 in the second wing 760.

Figure 21A:
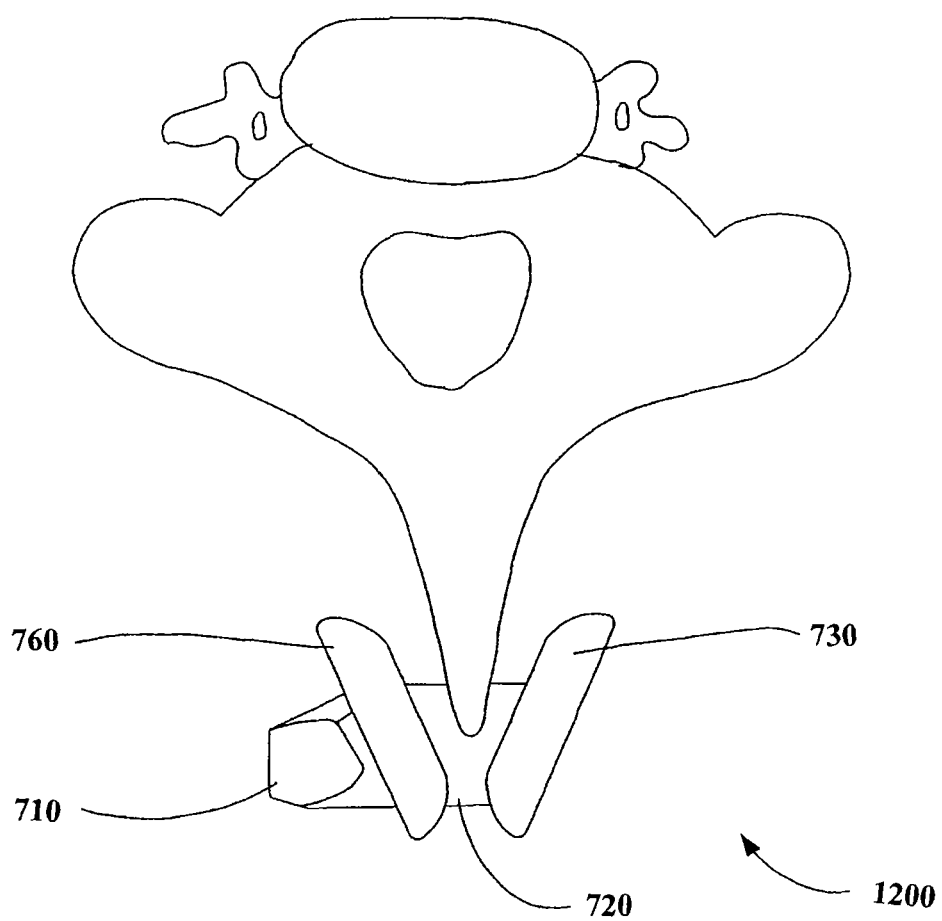
FIG. 21A is a top view of an embodiment of an implant in accordance with the present invention positioned between the spinous processes of adjacent cervical vertebrae.
Figure 21B:
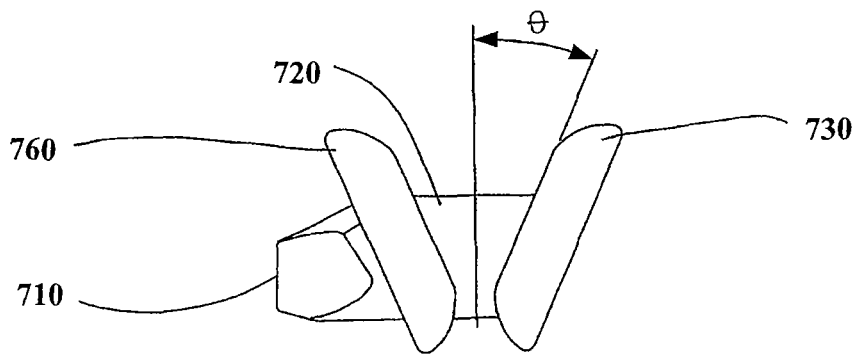
FIG. 21B is a top view of the implant of FIG. 21A.
Figure 22:
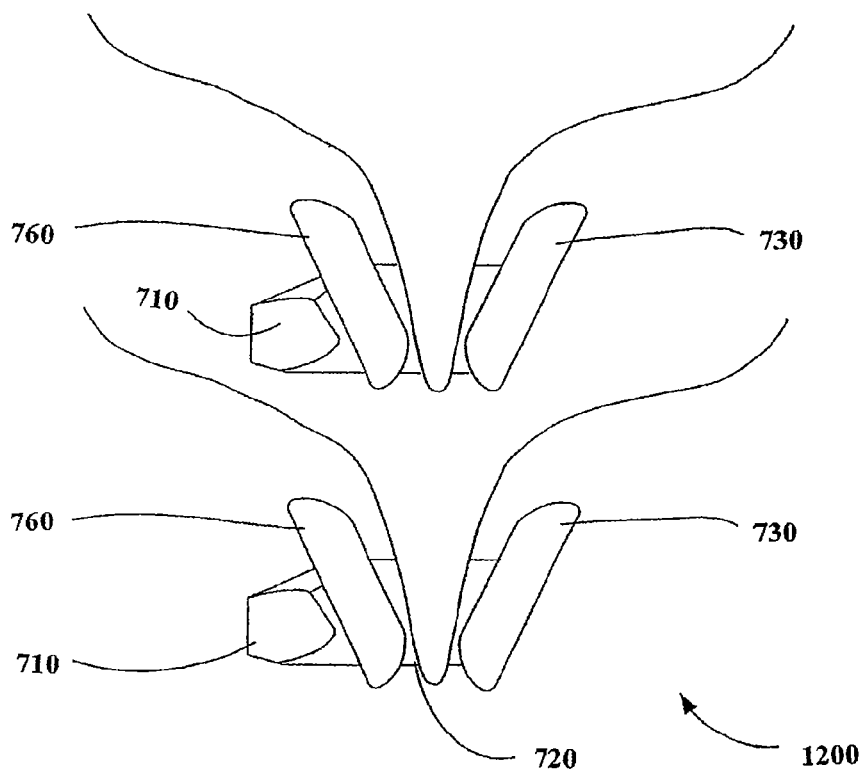
FIG. 22 is a top view of two such implants of the invention as seen in FIG. 21, positioned in the cervical spine.

FIGS. 21A-22 illustrate an embodiment of an implant 1200 wherein anterior ends of a first wing 730 and second wing 760 flare out at an angle away from the spacer 720 and away from each other. The cervical spinous processes are themselves wedge-shaped when seen from a top view. That the implant 1200 can roughly conform with the wedge shape so that the implant 1200 can be positioned as close as possible to the vertebral bodies of the spine where the load of the spine is carried. Thus the first 730 and the second wings 760 are positioned relative to the spacer, whether the spacer is fixed 720 or rotatable 810, so that the wings flare out as the wings approach the vertebral body of the spine. FIG. 21B depicts a top view of the implant 1200 of FIG. 21A. As is evident from FIG. 21B, the first wing 730 is aligned at an angle with respect to a line perpendicular to the longitudinal axis. In one embodiment, the angle is about 30°, however, the angle Θ can range from about 15° to about 45°. In other embodiments, other angles of the first wing 730 relative to the spacer 720 outside of this range are contemplated and in accordance with the invention. Likewise, the second wing 760 can be aligned along a similar, but oppositely varying range of angles relative to the line perpendicular to the longitudinal axis. The first and second wing 730,760 thus form an obtuse angle with respect to the spacer 720 in this embodiment. The second wing 760 defines an inner hole 770 which is outlined by the lip 780. As is evident, the lip 780 can be provided at an angle relative to the rest of the second wing 760 so that when the lip 780 is urged into contact with the spacer 720, the second wing 760 has the desired angle relative to the spacer 720. As discussed above, there are various ways that the second wing 760 is secured to the spacer 720. FIG. 21A depicts a top view of one such implant 1200 placed between the spinous processes of adjacent cervical vertebrae. FIG. 22 is a top view illustrating two layers of distracting implants 1200 with flared wings.

Figure 23:
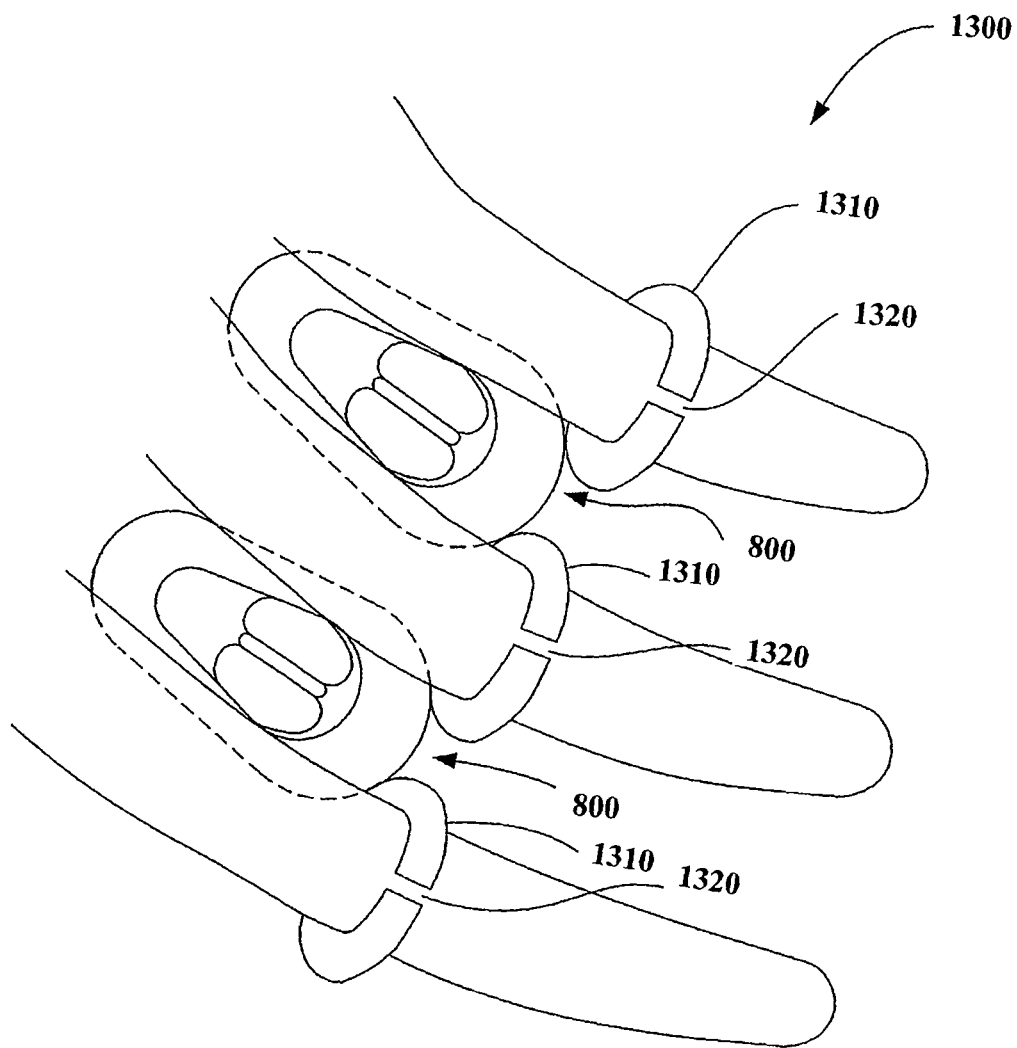
FIG. 23 is a side view of two implants of the invention positioned in the cervical spine, with stops or keeps at the distal ends of the spinous processes.

Systems and methods in accordance with the present invention can include devices that can be used in cooperation with implants of the present invention. FIG. 23 illustrates "stops" (also referred to herein as "keeps") 1310, which are rings of flexible biocompatible material, which can be positioned around the spinous processes of adjacent cervical vertebrae and located posteriorly to the implant. The keeps 1310 can prevent posterior displacement of the implants. In one embodiment, the keeps can include a ring 1310 having a slit 1320. The keeps 1310 can be somewhat sprung apart, so that the keep 1310 can be fit over the end of the spinous process and then allowed to spring back together in order to hold a position on the spinous process. The keep 1310 can act as a block to the spacer 720 in order to prevent the implant from movement in a posterior direction.

Distractible Interspinous Implants

Figure 24:
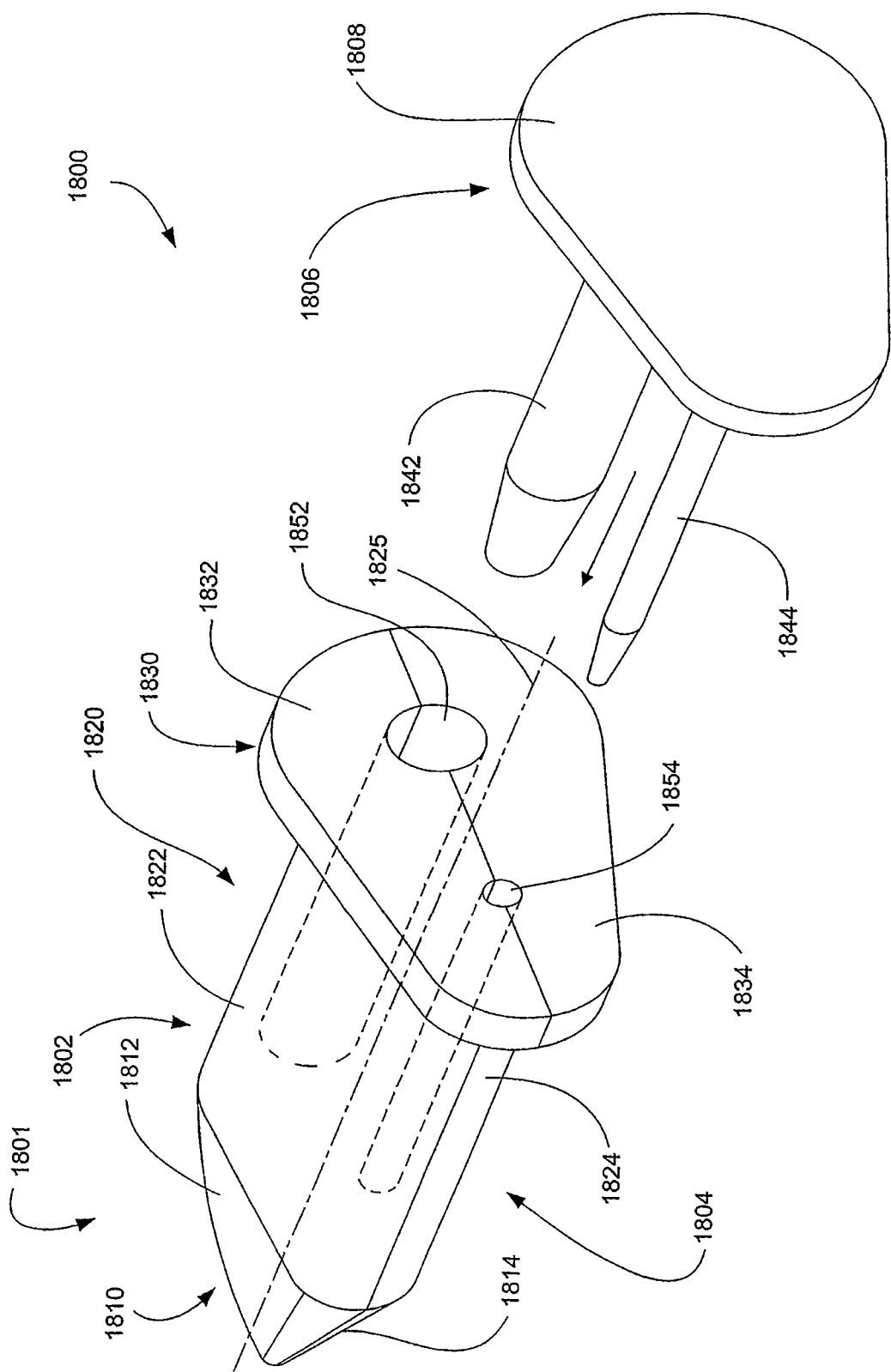
FIG. 24 is a perspective view of an alternative embodiment of an implant for use with systems and methods of the present invention.
Figure 25A:
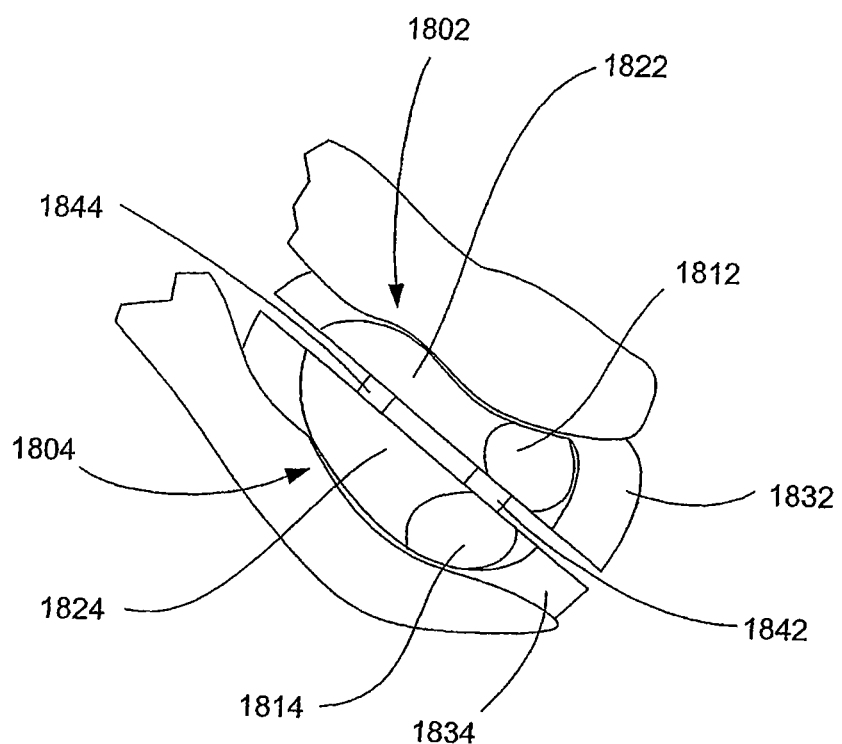
FIG. 25A is an end view of an implant in accordance with still another embodiment of the present invention having a first part shaped to conform roughly with a contact surface of the spinous process.

In still other embodiments, implants in accordance with the present invention can be distractible in situ. FIG. 24 is a perspective view of one such implant. The implant 1800 comprises a body 1801 adapted to be inserted between the spinous processes, and a distracting insert 1806. The body 1801 can include two substantially mirror parts: a first part 1802 adapted to contact and support an upper spinous process and a second part 1804 adapted to contact and support a lower spinous process. When positioned such that the first and second parts 1802,1804 align with and abut one another, the body 1801 can resemble implants described above in reference to FIGS. 7-23. In other embodiments, the body 1801 can have a shape other than those shown in FIGS. 7-23. Further, in some embodiments the first part 1802 and second part 1804 can have different shapes, such that when the first part 1802 and second part 1804 align with and abut one another, the body 1801 is nonsymmetrical about the plane of contact. For example, as shown in FIG. 25A, the first part 1802 can have a saddle-like, or concave shape conforming roughly with a shape of a contact surface of the second cervical, while the second part 1804 has a substantially convex shape.

The body 1801 can include a wing 1830 having a first and second portion 1832,1834, a spacer 1820 having a first and second portion 1822,1824, and a lead-in tissue expander (also referred to herein as a distraction guide) 1810 having a first and second portion 1812,1814. The distraction guide 1810 as shown is wedge-shaped, i.e., the distraction guide 1810 has an expanding cross-section from the proximal end of the body 1801 to a region where the distraction guide 1810 joins with the spacer 1820. As such, the distraction guide 1810 functions to initiate distraction of the soft tissue and the spinous processes when the body 1801 is surgically inserted between the spinous processes.

The spacer 1820, as shown, is teardrop-shaped in a cross-section perpendicular to the spacer's longitudinal axis 1825. The spacer 1820 can be shaped to roughly conform to a wedge-like space, or a portion of the space, between adjacent spinous processes, for example as between the spinous processes of the fourth and fifth cervical vertebrae. The shape of the spacer 1820 can be selected for a particular patient, and/or a particular pair of adjacent spinous processes, and can vary substantially. Thus, in other embodiments, the spacer 1820 can have other cross-sectional shapes, such as circular, wedge, oval, ovoid, football-shaped, and rectangular-shaped with rounded corners and other cross-sectional shapes and/or can be custom fabricated for the particular patient and the anatomy of the particular spinal processes between which the implant 1800 is to be placed.

In still other embodiments, the spacer 1820 can have a nonsymmetrical cross-sectional shape, for example where a space between adjacent spinous processes is nonsymmetrical.

The ability to select a size and shape of the spacer 1820 to suit a patient allows the physician to choose an implant 1800 that can be placed closer to the vertebral bodies than farther away for additional support. The shape selected for the spacer 1820 can define the contact surface area between the implant 1800 and the spinous processes that are subject to distraction.

Increasing the contact surface area between the implant 1800 and the spinous processes distributes the force and load between the spinous frame and the implant 1800. Generally, a teardrop or wedge-shaped spacer 1820 can allow for more load-bearing contact between the spacer 1820 and the spinous processes of the cervical vertebrae, and embodiments having such shapes will be more particularly described.

As shown, the wing 1830 can be tear-drop shaped in cross-section, although having a minor dimension that is larger than that of the spacer 1820, and can limit or block lateral displacement of the implant 1800 in the direction of insertion along the longitudinal axis 1825. However, the wing 1830 need not be teardrop shaped. In other embodiments, the wing 1830 can have some other shape, for example the wing 1830 can be elliptical, wedge, circular, oval, ovoid, football-shaped, and rectangular-shaped with rounded corners and other shapes, and be within the spirit and scope of the invention. Further, as with the spacer 1820, the wing 1830 can have a nonsymmetrical cross-sectional shape. The shape of the wing 1830 can be chosen to most easily fit into place while avoiding obstructions, such as soft tissue or bone, or other implants, while still blocking or limiting lateral displacement.

The wing 1830 can include one or more cavities 1852,1854 that extend through the wing 1830 and through at least a portion of the spacer 1820. The one or more cavities 1852, 1854 should comprise a first groove formed in the first part 1802 and a second groove formed in the second part 1804, so that the cross-section of the cavity 1852,1854 can be expanded during insertion of a distracting insert 1806, as described below. The body 1801 of FIG. 24 includes a first cavity 1852 and a second cavity 1854 to receive a first insert 1842 and a second insert 1844 of the distracting insert 1806. Having two or more cavities and corresponding inserts can prevent relative rotation between the body 1801 and the distracting insert 1806. In the embodiment shown in cross-section in FIG. 25B, each cavity has a substantially circular cross-section, and is sized roughly in proportion to the width of the spacer 1820, so that the first cavity 1852 is larger in diameter than the second cavity 1854.

Figure 25B:
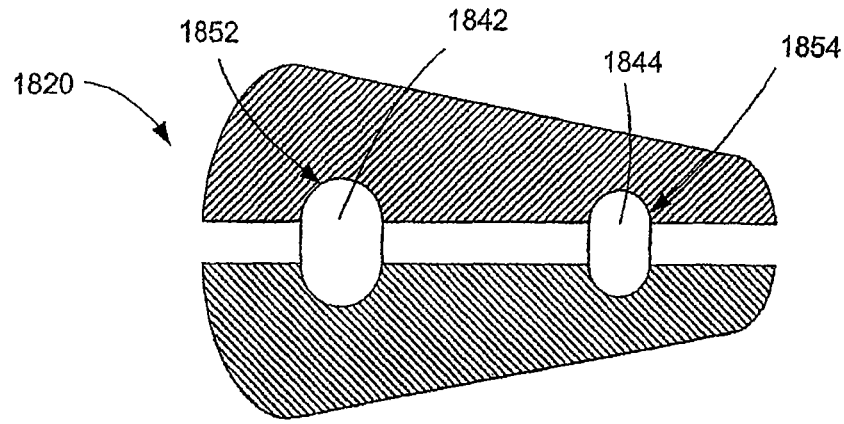
FIG. 25B is a cross-sectional view of a spacer and a distracting insert in accordance with one embodiment of the present invention.
Figure 25C:
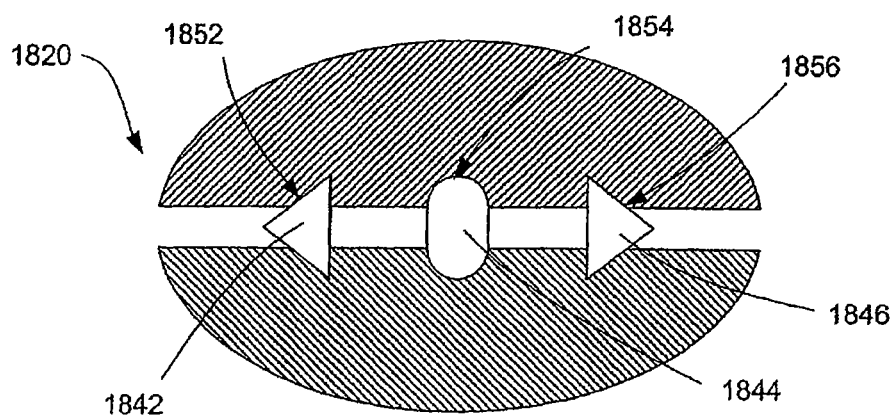
FIG. 25C is a cross-sectional view of a spacer and a distracting insert in accordance with an alternative embodiment of the present invention.
Figure 25D:
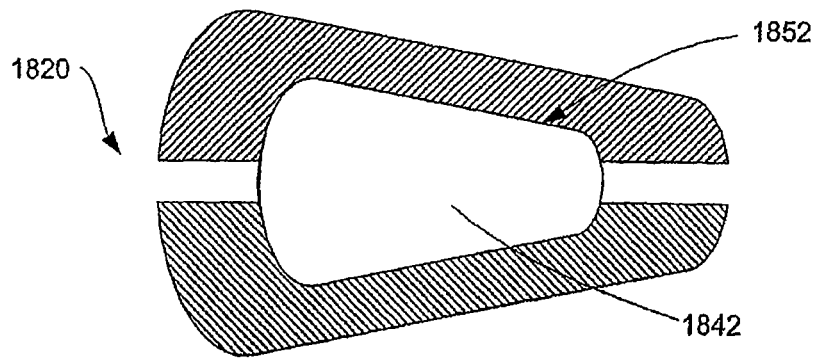
FIG. 25D is a cross-sectional view of a spacer and a distracting insert in accordance with still another embodiment of the present invention.

However, in other embodiments, the cavities need not be shaped as shown. For example, the cavities can be elliptical, dual-lobed, or otherwise shaped. Further, the cavities need not be sized as shown. For example, the cavities can be roughly the same size. As shown in FIG. 25C, in still further embodiments, the body 1801 can include more than two cavities 1852,1854, 1856, and each cavity can have similar, or different shape. As shown in FIG. 25D, in still other embodiments the body 1801 can include a single cavity 1852, such as a wedge-shaped cavity roughly corresponding to a shape of the spacer 1820. Myriad different cavity shapes and cavity configurations can be employed to achieve separation of a body 1801 positioned between spinous processes. However, it can be preferable that the shape of the cavities 1852,1854, 1856 should correspond roughly with the shape of the upper and lower surfaces of the inserts 1842,1844, 1846 of the. distracting insert 1806, so that, as shown in FIG. 25B-25D, a load applied to the body 1801 can be distributed relatively evenly over the surface of the cavities 1852,1854, 1856.

Once the body 1801 is positioned between adjacent spinous processes, the first and second parts 1802,1804 of the body 1801 can be separated, thereby expanding the width of the body 1801 and distracting the adjacent spinous processes. In one embodiment, separation of the first and second parts 1802,1804 can be accomplished, for example, by positioning the distracting insert 806 within the body 1801 such that the first and second parts 1802,1804 are urged apart. As mentioned above, the distracting insert 1806 can include one or more inserts associated with the one or more cavities, the one or more inserts being fixedly connected to a cap 1808. As shown in FIG. 24, the distracting insert 1806 includes a first insert 1842 and a second insert 1844, each of the inserts being fixedly connected with a cap 1808 having a shape roughly corresponding to a shape of the wing 1830. Inserts 1842,1844 have distracting tips that can initially urge the halves of the implant 1800 apart. In other words, the inserts 1842,1844 have tips with ever-increasing cross-section so that the tips can be easily inserted in the cavities 1852,1854 and the continual movement of the insert 1842,1844 urges the halves of the body 1801 apart. Thus, the tips of the insert 1842,1844 can be smaller than the cavities 1852,1854 in order to facilitate initial insertion into the cavities 1852,1854. As shown in FIGS. 25B-D, the one or more inserts 1842,1844, 1846 can be sized such that they have a height larger than a diameter (or height) of the one or more cavities 1852,1854, 1856, so that when positioning the inserts within the cavities, the first part 1802 and second part 1804 of the body 1801 are separated by the difference in height of the inserts and the diameter (or height) of the cavities (i.e., an additional distraction height).

Figure 26A:
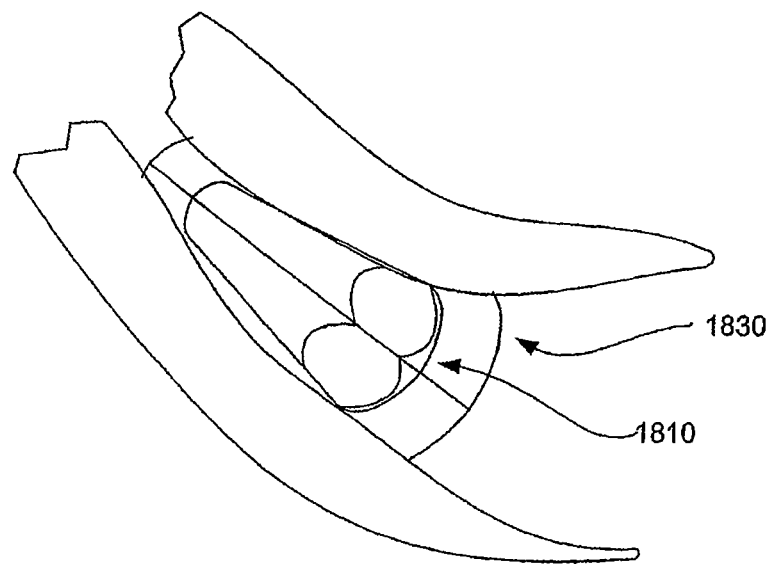
FIG. 26A is a front view of the implant of FIG. 24 inserted between spinous processes.

As shown in FIG. 26A, the body 1801 can be inserted between adjacent spinous processes by piercing and/or displacing the soft tissue (i.e., the interspinous ligament) with the distraction guide 1810 and stretching and/or displacing the tissue so that the spacer 1820 fits between the spinous processes. The height of the first part 1802 and second part 1804 of the body 1801 can be minimized by abutting the first part 1802 and the second part 1804 so that the body 1801 can be positioned between the spinous processes.

Figure 26B:
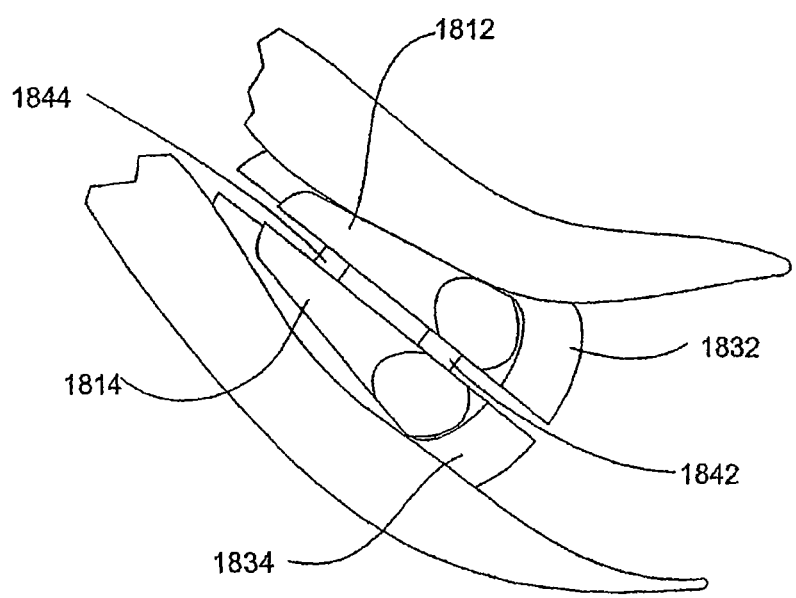
FIG. 26B is a front view of the implant of FIG. 26A having a distracting insert positioned within cavities of the implant.

As described above, and as can be seen in FIG. 26A, the shape of the body 1801 can resemble the shape of a space between adjacent spinous processes. With the body 1801 in place, the distracting insert 1806 can be inserted into the body 1801, causing the first part 1802 and second part 1804 to separate, as described above and shown in FIG. 26B. As discussed above, proximal ends of the inserts 1842, 1844 of the distracting insert 1806 can be tapered to assist in guiding the inserts 1842,1844 into the cavities 1852,1854, and to ease separation of the first and second parts 1802,1804. The distracting insert 1806 can have inserts 1842,1844 sized to achieve a desired amount of distraction of the spinous processes.

As with the body 1801, multiple distracting inserts 1806 can be made available to a physician, the physician choosing a distracting insert 1806 sized to suit a particular patient. A system in accordance with one embodiment of the present invention can comprise a plurality of bodies 1801, each body 1801 having different shape and/or height.

Such a system can further comprise a plurality of distracting inserts 1806, having inserts corresponding to cavities of the bodies 1801, and having different heights to achieve different amounts of distraction. Methods in accordance with embodiments of the present invention can apply such systems so that a physician can select implant components appropriate to the patient at the time of surgery, and can further substitute different bodies and/or different distracting inserts based on evaluation or reevaluation during surgery.

Figure 27A:
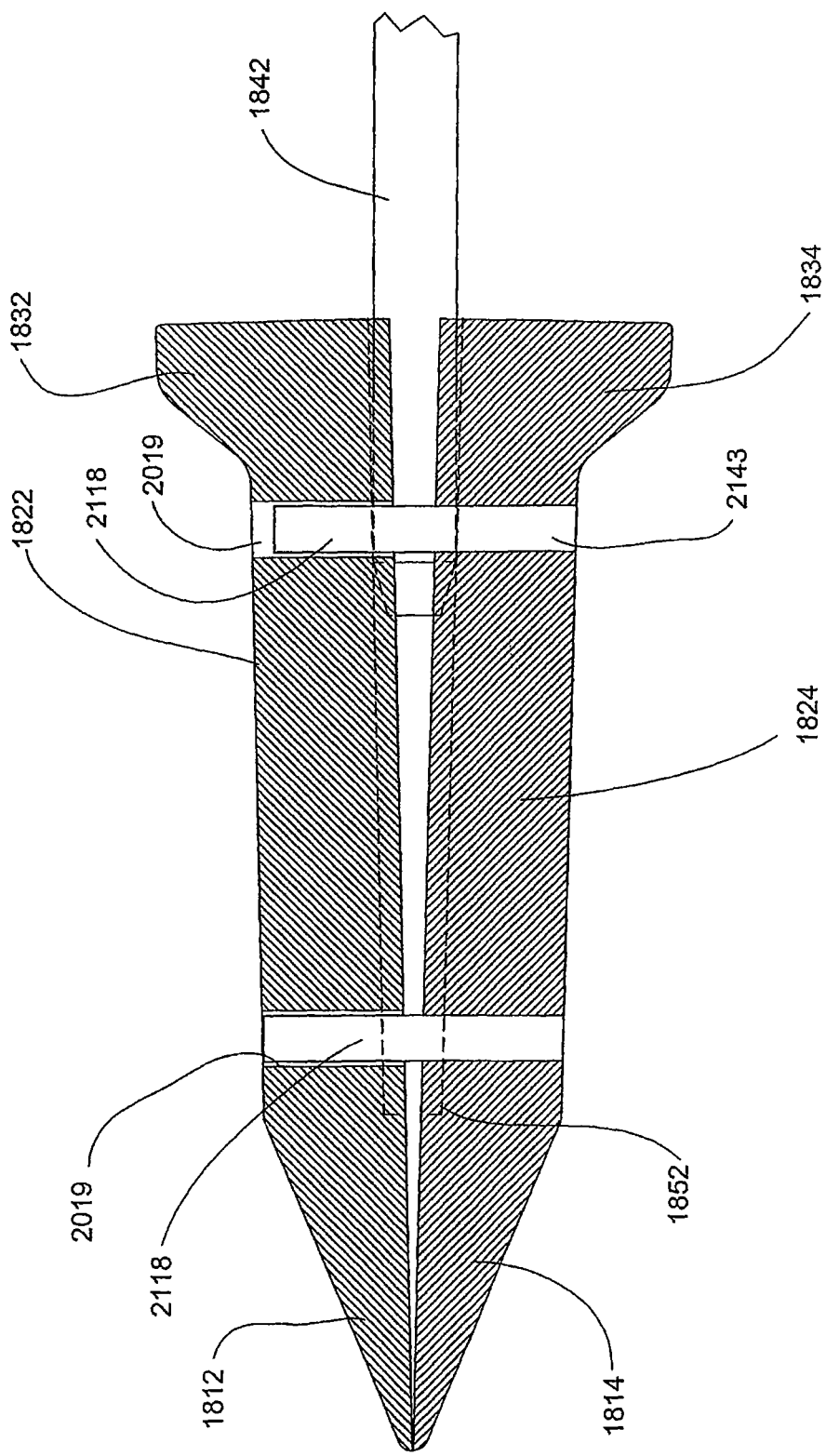
FIG. 27A is a cross-sectional side view of the implant of FIG. 24 showing a distracting insert partially inserted in a cavity of the implant having pins for aligning a first portion with a second portion.
Figure 27B:
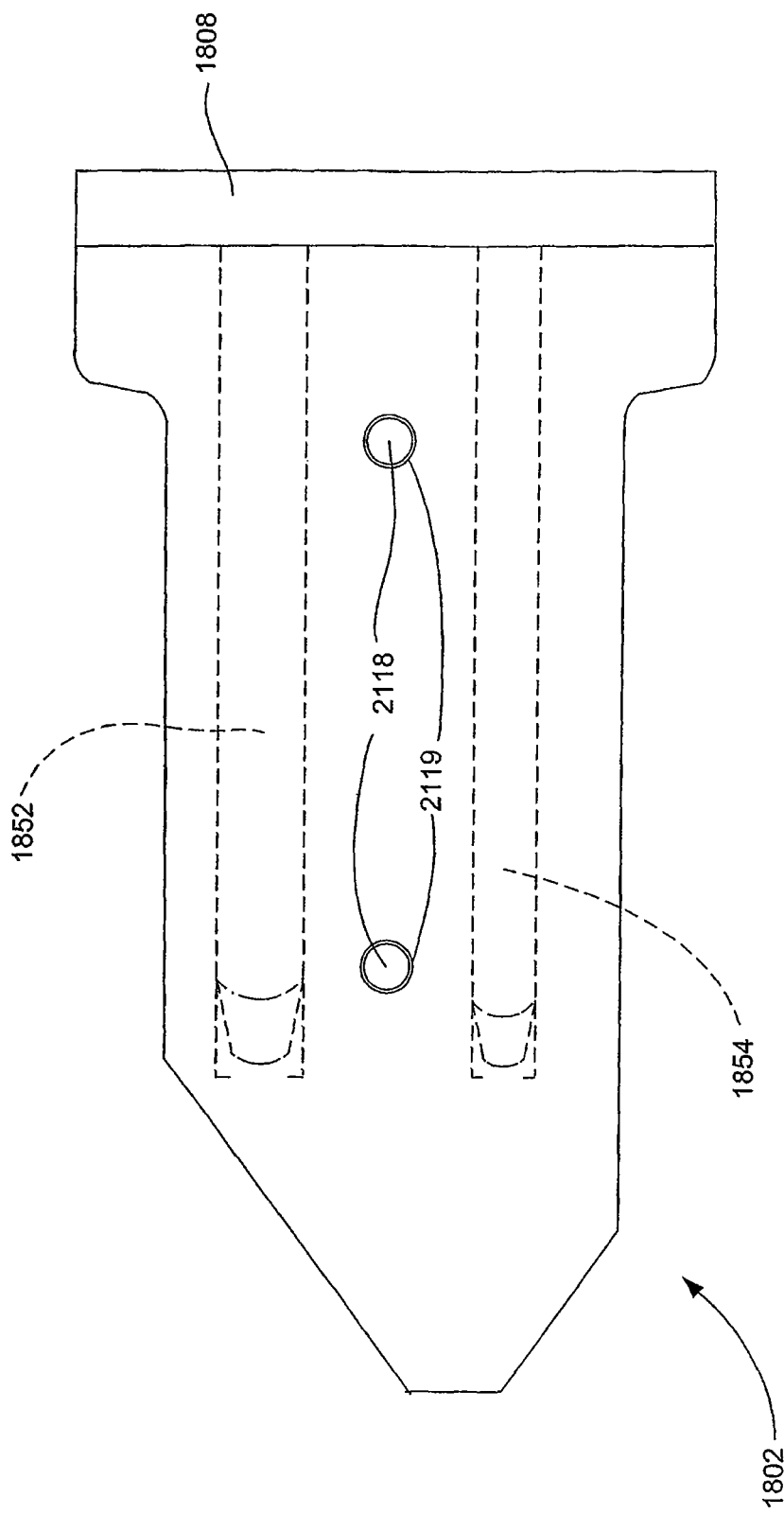
FIG. 27B is a top view of the implant of FIG. 27A showing positioning of pins for alignment of the first part and second part.

FIG. 27A is a cross-sectional side view of a distractible implant 1800 in accordance with one embodiment of the present invention positioned between adjacent spinous processes, and having an insert 1842 of the distracting insert 1806 partially inserted within a cavity 1852 of the body 1801. As described above, when inserted between spinous processes, the first part 1802 of the body 1801 is aligned and abutted with the second part 1804 of the body 1801. The first part 1802 and second part 1804 should remain aligned while the body 1801 is inserted between the spinous processes, and further should remain aligned while the distracting insert 1806 is mated with the body 1801. In order to maintain proper alignment, one of the first and second parts 1802,1804 can include alignment pins (or protrusions) 2118 that mate with corresponding holes 2119 of the other of the first and second parts 1802,1804. The pins 2118 can be made of the same or different material as the body 1801, and can be integrally formed or mated with the corresponding part. For example, where the pins 2118 are made of titanium, and the body 1801 is made of a biocompatible thermoplastic, the pins 2118 can be press fit into the second part 1804. The pins 2118 are free to slide in and out of the holes 2119, but are prevented from separating from the holes 2119 by pressure of the spinous processes. As an insert 1842 enters a cavity 1852 of the body 1801, the distal end of the body 1801 begins to separate, as shown. As the spinous processes are distracted, the pins 2118 move within the holes 2119, allowing separation of the first part 1802 and second part 1804. The pins 2118 prevent relative shifting or sliding along the longitudinal axis or along the length of the spinous process. The pins 2118 (and corresponding holes 2119) preferably have a height larger than the maximum distraction height, thereby preventing the pins 2118 from separating from the holes 2119 and allowing relative shifting of the first and second parts 1802,1804. FIG. 27B is a top view showing the position of the pins 2118 relative to a first and second cavity 1852,1854. Two pins 2118 are shown extending through holes 2119 of the second part 1802, however, in other embodiments, any number of pins 2118 or protrusions can be integrally formed or connected with one of the first and second parts 1802,1804.

In an alternative embodiment (not shown), the first part 1802 and second part 1804 of the body 1801 can be bound together by a flexible, artificial ligament or suture material. For example, the material can be a bio-compatible polymer having flexible properties. The artificial ligament or suture material can limit the shifting between the first part 1802 and second part 1804. In still other embodiments, some other device can be employed to maintain alignment of the first and second parts 1802,1804. It is intended that in some embodiments of the present invention, it is preferable to maintain alignment of the first and second parts 1802,1804 during distraction. As one of ordinary skill in the art can appreciate, many different devices can be employed to maintain alignment between the first and second parts 1802,1804 of the body 1801.

Figure 28A:
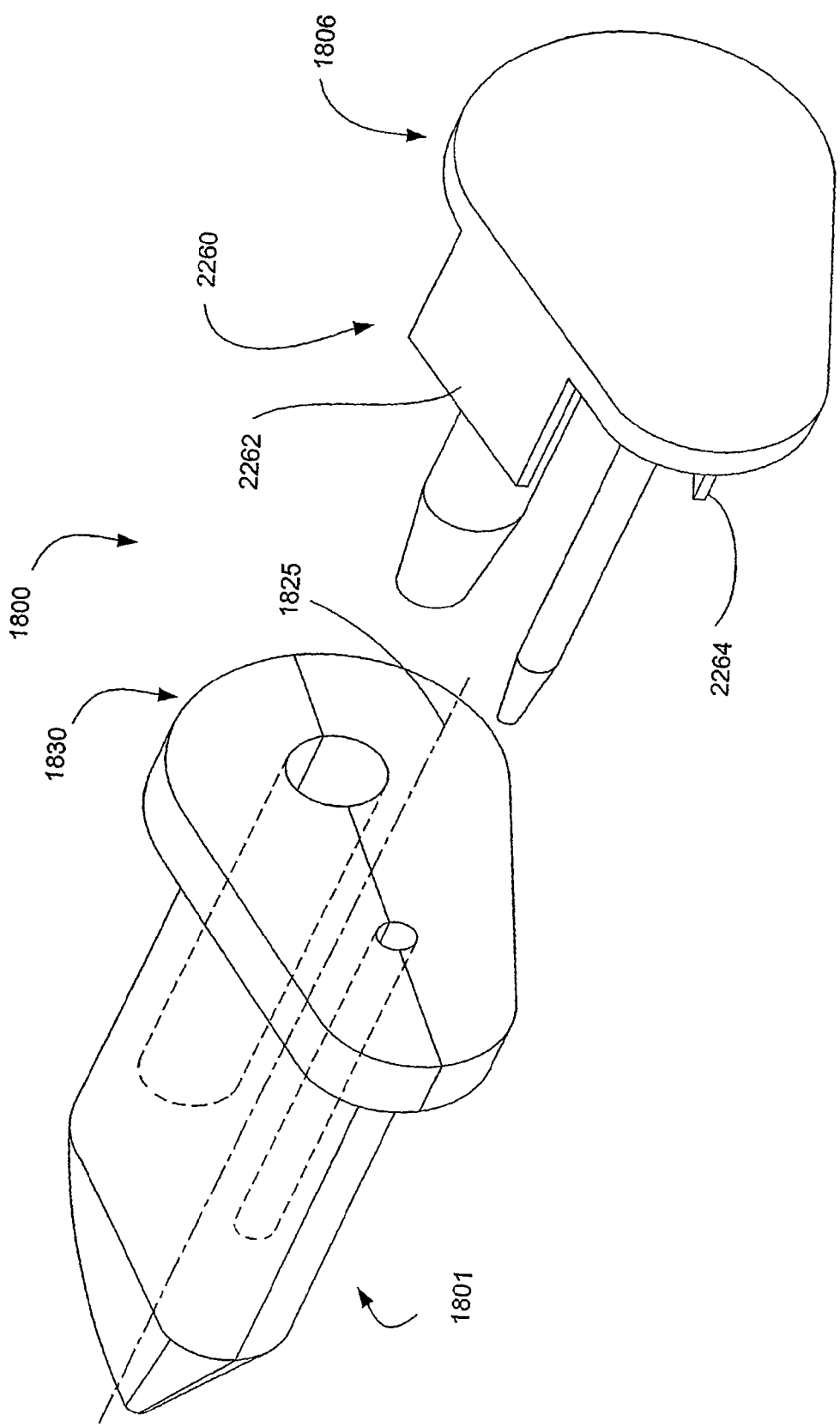
FIG. 28A is a perspective view of an alternative embodiment of an implant for use with systems and methods of the present invention, wherein the distracting insert includes a clip.
Figure 28B:
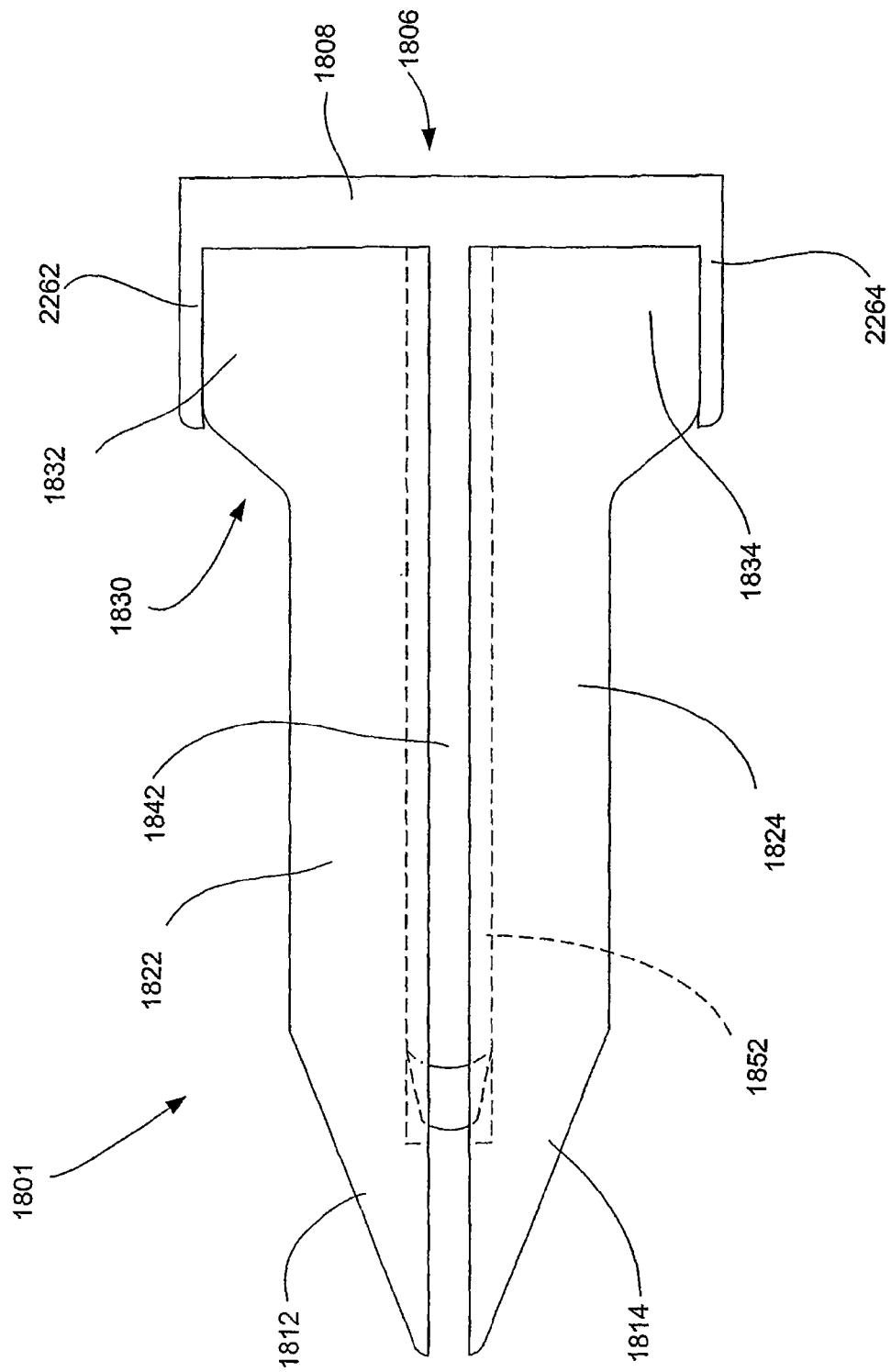
FIG. 28B is a side view of the implant of FIG. 28A showing a distracting insert mated with the implant.

As shown in FIGS. 28A and 28B, the distracting insert 1806 can be secured to the body 1801 by a clip 2260. The body 1801 as shown in FIGS. 28A-28D is the same as the body 1801 of FIG. 24. Commonly labeled components are as described above. However, it should be noted that other embodiments of a body 1801 can be used with distracting inserts 1806 described with reference to FIG. 28A-28D. In one embodiment, the clip 2260 can include a first tab 2262 and a second tab 2264. Each tab 2262,2264 can extend across at least a portion of the width of the respective portion of the wing 1830 along the longitudinal axis 1825. When the distracting insert 1806 is mated with the body 1801, the wing 1830 can be interference-fit with the distracting insert 1806 so that the wing 1830 is held between the tabs 2262,2264. The pressure applied to the surfaces of the wing 1830 should create sufficient frictional force to prevent relative movement between the body 1801 and distracting insert 1806. In other embodiments, the clip 2260 can comprise a single lip along a portion of, or the entire periphery of the cap (and wing 1830) and can extend across at least a portion of the width of the wing 1830 along the longitudinal axis 1825.

Figure 28C:
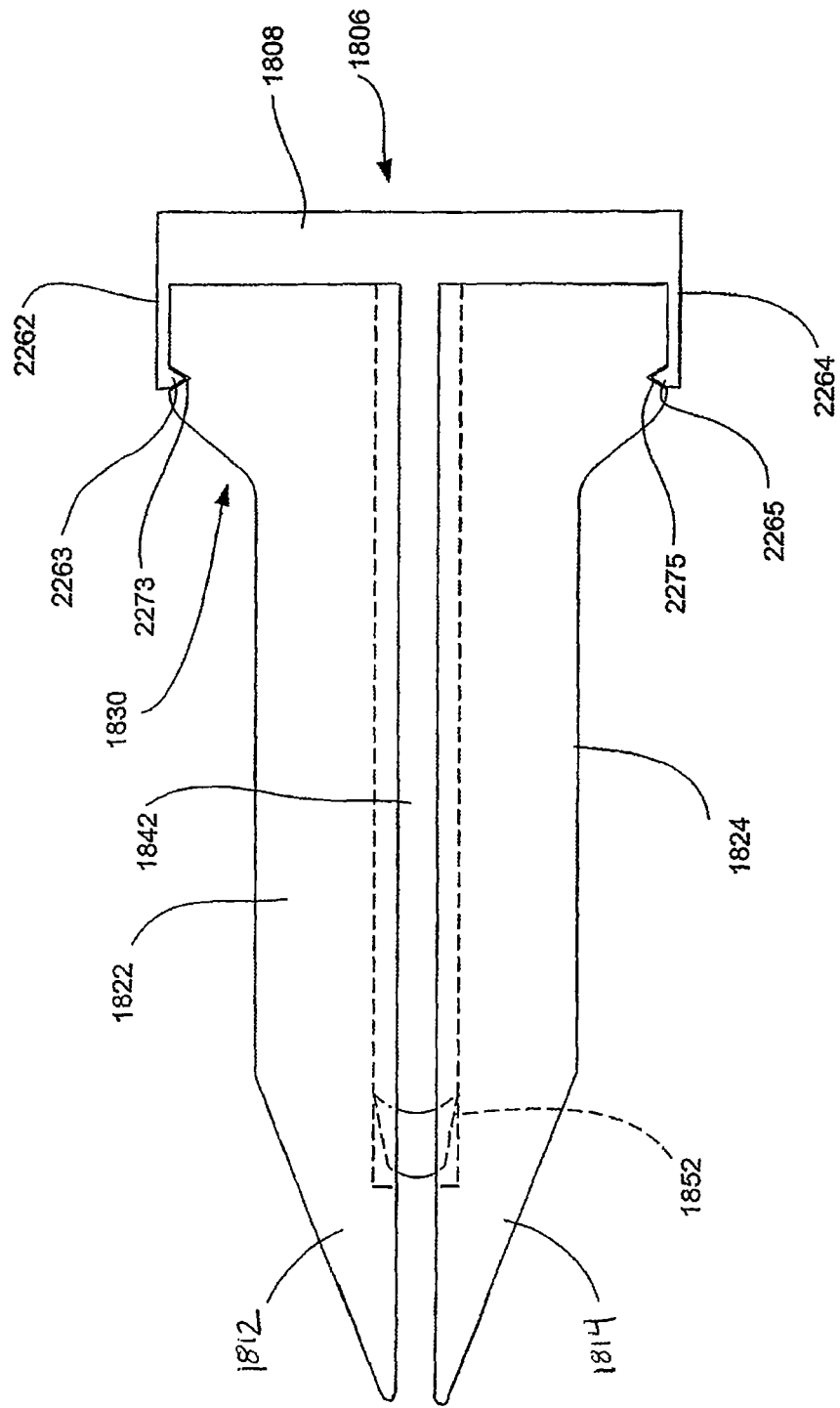
FIG. 28C is a side view of an alternative embodiment of an implant mated with an alternative embodiment of a distracting insert.

As shown in FIG. 28C, in still other embodiments, each tab 2262,2264 can include a protrusion 2263,2265 located at a proximal end of the tab 2262,2264. The wing 1830 can include indentations 2273,2275, or cavities, for receiving each of the protrusions 2263,2265 so that when the protrusions are positioned within the respective indentations, the clip 2260 is locked in place. Alternatively, the tab 2262,2264 can extend beyond a ledged wing 1830, so that the clip 2260 can be locked in place when the protrusions 2263,2265 clear the wing 1830. As described above, the distracting insert 1806 is mated with the positioned body 1801 by gradually urging the inserts of the distracting insert 1806 along the length of the cavities of the spacer 1820. The protrusions 2263,2265 can be beveled, so that as the protrusions contact an outer lip of the wing 1830, the tabs 2262,2264 deflect upward, allowing the distracting insert 1806 to continue moving into position along the longitudinal axis. When the protrusions 2263,2265 find the indentations 2273,2275 of the wing 1830 (or alternatively, when the protrusions clear the ledge), the clasp 2260 locks into place and the distracting insert 1806 is mated with the body 1801.

Figure 28D:
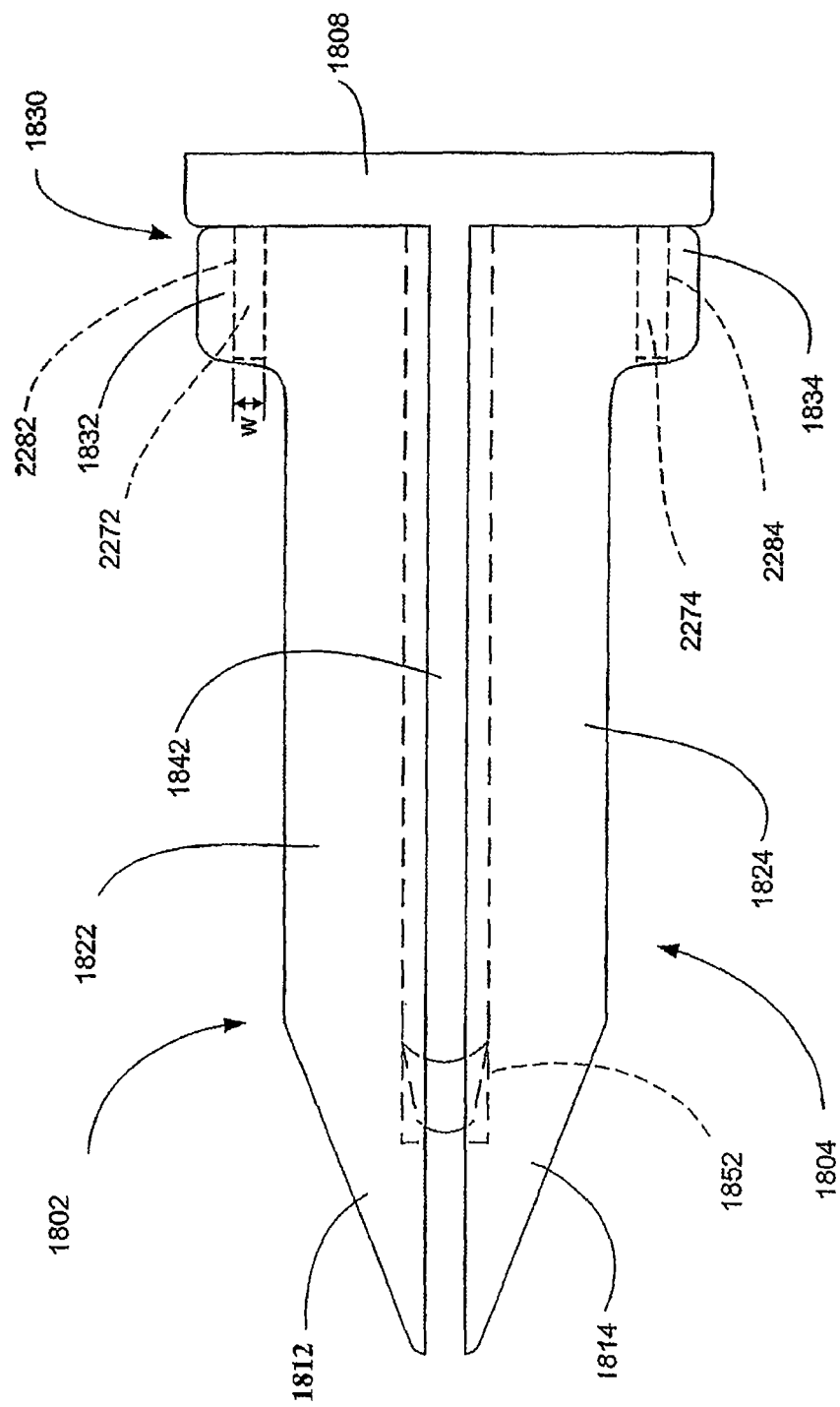
FIG. 28D is a side view of still another embodiment of an implant mated with still another embodiment of a distracting insert.

In still further embodiments, the distracting insert 1806 need not include a clip, but can be mated with the body 1801 using some other device. For example, as shown in FIG. 28D, an insert 1842 can include one or more pegs 2272,2274, and one or more corresponding through-holes 2282,2284 (or cavities) within the first wing 1830. The one or more pegs 2272,2274 can be sized such that a feature of the one or more pegs 2272,2274 is approximately the same width, or slightly larger than a width, w, of the one or more corresponding through-holes 2282,2284, so that an interference fit is created between the distracting insert 1806 and the body 1801, holding the distracting insert 1806 seated in place, and limiting the relative movement of the first part 1802 and second part 1804.

Figure 29:
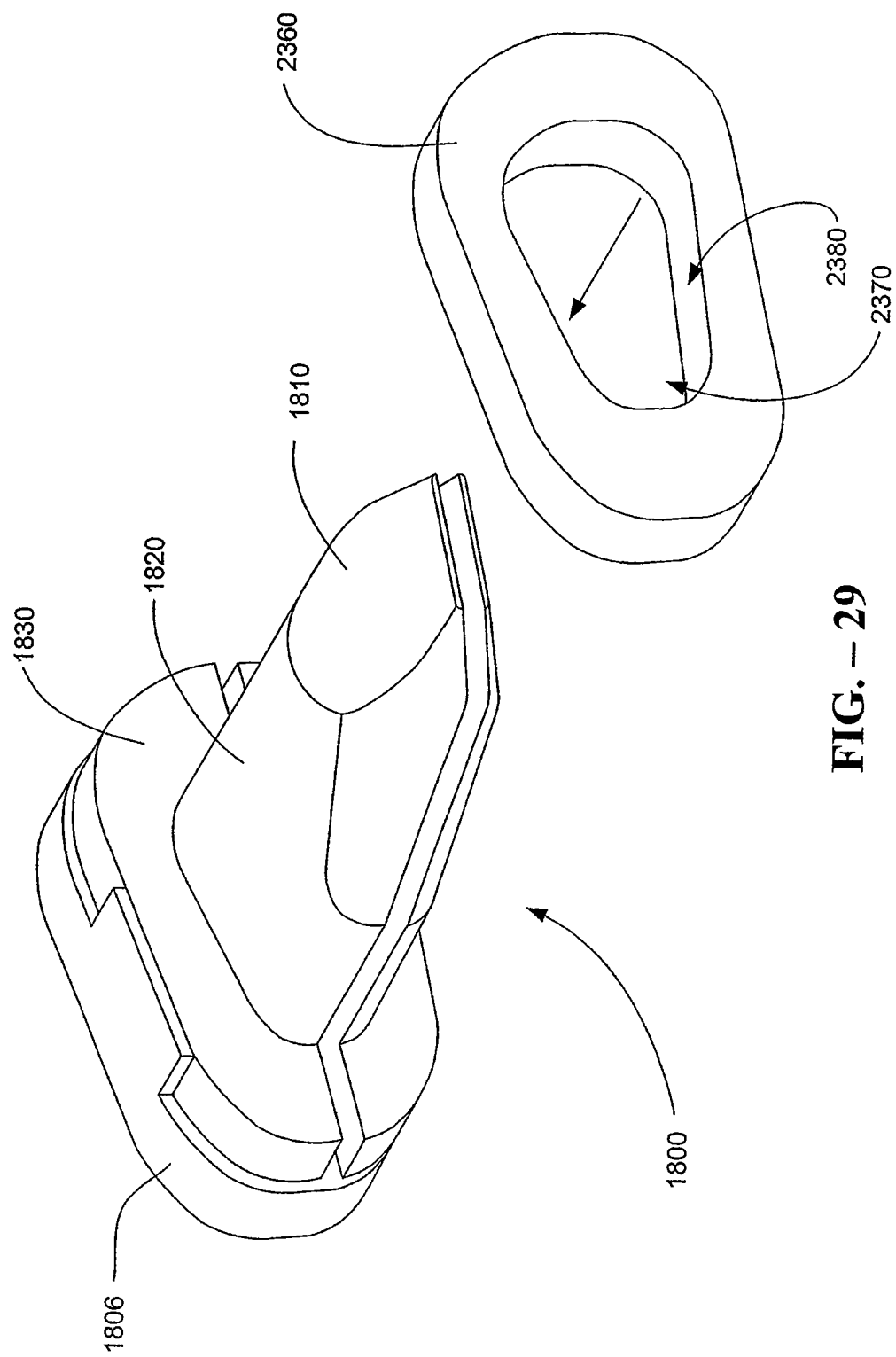
FIG. 29 is a perspective view of an embodiment of a distractible implant in accordance with the present invention having a second wing for limiting or blocking shifting along the longitudinal axis.

Referring to FIG. 29, the implant 1800 can further include a second wing 2360, similar to previously described embodiments. The second wing 2360 can be connected to the proximal end of the spacer 1820 so that portions of the adjacent spinous processes are sandwiched between the second wing 2360 and the first wing 1830. The second wing 2360, like the first wing 1830, can prevent lateral displacement of the body 1801 relative to the spinous processes. The second wing 2360 can be teardrop-shaped and sized to approximate the shape and size of the first wing 1830 when the distracting insert 1806 is mated with the body 1801. Likewise, the sides of the second wing 2360 define a space 2370 with a lip 2380 that allows the second wing 2360 to pass over the distraction guide 1810 to meet and connect with the spacer 1820. The space 2370 defined within the second wing 2360 should correspond with the distracted height of the body 1801. As described above, systems and methods in accordance with the present invention can comprise a plurality of bodies 1801 and a plurality of distracting inserts 1806 to suit a particular patient. Likewise, systems and methods in accordance with the present invention can further comprise a plurality of second wings 2360 corresponding in size and shape to the plurality of bodies 1801 and the plurality of distracting inserts 1806. The second wing 2360 can be secured to the spacer 1820, for example as described above. The second wing 2360 is implanted once the distraction guide 1810, spacer 1820, and first wing 1830 are inserted as a unit between the spinous processes of adjacent cervical vertebrae.

It is to be understood that the various features of the various embodiments can be combined with other embodiments of the invention and be within the spirit and scope of the invention. Thus, for example only, the embodiment of FIG. 24 can have truncated wings as depicted in other embodiments.

Materials for Use in Implants of the Present Invention

It is to be understood that implants in accordance with the present invention, and/or portions thereof can be fabricated from somewhat flexible and/or deflectable material.

In these embodiments, the implant and/or portions thereof can be made out of a polymer, such as a thermoplastic. For example, in one embodiment, the implant can be made from polyketone, known as polyetheretherketone (PEEK). Still more specifically, the implant can be made from PEEK 450G, which is an unfilled PEEK approved for medical implantation available from Victrex of Lancashire, Great Britain. Other sources of this material include Gharda located in Panoli, India. PEEK has the following approximate properties:

| Property | Value |
| --- | --- |
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

The material specified has appropriate physical and mechanical properties and is suitable for carrying and spreading a physical load between the adjacent spinous processes. The implant and/or portions thereof can be formed by extrusion, injection, compression molding and/or machining techniques.

In some embodiments, the implant can comprise, at least in part, titanium or stainless steel, or other suitable implant material which is radiopaque, and at least in part a radiolucent material that does not show up under x-ray or other type of imaging. For example, in one embodiment, a first wing, a second wing and a shaft can comprise a radiopaque material (e.g., titanium) and a rotatable spacer and a lead-in tissue expander can comprise a radiolucent material (e.g., PEEK). In such an embodiment, under imaging the implant looks like an "H". The physician can have a less obstructed view of the spine under imaging, than with an implant comprising radiopaque materials entirely. However, the implant need not comprise any radiolucent materials.

It should be noted that the material selected can also be filled. For example, other grades of PEEK are also available and contemplated, such as 30% glass-filled or 30% carbon-filled, provided such materials are cleared for use in implantable devices by the FDA, or other regulatory body. Glass-filled PEEK reduces the expansion rate and increases the flexural modulus of PEEK relative to that which is unfilled. The resulting product is known to be ideal for improved strength, stiffness, or stability. Carbon-filled PEEK is known to enhance the compressive strength and stiffness of PEEK and lower its expansion rate. Carbon-filled PEEK offers wear resistance and load carrying capability.

In this embodiment, as described above, the implant is manufactured from PEEK, available from Victrex. As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention.

The spacer can also be comprised of polyetherketoneketone (PEKK). Other material that can be used include polyetherketone (PEK), polyetherketoneetherketoneketone (PEKEKK), and polyetheretherketoneketone (PEEKK), and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials. "Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

Methods for Implanting Interspinous Implants

Figure 30:
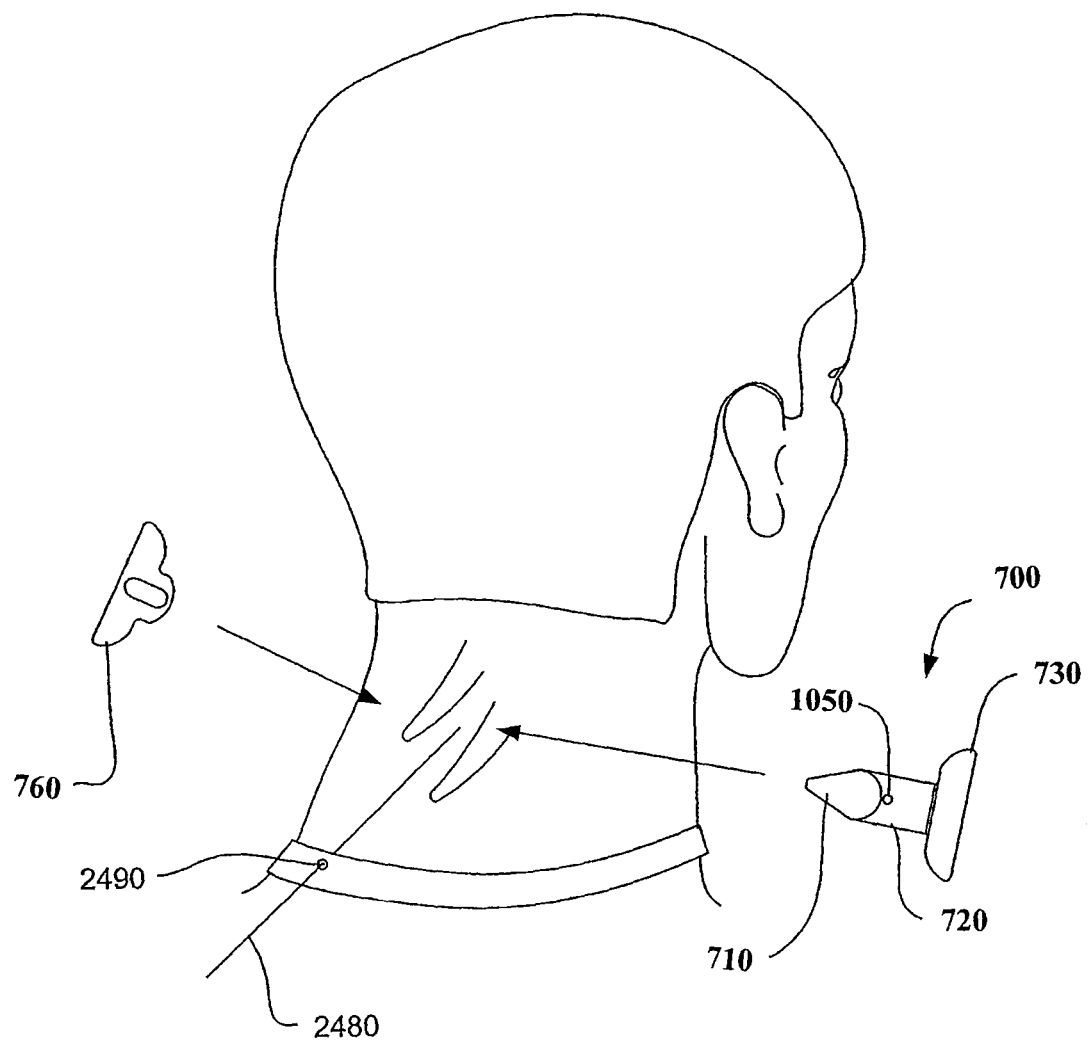
FIG. 30 illustrates an embodiment of a method for implanting an interspinous implant in accordance with the present invention.

A minimally invasive surgical method for implanting an implant 100, 1800 in the cervical spine is disclosed and taught herein. In this method, as shown in FIG. 30, preferably a guide wire 2480 is inserted through a placement network 2490 into the neck of the implant recipient. The guide wire 2480 is used to locate where the implant is to be placed relative to the cervical spine, including the spinous processes. Once the guide wire 2480 is positioned with the aid of imaging techniques, an incision is made on the side of the neck so that an implant in accordance with an embodiment of the present invention, can be positioned in the neck thorough an incision and along a line that is about perpendicular to the guide wire 2480 and directed at the end of the guide wire 2480. In one embodiment, the implant can be a sized implant 100 (i.e., having a body that is not distractible), such as described above in FIGS. 7-23 and including a distraction guide 710, a spacer 720, and a first wing 730. The implant 700 is inserted into the neck of the patient. Preferably during insertion, the distraction end pierces or separates the tissue without severing the tissue.

Once the implant 700 is satisfactorily positioned, a second wing 760 can be optionally inserted along a line that is generally collinear with the line over which the implant 700 is inserted but from the opposite side of the neck. The anatomy of the neck is such that it is most convenient and minimally invasive to enter the neck from the side with respect to the implant 700 and the second wing 760. The second wing 760 is mated to the implant and in this particular embodiment, the second wing 760 is snapped into engagement with the implant 700. In an alternative embodiment, the second wing 760 is attached to the implant by the use of a fastener, for example by a screw 1050. Where a screw is used, the screw 1050 can be positioned using a screw driving mechanism that is directed along a posterior to anterior line somewhat parallel to the guide wire 2480. This posterior to anterior line aids the physician in viewing and securing the second wing 160 to the implant.

Figure 31:
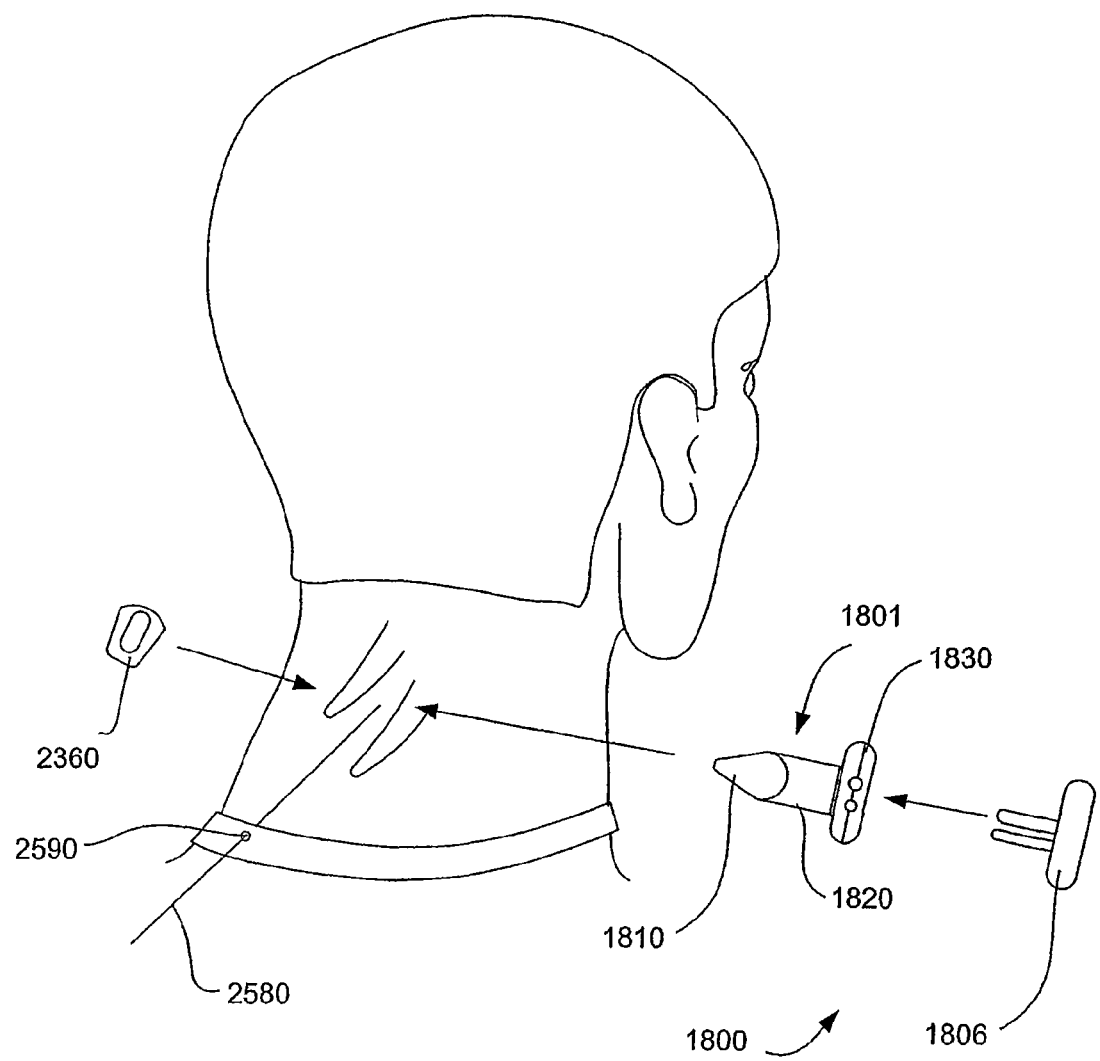
FIG. 31 illustrates an alternative embodiment of a method for implanting an interspinous implant in accordance with the present invention.

In other embodiments of methods in accordance with the present invention, the implant can be a distractible implant 1800, such as described above in FIGS. 24-29. In such embodiments, as shown in FIG. 31, preferably a guide wire 2580 is inserted through a placement network 2590 into the neck of the implant recipient (as shown and described above). Once the guide wire 2580 is positioned with the aid of imaging techniques, an incision is made on the side of the neck so that a distractible body 1801 in accordance with an embodiment of the present invention, can be positioned in the neck thorough an incision and along a line that is about perpendicular to the guide wire 880 and directed at the end of the guide wire. The distractible body 1801 can include a distraction guide 1810, a spacer 1820, and a first wing 1830. The body 1801 is inserted into the neck of the patient, between adjacent spinous processes. Preferably during insertion, the distraction guide 1810 pierces or separates the tissue without severing the tissue, and the body 1801 is positioned so that the spacer 1820 is between the adjacent spinous processes. A distracting insert 1806 is then positioned within the incision and urged into one or more cavities of the body 1801, distracting the spinous processes between which the body is positioned. As the distracting insert 1806 mates with the body 1801, the distracting insert 1806 locks in place.

Once the distractible implant 1800 is satisfactorily positioned and distracted, a second wing 2360 can optionally be inserted along a line that is generally collinear with the line over which the body 1801 is inserted but from the opposite side of the neck. The anatomy of the neck is such that it is most convenient and minimally invasive to enter the neck from the side with respect to the body 1801 and the second wing 2360. The second wing 2360 can be mated to the body 1801 through an interference fit, or alternatively by attaching to the body 1801 by the use of a fastener, or by some other device, as described above. For example, where a screw is employed, the screw can be positioned using a screw driving mechanism that is directed along a posterior to anterior line somewhat parallel to the guide wire. This posterior to anterior line aids the physician in viewing and securing the second wing 2360 to the body 1801.

The foregoing description of the present invention have been presented for purposes of illustration and description. It is not intended to be exhaustive or to limit the invention to the precise forms disclosed. Many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

Figure 32:
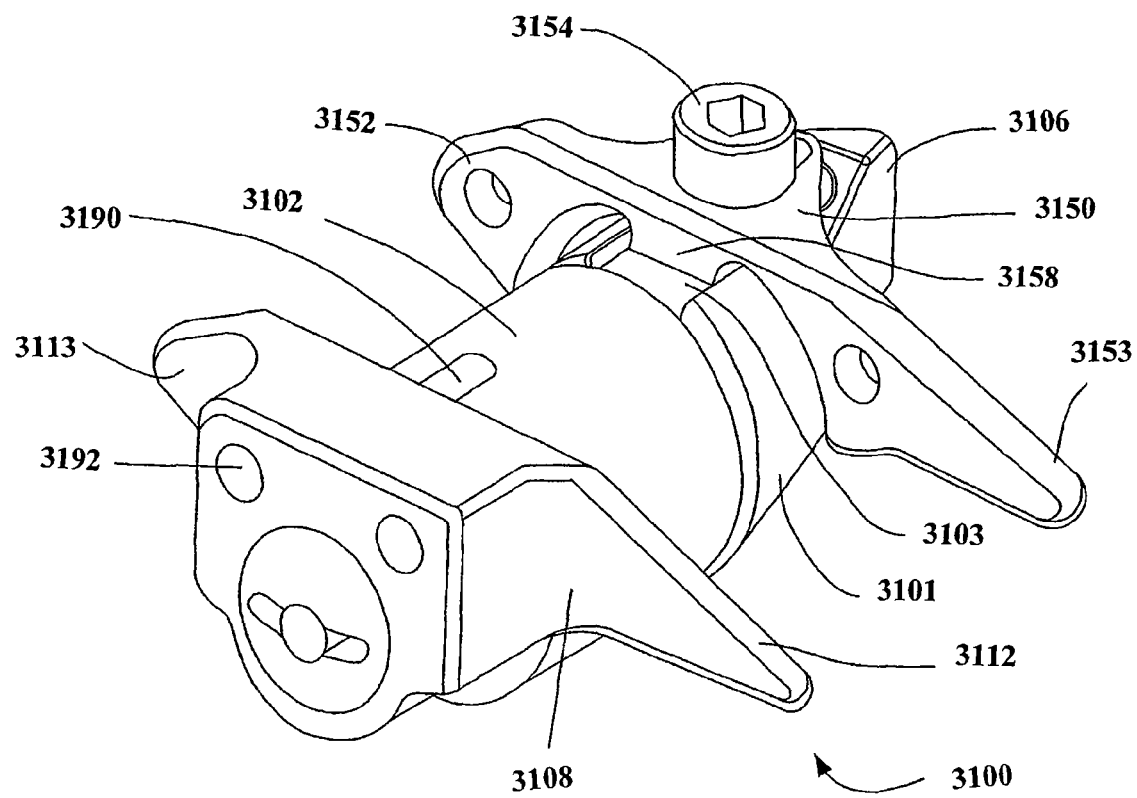
FIG. 32 is a perspective view of an interspinous implant capable of limiting or blocking relative movement of adjacent spinous processes during extension of the spine.

FIG. 32 is a perspective view of an implant as described in U.S. Pat. No. 6,695,842 to Zucherman, et al. and U.S. Pat. No. 6,712,819 to Zucherman et al., both incorporated herein by reference. The implant 3100 has a main body 3101. The main body 3101 includes a spacer 3102, a first wing 3108, a lead-in tissue expander 3106 (also referred to herein as a distraction guide) and an alignment track 3103. The main body 3101 is inserted between adjacent spinous processes. Preferably, the main body 3101 remains (where desired) in place without attachment to the bone or ligaments.

The distraction guide 3106 includes a tip from which the distraction guide 3106 expands, the tip having a diameter sufficiently small such that the tip can pierce an opening in an interspinous ligament and/or can be inserted into a small initial dilated opening. The diameter and/or cross-sectional area of the distraction guide 3106 then gradually increases until it is substantially similar to the diameter of the main body 3101 and spacer 3102. The tapered front end eases the ability of a physician to urge the implant 3100 between adjacent spinous processes. When urging the main body 3101 between adjacent spinous processes, the front end of the distraction guide 3106 distracts the adjacent spinous processes and dilates the interspinous ligament so that a space between the adjacent spinous processes is approximately the diameter of the spacer 3102.

The shape of the spacer 3102 is such that for purposes of insertion between the spinous processes, the spinous processes need not be altered or cut away in order to accommodate the spacer 3102. Additionally, associated ligaments need not be cut away and there is little or no damage to the adjacent or surrounding tissues. As shown in FIG. 32, the spacer 3102 is elliptically shaped in cross-section, and can swivel about a central body (also referred to herein as a shaft) extending from the first wing 3108 so that the spacer 3102 can self-align relative to the uneven surfaces of the spinous processes. Self-alignment can ensure that compressive loads are distributed across the surface of the bone. As contemplated in Zucherman '842, the spacer 3102 can have, for example, a diameter of six millimeters, eight millimeters, ten millimeters, twelve millimeters and fourteen millimeters. These diameters refer to the height by which the spacer distracts and maintains apart the spinous process. For an elliptically shaped spacer, the selected height (i.e., diameter) is the minor dimension measurement across the ellipse. The major dimension is transverse to the alignment of the spinous process, one above the other.

The first wing 3108 has a lower portion 3113 and an upper portion 3112. As shown in FIG. 32, the upper portion 3112 is shaped to accommodate the anatomical form or contour of spinous processes (and/or laminae) of the L4 (for an L4-L5 placement) or L5 (for an L5-S1 placement) vertebra. The same shape or variations of this shape can be used to accommodate other motion segments. The lower portion 3113 can also be rounded to accommodate the spinous processes. The lower portion 3113 and upper portion 3112 of the first wing 3108 act as a stop mechanism when the implant 3100 is inserted between adjacent spinous processes. The implant 3100 cannot be inserted beyond the surfaces of the first wing 3108. Additionally, once the implant 3100 is inserted, the first wing 3108 can prevent side-to-side, or posterior-to-anterior movement of the implant 3100. The first wing 3108 can further include one or more alignment holes 3103 and one or more locking pin holes 3104 for receiving pins of a main body insertion instrument (not shown).

Figure 33A:
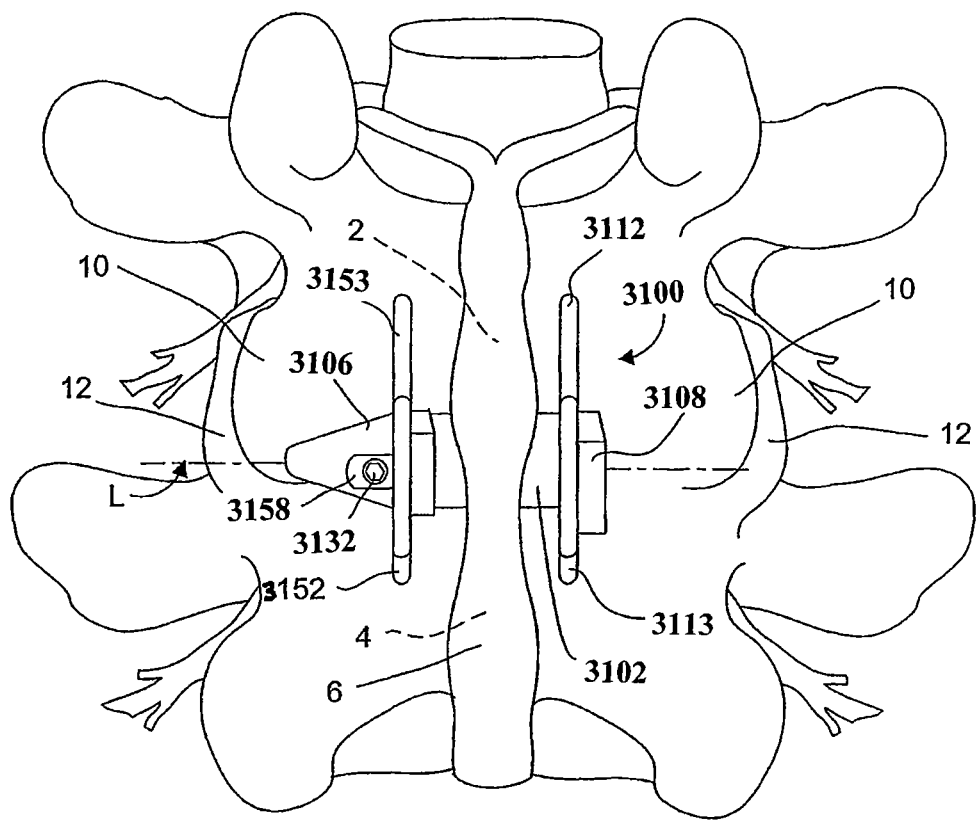
FIG. 33A is a posterior view of the implant of FIG. 32 positioned between adjacent spinous processes.

The implant 3100 further includes an adjustable wing 3150 (also referred to herein as a second wing). The adjustable wing 3150 has a lower portion 3152 and an upper portion 3153. Similar to the first wing 3108, the adjustable wing 3150 is designed to accommodate the anatomical form or contour of the spinous processes and/or lamina. The adjustable wing 3150 is secured to the main body 3101 with a fastener 3154. The adjustable wing 3150 also has an alignment tab 3158. When the adjustable wing 3150 is initially placed on the main body 3101, the alignment tab 3158 engages the alignment track 3103. The alignment tab 3158 slides within the alignment track 3103 and helps to maintain the adjustable wing 3150 substantially parallel with the first wing 3108. When the main body 3101 is inserted into the patient and the adjustable wing 3150 has been attached, the adjustable wing 3150 also can prevent side-to-side, or posterior-to-anterior movement. FIG. 33A illustrates an implant 3100 positioned between adjacent spinous processes extending from vertebrae of the lumbar region. The implant 3100 is positioned between inferior articular processes 10 associated with the upper vertebrae and superior articular processes 12 associated with the lower vertebrae. The supraspinous ligament 6 connects the upper and lower spinous processes 2,4. The implant 3100 can be positioned without severing or otherwise destructively disturbing the supraspinous ligament 6.

Figure 33B:
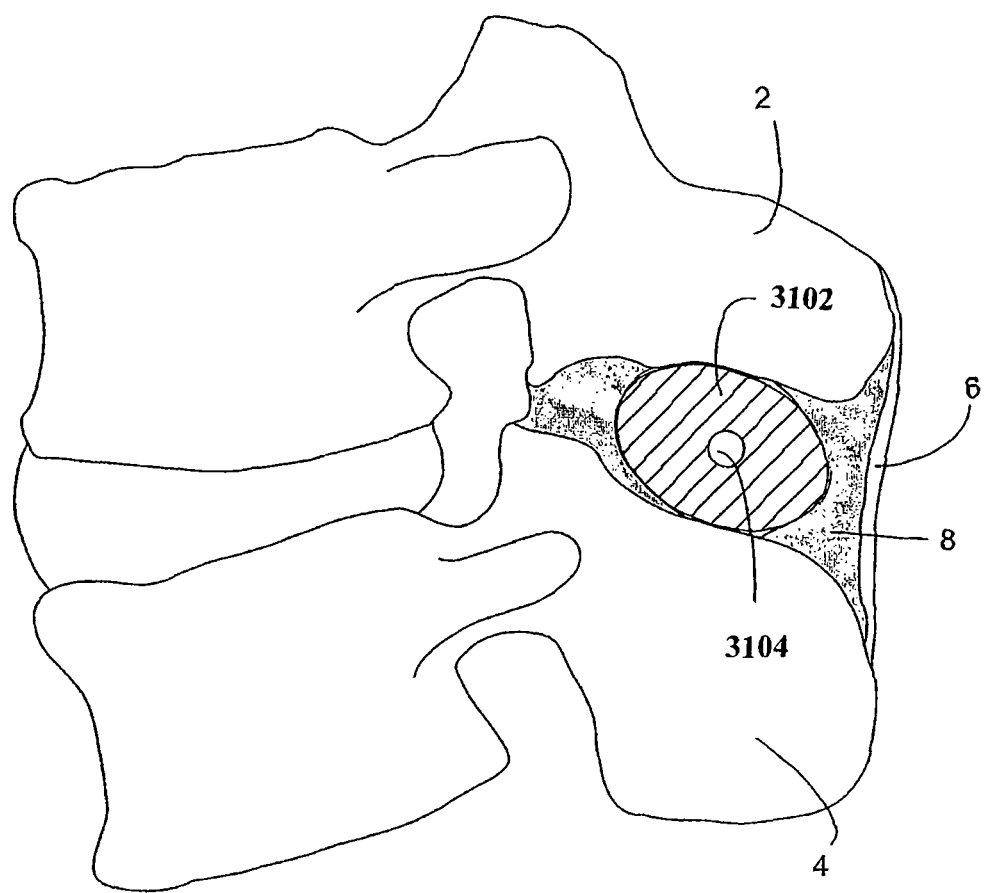
FIG. 33B is a cross-sectional side view of a spacer of the interspinous implant of FIGS. 32 and 33A positioned between spinous processes.

Referring to FIG. 33B, the spacer 3102 of the implant 3100 of FIG. 33A is shown in cross-section. The spacer 3102 defines a minimum space between adjacent spinous processes 2,4.

Figure 33C:
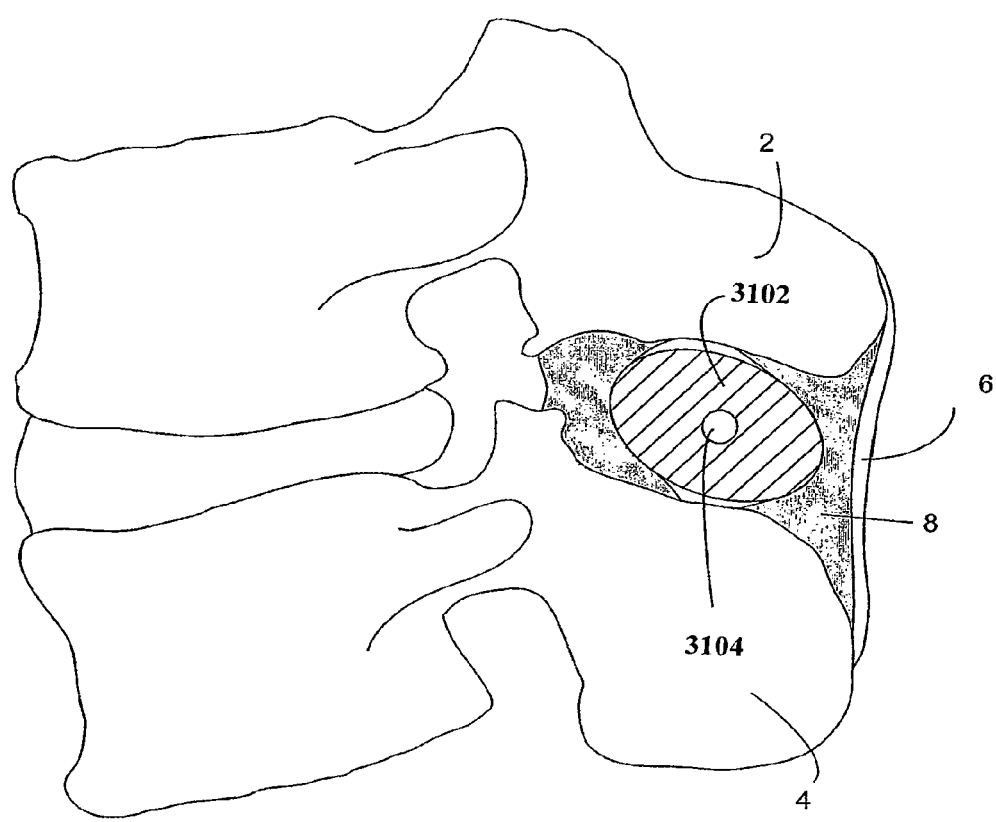
FIG. 33C is a cross-sectional view of the spacer of FIG. 33B during flexion of the spine.

During extension the spacer 3102 limits or blocks relative movement between the adjacent spinous processes 2,4, limiting or blocking the collapse of the space between the spinous processes 2,4. Such support can alleviate symptoms of degenerative disorders by preventing a reduction of the foraminal area and compression of the nerve roots, or by avoiding aggravation of a herniated disk, or by relieving other problems. However, as shown in FIG. 33C, the implant 3100 permits flexion, which in some degenerative disorders (for example in cases of spinal stenosis) can relieve some symptoms. As can be seen, during flexion the spacer 3102 can float between the spinous processes, held in position by the interspinous ligament 8, and/or other tissues and structures associated with the spine. The ability to float between the spinous processes 2,4 also permits varying degrees of rotation, as well as flexion. Implants as described in Zucherman '842 thus have the advantage that they permit a greater degree of movement when compared with primary and supplementary spinal fusion devices.

Figure 34A:
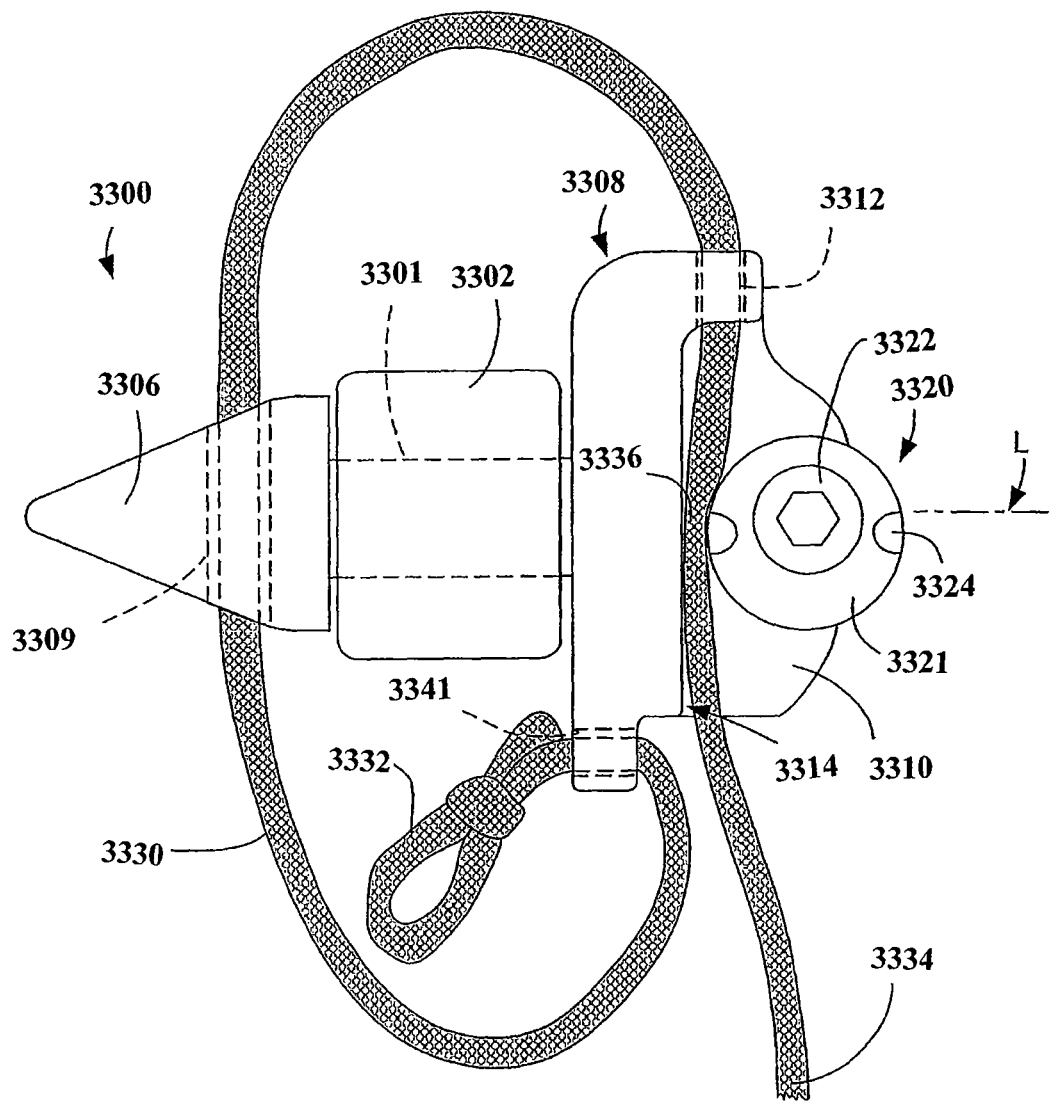
FIG. 34A is a side view of an embodiment of an implant in accordance with the present invention having a distraction guide, a spacer, a brace, and a binder associated with the brace and fixable in position by a capture device.

In some circumstances, for example where a patient develops spondylosis or other degenerative disorder that makes both flexion and extension painful and uncomfortable, it can be desired that the spinous processes be further immobilized, while providing the same ease of implantation as provided with implants described above. Referring to FIG. 34A, an embodiment of an implant 3300 in accordance with the present invention is shown. The implant 3300 includes a distraction guide 3306, a spacer 3302, and a brace 3308. As shown, the spacer 3302 is rotatable about a central body 3301 extending from the brace 3302, although in other embodiments the spacer 3302 can be fixed is position. A binder 3330 can be fixedly connected with the brace 3308 at a proximal end 3332 of the binder 3330. The binder 3330 is flexible, or semi-flexible, and can be positioned around adjacent spinous processes so that the binder 3308 engages the spinous processes during flexion of the spine. Once positioned around adjacent spinous processes, tension of the binder 3330 can be set when the binder 3330 is secured to the brace 3308 so that relative movement of the adjacent spinous processes during flexion is limited or prevented, as desired.

As can be seen in FIG. 34A, in an embodiment the brace 3308 can include a first end having a slot 3341 through which the proximal end 3332 of the binder 3330 can be threaded and subsequently sutured, knotted or otherwise bound so that the proximal end 3332 of the binder 3330 cannot be drawn through the slot 3341. In other embodiments (not shown), the proximal end 3332 can be looped or can include a connector, such as a clasp or other device, and can be fixed to the brace 3308 via a fastener that engages the connector. One of ordinary skill in the art can appreciate the myriad different ways in which the proximal end 3332 of the binder 3330 can be associated with the brace 3308 so that tension can be applied to the binder 3330, and implants in accordance with the present invention are not intended to be limited to those schemes described in detail herein. The brace 3308 can include a height along the spine greater than a height of the spacer 3302 so that movement along a longitudinal axis L in the direction of insertion is limited or blocked by the brace 3308 when the brace 3308 contacts the lateral surfaces of the spinous processes. In this way, the brace 3308 can function similarly to the wing 3108 of the above described implant 3300. In other embodiments, the brace 3308 can have a height greater or smaller than as shown. Once the binder 3330 is positioned around the spinous processes and secured, movement of the implant 3300 relative to the spinous processes is limited by the binder 3330 along the longitudinal axis as well as along the spinous processes (i.e., anterior-to-posterior movement).

A free end of the binder 3330 can be secured to the brace 3308 by a capture device 3320 associated with the brace 3308. The brace 3308 can include a flange 3310 from which the capture device 3320 can extend, hi the embodiment shown in FIG. 34A, the capture device 3320 comprises a rotatable cam 3321 having a fastener 3322 and one or more cut-outs 3324. A tool can be mated with the cut-outs 3324 and rotated to pivot the rotatable cam 3321. When the cam 3321 is rotated, the eccentric shape of the cam 3321 causes a gap to close between the cam 3321 and a wall 3314 of the brace 3330 from which the flange 3310 extends. When the binder 3330 is positioned between the cam 3321 and the wall 3314, the rotation of the cam 3321 can pinch the binder 3330 between the cam 3321 and the wall 3314, defining a secured end 3336 of the binder 3330. Optionally, the fastener 3322 can be screwed (i.e., rotated) so that the fastener 3322 is further seated, tightening against the cam 3321 to fix the cam 3321 in position. Further, optionally, one or both of the wall 3314 and the rotatable cam 3321 can include knurls, or some other texture (e.g., teeth) to prevent slippage (i.e., the slipping of the binder 3330 between the cam 3321 and the wall 3314). The brace 3308 can further include a guide 3312, such as a channel or slot (a slot as shown) at a second end of the brace 3308 to align the binder 3330 with the capture device 3320. The binder 3330 can comprise a strap, ribbon, tether, cord, or some other flexible (or semi-flexible), and preferably threadable structure. The binder 3330 can be made from a biocompatible material, hi an embodiment, the binder 3330 can be made from a braided polyester suture material. Braided polyester suture materials include, for example, Ethibond, Ethiflex, Mersilene, and Dacron, and are nonabsorbable, having high tensile strength, low tissue reactivity and improved handling. In other embodiments, the binder 3330 can be made from stainless steel (i.e., surgical steel), which can be braided into a tether or woven into a strap, for example. In still other embodiments, the binder 3330 can be made from some other material (or combination of materials) having similar properties.

The distraction guide 3306 can optionally include a slot, bore, cut-out or other cavity 3309 formed in the distraction guide 3306 through which the binder 3330 can be threaded or positioned. Such a cavity can allow on-axis positioning of the binder 3330 (i.e., the binder can be substantially aligned with the longitudinal axis L of the implant 3300). Further, capturing the binder 3330 within a slot or bore can prevent or limit shifting of the distraction guide 3306 relative to the binder 3330 to further secure the implant 3300 between the spinous processes.

As will be readily apparent to one of skill in the art, implants in accordance with the present invention provide significant benefits to a physician by simplifying an implantation procedure and reducing procedure time, while providing an implant that can limit or block flexion and extension of the spine. A physician can position an implant between adjacent spinous processes and can position a binder 3330 connected with the brace 3308 around the spinous processes without requiring the physician to measure an appropriate length of the binder 3330 prior to implantation. The capture device 3320 allows the binder 3330 to be secured to the brace 3308 anywhere along a portion of the binder 3330, the portion being between a distal end 3334 of the binder 3330 and the proximal end 3332. The physician can secure the binder 3330 to the brace 3308 to achieve the desired range of movement (if any) of the spinous processes during flexion.

Figure 34B:
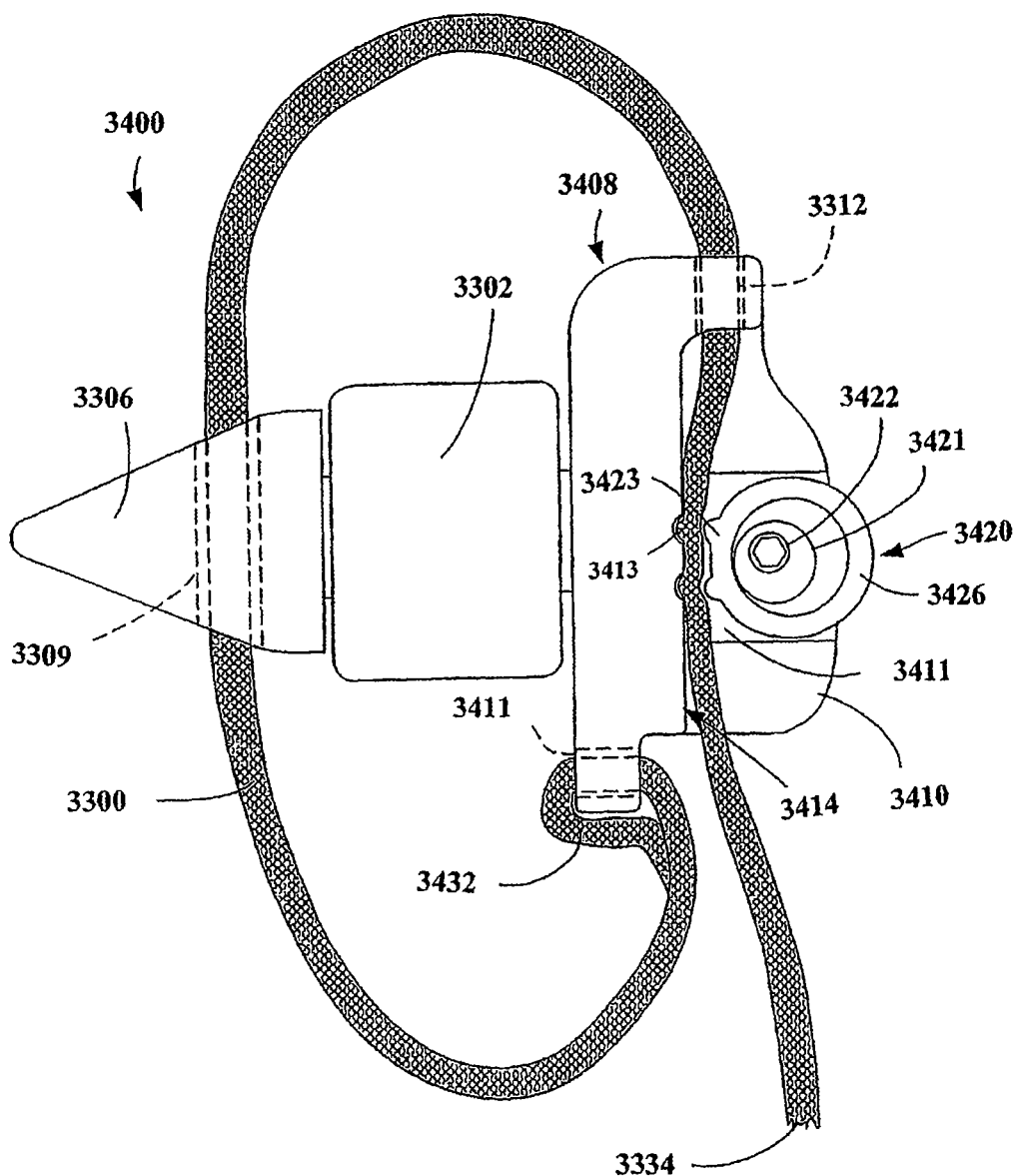
FIG. 34B is a side view of an alternative embodiment of an implant in accordance with the present invention including a brace wall having recesses for receiving lobes of a capture device.

The capture device 3320 and brace 3308 can have alternative designs to that shown in FIG. 34A. A side view of an implant 3400 in accordance with an alternative embodiment of the present invention is shown in FIG. 34B, the implant 3400 including a capture device 3420 comprising a cam 3421 positioned within a ring 3426 having one or more lobes 3423 corresponding with one or more recesses 3413 in a wall 3414 of the brace 3408. The binder 3330 is positioned between the capture device 3420 and the brace 3408. Once the binder 3330 is positioned as desired, the fastener 3422 and cam 3421 can be rotated using an appropriate tool, with the cam 3421 forcing the lobes 3423 of the ring 3426 to mate with the recesses 3413 of the brace 3408, preventing the ring 3426 from shifting in position and defining a secure end 3336 of the binder 3330. Rotating the fastener 3422 rotates and optionally tightens down the cam 3421. Such a capture device 3420 can provide a physician a visual indication that the binder 3330 is properly secured to the brace 3408, as well as preventing slippage.

Figure 34C:
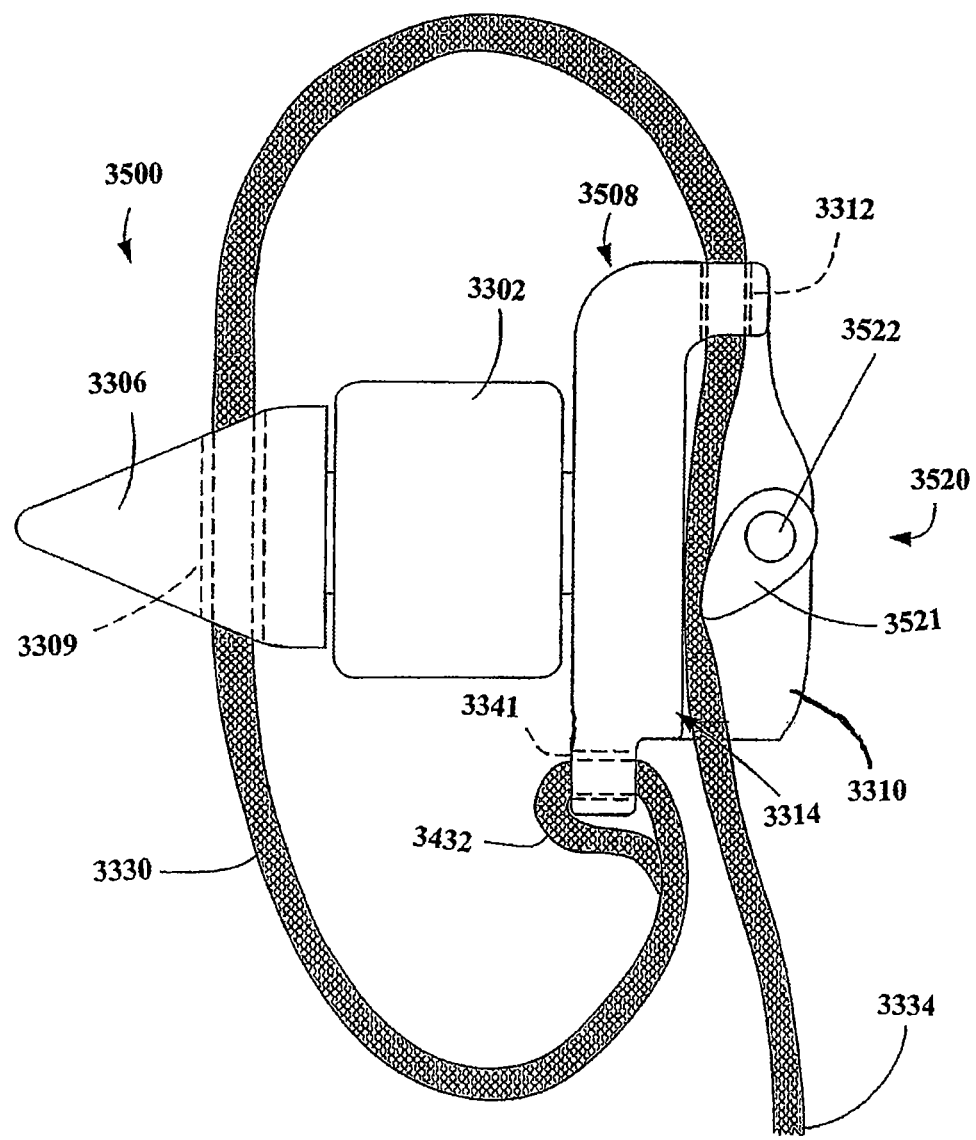
FIG. 34C is a side view of still another embodiment of an implant in accordance with the present invention including a capture device having a spring-loaded cam for securing a binder against a brace wall.
Figure 34D:
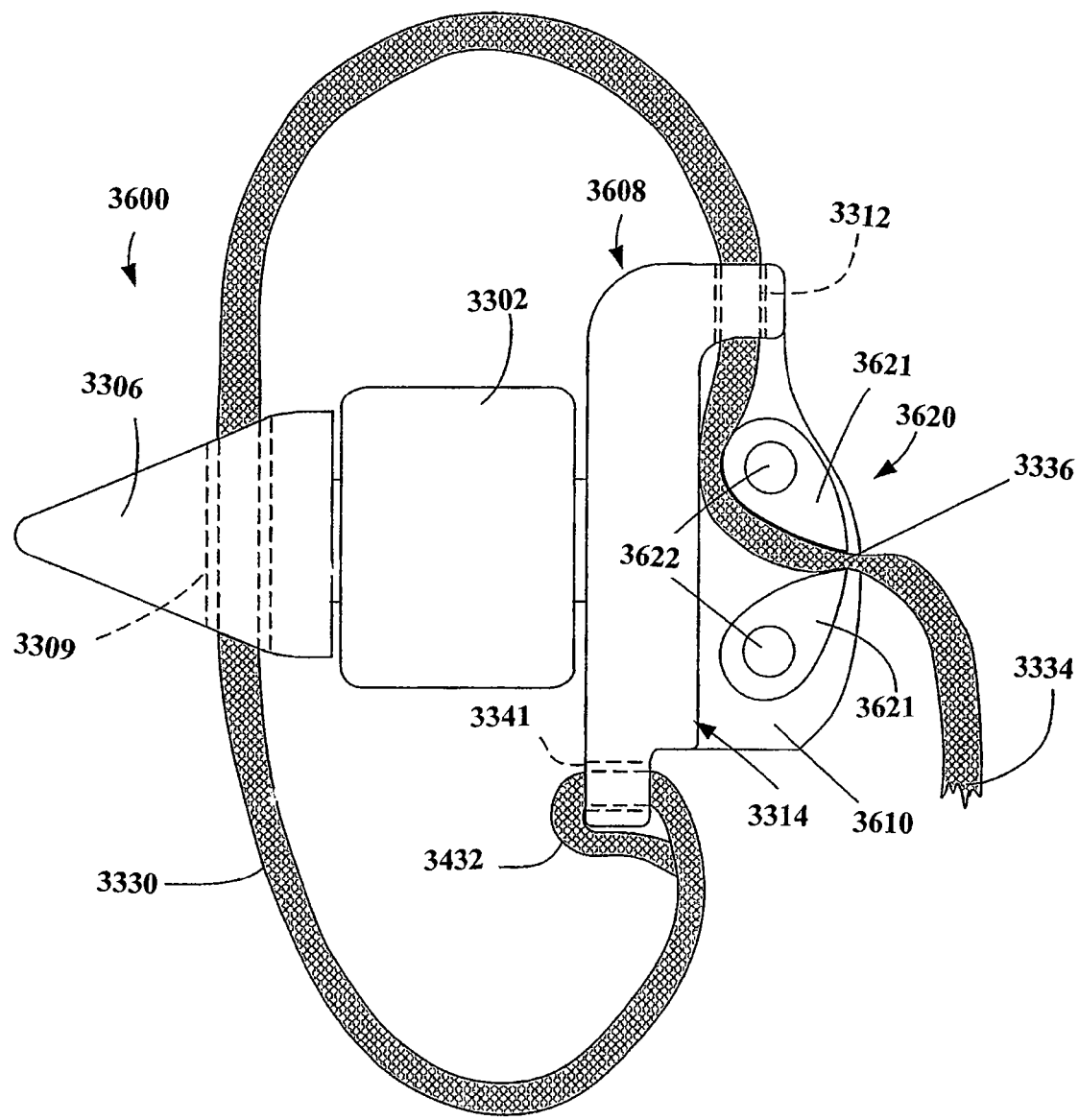
FIG. 34D is a side view of a still further embodiment of an implant in accordance with the present invention including a capture device having dual spring-loaded cams for securing a binder in position.

Referring to FIGS. 34C and 34D, in still other embodiments, the implant can include a capture device comprising a spring-loaded mechanism. FIG. 34C illustrates an implant 3500 including a capture device 3520 comprising a single spring-loaded cam 3521 pivotally connected with the flange 3310 and biased to rotate in one direction. The distance between the pivot point of the cam 3510 and the wall 3314 is sufficiently narrow that the rotation of the cam 3521 in the direction of bias is blocked (or nearly blocked) by the wall 3314. The eccentricity of the cam 3521 is large enough that a maximum gap between the wall 3314 and the cam 3521 is sufficiently wide as to allow the binder 3330 to be threaded between the cam 3521 and the wall 3314. A physician can position the binder 3330 between the cam 3521 and the wall 3514 by overcoming the spring-force of the spring-loaded cam 3521. Once the binder 3330 is position as desired, the physician need only allow the bias force of the spring-loaded cam 3520 to force the cam 3521 against the wall 3314, so that the cam 3521 pinches and secures the binder 3330 between the cam 3521 and the wall 3314. Optionally, one or both of the cam 3521 and the wall 3314 can be knurled or otherwise textured to limit or prevent slippage. Further, the wall 3314 can optionally include a recess (not shown) to receive the cam 3521 so that the binder 3330 is pinched within the recess (similar to the lobe and recess arrangement of FIG. 34B), thereby further limiting slippage. FIG. 34D illustrates an implant 3600 including a capture device 3620 comprising dual spring-loaded cams 3621, the dual spring-loaded cams 3621 being pivotally connected with the flange 3310. The dual spring-loaded cams 3621 are biased in opposition to one another so that the cams 3621 abut one another, similar to cam cleats commonly used for securing rope lines on boats. During surgery, the binder 3330 can be loosely positioned around the adjacent spinous processes and threaded between the cams 3621. Tension can be applied to the binder 3330, as desired, by drawing the binder 3330 through the cams 3621. The force of the binder 3330 being pulled through the cams 3621 can overcome the bias force to allow the binder 3330 to be tightened, while releasing the binder 3330 can define a secure end 3336 of the binder 3330 as the cams 3621 swivel together. As above, one or both of the cams 3621 can be knurled or otherwise textured to limit or prevent slippage.

Embodiments of implants have been described in FIGS. 34A-34D with some level of specificity; however, implants in accordance with the present invention should not be construed as being limited to such embodiments. Any number of different capture devices can be employed to fix a binder to a brace by defining a secure end of the binder, and such capture devices should not be construed as being limited to capture devices including cams, as described above. The capture device need only be a device that allows a physician to fit a binder having a generic size, or estimated size, around adjacent spinous processes with a desired level of precision in tension.

Figure 35A:
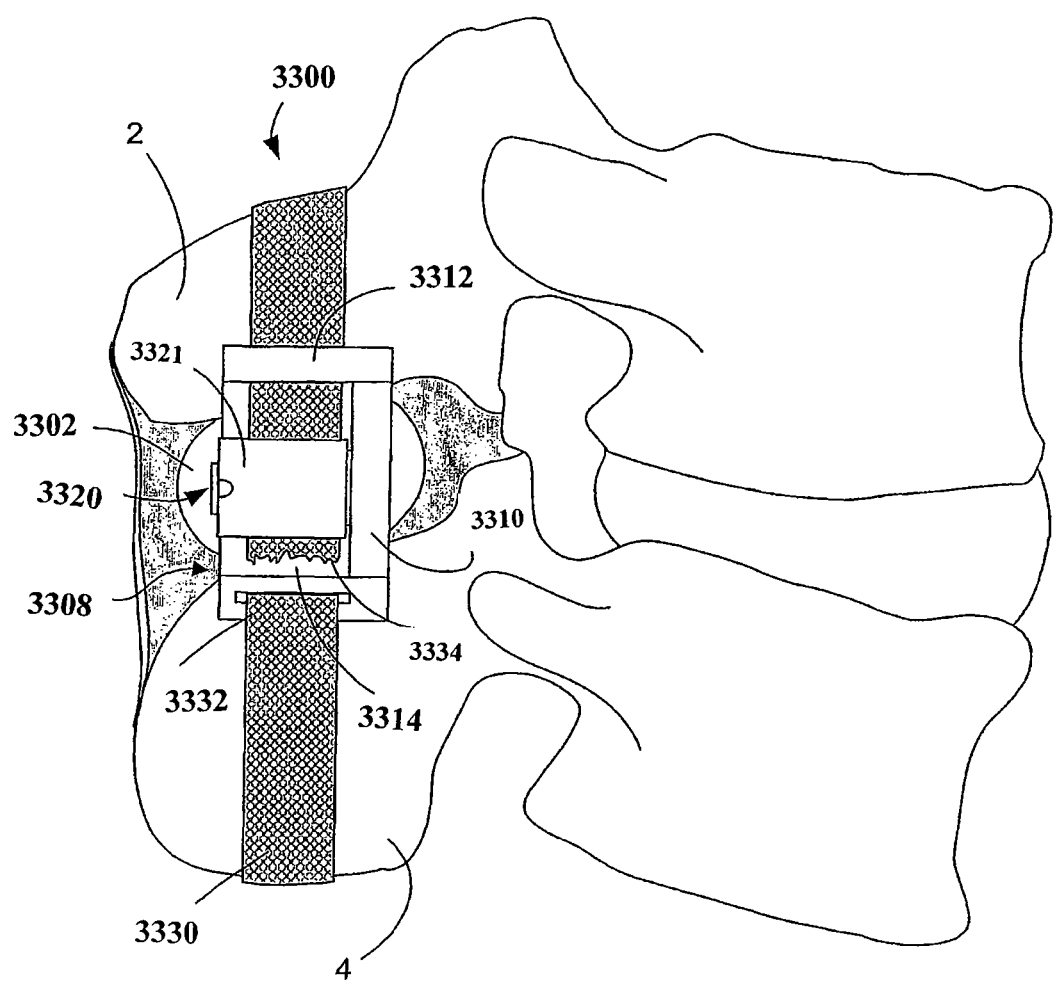
FIG. 35A is an end view of the implant of FIG. 34A positioned between adjacent spinous processes.
Figure 35B:
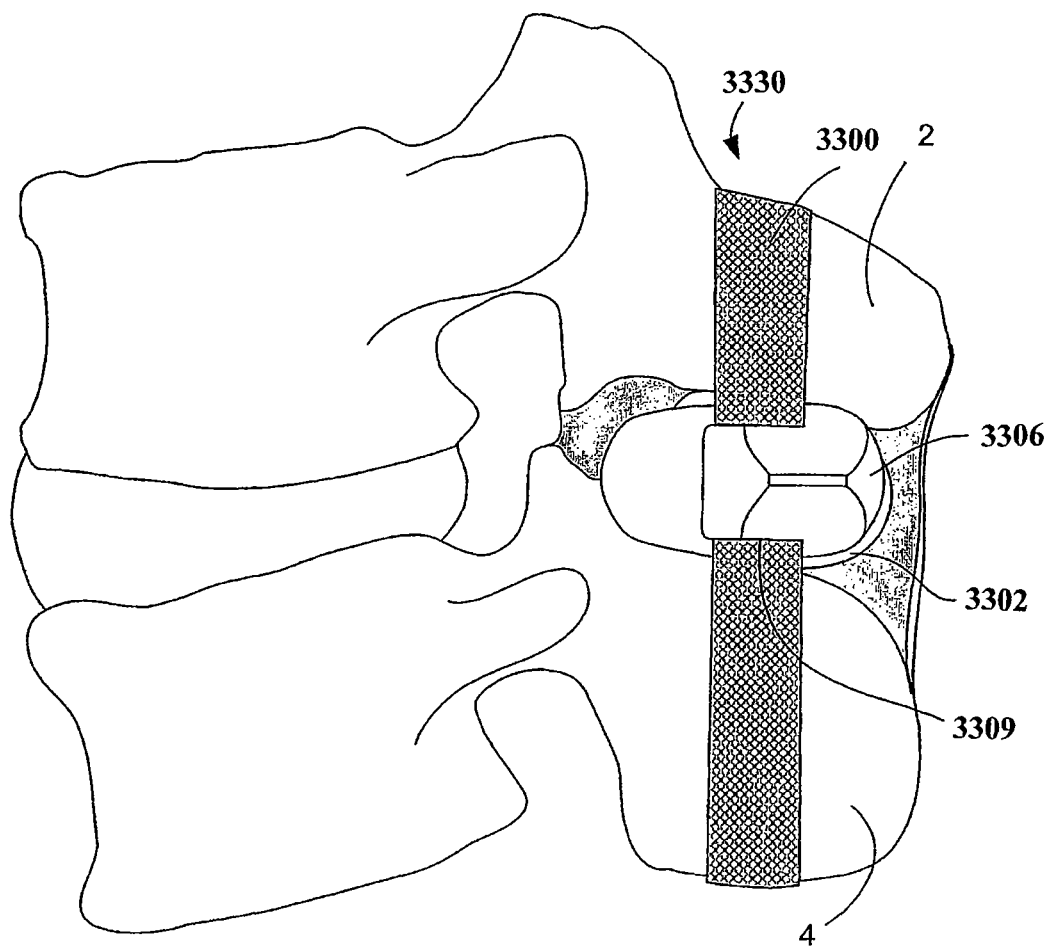
FIG. 35B is an end view of the implant of FIG. 34A positioned between adjacent spinous processes.

FIGS. 35A and 35B are an opposite end views of the implant of FIG. 34A positioned between adjacent spinous processes extending from vertebrae of the lumbar region. The contours of a space between adjacent spinous processes can vary between patients, and between motion segments. A rotatable spacer 3302 can rotate to best accommodate the shape of the space so that the implant 3300 can be positioned as desired along the spinous processes. For example, it can be desirable to position the spacer 3302 as close to the vertebral bodies as possible (or as close to the vertebral bodies as practicable) to provide improved support. Once the implant 3300 is positioned as desired, the binder 3330 can be threaded through interspinous ligaments associated with motion segments (i.e., pairs of adjacent vertebrae and associated structures and tissues) above and below the targeted motion segment so that the binder 3330 is arranged around the upper and lower spinous processes 2,4. The binder 3330 can then be threaded through the slot 3312 of the brace 3308 and positioned between the capture device 3320 and the brace wall 3314. A first tool (not shown) can be inserted into the incision formed to insert the implant 3300 between the spinous processes 2,4. Though not shown, the spacer 3302 can include a notch, similar to a notch 3190 of the spacer 3102 of FIG. 32, and the brace 3308 can include recesses, similar to recesses 103,104 of the first wing 3108 of FIG. 32, that can be engaged by the first tool for grasping and releasing the implant 3300 during insertion. (See U.S. Pat. No. 6,712,819, which is incorporated herein by reference.) Alternatively, some other technique for grasping and releasing the implant 3300 can be employed. Once the implant 3300 is positioned and the binder 3330 is arranged as desired, a second tool (not shown), such as a forked tool having spaced apart tines, can engage the cam 3321 of the capture device 3320 to rotate the cam 3321, thereby securing the binder 3330 to the brace 3308. A hex wrench can tighten down the fastener 3322 if desired. Alternatively, a single tool can be employed to perform both the function of insertion of the implant 3300 and rotation of the cam 3321, as depicted in the above referenced patent. Optionally, the binder 3330 can then be trimmed so that the distal end 3334 of the binder 3330 does not extend undesirably away from the brace 3308.

As can be seen, the spacer 3302 is rotated relative to the distraction guide 3306 and the brace 3308. Because the spacer 3302 can rotate relative to the distraction guide 3306 and the brace 3308, the brace 3308 can be positioned so that the binder 3330 can be arranged around the upper and lower spinous processes 2,4 without twisting the binder 3330. The binder 3330 is positioned around the lower spinous process 4, threaded or positioned at least partially within a slot 3309 of the distraction guide 3306, and positioned around the upper spinous process 2 so that the binder 3330 can be secured to the brace 3308, as described above.

Figure 35C:
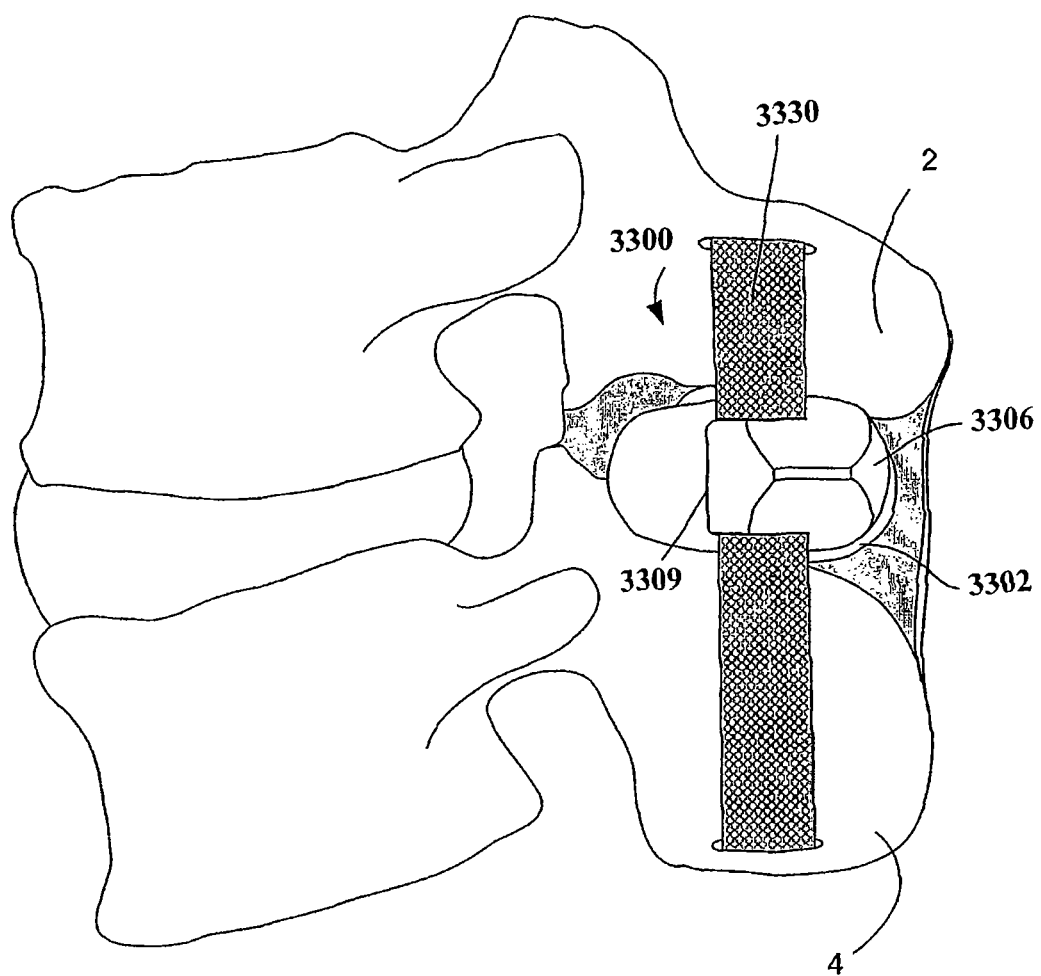
FIG. 35C is an end view of the implant of FIG. 34A positioned between adjacent spinous processes wherein the spinous processes are surgically modified to receive a binder.

Implants in accordance with the present invention can enable a physician to limit or block flexion and extension in a targeted motion segment while minifying invasiveness of an implantation procedure (relative to implantation procedures of the prior art). However, such implants can also be used where more extensive implantation procedures are desired. For example, as shown in FIG. 35C, it can be desired that the adjacent spinous processes 2,4 be surgically modified to receive the binder 3330, thereby insuring that the binder 3330 does not shift or slide relative to the spinous processes 2,4. The binder 3330 is threaded directly through the respective spinous processes 2,4 rather than through the interspinous ligaments of adjacent motion segments. The amount of bone removed from the spinous processes 2,4 can be reduced where a cord or tether is used as a binder 3330 rather than a strap. While such applications fall within the contemplated scope of implants and methods of implantation of the present invention, such application may not realize the full benefit that can be achieved using such implants due to the modification of the bone.

Figure 36:
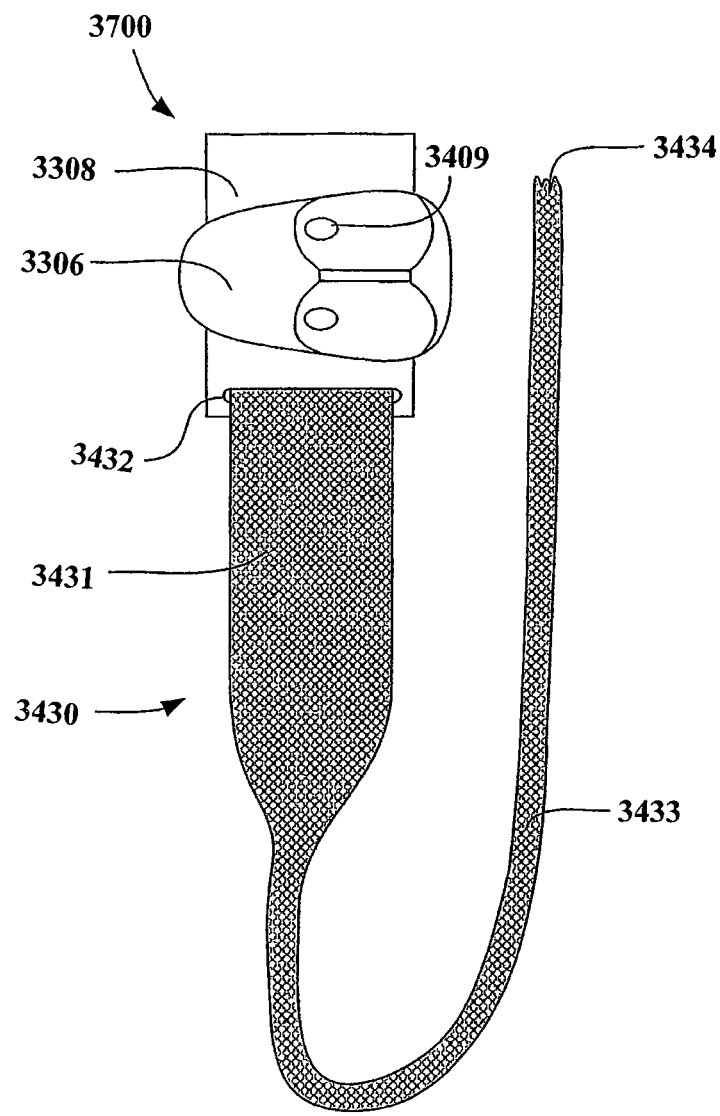
FIG. 36 is an end view of an alternative embodiment of an implant in accordance with the present invention having a binder that varies in shape along the binder's length.
Figure 37A:
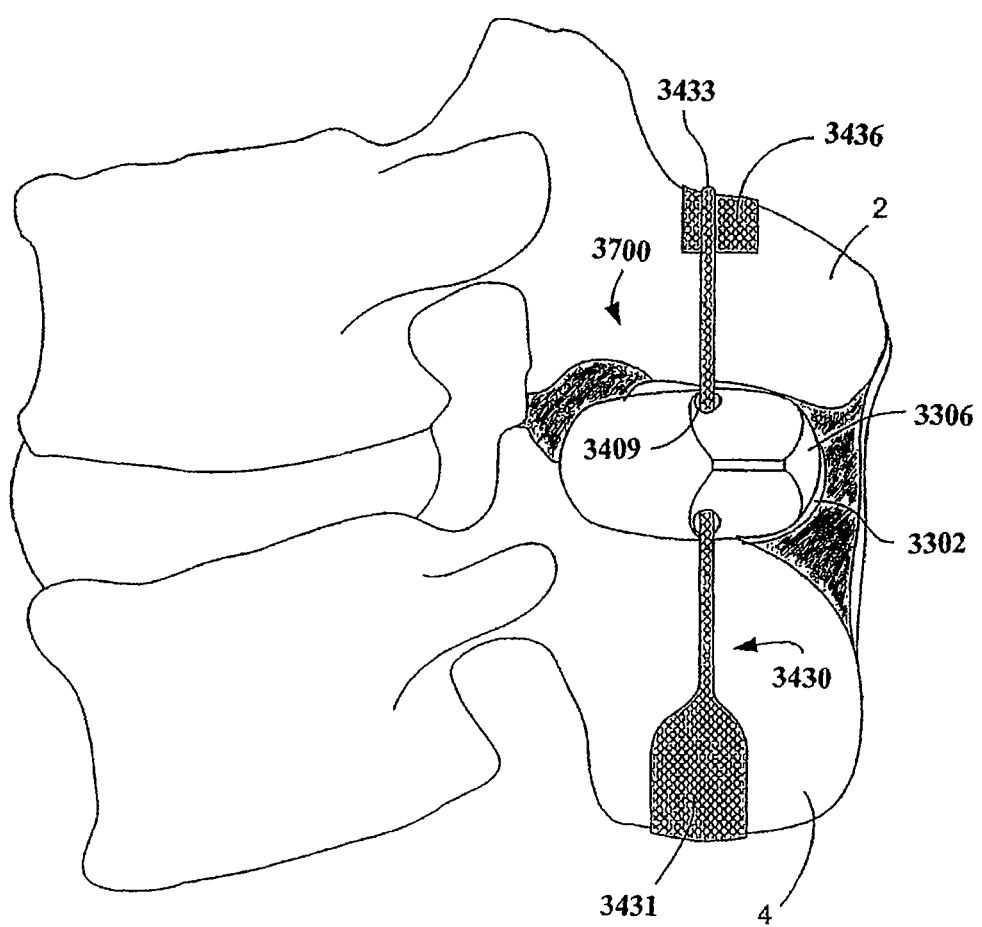
FIG. 37A is an end view of the implant of FIG. 36 positioned between adjacent spinous processes.
Figure 37B:
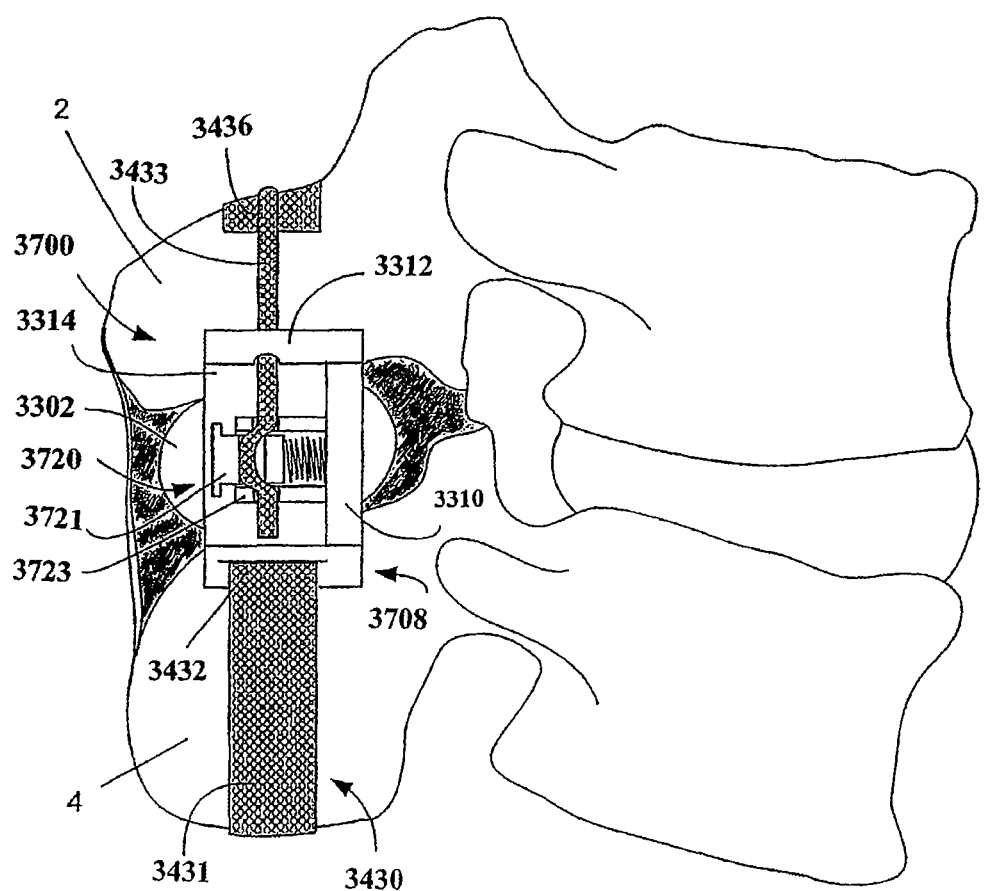
FIG. 37B is an opposite end view of the implant of FIG. 37A.

Still another embodiment of an implant 3700 in accordance with the present invention is shown in the end view of FIG. 36. In such an embodiment the binder 3430 can comprise a first portion 3431 formed as a strap for arrangement around one of the upper and lower spinous processes 2,4, and that tapers to a second portion 3433 formed as a cord. The distraction guide 3406 can include a bore 3409 or other cavity for receiving the second portion 3433. As can be seen in FIG. 37A, once the binder 3430 is threaded through the distraction guide 3406, a pad 3436 of biocompatible material can be associated with the binder 3430, for example by slidably threading the binder 3430 through a portion of the pad 3436, and the pad 3436 can be arranged between the binder 3430 and the respective spinous process 2 so that a load applied by the binder 3430 is distributed across a portion of the surface of the spinous process 2. Referring to FIG. 37B, once the binder 3430 is arranged as desired relative to the adjacent spinous processes 2,4, the binder 3330 can be secured by the brace 3708. The brace 3708 as shown is still another embodiment of a brace for use with implants of the present invention, in such an embodiment, the brace 3708 includes a capture device 3720 comprising a clip including a spring-loaded button 3721 having a first hole therethrough and a shell 3723 in which the button 3721 is disposed, the shell 3723 having a second hole. A physician depresses the button 3721 so that the first and second holes align. The binder 3430 can then be threaded through the holes, and the button 3721 can be released so that the spring forces the holes to misalign, pinching the binder 3430 and defining a secure end of the binder 3430.

Figure 37C:
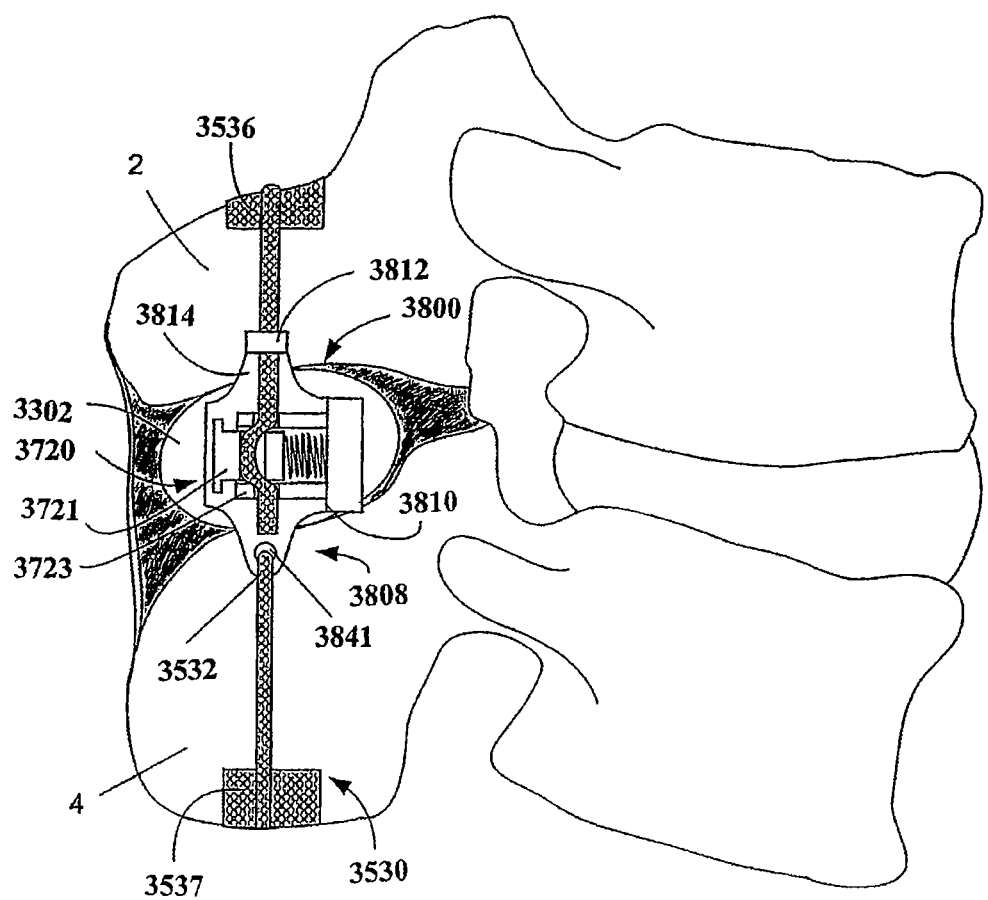
FIG. 37C is an end view of still another embodiment of an implant in accordance with the present invention having a cord for a binder.

FIG. 37C is an end view of a still further embodiment of an implant 3800 in accordance with the present invention. In such an embodiment the binder 3530 can comprise a cord. An upper pad 3536 and a lower pad 3538 can be slidably associated with the binder 3530 and arranged so that a load applied by the binder 3530 is distributed across a portion of the upper and lower spinous processes 2,4. As can be seen, such an embodiment can include a brace 3808 having a substantially different shape than braces previously described. It should be noted that the brace 3808 of FIG. 37C is shown, in part, to impress upon one of ordinary skill in the art that a brace and capture device for use with implants of the present invention can include myriad different shapes, mechanisms and arrangements, and that the present invention is meant to include all such variations. As shown, the footprint of the brace 3808 is reduced by shaping the wall 3814 of the brace 3808 to taper at an upper end to form a guide 3812 for aligning the binder 3530 and to taper at a lower end to an eyelet 3841 for capturing a proximal end 3532 of the binder 3530. The brace 3808 includes a height from eyelet 3841 to guide 3812 such that movement of the implant 3800 in the direction of insertion is blocked or limited by the brace 3808.

Use of a binder to limit or prevent flexion can provide an additional benefit of limiting movement along the longitudinal axis L (shown in FIG. 34A). However, implants in accordance with the present invention can optionally further include a second wing for limiting or blocking movement in the direction opposite insertion. Inclusion of such a structure can ensure that the implant remains in position, for example where the binder slips out of a slot of the distraction guide, or where the binder becomes unsecured.

Figure 38A:
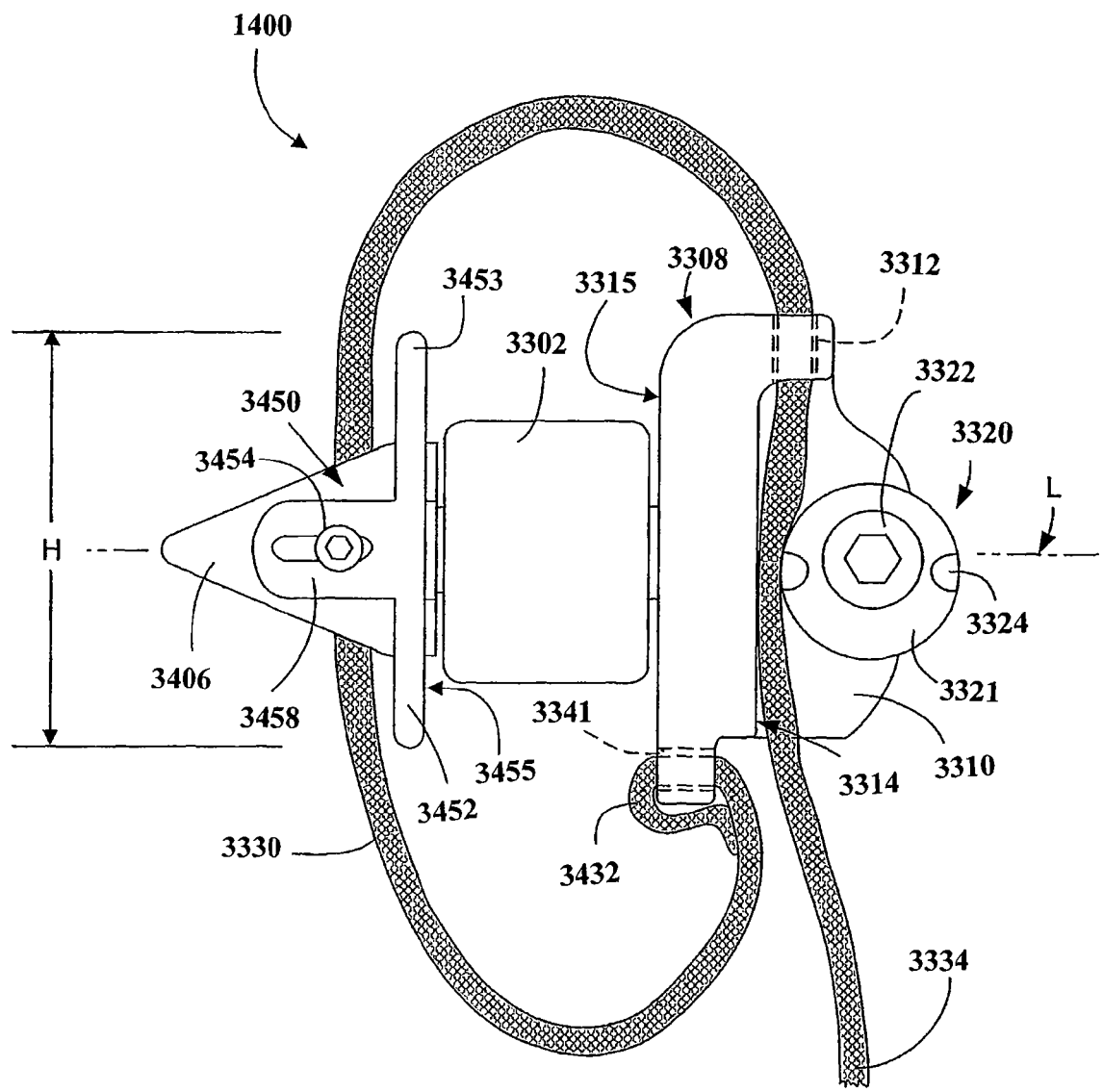
FIG. 38A is a side view of an embodiment of an implant in accordance with the present invention including a wing associated with the distraction guide to further limit or block movement of the implant.

Referring to FIG. 38A, an implant in accordance with an embodiment can include a second wing 3450 connected with the distraction guide 3406 of the implant 3900 by a fastener 3454. The second wing 3450 is similar to the second wing 3150 described above in reference to FIG. 32. The second wing 3450 can include an alignment tab 3458 allowing a position of the second wing 3450 to be adjusted along a longitudinal axis L of the implant 3900, and a fastener 3454 (for example a hex headed bolt) for affixing the second wing 3450 to the implant 3900 in the position along the longitudinal axis L desired. The distraction guide 3406 can include an alignment groove (not shown) corresponding to the alignment tab 3458. The alignment tab 3458 fits within, and is movable along, the alignment groove so that a contact surface 3455 of the second wing 3450 can be arranged as desired. As shown, the second wing 3450 includes a substantially planar contact surface arranged so that the contact surface 3455 of the second wing 3450 is perpendicular to the longitudinal axis L. However, in other embodiments, the contact surface 3455 need not be planar, and can be shaped and oriented to roughly correspond with a contact surface of the upper and lower spinous processes. Likewise, a contact surface 3315 of the binder 3308 can be shaped and oriented to roughly correspond with a contact surface of the upper and lower spinous processes. As shown, the upper portion 3453 and the lower portion 3452 of the second wing 3450 do not extend from the distraction guide 3406 as substantially as the upper portion 3153 and lower portion 3152 of the second wing 3150 of FIG. 32. As such, the second wing 3450 includes a height H along the spine smaller than that of the second wing 3150 of FIG. 32. It has been observed that benefits can be gained by including a wing 3450, though the wing 3450 does not extend from the distraction guide 3406 as significantly as shown in FIG. 32 (i.e., the wing 3450 includes "nubs" extending above and/or below the height of the spacer 3302). Such wings 3450 will also be referred to herein as winglets. Including a second wing 3450 having an overall height along the spine smaller than that of FIG. 32 can limit movement along the longitudinal axis without interfering with (or being interfered by) the arrangement of the binder 3330.

Figure 38B:
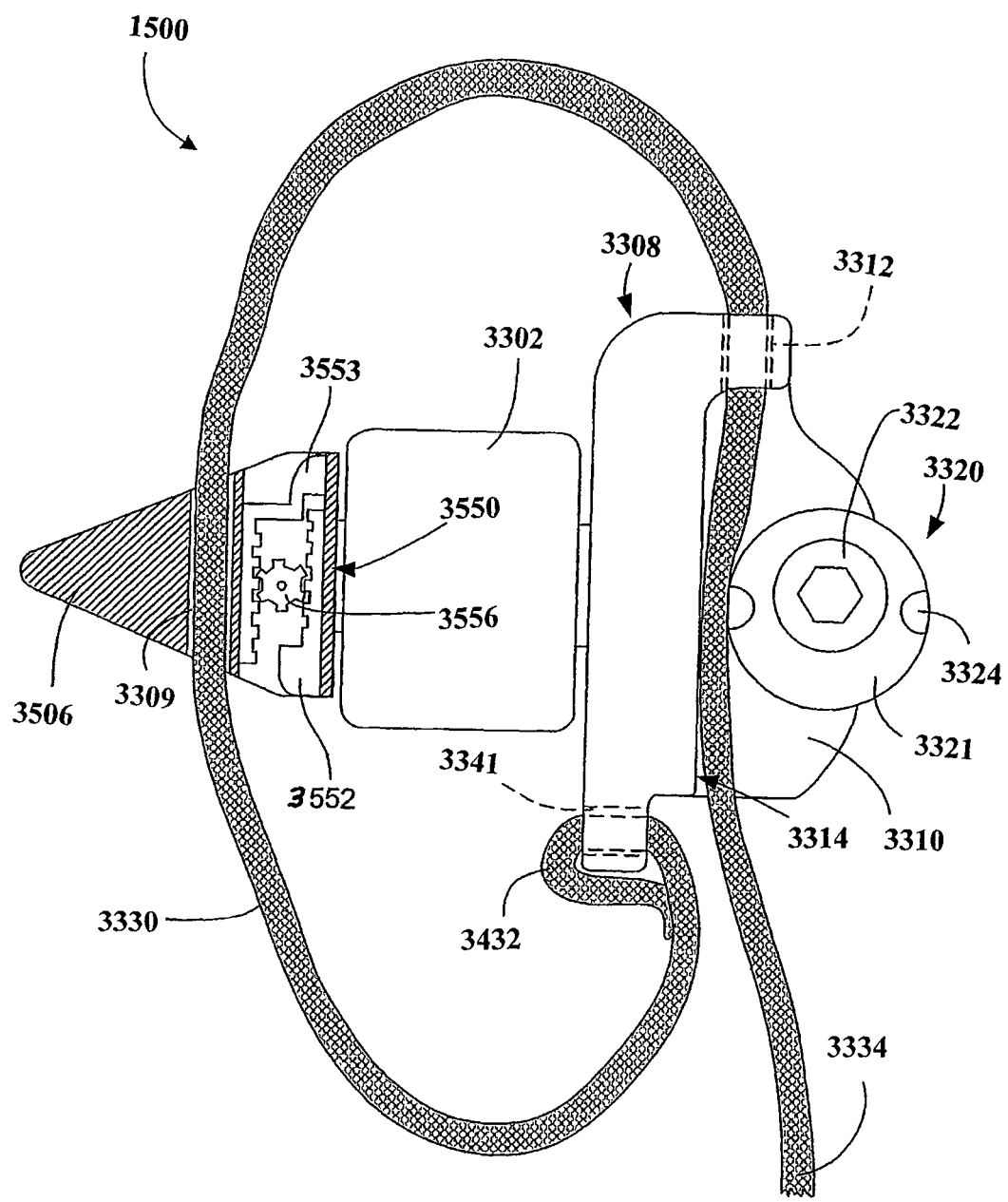
FIG. 38B is a partial cross-sectional side view of an alternative embodiment of an implant in accordance with the present invention include an extendable wing associated with the distraction guide, the extendable wing being in a retracted position.
Figure 38C:
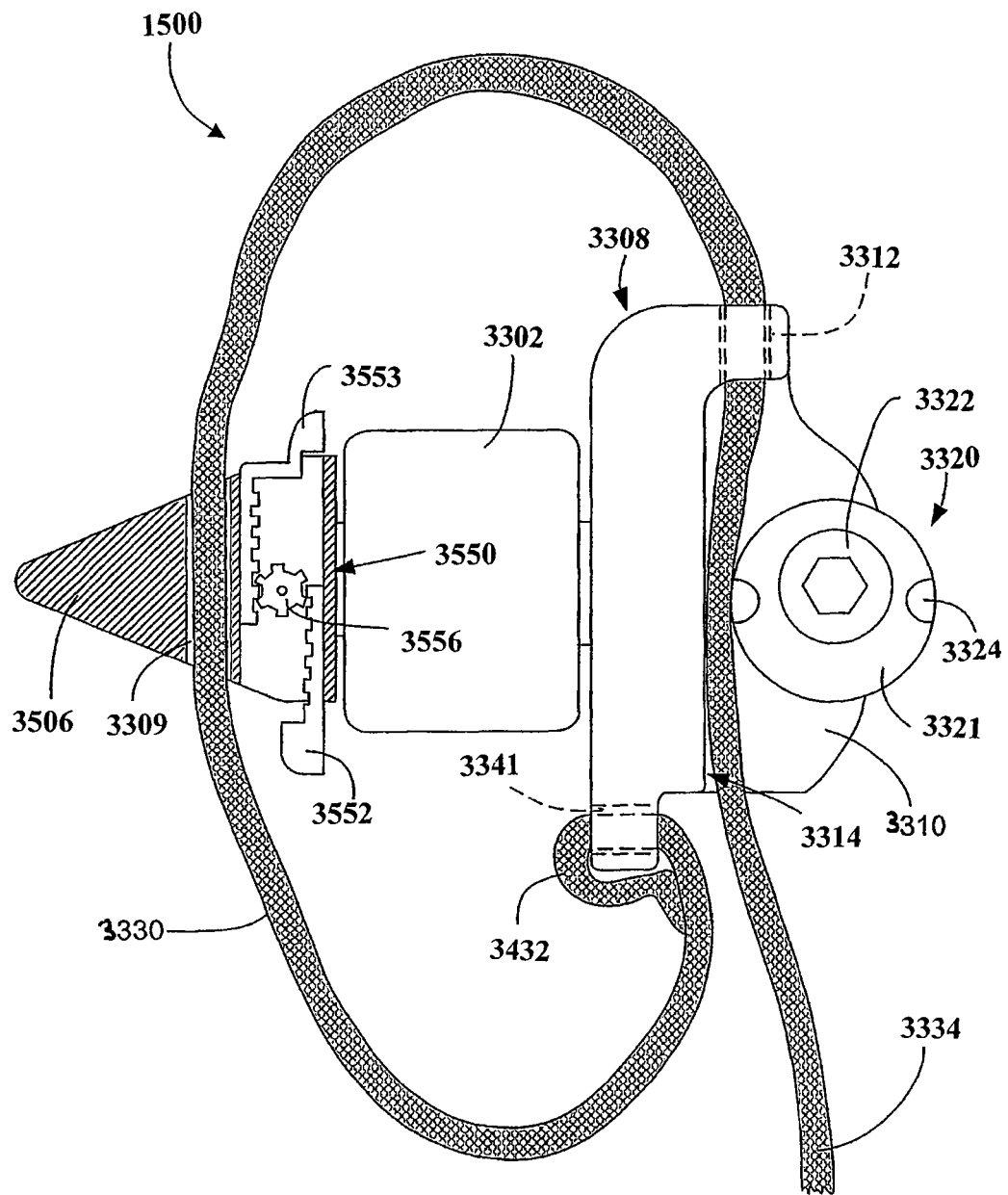
FIG. 38C is a partial cross-sectional side view of the implant of FIG. 38B wherein the extendable wing is in an extended position.

In other embodiments, implants in accordance with the present invention can include a second wing (or an upper portion and/or lower portion) extendable from the distraction guide. In this way an implant and a device for limiting or blocking movement along a longitudinal axis of the implant can be included in a single piece, possibly simplifying implantation. Referring to FIGS. 38B and 38C, implants 1500 in accordance with the present invention can include a distraction guide 3506 having a selectably extendable upper portion 3553 and lower portion 3552 disposed within a cavity of the distraction guide 3506. The upper and lower portions 3553,3552 can be extended by actuating a nut, knob or other mechanism operably associated with a gear 3556 so that the gear 3556 rotates. The teeth of the gear 3556 engage teeth of the upper and lower portions 3553,3552, causing the upper and lower portions 3553,3552 to extend sufficiently that the upper and lower portions 3553,3552 form winglets for preventing motion of the implant 1500 in a direction opposite insertion (shown in FIG. 38C). Rotating the gear 3556 in an opposite direction can retract the upper and lower portions 3553,3552.

Figure 38D:
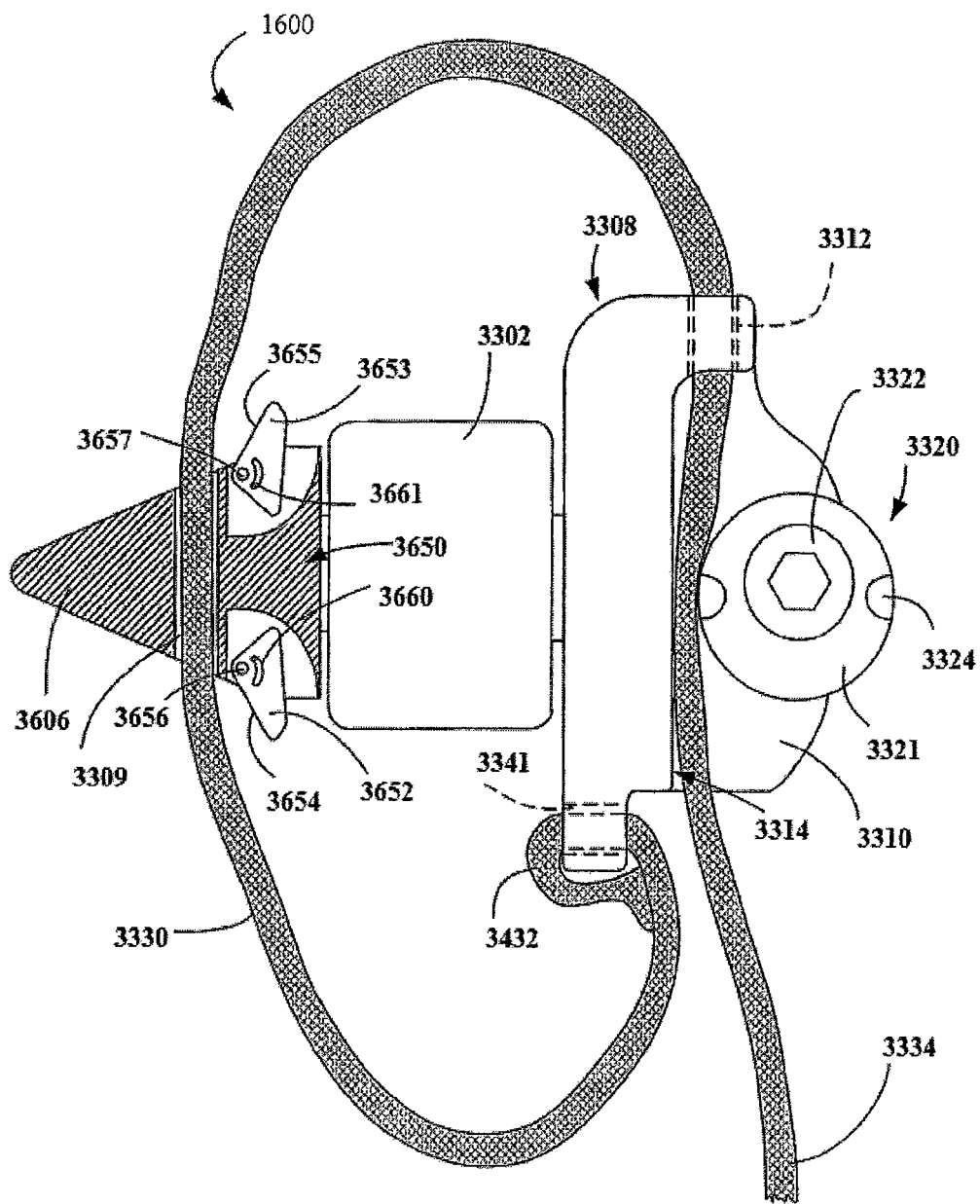
FIG. 38D is a partial cross-sectional side view of still another embodiment of an implant in accordance with the present invention including a spring-loaded wing associated with the distraction guide, the wing being in an extended position.
Figure 38E:
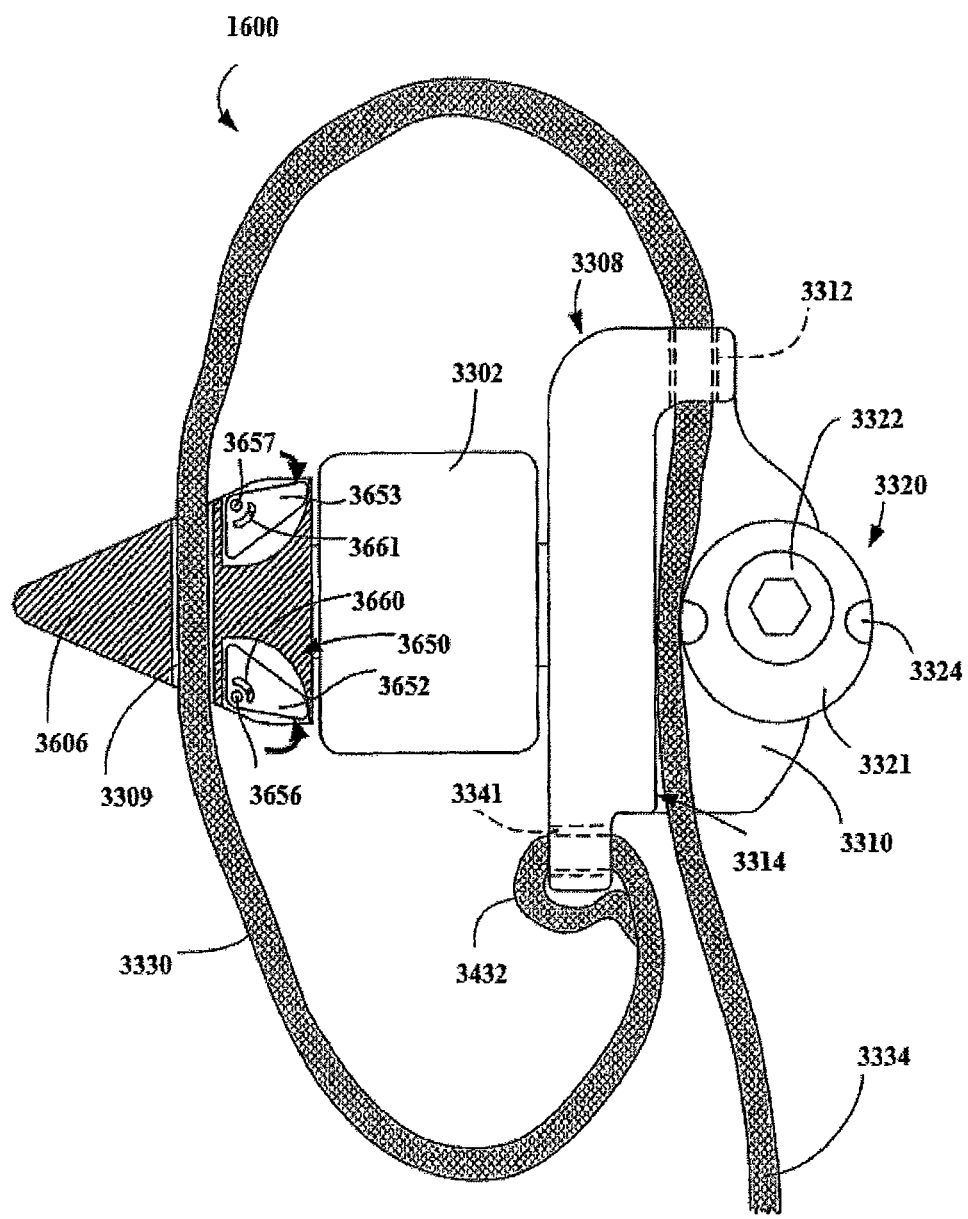
FIG. 38E is a partial cross-sectional side view of the implant of FIG. 38D wherein the spring-loaded wing is in a collapsed position.

In an alternative embodiment, implants 1600 in accordance with the present invention can include spring-loaded upper and/or lower portions 3653,3652 such as shown in FIGS. 38D and 38E. In such an embodiment the upper and lower portions 3653,3652 can be fin-shaped, having sloping forward surfaces 3655,3654 and being spring-biased to an extended position, as shown in FIG. 38D. As the implant 1600 is positioned between adjacent spinous processes, the spinous processes and/or related tissues can contact the forward surface 3655, 3654 of the upper and lower portions 3653,3652, causing the upper and lower portions 3653,3652 to pivot about respective hinge points 3657,3656 and collapse into cavities disposed within the distraction guide 3606, as shown in FIG. 38E. Once the implant 1600 clears the obstruction, the upper and lower portions 3653,3652 re-extend out of the distraction guide 3650. A slot and pin mechanism 3660,3661 or other mechanism can lock the upper and lower portion 3653,3652 in place once extended, disallowing over-extension of the upper and lower portion 3653,3652 in the direction of bias. The extended upper and lower portions 3653,3652 limit or block movement of the implant 1600 in an a direction opposite insertion.

In still further embodiments, implants in accordance with the present invention can optionally employ some other additional mechanism for limiting or blocking motion along the longitudinal axis of the implant. Mechanisms shown and described in FIGS. 38A-38E are merely provided as examples of possible mechanisms for use with such implants, and are not intended to be limiting.

Figure 39:
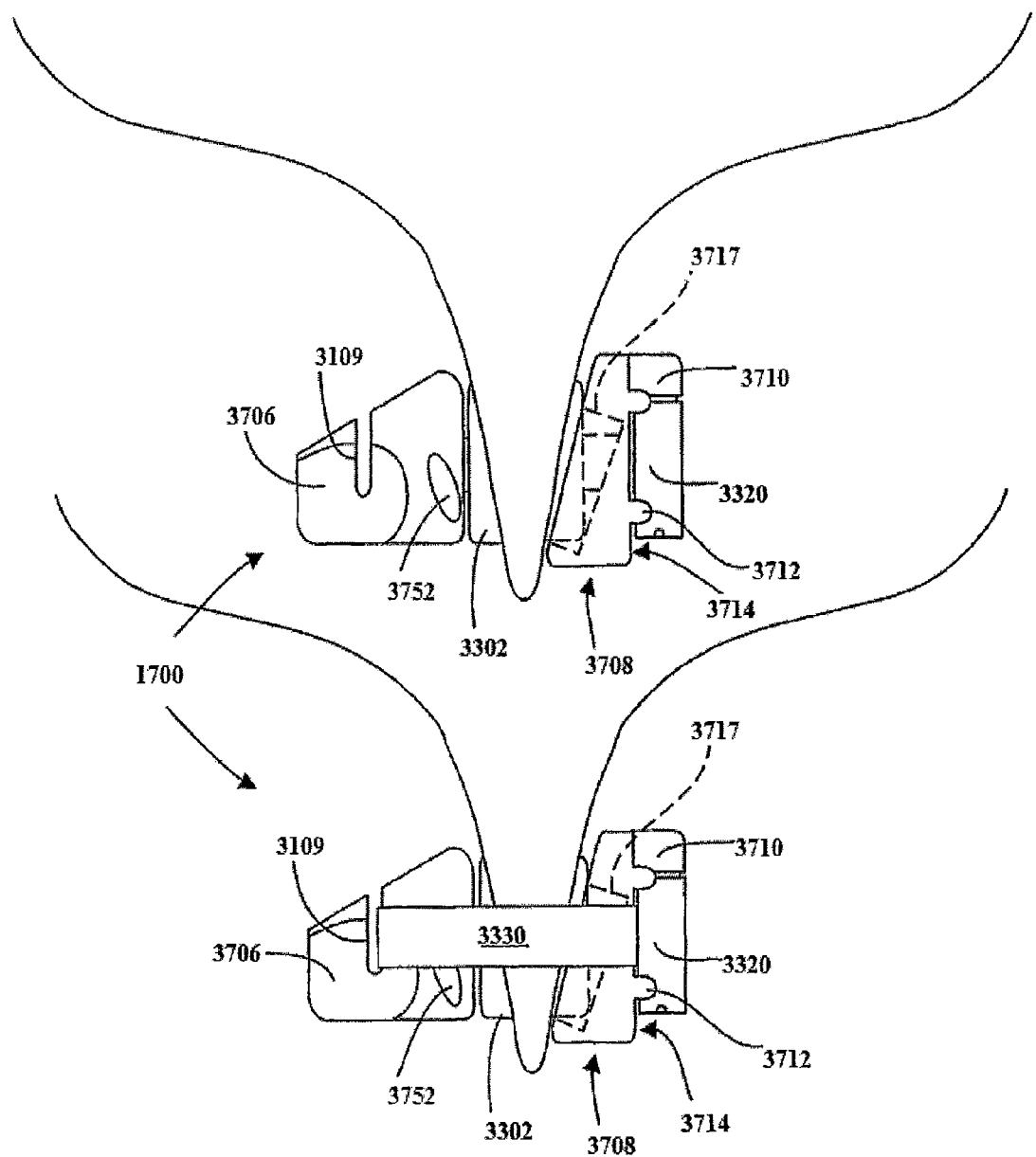
FIG. 39 is a top view of two implants in accordance with an embodiment of the present invention positioned between the spinous processes of adjacent vertebrae, one of the implants having a binder arranged around the adjacent spinous processes.

FIG. 39 is a top-down view of still another embodiment of an implant in accordance with the present invention including a brace 3708 arranged at an angle along the spinous process relative to the longitudinal axis L of the implant 1700. The brace 3708 is arranged at such an angle to roughly correspond to a general shape of the adjacent spinous processes. Such a general shape can commonly be found in spinous processes extending from vertebrae of the cervical and thoracic region, for example. The implant 1700 further includes a second wing 3752 extending from distraction guide 3706 at an angle roughly corresponding to a general shape of the adjacent spinous processes. Identical implants 1700, one above the other, are shown. The lower implant 1700 includes a binder 3330 arranged around the adjacent spinous processes (only the upper spinous process is shown) and positioned in a slot 3309 of the distraction guide 3706. The binder 3330 includes a capture device 3320 for securing the binder 3330 to the brace 3708, and a channel formed by guides 3712 on the brace 3708 for aligning the binder 3330 with the capture device 3320. Unlike previously illustrated embodiments, the brace wall includes a recess 3717 to accommodate rotation of the rotatable spacer 3302. Alternatively, the implants can include fixed spacers, for example integrally formed with the brace 3708 and the distraction guide 3706.

Figure 40A:
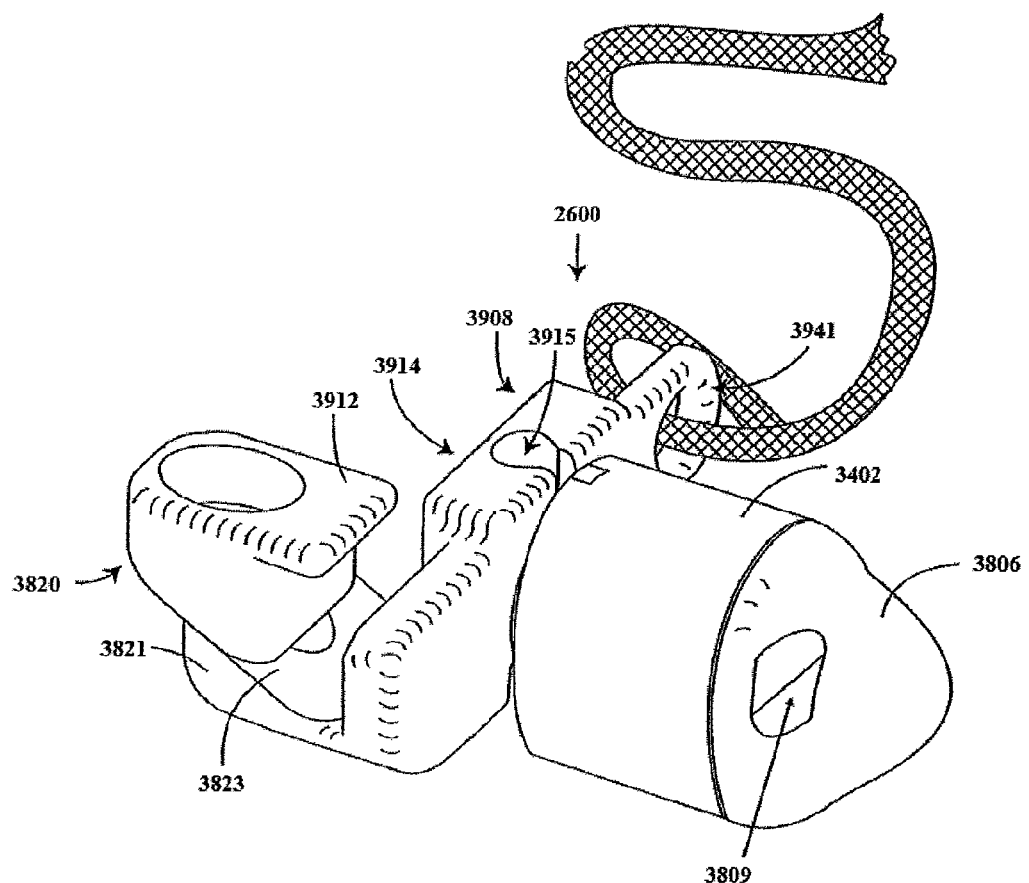
FIG. 40A is a perspective view of a further embodiment of an implant in accordance with the present invention having a distraction guide, a spacer, a brace, and a binder associated with the brace and fixable in position by a capture device.
Figure 40B:
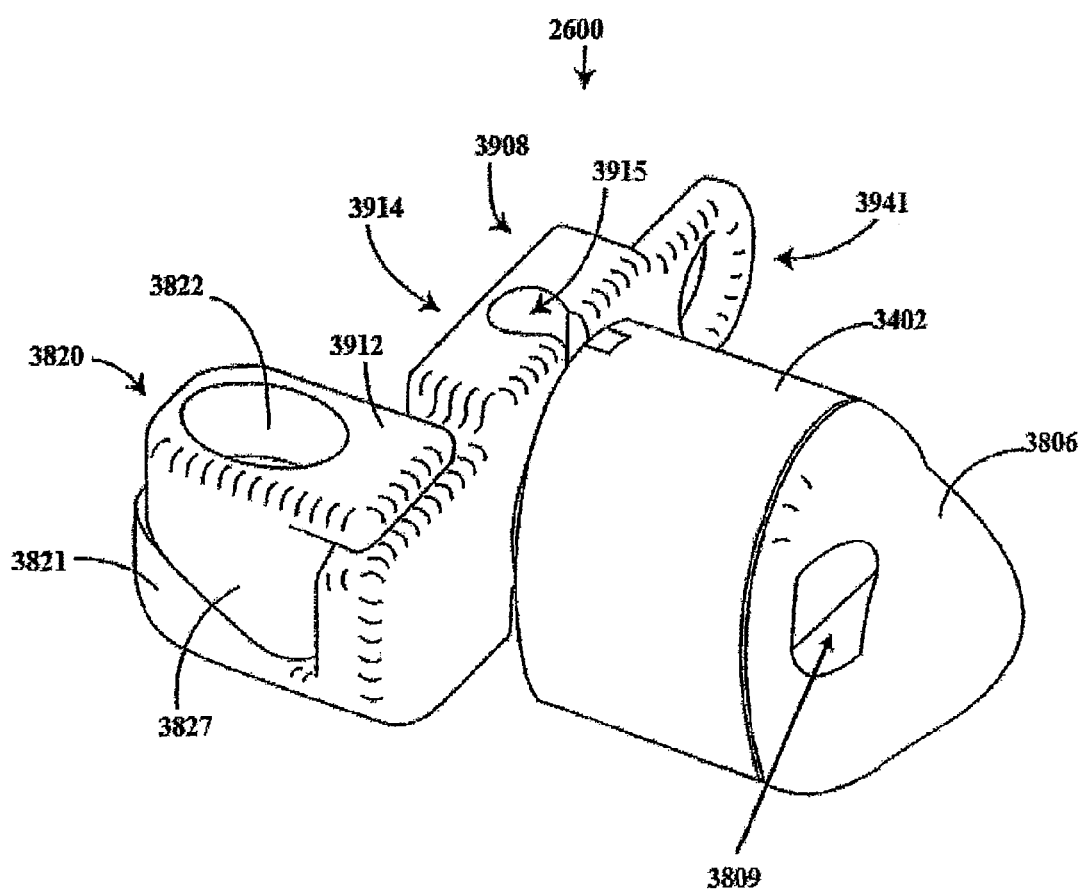
FIG. 40B is a perspective view the implant of FIG. 40A wherein the capture device is arranged to secure a binder between the capture device and the brace.
Figure 40C:
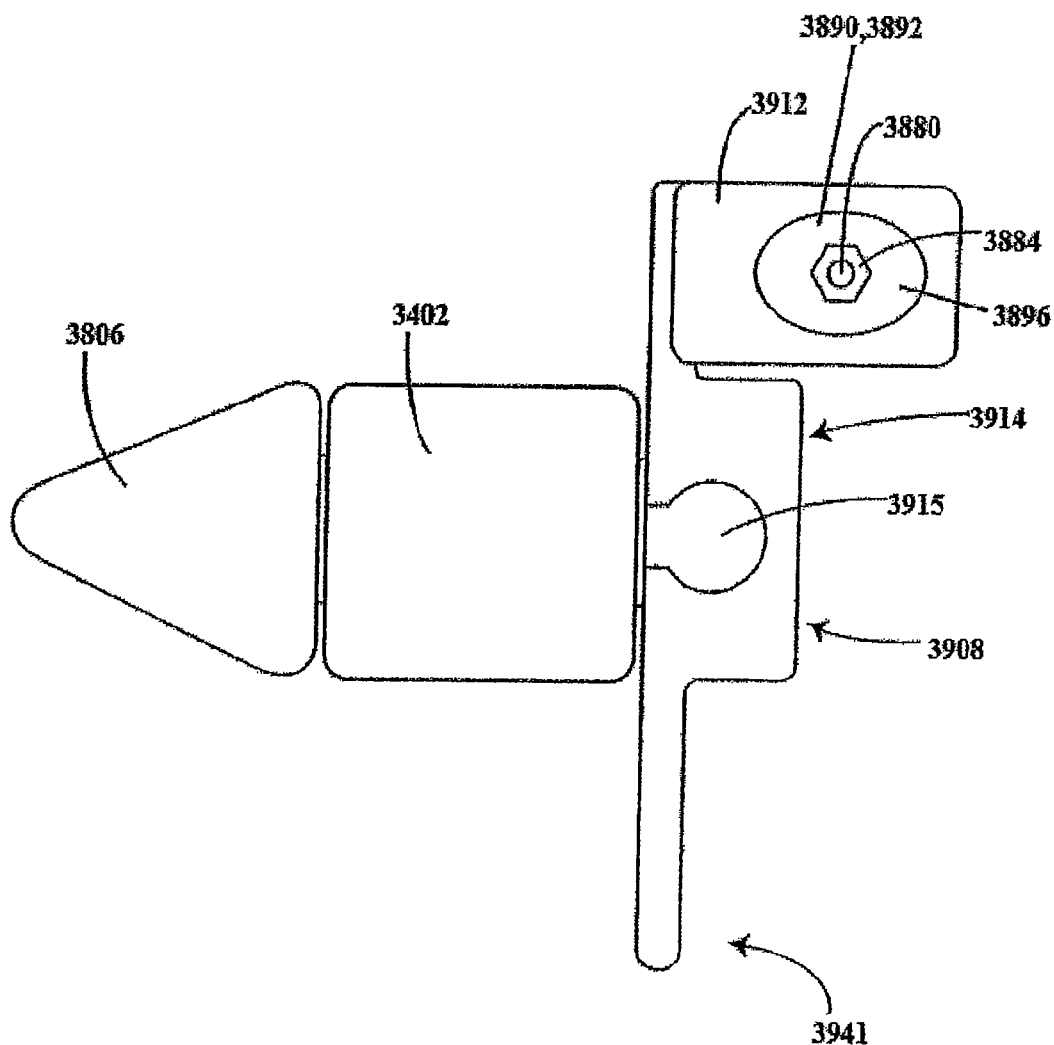
FIG. 40C is a side view of the implant of FIGS. 40A and 40B.

FIGS. 40A and 40B are perspective views, and FIG. 40C is a side view of a still further embodiment of an implant in accordance with the present invention. The implant 2600 includes a distraction guide 806, a rotatable spacer 3302, and a brace 3908. As above, a binder 3330 can be fixedly connected with the brace 3908 at a proximal end 3332 of the binder 3330. Once positioned around adjacent spinous processes, tension of the binder 3330 can be set when the binder 3330 is secured to the brace 3908 so that relative movement of the adjacent spinous processes during flexion is limited or prevented, as desired.

As can be seen in FIG. 40A, the brace 33908 can include a first end having an eyelet 3941 through which the proximal end 3332 of the binder 3330 can be threaded and subsequently sutured, knotted or otherwise bound, or alternatively looped through the eyelet 3941 and secured to itself (e.g., using a clasp) so that the proximal end 3332 of the binder 3330 cannot be drawn through the eyelet 3941. One of ordinary skill in the art can appreciate the myriad different ways in which the proximal end 3332 of the binder 3330 can be associated with the brace 3908 so that tension can be applied to the binder 3330. As in previous embodiments, a free end of the binder 3330 can be secured to the brace 3908 by a capture device 3820 associated with the brace 3908. The capture device 3820 of FIGS. 40A-42 is arranged at a second end of the brace 3908 opposite the eyelet 3941, rather than approximately centered along the brace wall 3914. The brace 3908 can optionally include a locking pin hole 3915 that can be engaged by a locking pin of an insertion instrument (not shown), for example as described in U.S. Pat. No. 6,712,819 to Zucherman, et al., incorporated herein by reference. Further, similar to implants described in Zucherman '819, the brace wall 3914 can optionally include one or more holes 3916 (shown in FIG. 42) adapted to receive alignment pins of such an insertion instrument, and the spacer 3402 can include a spacer engagement hole 3403 adapted to receive a spacer engagement pin of such an insertion instrument. When a spacer engagement pin engages the spacer engagement hole 3403, rotation of the spacer 3402 can be limited or blocked. Once the spacer engagement pin is released from the spacer engagement hole 3403, the spacer 3402 can rotate and/or swivel about a central body 3917 without impedance from the spacer engagement pin. Such an arrangement can provide a physician additional control over the positioning of the implant 2600, although in other embodiments the spacer 3402 need not include an engagement hole 3403. Arranging the captured device 3820 at a second end of the brace 3908 can allow an insertion instrument, having a configuration as described in Zucherman '819 or having some other configuration, to releasably engage the implant 2600 to assist in implantation without interference from the capture device 3820.

The distraction guide 3806 of the implant 2600 can be wedge-shaped, as described above, or approximately conical, as shown in FIGS. 40A-40C, and can include a slot 3809 disposed through the distraction guide 3806 and adapted to receive the binder 3330 during implantation. Also as described above, the rotatable spacer 3402 can be elliptical in cross-section, or otherwise shaped, and can rotate relative to the distraction guide 3806 to roughly conform with a contour of a space between the targeted adjacent spinous processes.

Figure 41A:
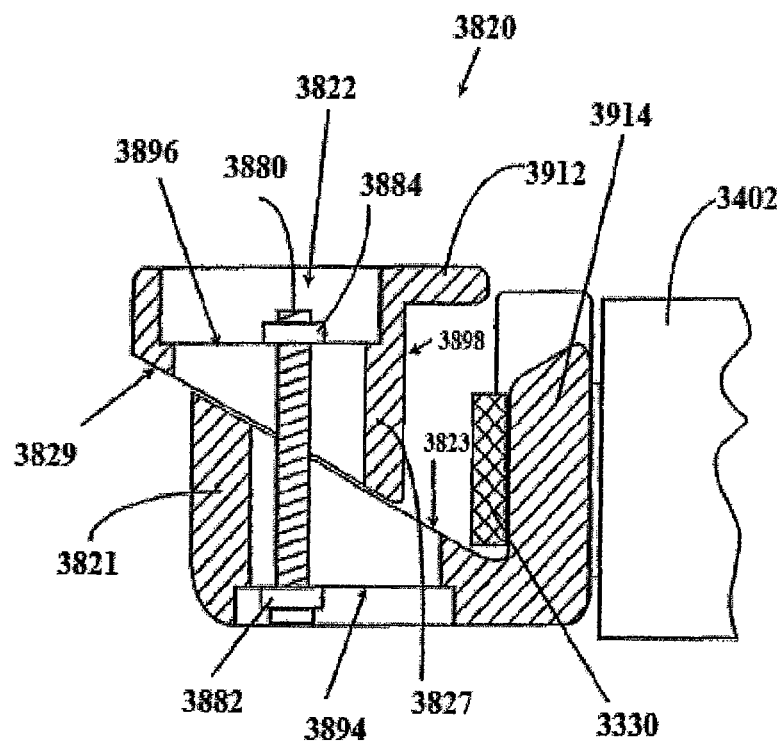
FIG. 41A is a cross-sectional top view of a binder loosely positioned within the capture device of the implant of FIGS. 40A and 40B.
Figure 41B:
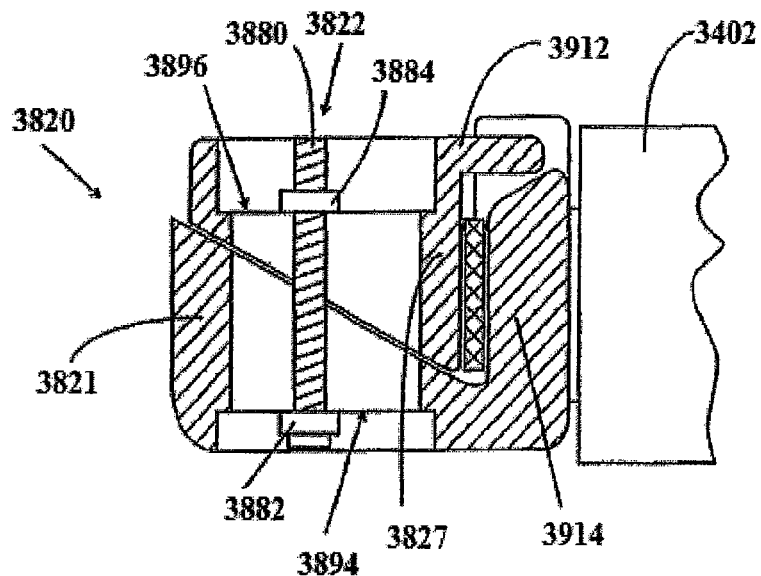
FIG. 41B is a cross-sectional top view of the binder secured to the brace by the capture device of the implant of FIGS. 40A and 40B.
Figure 41C:
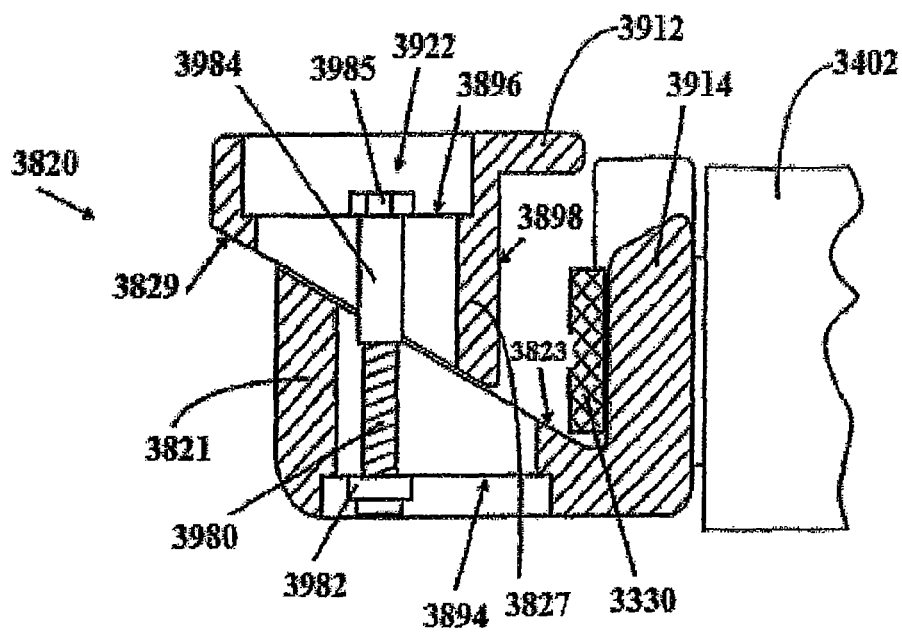
FIG. 41C is a cross-sectional top view of a binder loosely positioned within an alternative embodiment of a capture device of the implant of FIGS. 40A and 40B.
Figure 41D:
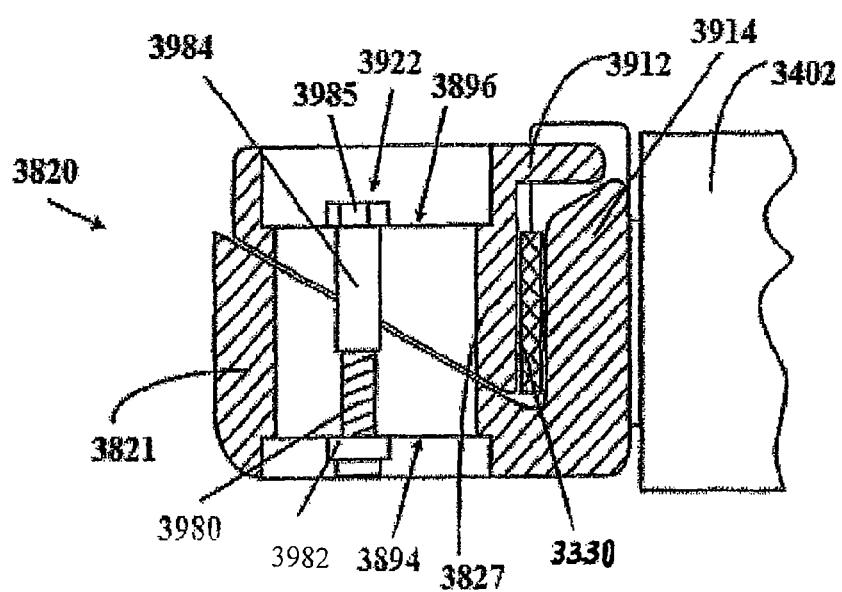
FIG. 41D is a cross-sectional top view of the binder and capture device of FIG. 41C wherein the binder is secured to the brace.

The capture device 3820 is shown in cross-section in FIGS. 41A and 41B. The capture device 3820 can comprise, for example, two pieces slidably associated with one another by an adjustable fastener 3822 (as shown, the adjustable fastener is a hex screw). A fixed piece 3821 of the capture device can extend from the brace wall 3914. The fixed piece 3821 can include a beveled surface 3823 that can function as a ramp. A slidable piece 3827 of the capture device can be slidably associated with the fixed piece 3821, and can likewise included a beveled surface 3829 positioned in opposition to the beveled surface 3823 of the fixed piece 3821. As shown, the slidable piece 3827 is associated with the fixed piece 3821 via an adjustable fastener 3822. The fastener 3822 can be positioned within slots 3890,3892 of the fixed piece 3821 and the slidable piece 3827 and can include a threaded shaft 3880, a head 3882, and a nut 3884. The head 3882 of the fastener 3822 can engage an anterior surface 3894 of the fixed piece 3821 and the nut 3884 can be threaded onto the threaded shaft 3880 so that the nut 3884 can engage a posterior surface 3896 of the slidable piece 3827. The slidable piece 3827 is free to slide along the beveled surface 3823 of the fixed piece 3821 until both the nut 3884 engages the posterior surface 3896 and the head 3882 engages the anterior surface 3894, blocking further movement in one direction. The distance between the anterior surface 3894 and the posterior surface 3896 increases or decreases as the slidable piece 3827 slides along the beveled surface 3823 and a distance between a capture surface 3898 of the slidable piece 3827 and the brace wall 3914 likewise increases or decreases. The maximum distance the slidable piece 3827 can travel can be defined by the distance between the nut 3884 and the head 3882. A physician can adjust the maximum distance by rotating the nut 3884 so that the nut 3884 travels closer to, or farther from the head 3882 along the threaded shaft 3880, possibly urging the capture surface 3898 toward the brace wall 3914. Thus, when the implant 2600 is positioned between spinous processes, the physician can set the maximum distance so that the free end of the binder 3330 can be threaded between the capture surface 3898 and the brace wall 3914. As shown in FIG. 41B, the physician can then adjust the fastener 3822 so that the posterior surface 3896 and the anterior surface 3894 are urged together, the maximum distance decreases and the distance between the capture surface 3898 and the brace wall 3914 decreases, thereby pinching the binder 3330 between the capture surface 3898 and the brace wall 3914 and defining a secure end of the binder 3330. In some embodiments, one or both of the capture surface 3898 and the brace wall 3914 can include texture so that the binder 3330 is further prevented from sliding when the binder 3330 is placed under increasing tension (e.g., during flexion).

The slidable piece 3827 can optionally further include a guide 3912 extending from the slidable piece 3827 so that the guide 3912 overlaps a portion of the brace 3908. The guide 3912 can extend, for example, a distance roughly similar to the maximum distance between the capture surface 3898 and the brace wall 3914, and can help ensure that the binder 3330 is captured between the capture surface 3898 and the brace wall 3914. In other embodiments, the capture device 3820 of FIGS. 40A-41B can include some other shape or configuration and still fall within the contemplated scope of the invention. For example, the fastener need not include a nut. In one embodiment, shown in FIGS. 41C and 41D, the fastener 3922 can include a threaded shaft 3980 associated with a sleeve 3984. As one of the threaded shaft 3980 and the sleeve 3984 is rotated, the distance between a head 3982 of the threaded shaft 3980 and the head 3985 of the sleeve 3984 can decrease or increase. In still other embodiments, the fastener need not include a threaded shaft, but rather can include a smooth shaft having a retaining clip frictionally associated with the smooth shaft. One of ordinary skill in the art will appreciate the myriad different devices that can be employed to selectively close a gap between a capture surface 3898 and the brace wall 3914.

Figure 42:
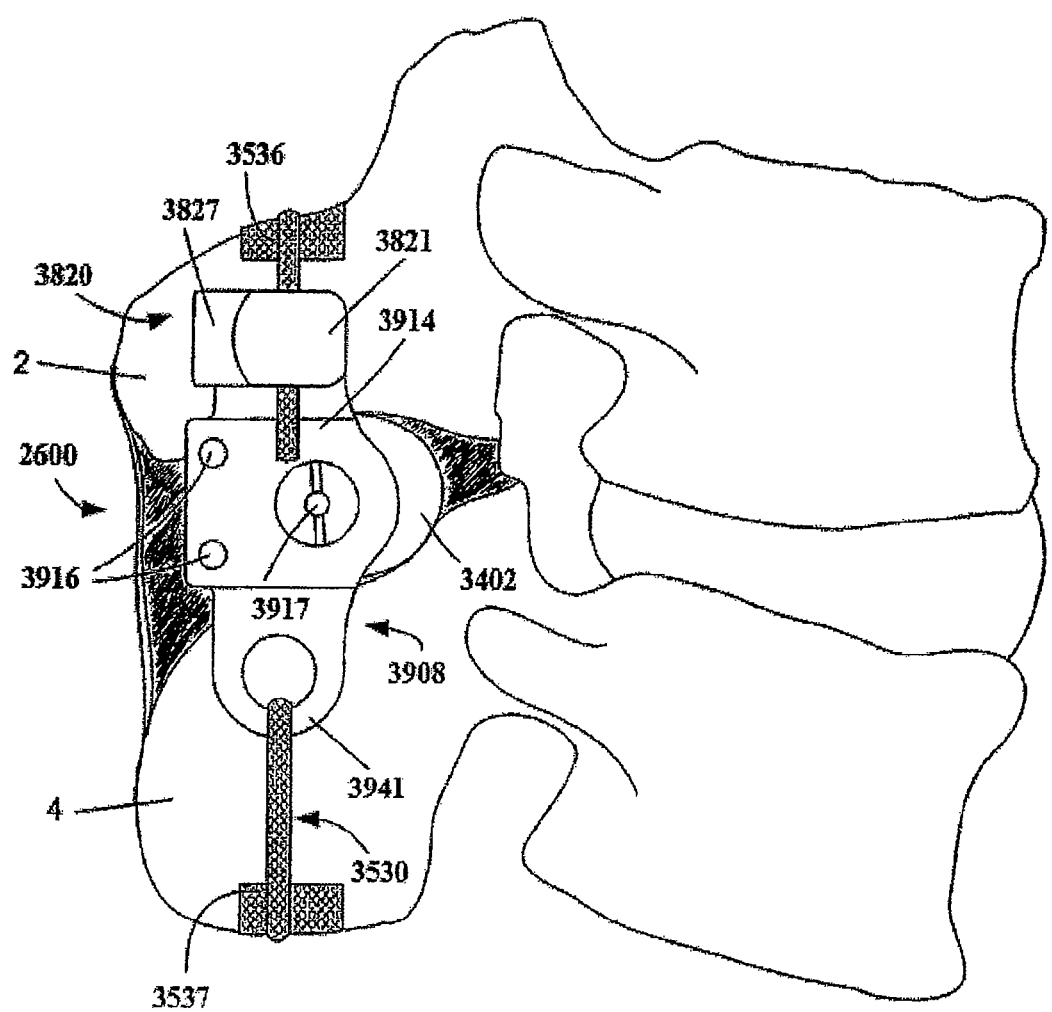
FIG. 42 is an end view of the implant of FIGS. 40A and 40B positioned between adjacent spinous processes.

FIG. 42 is an end view of the implant 2600 of FIGS. 40A-41D positioned between adjacent spinous processes. As shown, the binder 3530 is a cord, but in other embodiments can have some other geometry. As described above in reference to previous embodiments, where a cord, a tether, or the like is used as a binder, a pad 3536 can be arranged along a contact surface of the respective spinous process so that a load applied to the contact surface by the tension in the binder 3530 can be distributed across a portion of the contact surface wider than the binder 3530, thereby reducing stress on the portion. The capture device 3820 is arranged so that the slidable piece 3827 is posteriorly located relative to the fixed piece 3821. A fastener 3822 can be accessed by the physician using a substantially posterior approach.

Figure 43:
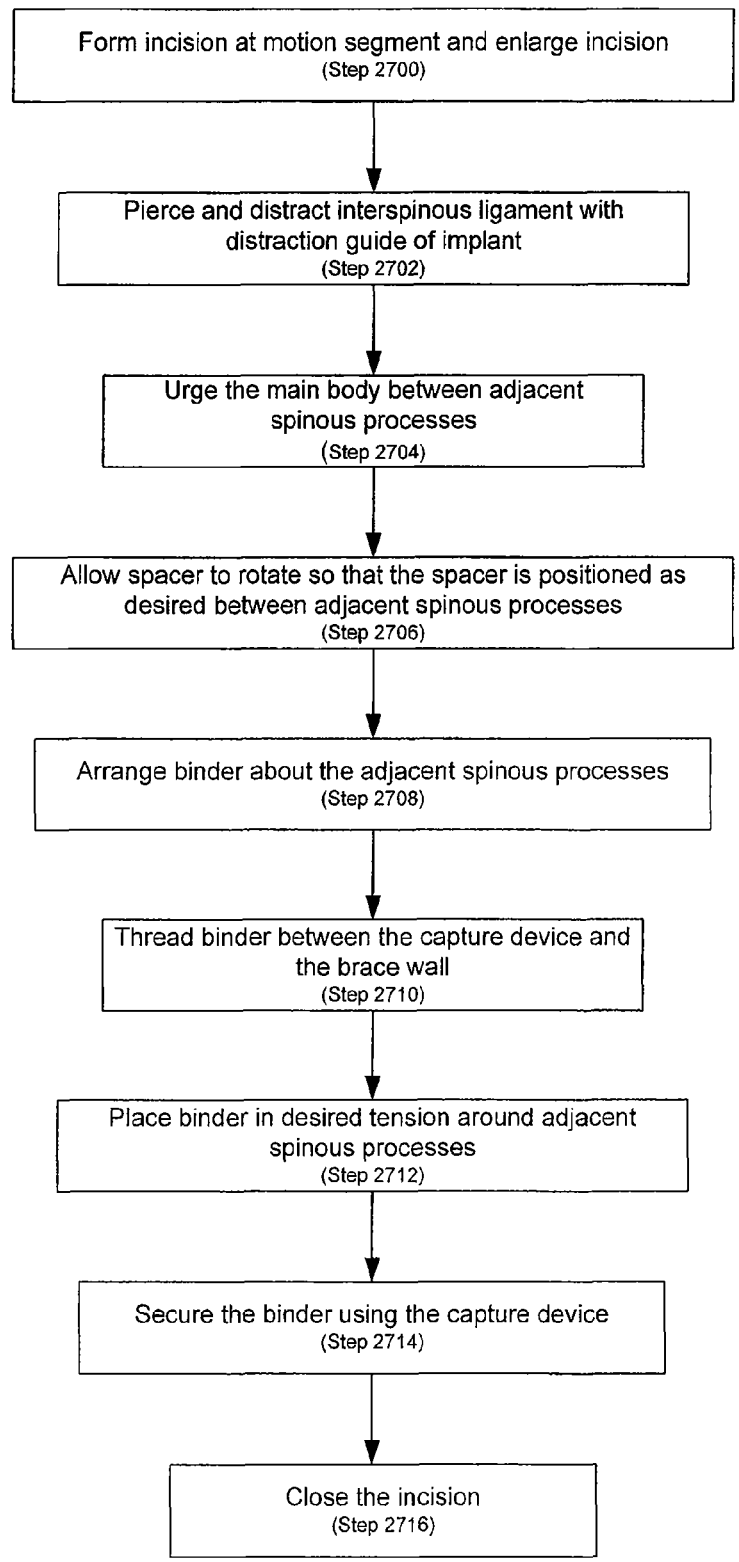
FIG. 43 is a block diagram illustrating a method of positioning the implant of FIG. 40A between adjacent spinous processes.

A method of surgically implanting an implant 2600 in accordance with an embodiment as described above in FIGS. 40A-42 of the present invention is shown as a block diagram in FIG. 43. The method can include forming an incision at the target motion segment, and enlarging the incision to access the target motion segment (Step 2700). The interspinous ligament between targeted adjacent spinous processes can then be distracted by piercing or displacing the interspinous ligament with the distraction guide 3106 (Step 2702) and urging the implant 2600 between the adjacent spinous processes (Step 2704). As the interspinous ligament is displaced, the spacer 3302 can be positioned between the spinous processes such that the spacer 3302 can rotate to assume a preferred position between the spinous processes (Step 2706).

Once the implant 2600 is positioned, the binder 3330 can be threaded between interspinous ligaments of adjacent motion segments so that the targeted adjacent spinous processes are disposed within a loop formed by the binder 3330 (Step 2708). The physician can then thread the binder 3330 between the capture surface 3898 of the capture device 3820 and the brace wall 3914 (Step 2710). Once a desired tension of the binder 3330 is applied (Step 2712), the physician can adjust the fastener 3822 of the capture device 3820 so that the binder 3330 is secured between the captured surface 3898 and the brace wall 3914 (Step 2714). The incision can subsequently be closed (Step 2716).

Figure 44A:
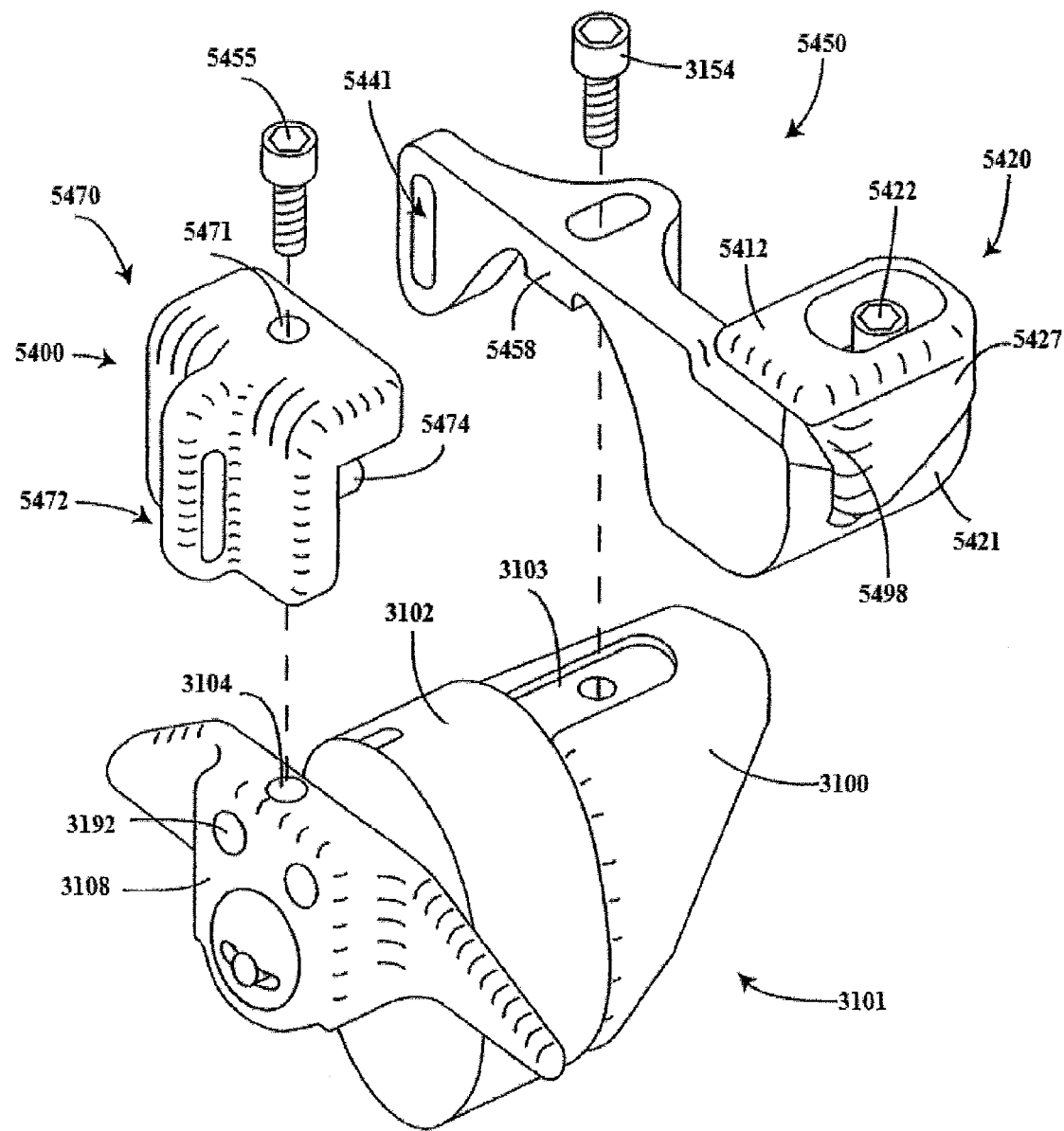
FIG. 44A is a perspective view of an still another embodiment of an implant in accordance with the present invention having a distraction guide, a spacer, a first wing, and a second wing including a capture device.
Figure 44B:
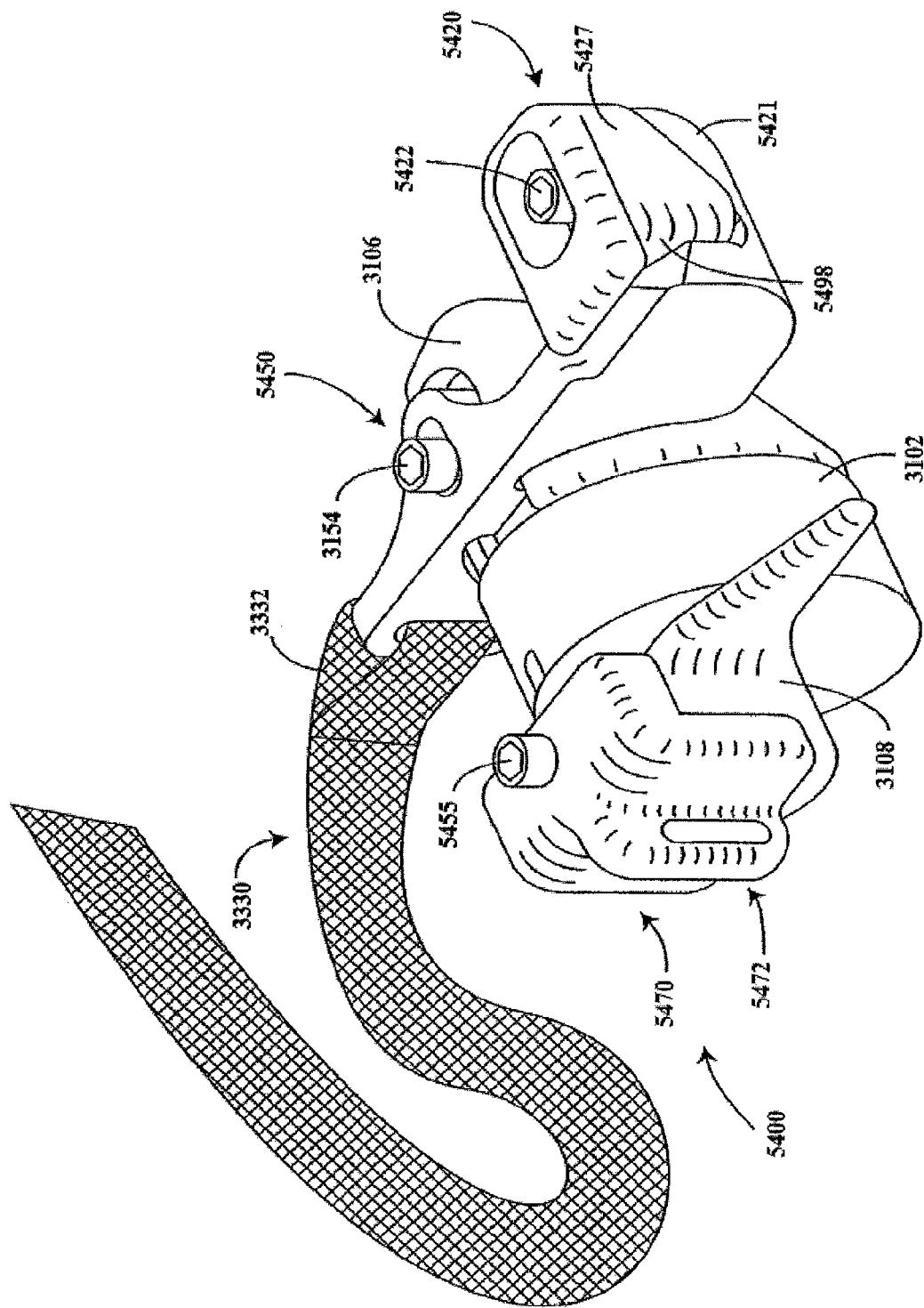
FIG. 44B is a perspective view of the implant of FIG. 44A in accordance with the present invention having a distraction guide, a spacer, a first wing, and a second wing including a capture device.

FIGS. 44A and 44B are perspective views of still another embodiment of an implant 5400 in accordance with the present invention. In such an embodiment, the implant 5400 can include a main body 3101 similar to the main body 3101 described above in reference to FIG. 32. As above, the main body 3101 (also referred to herein as a first unit) includes a spacer 3102, a first wing 3108, a distraction guide 3106 and an alignment track 3103. The main body 3101 is inserted between adjacent spinous processes. Preferably, the main body 3101 remains (where desired) in place without attachment to the bone or ligaments.

Figure 46:
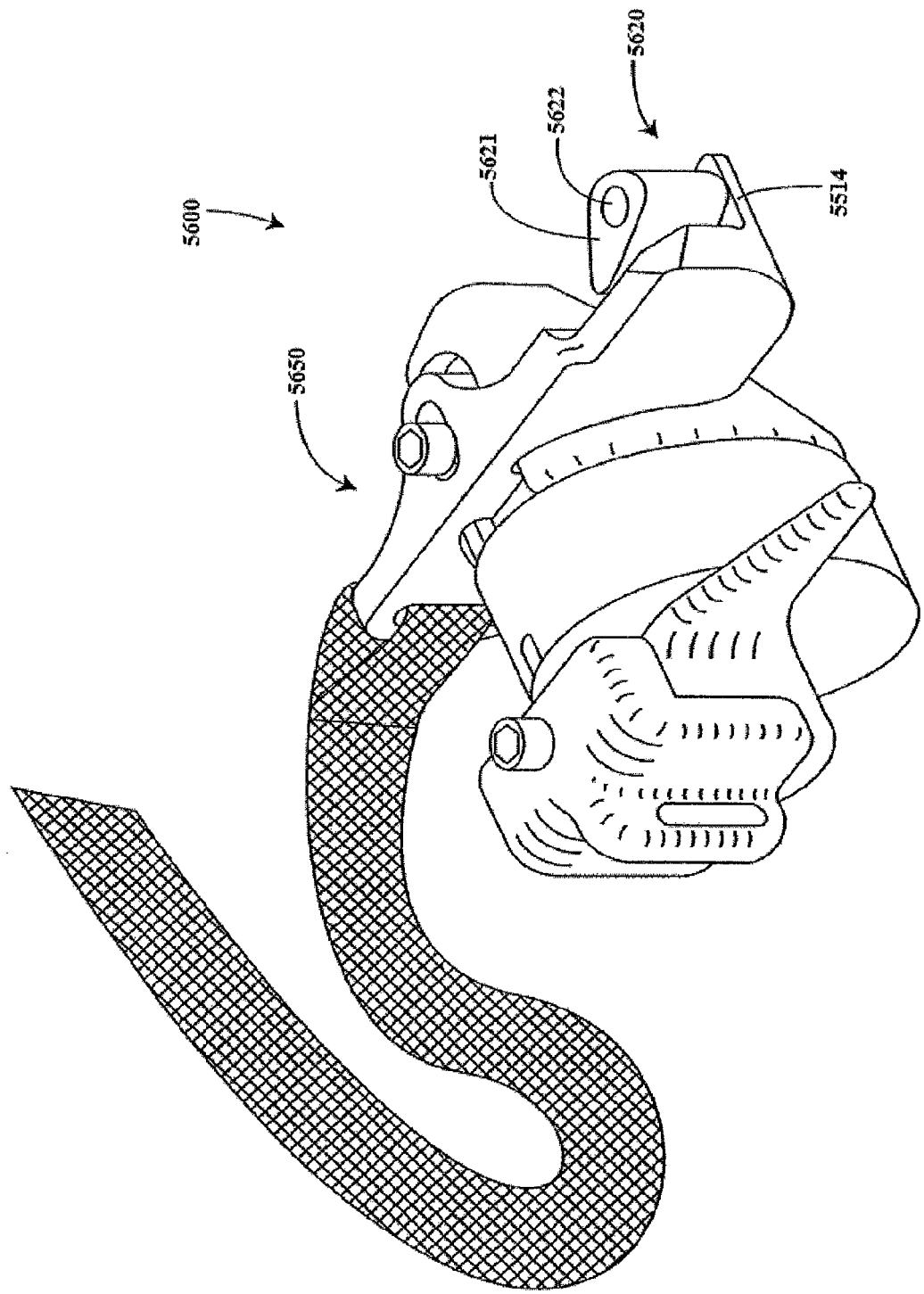
FIG. 46 is a perspective view of an still another embodiment of an implant in accordance with the present invention having a distraction guide, a spacer, a first wing, and a second wing including a capture device.

The alignment track 3103 includes a threaded hole for receiving a fastener. The alignment track 3103 need not include a threaded hole, but rather alternatively can include some other mechanism for fixedly connecting an additional piece (such as a second wing for limiting or blocking movement of an implant along the longitudinal axis). For example, in an alternative embodiment, the alignment track 5403 can include a flange so that the second wing 5450 can be slidably received, as shown in FIG. 46.

As further shown in FIGS. 44A and 44B, the implant 5400 includes a second wing 5450 removably connectable with the implant 5400. The second wing 5450 includes an alignment tab 5458 adapted to be received in the alignment track 3103 of the main body 3101, the alignment tab 5458 optionally including a slot for receiving the fastener so that the alignment tab 5458 is disposed between the fastener and the alignment track 3103. In alternative embodiments, the alignment tab 5458 need not include a slot but rather can include some other mechanism for mating with the main body 3101. The second wing 5450 can include a first end having a slot (or eyelet) 5441 through which the proximal end (also referred to herein as an anchored end) 3332 of a binder 3330 can be threaded and subsequently sutured, knotted or otherwise bound, or alternatively looped through the slot 5441 and secured to itself (e.g., using a clasp) so that the proximal end 3332 of the binder 3330 cannot be withdrawn through the slot 5441. One of ordinary skill in the art can appreciate the myriad different ways in which the proximal end 3332 of the binder 3330 can be associated with the second wing 5450 so that tension can be applied to the binder 3330. The binder 3330 can be disposed around adjacent spinous processes and a portion of the length of the binder 3330 (the length of the binder being that portion of the binder extending from the proximal end of the binder) can be secured to the second wing 5450 by a capture device 5420 associated with the second wing 5450.

The capture device 3820 of FIGS. 44A and 44B is arranged at a second end of the second wing 5450 opposite the slot 5441. The capture device 5420 can be substantially similar to capture devices 5420 as described above in reference to FIGS. 41A and 41B, and can comprise, for example, two pieces slidably associated with one another by an adjustable fastener. As above, a fixed piece 5421 of the capture device can extend from the second wing 5450. The fixed piece 5421 can include a beveled surface that can function as a ramp. A slidable piece 5427 of the capture device can be slidably associated with the fixed piece 5421 (for example, via the adjustable fastener) and can likewise included a beveled surface positioned in opposition to the beveled surface of the fixed piece 5421. As the slidable piece 5427 slides along the beveled surface of the fixed piece 5421, a distance between a capture surface 5498 of the slidable piece 5427 and the second wing 5450 increases or decreases. As above, the slidable piece 5427 can optionally further include a guide 5412 extending from the slidable piece 5427 so that the guide 5412 overlaps a portion of the second wing 5450. The guide 5412 can extend, for example, a distance roughly similar to the maximum distance between the capture surface 5498 and the second wing 5450, and can help ensure that the binder 3330 is arranged between the capture surface 5498 and the second wing 5450. A physician can position the binder 3330 so that the binder 3330 is disposed between adjacent spinous processes, threading the binder 3330 between the slidable piece 5427 and the second wing 5450. The physician can then adjust the fastener 5422 so that the distance between the capture surface 5498 and the second wing 5450 decreases, thereby pinching the binder 3330 between the capture surface 5498 and the second wing 5450 and defining a secure end of the binder 3330. In some embodiments, one or both of the capture surface 5498 and the second wing 5450 can include texture so that the binder 3330 is further prevented from sliding when the binder 3330 is placed under increasing tension (e.g., during flexion).

The implant 5400 can further include a binder aligner 5470 selectably connectable with the first wing 3108 of the main body 3101. The binder aligner 5470 can be connected with the first wing 3108 by fastening the binder aligner 5470 to the locking pin hole 3104 of the first wing 3108. In such embodiments where a fastener 5455 is used to connect the binder aligner 5470 with the first wing 3108 through a hole 5471 in the binder aligner 5470, it is desirable that the locking pin hole 3104 be threaded, or otherwise adapted to receive the fastener 5455. The locking pin hole 3104 can thus be adapted to function as a hole to slidably (and temporarily) receive a locking pin of an insertion tool (not shown), thereby facilitating insertion and positioning of the main body 3101, and can also be adapted to function to fixedly receive a fastener 5455 for positioning the binder aligner 5470. The binder aligner 5470 can optionally include pins 5474 corresponding to the alignment holes 3192 of the main body 3101 to further secure the binder aligner 5470 to the main body 3101 and limit undesired movement of the binder aligner 5470 relative to the main body 3101.

The binder aligner 5470 includes a guide 5472 extending from the binder aligner 5470 to limit or block shifting of the binder 3330 in a posterior-anterior direction. The guide 5472 can include a loop, as shown in FIG. 44A, or alternatively some other structure, closed or unclosed, for limiting or blocking shifting of the binder 3330. Such a structure can prevent undesired relative movement between the binder 3330 and the main body 3101, and can additionally ease arrangement of the binder 3330 during an implantation procedure, by helping to aid proper positioning of the binder 3330.

Figure 45:
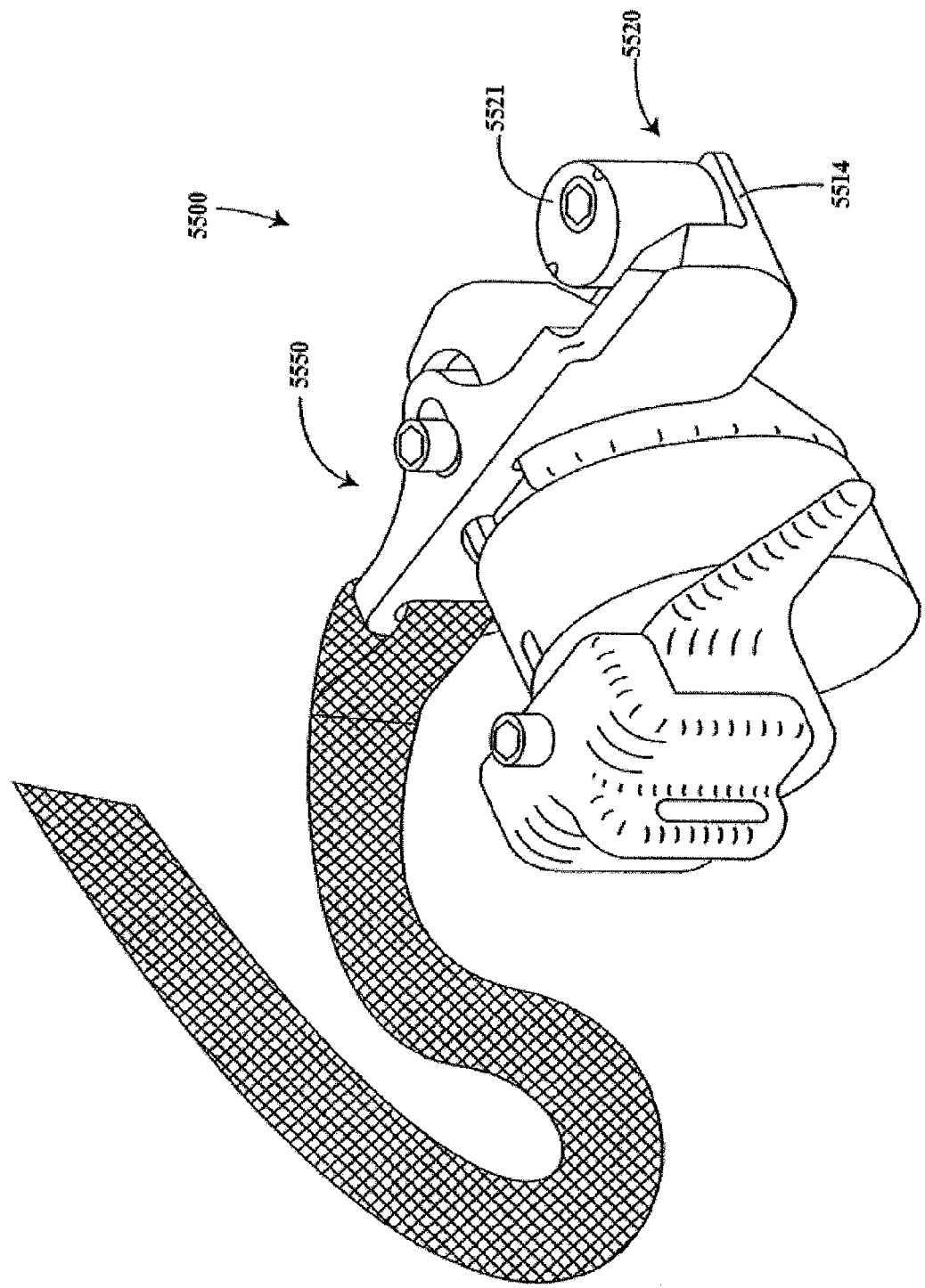
FIG. 45 is a perspective view of an still another embodiment of an implant in accordance with the present invention having a distraction guide, a spacer, a first wing, and a second wing including a capture device.
Figure 47:
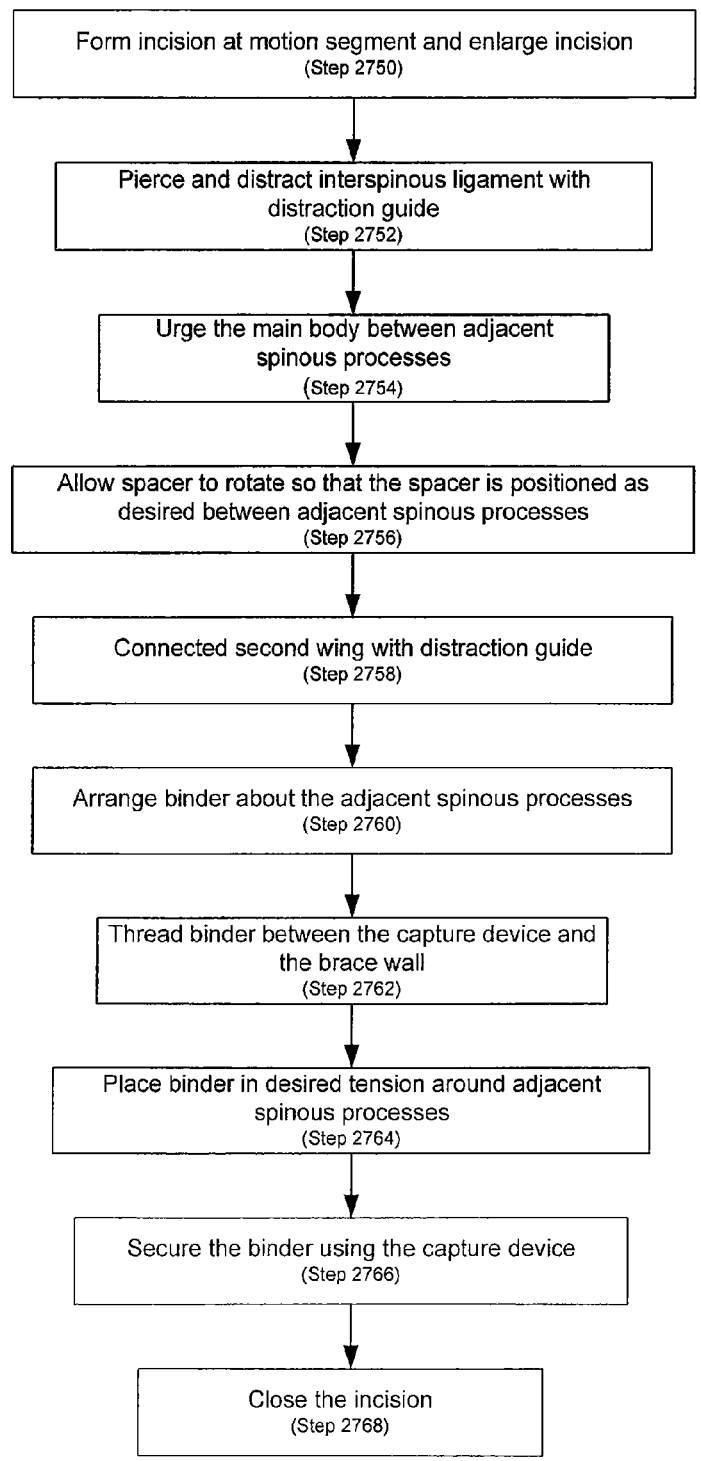
FIG. 47 is a block diagram illustrating a method of positioning the implant of FIGS. 44A-46 between adjacent spinous processes.

In other embodiments, the capture device of FIGS. 44A and 44B can include some other shape, configuration, and mechanism and still fall within the contemplated scope of the invention. For example, referring to FIG. 45, in other embodiments, a flange 5514 can extend from the second wing 5550, from which a rotatable cam 5521 extends so that the binder 3330 can be captured between the second wing 5550 and the cam 5521. Such a capture device can resemble capture devices 5520 as described above in FIGS. 34C and 34B. Referring to FIG. 46, in still other embodiments, a spring-loaded cam 5621 extends from the flange 5514 so that the binder 3330 can be captured between the second wing 5514 and the spring-loaded cam 5621. Such a capture device can resemble capture devices 5520 as described above in FIGS. 34C and 34D. In still further embodiments in accordance with the present invention, some other mechanism can be employed as a capture device associated with the second wing 5550 for securing the length of the binder 3330, for example as otherwise described in herein, and other obvious variations. One of ordinary skill in the art will appreciate the myriad different mechanisms for securing the binder 3330 to the second wing 5450. A system in accordance with the present invention can comprise a second wing 5450 including a capture device 5420 as described above and optionally a binder aligner 5470. The system can be used with a main body 3101 in substitution for a second wing 3150 as described above in FIG. 32. Alternatively, the system can optionally be used to modify a main body 3101 previously implanted in a patient, for example by removing an existing second wing 3150 and replacing the second wing 3150 with the system, to additionally limit flexion as well as extension. Such a system can provide flexibility to a physician by allowing the physician to configure or reconfigure an implant according to the needs of a patient. Further, such a system can reduce costs by reducing the variety of components that need be manufactured to accommodate different procedures and different treatment goals. A method of surgically implanting an implant 5400 in accordance with an embodiment as described above in FIGS. 44A-46 of the present invention is shown as a block diagram in FIG. 47. The method can include forming an incision at the target motion segment, and enlarging the incision to access the target motion segment (Step 2700). The interspinous ligament between targeted adjacent spinous processes can then be distracted by piercing or displacing the interspinous ligament with the distraction guide 106 (Step 2702) and urging the implant 5400 between the adjacent spinous processes (Step 2704). As the interspinous ligament is displaced, the spacer 3102 can be positioned between the spinous processes such that the spacer 3102 can rotate to assume a preferred position between the spinous processes (Step 2706).

Once the implant 5400 is positioned, the second wing 5450 can be fixedly connected with the distraction guide 3106 (Step 2708). A binder 3330 associated with the second wing 5450 can be threaded between interspinous ligaments of adjacent motion segments so that the targeted adjacent spinous processes are disposed within a loop formed by the binder 3330 (Step 2710).

The physician can then thread the binder 3330 between the capture surface 5498 of the capture device 5420 and the second wing 5450 (Step 2712). Once a desired tension of the binder 3330 is applied (Step 2714), the physician can adjust the fastener 5422 of the capture device 5420 so that the binder 3330 is secured between the captured surface 5498 and the second wing 5450 (Step 2716). The incision can subsequently be closed (Step 2718).

Material for Use in Implants of the Present Invention

In some embodiments, the implant can be fabricated from medical grade metals such as titanium, stainless steel, cobalt chrome, and alloys thereof, or other suitable implant material having similar high strength and biocompatible properties. Additionally, the implant can be at least partially fabricated from a shape memory metal, for example Nitinol, which is a combination of titanium and nickel. Such materials are typically radiopaque, and appear during x-ray imaging, and other types of imaging. Implants in accordance with the present invention, and/or portions thereof can also be fabricated from somewhat flexible and/or deflectable material, m these embodiments, the implant and/or portions thereof can be fabricated in whole or in part from medical grade biocompatible polymers, copolymers, blends, and composites of polymers. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer. Many polymers, copolymers, blends, and composites of polymers are radiolucent and do not appear during x-ray or other types of imaging. Implants comprising such materials can provide a physician with a less obstructed view of the spine under imaging, than with an implant comprising radiopaque materials entirely. However, the implant need not comprise any radiolucent materials.

One group of biocompatible polymers is the polyaryletherketone group which has several members including polyetheretherketone (PEEK), and polyetherketoneketone (PEKK).

PEEK is proven as a durable material for implants, and meets the criterion of biocompatibility. Medical grade PEEK is available from Victrex Corporation of Lancashire, Great Britain under the product name PEEK-OPTIMA. Medical grade PEKK is available from Oxford Performance Materials under the name OXPEKK, and also from CoorsTek under the name BioPEKK. These medical grade materials are also available as reinforced polymer resins, such reinforced resins displaying even greater material strength, hi an embodiment, the implant can be fabricated from PEEK 450G, which is an unfilled PEEK approved for medical implantation available from Victrex. Other sources of this material include Gharda located in Panoli, India. PEEK 450G has the following approximate properties:

| Property | Value |
| --- | --- |
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

PEEK 450G has appropriate physical and mechanical properties and is suitable for carrying and spreading a physical load between the adjacent spinous processes. The implant and/or portions thereof can be formed by extrusion, injection, compression molding and/or machining techniques.

It should be noted that the material selected can also be filled. Fillers can be added to a polymer, copolymer, polymer blend, or polymer composite to reinforce a polymeric material. Fillers are added to modify properties such as mechanical, optical, and thermal properties. For example, carbon fibers can be added to reinforce polymers mechanically to enhance strength for certain uses, such as for load bearing devices. In some embodiments, other grades of PEEK are available and contemplated for use in implants in accordance with the present invention, such as 30% glass-filled or 30% carbon-filled grades, provided such materials are cleared for use in implantable devices by the FDA, or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to have enhanced compressive strength and stiffness, and a lower expansion rate relative to unfilled PEEK. Carbon-filled PEEK also offers wear resistance and load carrying capability.

As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. As mentioned, the implant can be comprised of polyetherketoneketone (PEKK). Other material that can be used include polyetherketone (PEK), polyetherketoneetherketoneketone (PEKEKK), polyetheretherketoneketone (PEEKK), and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials." Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

As described above, the binder can be made from a biocompatible material. In an embodiment, the binder can be made from a braided polyester suture material. Braided polyester suture materials include, for example, Ethibond, Ethiflex, Mersilene, and Dacron, and are nonabsorbable, having high tensile strength, low tissue reactivity and improved handling. In other embodiments, the binder can be made from stainless steel (i.e., surgical steel), which can be braided into a tether or woven into a strap, for example. In still other embodiments, the binder can be made from some other material (or combination of materials) having similar properties. The foregoing description of the present invention have been presented for purposes of illustration and description. It is not intended to be exhaustive or to limit the invention to the precise forms disclosed. Many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

Interspinous Implants

Figure 48A:
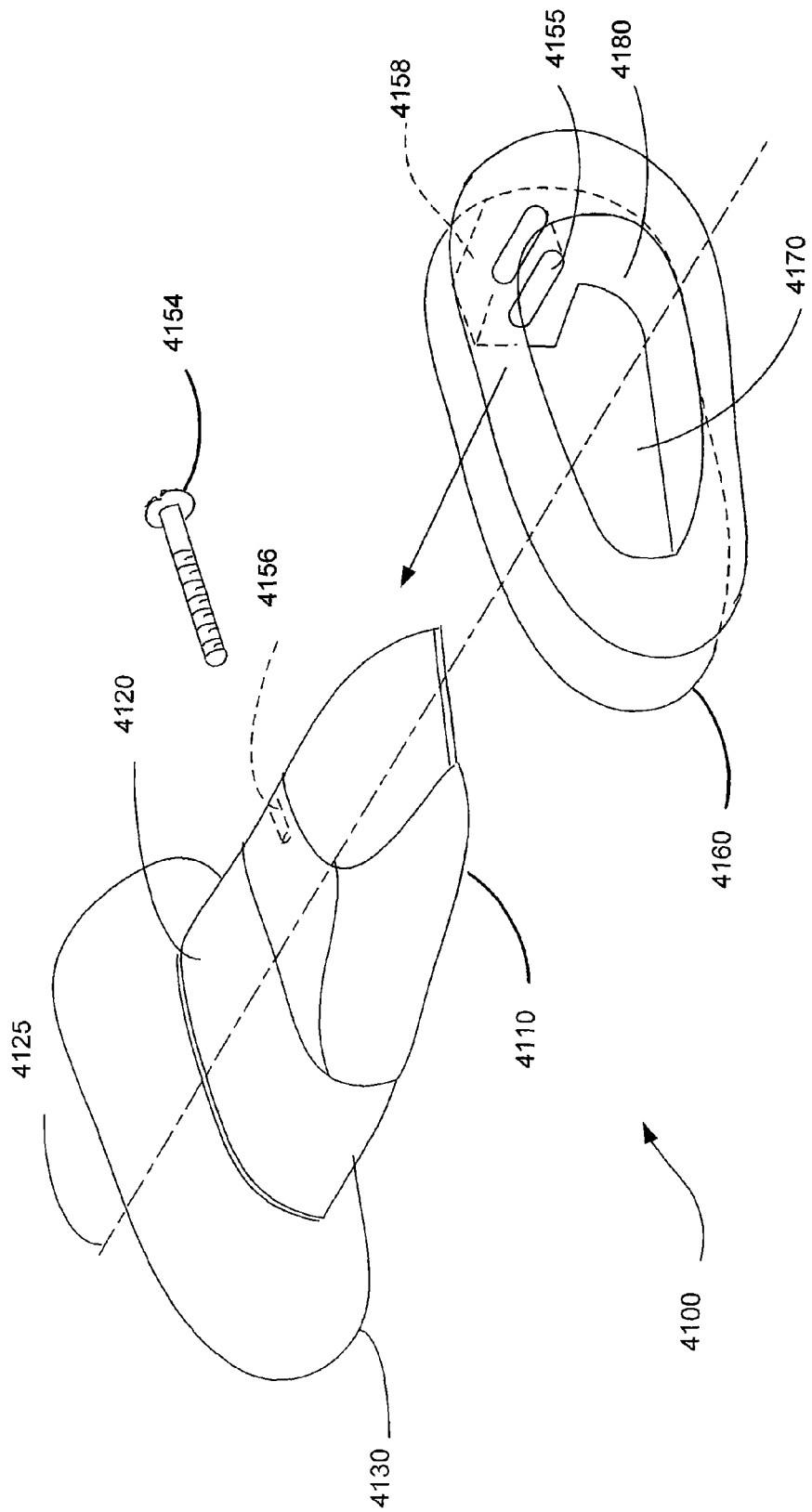
FIG. 48A is a perspective view of an implant including a spacer having a tear-drop shaped cross-section, a distraction guide, a first wing, and a second wing connectable with the distraction guide.

FIG. 48A is a perspective view of an implant as described in U.S. patent application Ser. No. 10/850,267, filed May 20, 2004, incorporated herein by reference. The implant 4100 comprises a first wing 4130, a spacer 4120, and a lead-in tissue expander (also referred to herein as a distraction guide) 4110.

The distraction guide 4110 in this particular embodiment is wedge-shaped, i.e., the implant has an expanding cross-section from a proximal end of the implant 100 to a region 4150 where the guide 4110 joins with the spacer 4120 (referencing for the figures is based on the point of insertion of the implant between spinous processes). As such, the distraction guide 4110 functions to initiate distraction of the soft tissue and the spinous processes when the implant 4100 is surgically inserted between the spinous processes. It is to be understood that the distraction guide 4110 can be pointed and the like, in order to facilitate insertion of the implant 4100 between the spinous processes of adjacent cervical vertebrae. It is advantageous that the insertion technique disturb as little of the bone and surrounding tissue or ligaments as possible in order to reduce trauma to the site and promote early healing, and prevent destabilization of the normal anatomy. For embodiments such as those of FIGS. 48A and 48B, there is no requirement to remove any of the bone of the spinous processes and no requirement to sever, or remove from the body, ligaments and tissues immediately associated with the spinous processes. For example, it is unnecessary to sever the supraspinal ligament of the lower vertebrae or the ligamentum nuchae (which corresponds to the supraspinal ligament) which partially cushions the spinous processes of the upper cervical vertebrae.

As can be seen, the spacer 4120 can be teardrop-shaped in cross-section perpendicular to a longitudinal axis 4125 of the implant 4100. In this way, the shape of the spacer 4120 can roughly conform to a wedge-shaped space, or a portion of the space, between adjacent spinous processes within which the implant 4100 is to be positioned. As shown in FIG. 48A, the spacer 4120 (and the first wing 4108) is shaped to accommodate the anatomical form or contour of spinous processes (and/or laminae) of preferably the C6 and C7 vertebra for placement between such spinous processes (i.e., the C6-C7 motion segment). The same shape or variations of this shape can be used to accommodate other motion segments, for example in the thoracic or lumbar regions. In other embodiments the spacer 4120 can have alternative shapes such as circular, wedge, oval, ovoid, football, and rectangular with rounded corners, and other shapes. The shape of the spacer 4120 can be selected for a particular patient so that the physician can position the implant 4100 as close as possible to the anterior portion of the surface of the spinous process. The shape selected for the spacer 4120 can affect the contact surface area of the implant 4100 and the spinous processes that are to be subject to distraction. Increasing the contact surface area between the implant 4100 and the spinous processes can distribute a load force between the spinous frame and the implant 4100.

The first wing 4130 is likewise teardrop-shaped in cross-section perpendicular to a longitudinal axis 4125 of the spacer 4120 and distraction guide 4110. The dimensions of the first wing 4130 can be larger than that of the spacer 4120, particularly along the axis of the spine, and can limit or block lateral displacement of the implant 4100 in the direction of insertion along the longitudinal axis 4125. As with the spacer 4120, the first wing 4130 can have other cross-sectional shapes, such as elliptical, wedge, circular, oval, ovoid, football, and rectangular with rounded corners and other shapes.

The implant 4100 of FIG. 48A further includes an adjustable wing 4160 (also referred to herein as a second wing) separate from the distraction guide 4110, the spacer 4120 and the first wing 4130. The second wing 4160 is connectable with the distraction guide 4110 (and/or the spacer 4120) once the implant 4100 is positioned between adjacent spinous processes. The second wing 4160, similar to the first wing 4130, can limit or block lateral displacement of the implant 4100, however displacement is limited or blocked in the direction opposite insertion. When both the first wing 4130 and the second wing 4160 are connected with the implant 4100 and the implant 4100 is positioned between adjacent spinous processes, a portion of the spinous processes can be sandwiched between the first wing 4130 and the second wing 4160, limiting displacement along the longitudinal axis 4125. As can be seen, the second wing 4160 can be teardrop-shaped in cross-section. A lip 4180 defining a space 4170 through the second wing 4160 allows the second wing 4160 to pass over the distraction guide 4110 to meet and connect with the distraction guide 4110 and/or the spacer 4120. The second wing 4160 is then secured to the distraction guide 4110 and/or the spacer 4120. The second wing 4160, can be designed to be interference-fit onto the spacer 4120 or a portion of the distraction guide 4110 adjacent to the spacer 4120. Where the second wing 4160 is interference-fit, there is no additional attachment device to fasten the second wing 4160 relative to the remainder of the implant 4100.

Alternatively, various fasteners can be used to secure the second wing 4160 relative to the remainder of the implant 4100. For example, FIG. 48A illustrates an embodiment of an implant 4100 including a teardrop-shaped second wing 4160 having a tongue 4158 at the posterior end of the second wing 4160. A bore 4155 is disposed through the tongue 4158, and is aligned with a corresponding bore 4156 on the spacer 4120 when the second wing 4160 is brought into position by surgical insertion relative to the rest of the implant 4100. A threaded screw 4154 can be inserted through the aligned bores 4155,4156 in a posterior-anterior direction to secure the second wing 4160 to the spacer 4120. The direction of insertion from a posterior to an anterior direction has the screw 4154 engaging the bores 4155,4156 and the rest of the implant 4100 along a direction that is generally perpendicular to the longitudinal axis 4125. This orientation is most convenient when the physician is required to use a screw 4154 to secure the second wing 4160 to the rest of the implant 4100. The second wing 4160 can further be secured to the spacer 4120 by some other mechanism, for example such as a flexible hinge (not shown) with a protrusion that engages an indentation of one of the distraction guide 4110 and the spacer 4120. Alternatively, the second wing 4160 can be secured to one of the distraction guide 4110 and the spacer 4120 by still some other mechanism.

Figure 48B:
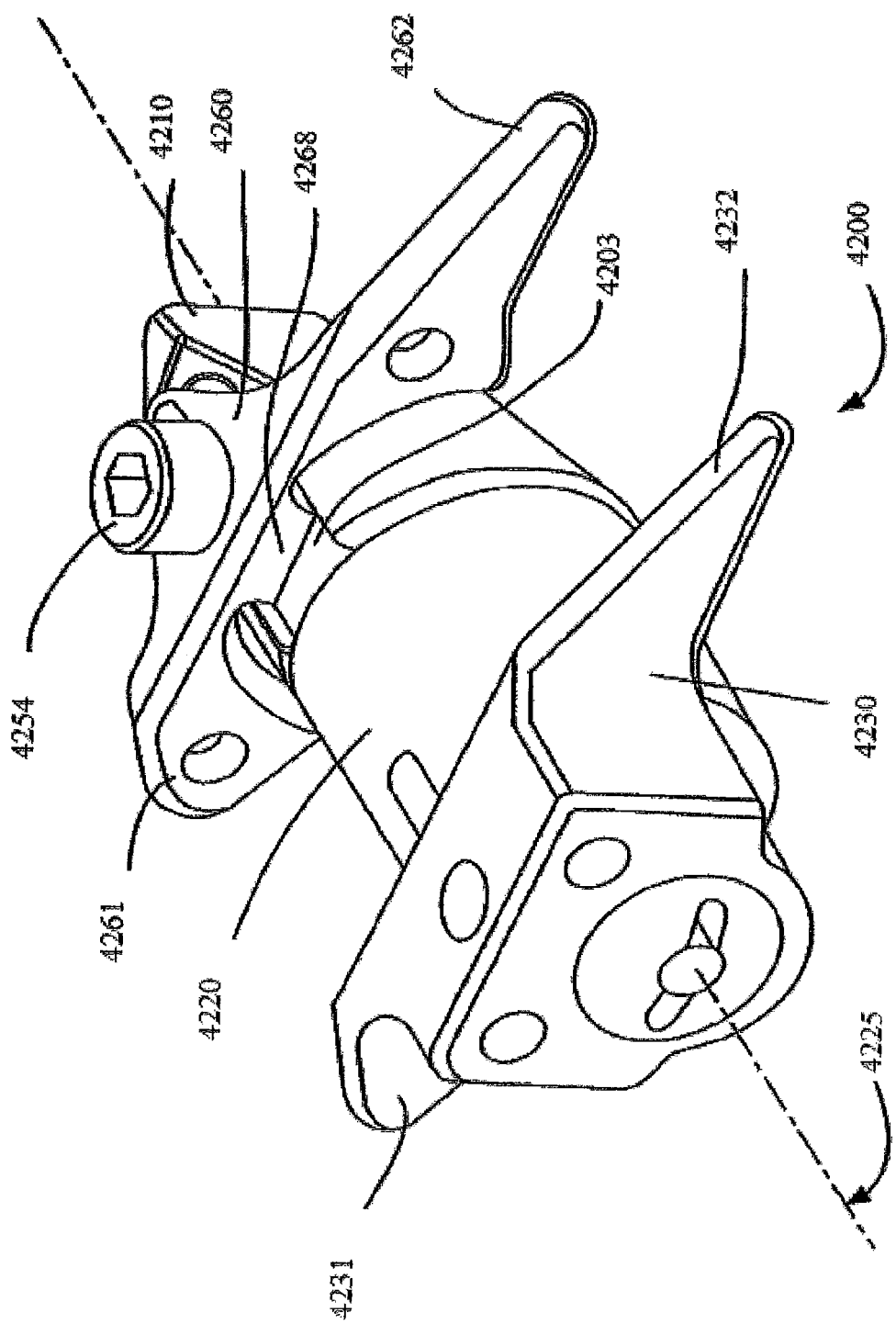
FIG. 48B is a perspective view of an implant including a rotatable spacer having an elliptical cross-section, a distraction guide, a first wing, and a second wing connectable with the distraction guide.

FIG. 48B is a perspective view of an implant as described in U.S. Pat. No. 6,695,842 to Zucherman, et al, incorporated herein by reference. The implant 4200 has a main body that includes a spacer 4220, a first wing 4230, a lead-in tissue expander 4210 (also referred to herein as a distraction guide) and an alignment track 4203. The main body of the implant 4200 is inserted between adjacent spinous processes and remains in place (where desired) without attachment to the bone or ligaments. The distraction guide 4210 includes a tip from which the distraction guide 4210 expands, the tip having a diameter sufficiently small such that the tip can pierce an opening in an interspinous ligament and/or can be inserted into a small initial dilated opening. The diameter and/or cross-sectional area of the distraction guide 4210 gradually increases until it is substantially similar to the diameter of the spacer 4220. The tapered front end eases the ability of a physician to urge the implant 4200 between adjacent spinous processes. When urging the main body of the implant 4200 between adjacent spinous processes, the front end of the distraction guide 4210 distracts the adjacent spinous processes and dilates the interspinous ligament so that a space between the adjacent spinous processes is approximately the diameter of the spacer 4220.

As shown in FIG. 48B, the spacer 4220 is elliptically shaped in cross-section, and can swivel so that the spacer 4220 can self-align relative to the uneven surfaces of the spinous processes. Self-alignment can ensure that compressive loads are distributed across the surface of the bone. As contemplated in Zucherman '842, the spacer 4220 can have, for example, a diameter of six millimeters, eight millimeters, ten millimeters, twelve millimeters and fourteen millimeters. These diameters refer to the height by which the spacer 4220 distracts and maintains apart the spinous process. For an elliptically shaped spacer 4220, the selected height (i.e., diameter) is the minor dimension measurement across the ellipse. The major dimension is transverse to the alignment of the spinous process, one above the other.

The first wing 4230 has a lower portion 4231 and an upper portion 4232. The upper portion 4232 is shaped to accommodate the anatomical form or contour of spinous processes (and/or laminae) of preferably the L4 (for an L4-L5 placement) or L5 (for an L5-S1 placement) vertebra. The same shape or variations of this shape can be used to accommodate other motion segments, such as motion segments in the cervical and thoracic regions. The lower portion 4231 can also be rounded to accommodate the spinous processes. The lower portion 4231 and upper portion 4232 of the first wing 4230 act as a stop mechanism when the implant 4200 is inserted between adjacent spinous processes. The implant 4200 cannot be inserted beyond the surfaces of the first wing 4230. Additionally, once the implant 4200 is inserted, the first wing 4230 can prevent some side-to-side, or posterior-to-anterior movement of the implant 4200.

As with the implant 4100 of FIG. 48A, the implant 4200 of FIG. 48B further includes a second wing 4260. Similar to the first wing 4230, the second wing 4260 includes a lower portion 4261 and an upper portion 4262 sized and/or shaped to accommodate the anatomical form or contour of the spinous processes and/or lamina. The second wing 4260 can be secured to the main body of the implant 4200 with a fastener 4254. The second wing 4260 also has an alignment tab 4268. When the second wing 4260 is initially placed on the main body of the implant 4200, the alignment tab 4268 engages the alignment track 4203. The alignment tab 4268 slides within the alignment track 4203 and helps to maintain the adjustable wing 4260 substantially parallel with the first wing 4230. When the main body of the implant 4200 is inserted into the patient and the second wing 4260 has been attached, displacement along the longitudinal axis 4225 in either the direction of insertion or the direction opposite insertion can be limited or blocked.

Further, the second wing 4260 also can prevent some side-to-side, or posterior-to-anterior movement.

For both the implant 4100 of FIG. 48A and the implant 4200 of FIG. 48B, where a second wing 4160,4260 is connected with the implant 4100,4200 after the implant 4100, 4200 is positioned between the spinous processes, a procedure for positioning such an implant 4100,4200 and subsequently connecting the second wing 4160,4260 with the implant 4100,4200 can require a bilateral approach wherein a physician must access both sides of the interspinous ligament, a first side to pierce and/or distract the interspinous ligament and position the implant 4100,4200 so that the movement in the direction of insertion is satisfactorily limited by the first wing 4130,4230, and a second side to attach the second wing 4160,4260 such that movement in the direction opposite insertion is satisfactorily limited by the second wing 4160, 4260.

Implants Having Deployable Second Wing

Figure 49A:
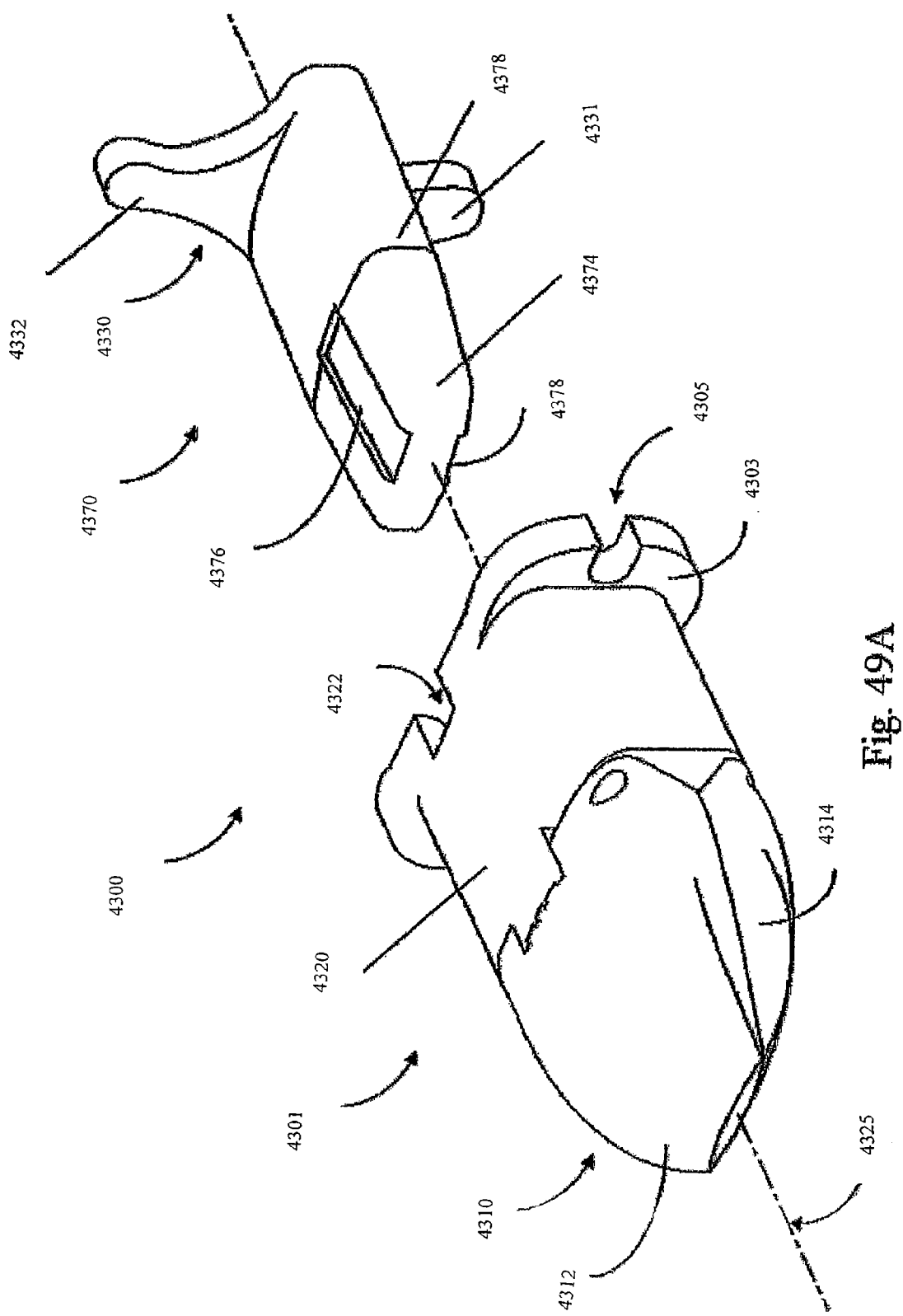
FIG. 49A is a perspective view of an implant in accordance with an embodiment of the present invention including a main body and an insert, the main body having a distraction guide, a spacer, and a first wing.
Figure 49B:
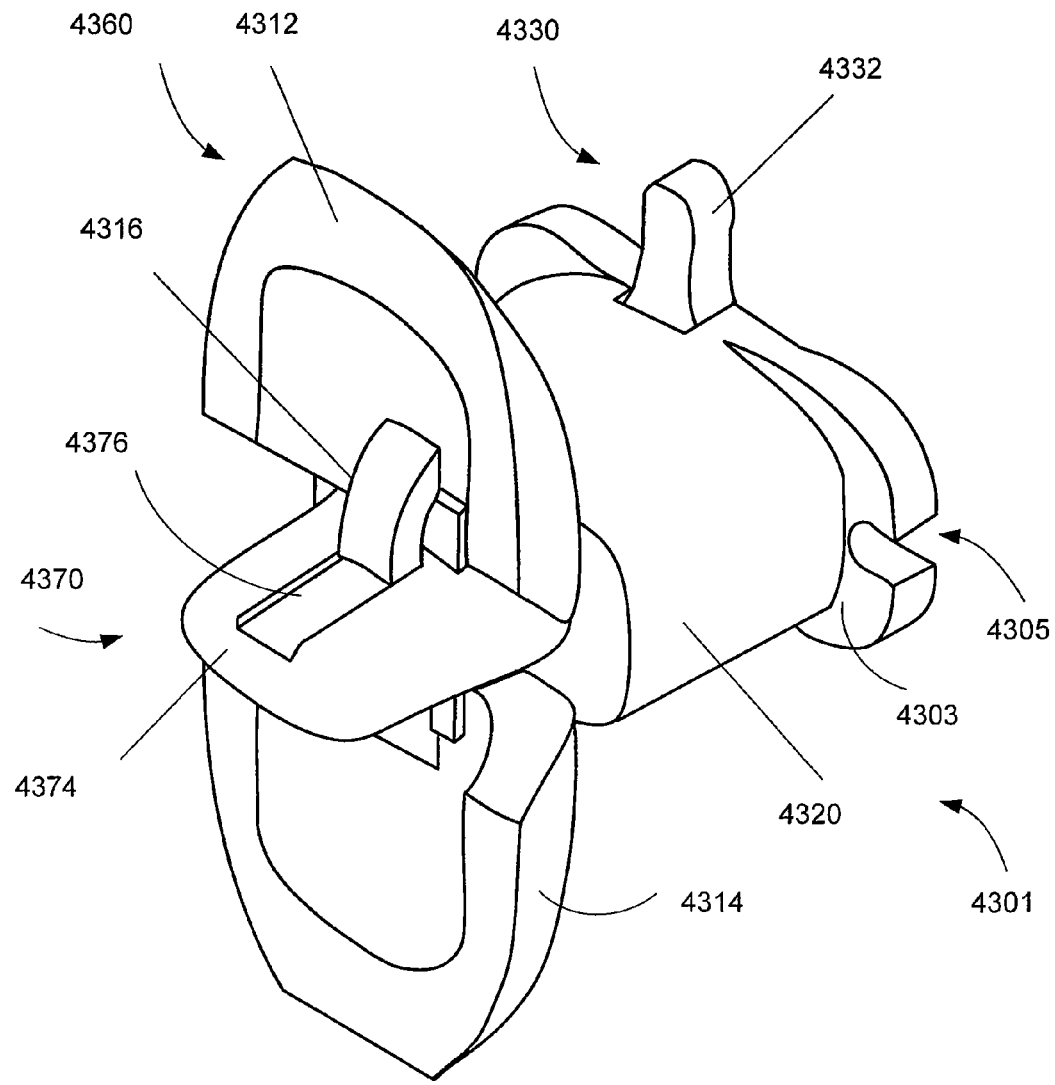
FIG. 49B is a perspective view of the implant of FIG. 49A wherein the insert is positioned within the main body, causing the distraction guide associated with the main body to limit or block movement of the implant when positioned between adjacent spinous processes.

Referring to FIGS. 49A through 49B, implants 4300 and methods for positioning such implants in accordance with the present invention can, in an embodiment, include a deployable second wing 4360 associated with a main body 4301 such that the second wing 4360 can be deployed with a physician needing only to access a first side of spinous processes to limit or block movement along the longitudinal axis 4325. As shown in FIG. 49A, the implant 4300 includes a main body 301 having a fixed spacer 4320 and a distraction guide 4310. The distraction guide 4310 comprises a first winglet (also referred to herein as an upper winglet) 4312 and a second winglet (also referred to herein as a lower winglet) 4314, and when arranged in a first configuration can include a tip from which the distraction guide 4310 expands, the tip having a diameter sufficiently small such that the tip can pierce an opening in an interspinous ligament and between spinous processes and/or can be inserted into a small initial dilated opening. The diameter and/or cross-sectional area of the distraction guide 4310 is then gradually increased until it is substantially similar to the diameter of the spacer 4320. In this respect, the distraction guide 4310 of FIG. 49A can resemble a distraction guide as described above when arranged in the first configuration. The winglets 4312,4314 can be hinged or otherwise pivotably connected with the main body 4301 such that the winglets 4312,4314 can be arranged in a second configuration (FIG. 49B) once the implant 4300 is positioned between spinous processes. In a second configuration one or both of the winglets 4312,4314 abut at least one of the spinous processes and/or related tissues when urged in a direction opposite from insertion, thereby limiting motion along the longitudinal axis 4325. Thus when arranged in a second configuration, the distraction guide 4310 becomes a second wing 4360, as shown in FIG. 49B.

The implant 4300 includes an insert 4370 having an insert body 4372 and a first wing 4330. As shown in FIG. 49B, the insert 4370 can be mated with the main body 4301 to arrange the distraction guide 4310 of the implant 4300 in the second configuration, thereby deploying the second wing 4360. To facilitate mating of the main body 4301 and the insert 4370, the spacer 4320 includes a cavity sized and shaped for receiving the insert body 4372 and accessible from a distal end of the main body 4301. A portion of the upper winglet 4312 and the lower winglet 4314 can extend at least partially into the cavity so that when the insert body 4372 is received within the cavity, the insert body 4372 displaces the portions, causing the distraction guide 4310 to be arranged in the second configuration. In the embodiment shown, the upper winglet 4312 and the lower winglet 4314 each include a lever 4316,4318 comprising a curved protrusion that protrudes into the cavity when the distraction guide 4310 is in the first configuration. As the insert body 4372 of the insert 4370 fills the cavity, the insert body 4372 contacts the first lever 4316 and the second lever 4318, applying a force to the first lever 4316 and the second lever 4318 which translates into a pivoting motion of the hinged upper winglet 4312 and the hinged lower winglet 4314. The insert body 4372 can optionally have a tapered proximal end 4374 having a first groove 4376 and a second groove 4378 corresponding to the first lever 4316 and the second lever 4318, respectively. The tapered shape of the proximal end 4374 allows the upper winglet 4312 and lower winglet 4314 to be deployed gradually, fully deploying as the insert body 4372 is fully seated within the cavity. The main body 4301 is shown including a flange 4303 in which is formed notches 4305 to receive an insertion tool (not shown), for example. As the insert body 4372 is seated within the cavity, an upper tab 4332 and a lower tab 4331 of the first wing 4330 seats within cut-outs 4322 of the flange 4303.

Figure 50A:
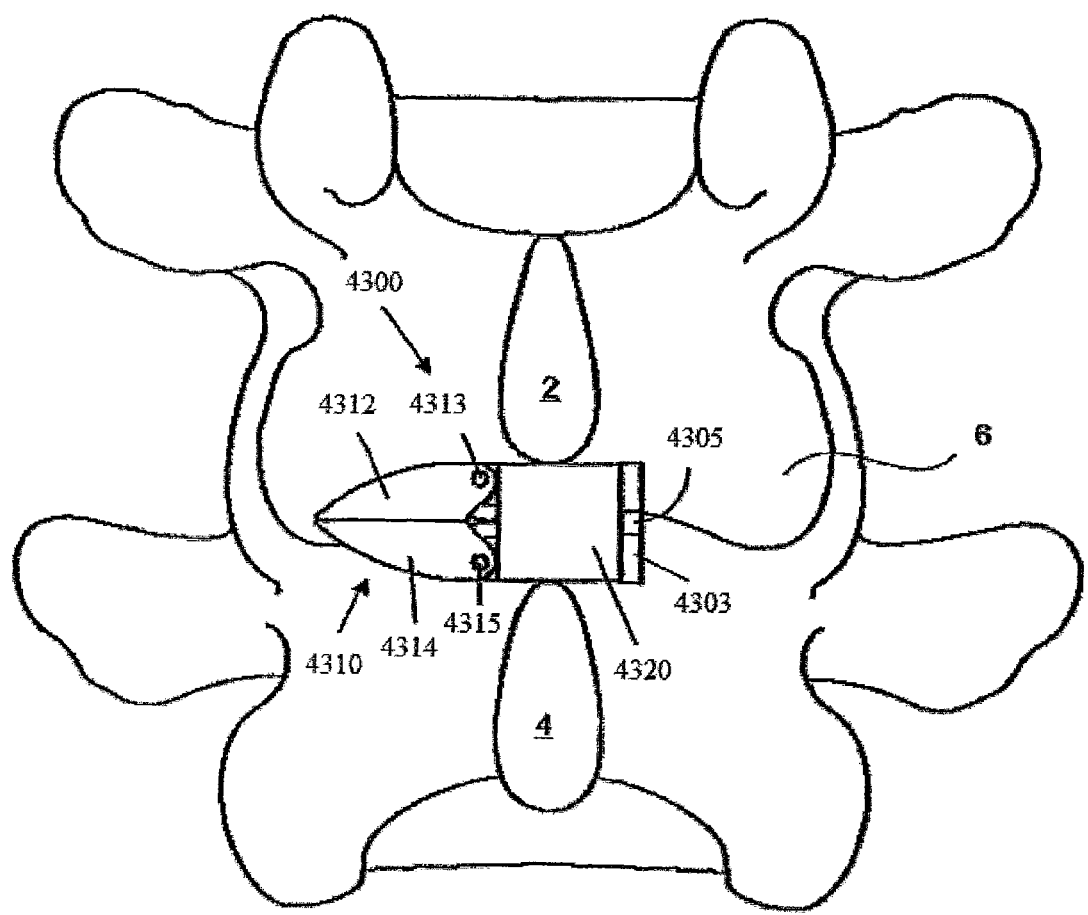
FIG. 50A is a side view of the main body of the implant of FIGS. 49A and 49B positioned between adjacent spinous processes.

Referring to FIG. 50A, the main body 4301 of the implant 4300 is shown positioned between adjacent spinous processes of the targeted motion segment. The motion segment shown is within the lumbar region, but in other embodiments, particularly where a fixed spacer 4320 is used, implants 4300 in accordance with the present convention can be positioned at motion segments of the thoracic and cervical region. The main body 4301 is positioned as shown by initially approaching the interspinous ligament between the upper and lower adjacent spinous processes 2,4 through an opening to the right of the interspinous ligament, roughly posterior to the right inferior articular facet 6 of the vertebrae from which the upper spinous process 2 extends. The main body 4301 can be associated with one or more insertion tools (not shown), and the distraction guide 4310 can be arranged in the first configuration. The tip of the distraction guide 4310 is positioned roughly adjacent to a point along the interspinous ligament, and the distraction guide 4310 is then urged through the interspinous ligament, piercing the interspinous ligament and/or separating and distracting fibers of the interspinous ligaments. The main body 4301 is then urged through the interspinous ligament until the spacer 4320 is positioned between the adjacent spinous processes 2,4 so that the spacer 4320 supports a load applied by the spinous processes 2,4.

Figure 50B:
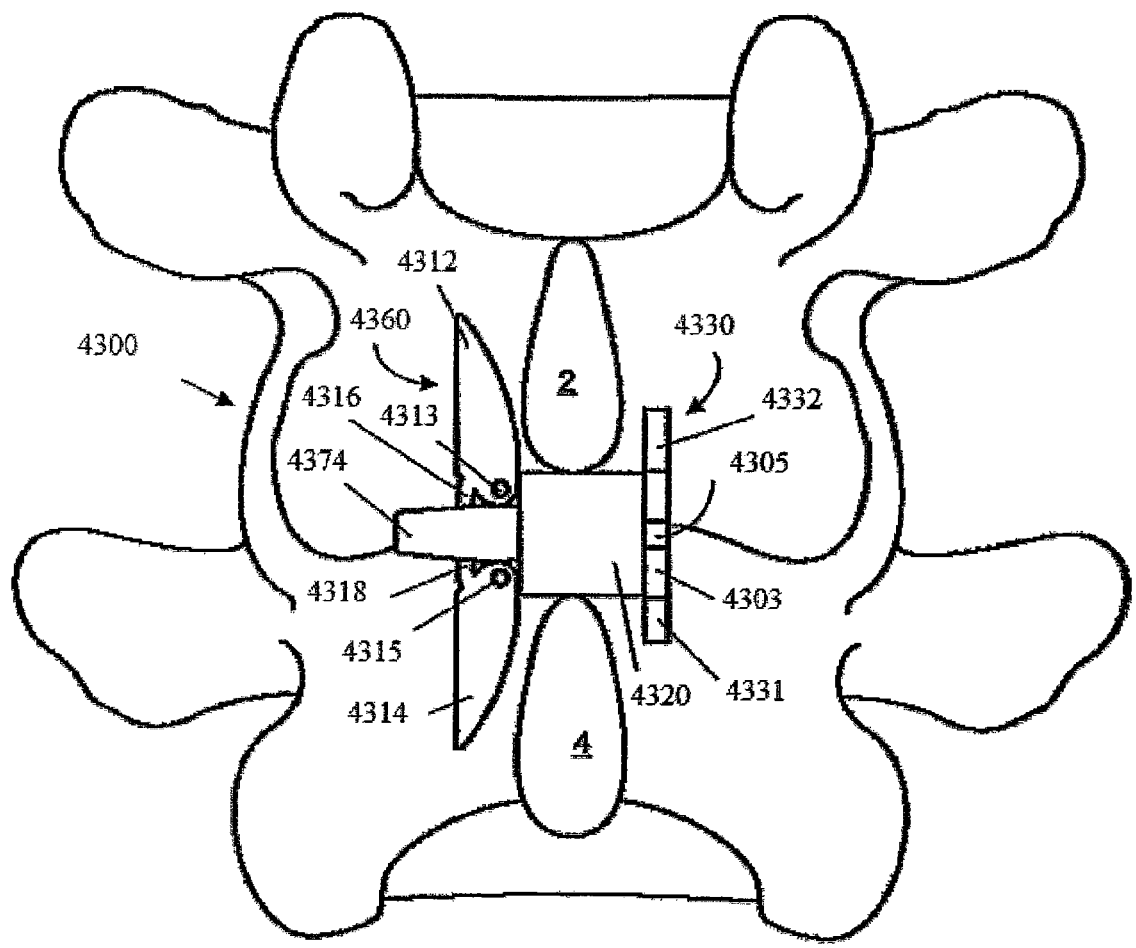
FIG. 50B is a side view of the implant of FIG. 50A wherein the insert is positioned within the main body.

Referring to FIG. 50B, once the implant 4300 is positioned as desired, the insertion tools can be removed from the opening and the insert 4370 can be positioned at the distal end of the main body 4301. The insert body 4372 can be urged into the cavity within the main body 4301 until the proximal end 4374 of the insert body 4372 contacts the first lever 4316 and the second lever 4318. The insert 4370 can then be further urged along the longitudinal axis 4325 so that the insert body 4372 urges the first lever 4316 and the second lever 4318 away from the insert body 4372, causing the upper winglet 4312 and the lower winglet 4314 to pivot about the first hinge 4313 and the second hinge 4315, respectively. As the first lever 4316 and the second lever 4318 are displaced from the cavity, the first lever 4316 and the second lever 4318 are guided along corresponding grooves 4376,4378 of the tapered proximal end 4374. As the insert body 4372 seats within the cavity of the main body 4301, the upper winglet 4312 and the lower winglet 4314 deploy as a second wing 4360. The insertion tool can be removed from the incision once the insert body 4372 is seated within the main body 4301. As can be seen a portion of the upper spinous process and a portion of the lower spinous process are sandwiched between the first wing 330 and the second wing 4360, limiting motion along the longitudinal axis 4325. Implants and methods for positioning such implants between spinous processes in accordance with the present invention are not meant to be limited to embodiments as described above and otherwise herein, but rather are meant to include any implant having a second wing deployable by urging an insert within a main body positioned between adjacent spinous processes. Myriad different variations may be readily apparent to one of ordinary skill in the art. For example, in an alternative embodiment, the main body 4301 of the implant 4300 of FIGS. 49A through 50B can include a lower winglet 4314 pivotably associated with the main body 4301 while an upper winglet 4312 is fixedly associated with the main body 4301. An insert 4370 can be adapted to deploy only the lower winglet 4314 when seated within the cavity of the main body 4301.

In other embodiments, a first wing 4310 can extend from the main body 4301 rather than, or in addition to, a first wing extending from the insert 4370. When the main body 4301 is initially positioned between the adjacent spinous processes, movement of the main body 4301 along the longitudinal axis 4325 can be limited in the direction of insertion. As the first wing 4310 extending from the main body 4301 contacts one or both of the adjacent spinous processes, further movement of the main body 4301 in the direction of insertion can be limited or blocked. The first wing 4310 can thus act as a hard stop, allowing the main body 4301 to be positioned without requiring a position of the main body 4301 along the spinous processes to be estimated, thereby easing implantation.

Figure 51:
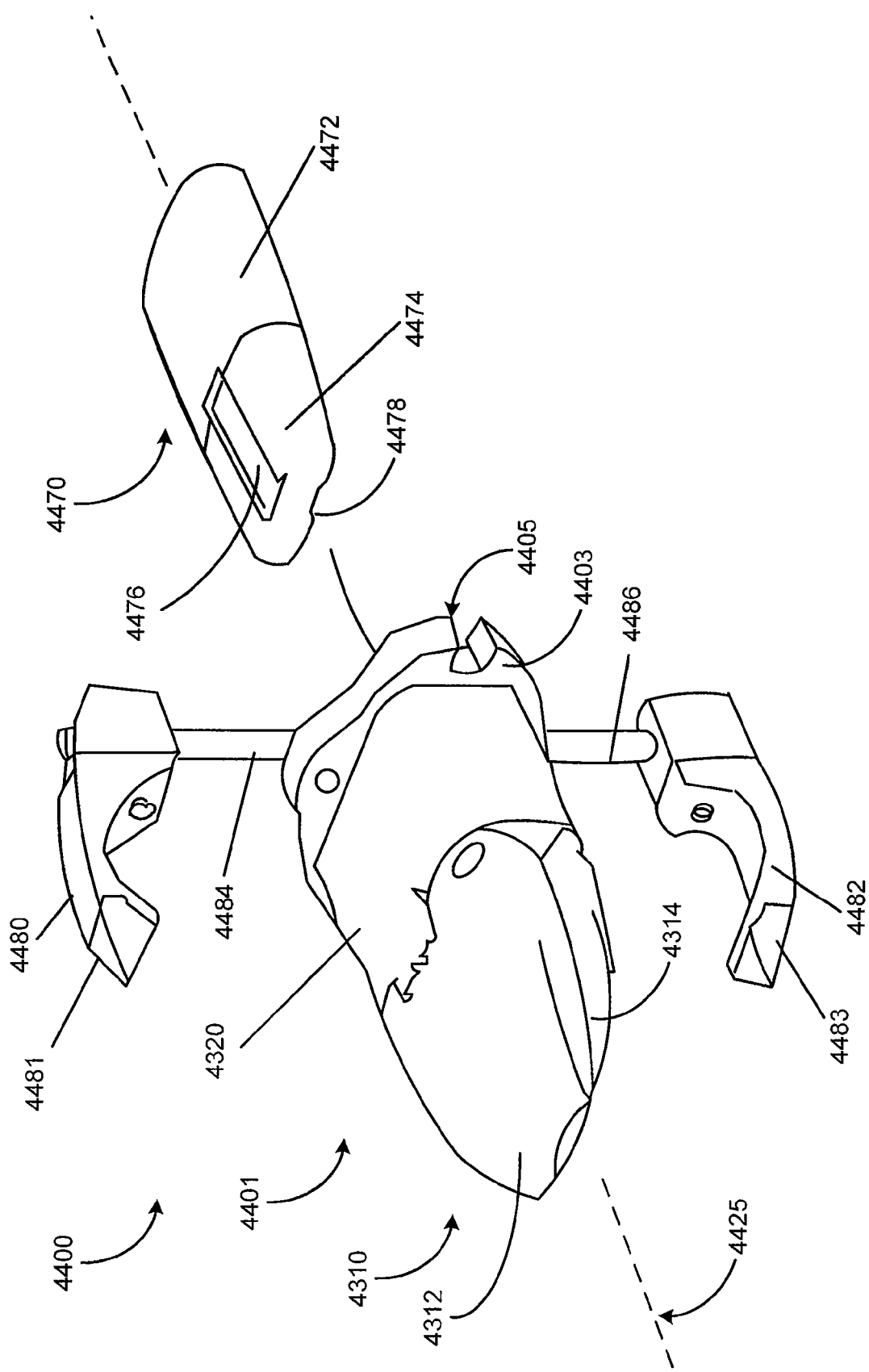
FIG. 51 is a perspective view of an implant in accordance with an alternative embodiment wherein the main body includes hooks to limit relative movement of adjacent spinous processes during flexion motion.

Referring to FIG. 51, in still further embodiments implants 4400 in accordance with the present invention can include one or both of a first engagement element (also referred to herein as an upper hook) 4480 and a second engagement element (also referred to herein as a lower hook) 4482 for limiting flexion motion in a motion segment. For example, similar hooks have been described in greater detail in U.S. Pat. No. 6,451,019 issued Sep. 17, 2002 to Zucherman et al. and U.S. Pat. No. 6,652,527 issued Nov. 25, 2003 to Zucherman et al., both incorporated herein by reference. Implants in accordance with the present invention can include such arrangements. The implant 4400 shown in FIGS. 51 and 52 includes an upper hook 4480 extending from an upper connection rod 4484 rotatably associated with the main body 4401 and a lower hook 4482 extending from a lower connection rod 4486 rotatably associated with the main body 4401. Alternatively, the connection rods 4484,4486 can be fixedly associated with the main body 4401.

The hooks 4480,4482 include tapered proximal ends 4481, 4483 that act as lead-in tissue expanders to distract interspinous ligaments of the motion segments above and below the targeted motion segment. As the main body 4401 is positioned between adjacent spinous processes, the tapered proximal ends 4481,4483 of the upper and lower hooks 4480,4482 can likewise pierce and/or distract interspinous ligaments so that the upper and lower hooks 4480,4482 can be properly positioned to limit or restrain flexion motion of the targeted motion segment when the main body 4401 is in place. As shown, the hooks 4480,4482 can be pivotably associated with the connection rods 4484,4486 so that the hooks 4480,4482 can be rotated relative to the connection rods 4484,4486, thereby allowing a physician to improve contact and spread loads between the hooks 4480,4482 and corresponding spinous processes 2,4. The rotatable upper connection rod 4484 and lower connection rod 4486 can provide flexibility in placement, so that where an anatomy varies between patients and varies between motion segments such that the arrangement of a minor dimension and major dimension of the implant 44400 about the longitudinal axis 4425 varies, the implant 4400 can be accommodated.

Figure 52:
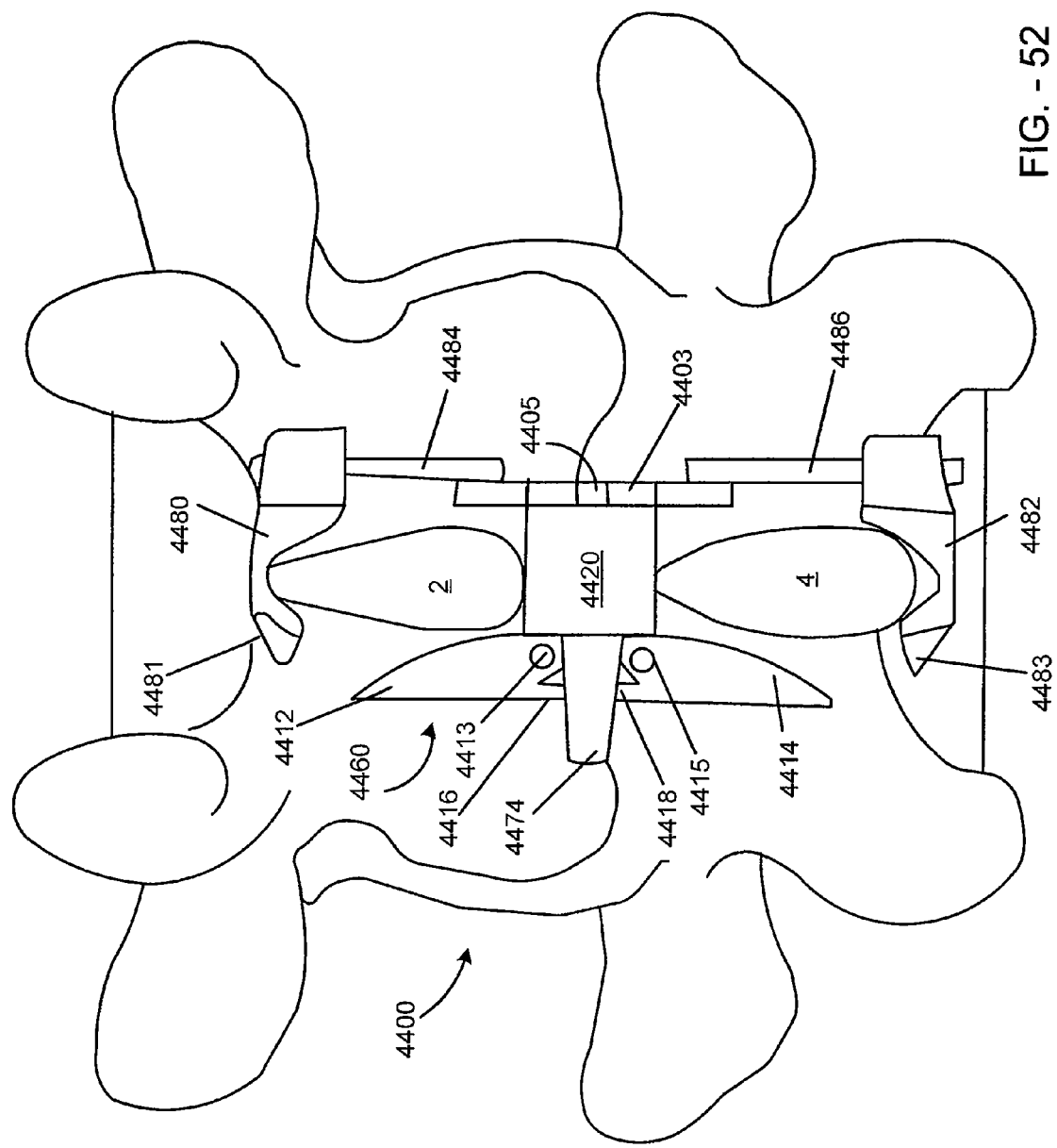
FIG. 52 is a side view of the implant of FIG. 51 positioned between adjacent spinous processes and arranged so that the hooks confine the adjacent spinous processes.

FIG. 52 is a posterior view of the implant 4400 positioned between adjacent spinous processes 2,4 and having an upper hook 4480 and a lower hook 4482 arranged so that both flexion and extension is limited as desired. Further, the second wing 4460 is deployed to limit movement of the implant 4400 along the longitudinal axis 4425. The upper hook 4480 and the lower hook 4482 prevent movement along the longitudinal axis 4425 in the direction opposite insertion, making a first wing unnecessary.

Figure 53A:
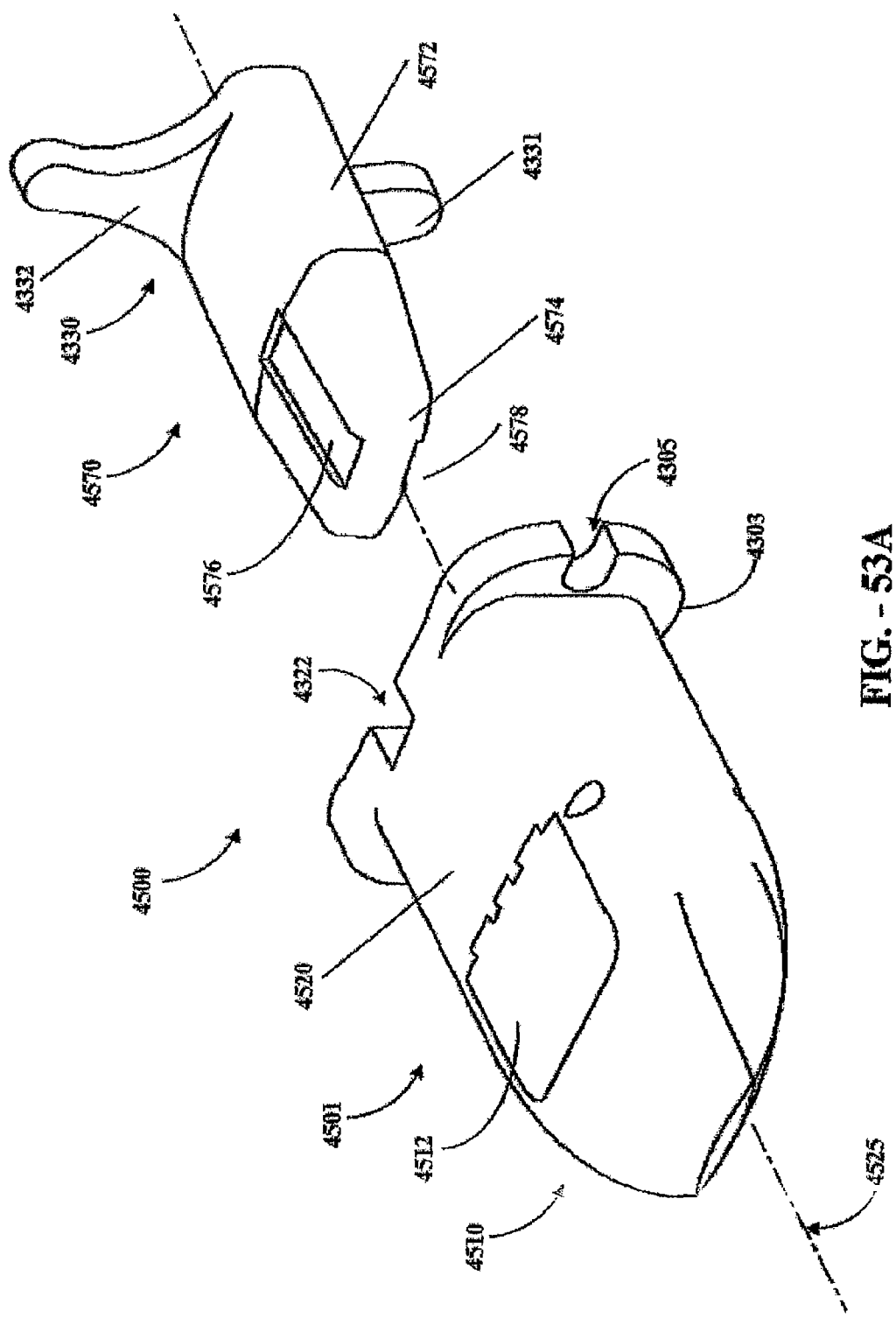
FIG. 53A is a perspective view of still another embodiment of an implant in accordance with the present invention, wherein a first section and a second section of a distraction guide are deployable to form a second wing.
Figure 53B:
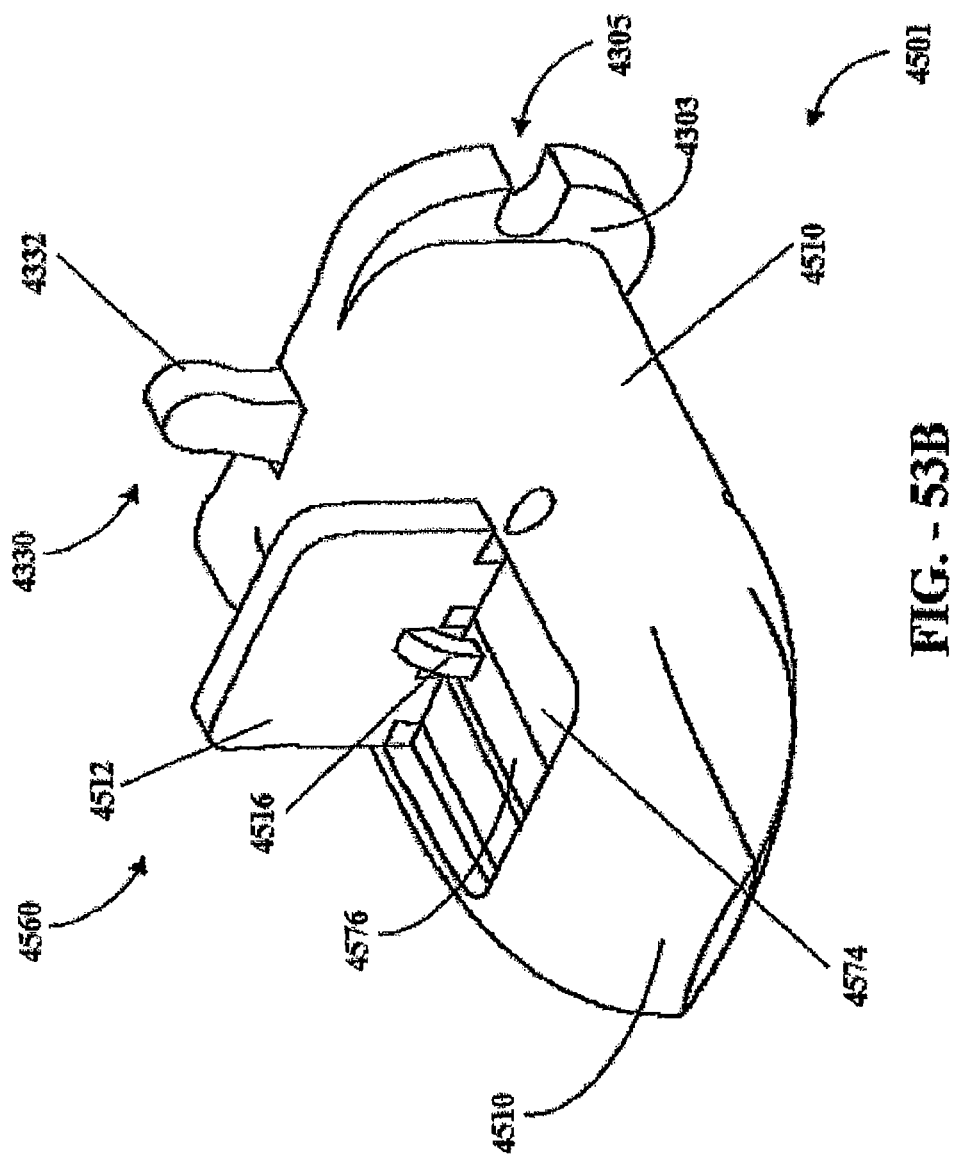
FIG. 53B is a perspective view of the implant of FIG. 53A wherein the insert is positioned within the main body, causing the first section and the second section of the distraction guide to deploy.
Figure 54A:
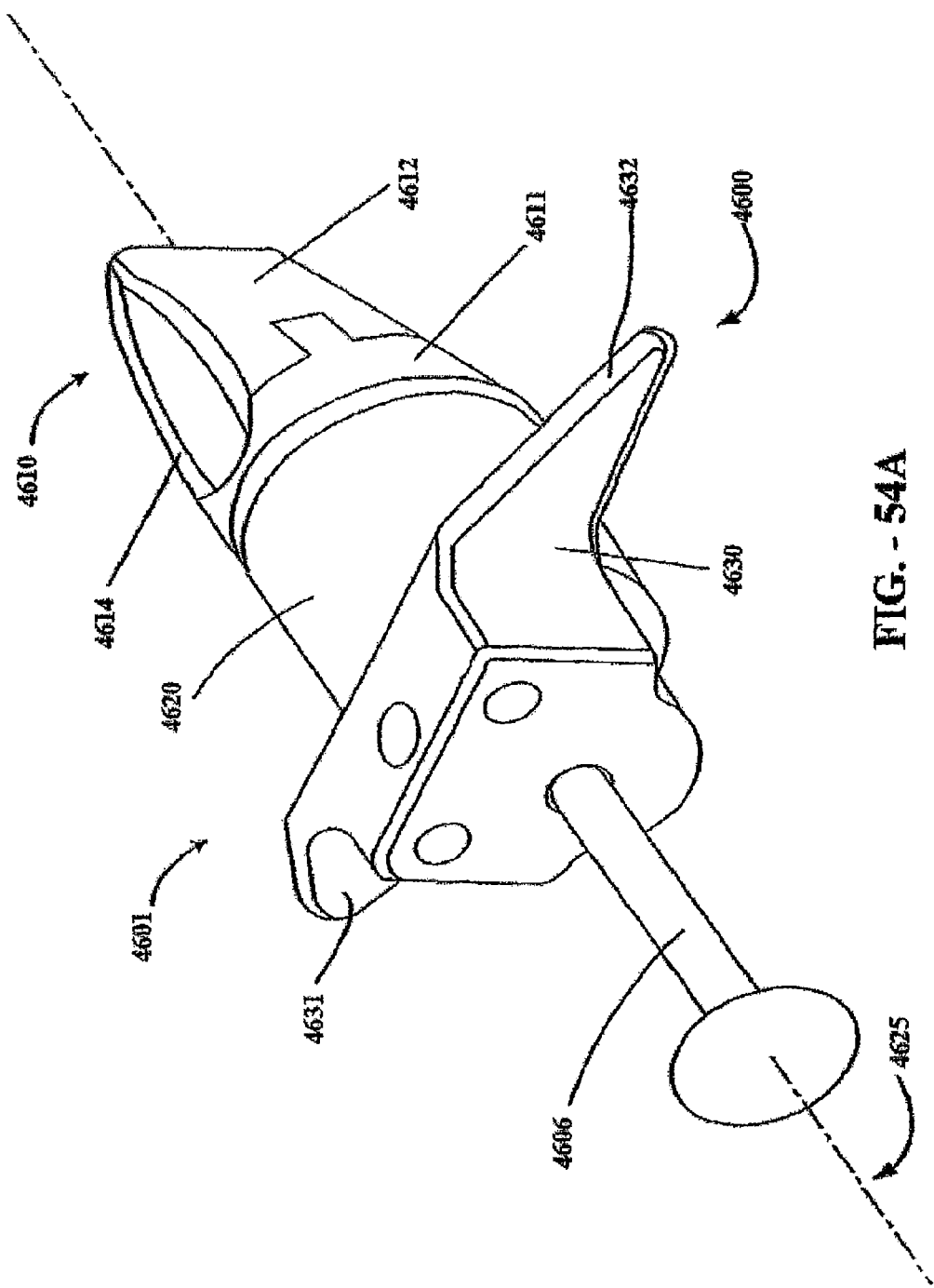
FIG. 54A is a perspective view of a still further embodiment of an implant in accordance with the present invention including a rotatable spacer.
Figure 54B:
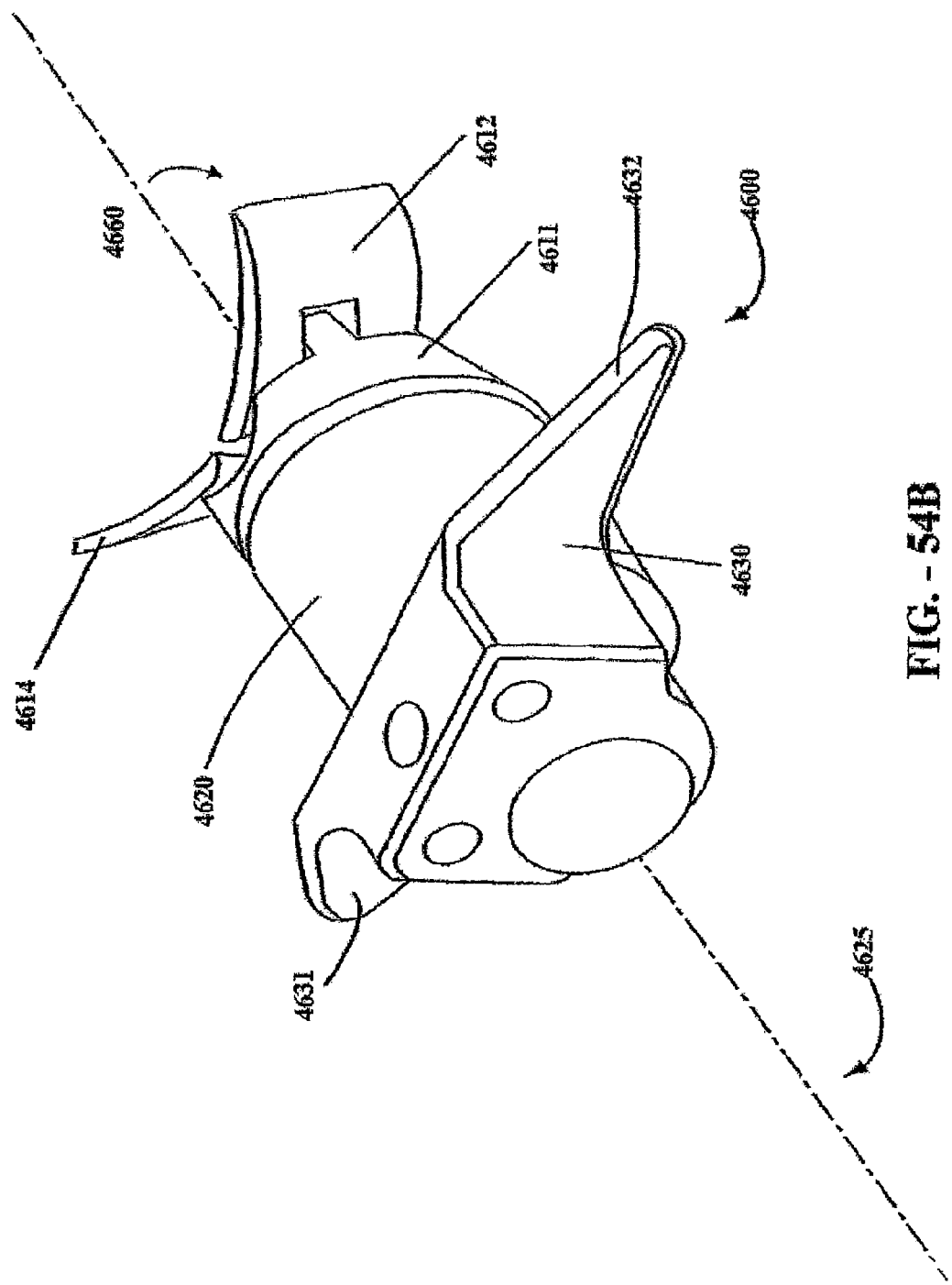
FIG. 54B is a perspective view of the implant of FIG. 54A wherein the insert is positioned within a central body so that the distraction guide deploys as a second wing.

Referring to FIGS. 53A and 53B, in still other embodiments implants 4500 and methods for positioning such implants 4500 between spinous processes in accordance with the present invention can include a distraction guide 4510 wherein portions of the distraction guide 510 can be extended from the distraction guide 4510 to form an upper winglet 4512 and a lower winglet 4514, respectively, of a second wing 4560 by positioning an insert 4570 within a cavity of the main body 4501. This is in contrast to the above embodiment where the entire distraction guide is formed by the winglets. In this embodiment, the winglet 4512,4514 extend out the side of the distraction guide 4510. When not extended, as seen in FIG. 53A, the winglet 4512,4514 partially form the sides of the distraction guide 4510. Such embodiments are contemplated to be useful where it is desired that the second wing 4560 have a limited height relative to implants 4300,4400 as described above where the entire distraction guide 4310 is deployed (see FIG. 49A through 50B). For example, where implants 4500 are to be positioned at adjacent motion segments, it can be desired that the second wings 4560 of the implants 4500 do not interfere with one another implant, for example during an extension motion when compressive loads are applied to the implants 4500. As with implants described above, one of ordinary skill in the art can appreciate the myriad different variations of the implant 4500 of FIGS. 53A and 53B. For example, in alternative embodiments the upper winglet 4512 and the lower winglet 4514 can have some other shape. For example, the positions of the upper winglet 4512 and lower winglet 4514 are staggered so that implants 4500 positioned at adjacent motion segments can be more easily positioned without interfering with one another. Such staggering can also accommodate anatomies where one of the upper and lower spinal processes is wider than the other. With staggering, for example, the upper winglet 4512 can be pivotably mounted on the distraction guide 4510 at a position less distant from the distraction end 4511 than the location where the lower winglet 4514 is pivotably mounted on the distraction guide 4510. In still other embodiments, the upper winglet 4512 and the lower winglet 4514 can have some other shape. Referring to FIGS. 54A through 55, in still further embodiments of implants 4600 in accordance with the present invention, the main body 4601 can include a hollow central body 4605 (shown in FIGS. 54C and 54D) extending from a first wing 4630. A rotatable spacer 4620 is disposed about the hollow central body 4605. The implant 4600 can include a spacer 4620 that resembles spacers, for example, as described above in FIG. 48B. A distraction guide 4610 can extend from the hollow central body 4605 and can include an upper winglet 4612 and a lower winglet 4614, one or both of which can be pivotably associated with a main portion 4611 of the distraction guide 4610 so that the upper winglet 4612 and/or the lower winglet 4614 can be deployed as a second wing 4660. A pin 4606 can be inserted into the hollow central body 4605 to deploy the second wing 4630. Referring to FIG. 54B, once the pin 4606 is seated within the main body 4601, the upper winglet 4612 and the lower winglet 4614 can be pivoted away from each other so that the upper winglet 4612 and the lower winglet 4614 limit or block motion along the longitudinal axis 4625 in the direction opposite from insertion. The upper winglet 4612 and the lower winglet 4614 thus act as a second wing 4660.

Figure 54C:
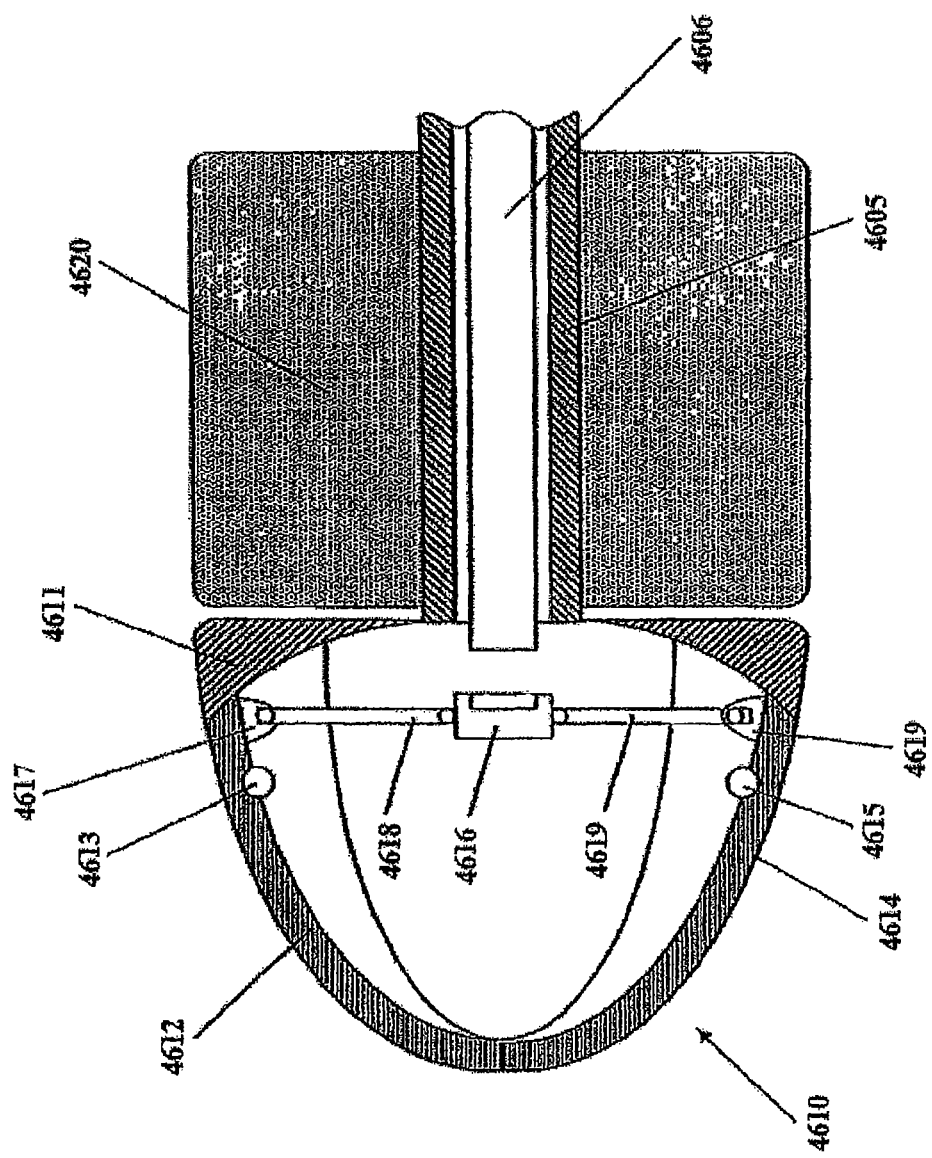
FIG. 54C is a cross-sectional side view of distraction guide of FIG. 54A.
Figure 54D:
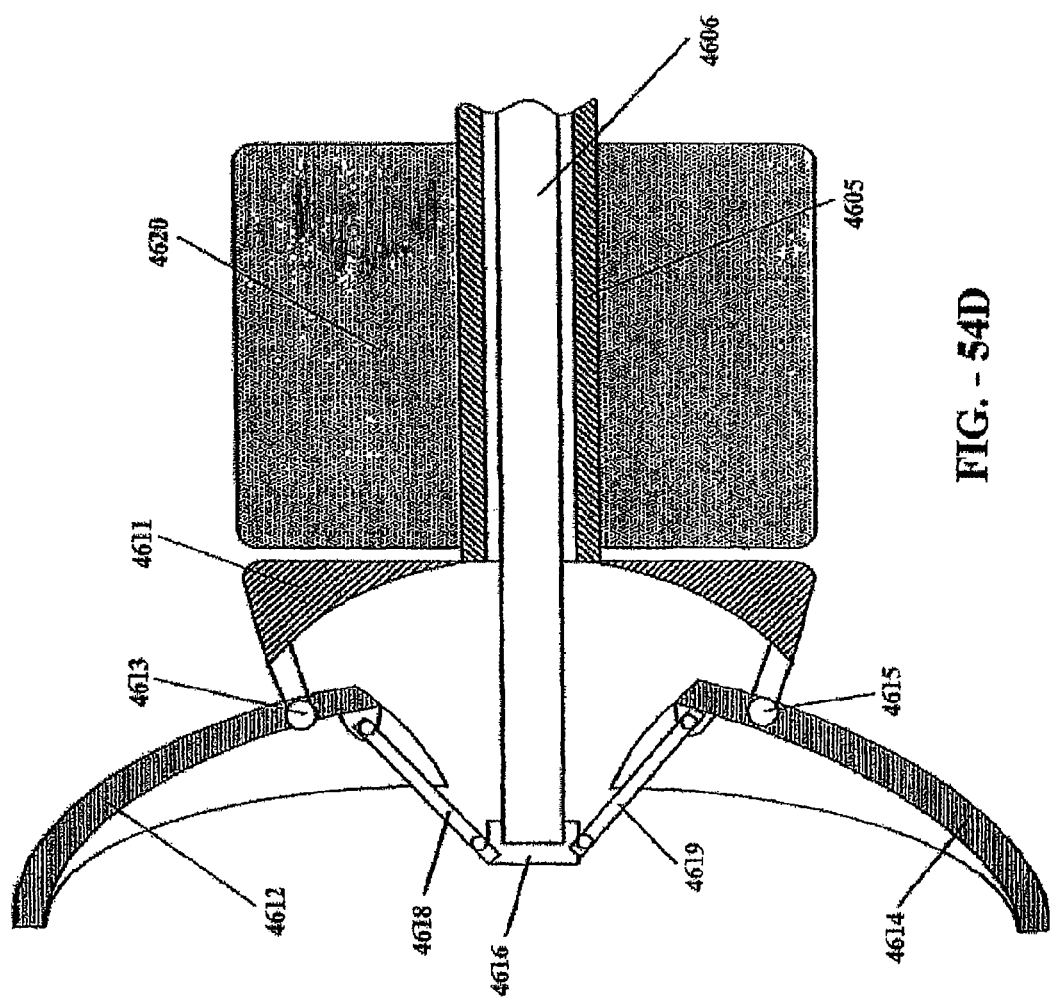
FIG. 54D is a cross-sectional side view of distraction guide of FIG. 54B.
Figure 55:
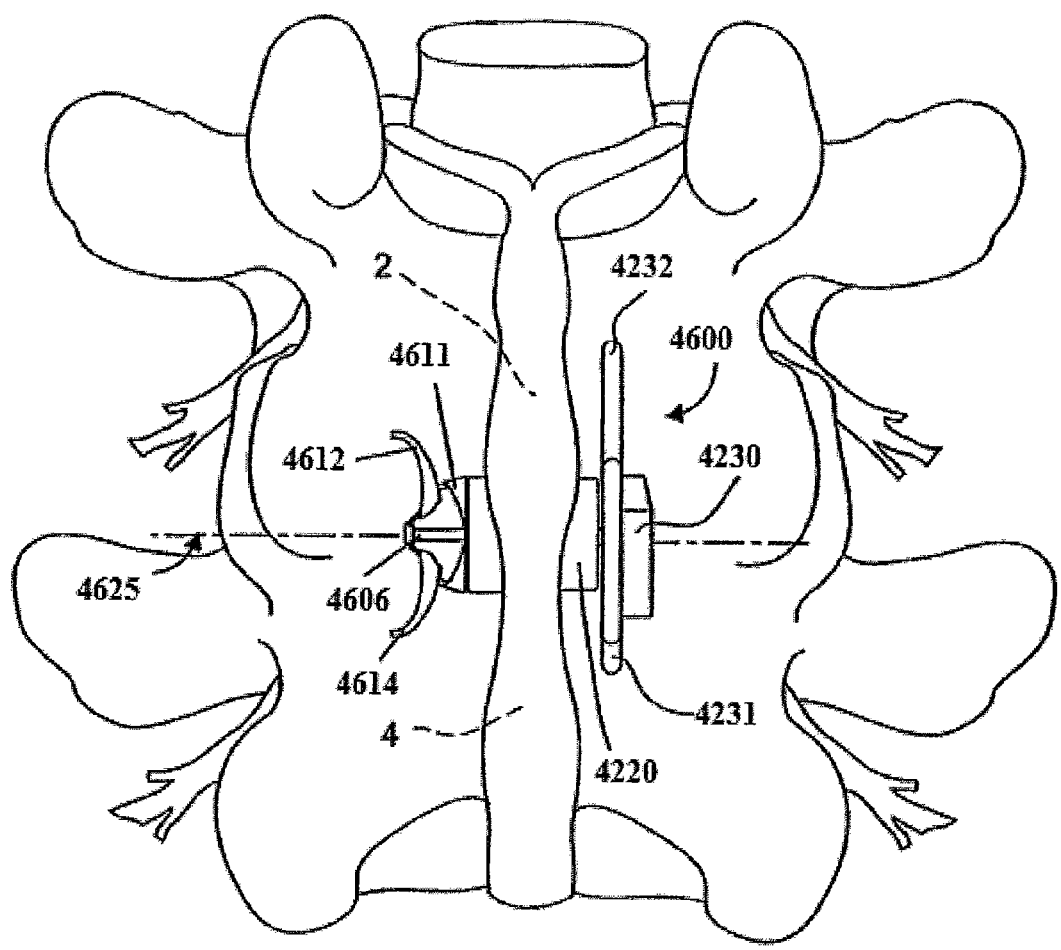
FIG. 55 is a side view of the implant of FIGS. 54A-54D positioned between adjacent spinous processes.

Referring to the partial cross-sections of FIGS. 54C and 54D, in an embodiment the distraction guide 4610 can include a cup 4616 structure sized and arranged to receive the pin 4606. Bar structures 4618,4619 can be pivotably connected between the cup structure 4616 and one or both of the upper winglet 4612 and the lower winglet 4614 so that when a force is applied to the cup structure 4616 by the pin 4606, the force is further transferred to the upper winglet 4612 and the lower winglet 4614, causing the upper winglet 4612 and the lower winglet 4614 to pivot on hinges 4613,4615 associated with the main portion 4611 of the distraction guide 4610 so that the second wing 4660 is deployed. As can be seen, the pivot points 4613,4615 of the upper winglet 4612 and the lower winglet 4614 are arranged proximally relative to the mount points 4617,4619 of the bar structures 4618,4619, causing the upper winglet 4612 and the lower winglet 4614 to pivot away from one another when the mount points 4617, 4619 are urged together by the insertion of the pin 4606 (as seen in FIG. 54D). In other embodiments, the upper winglet 4612 and the lower winglet 4614 can be caused to pivot away from one another using some other mechanism. Implants in accordance with the present invention are not intended to be limited to such second wing deployment mechanisms as are described in detail herein.

Figure 56A:
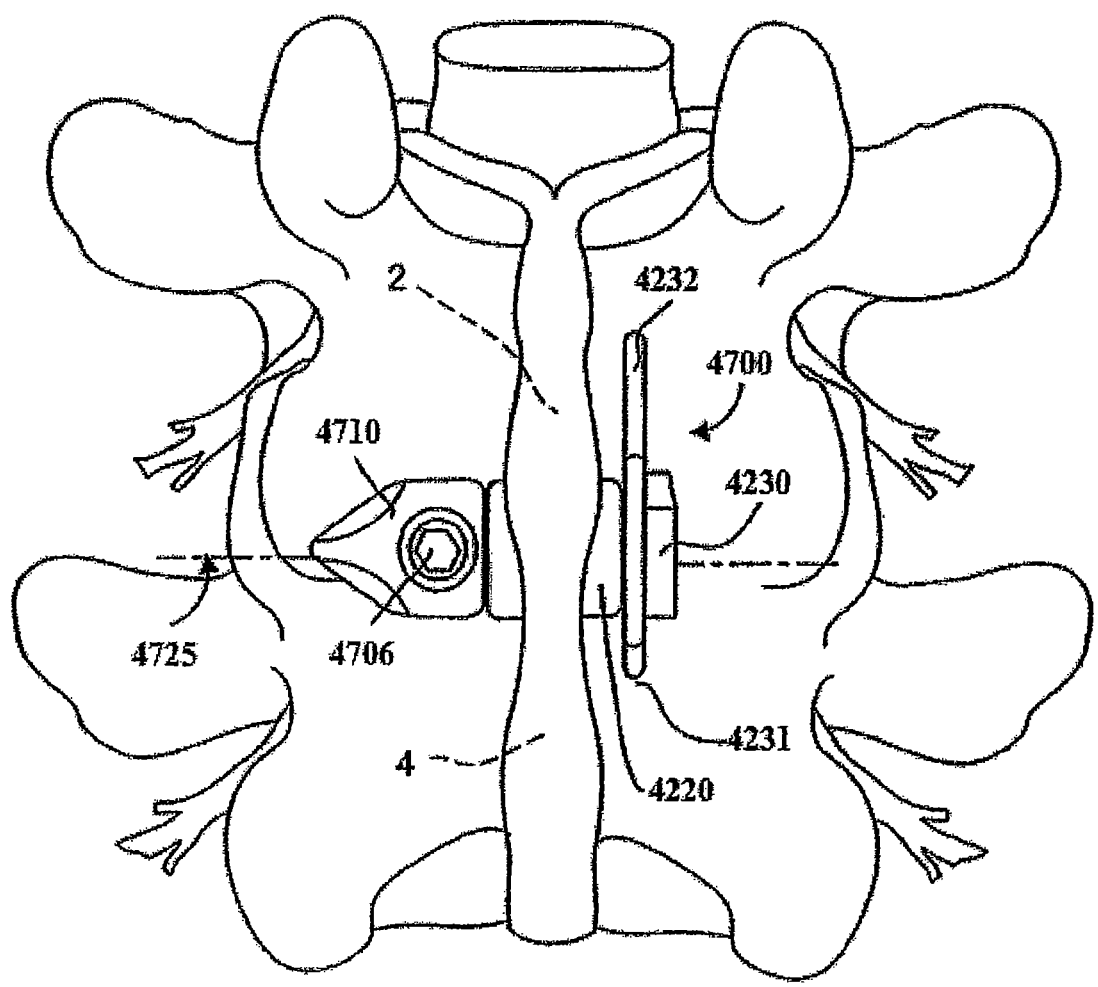
FIG. 56A is a side view of an alternative embodiment of the implant positioned between adjacent spinous processes.
Figure 56B:
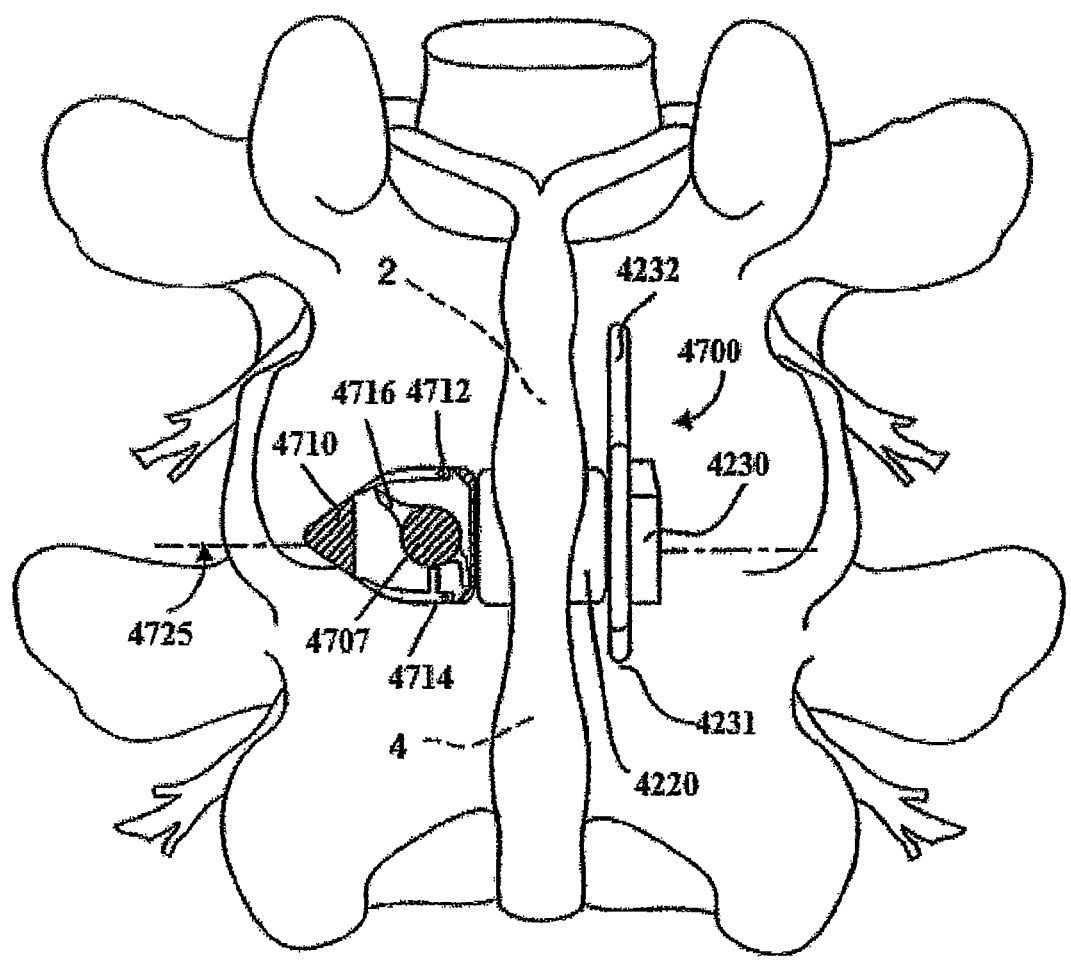
FIG. 56B is a partial cross-section side view of the implant of FIG. 56A showing deployable winglets disposed within a distraction guide of the implant.
Figure 56C:
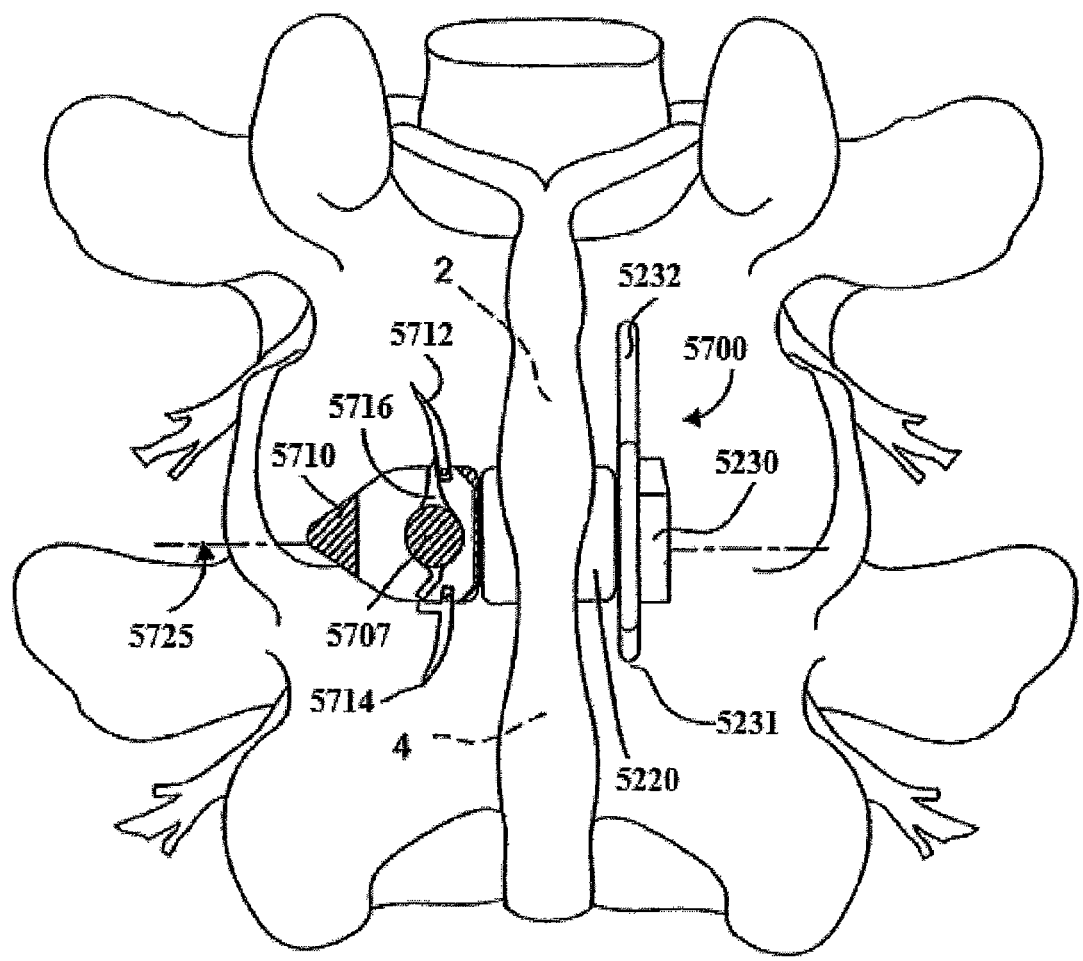
FIG. 56C is a partial cross-sectional side view of the implant of FIG. 56B wherein the winglets deployed.

Referring to FIG. 55, the implant 4600 is shown positioned between adjacent spinous processes 2,4. The second wing 4660 as shown is sized such that when arranged in a first configuration (i.e., as a distraction guide 4610) the upper winglet 4612 and the lower winglet 4614 do not extend undesirably into the adjacent tissues. However, the upper winglet 4612 and the lower winglet 4614 can be sized and shaped other than as shown in FIG. 55. The upper winglet 4612 and the lower winglet 4614 need only be sized and shaped such that when arranged in a second configuration, the upper and lower winglets 4612,4614 limit or block movement along the longitudinal axis 4625 in a direction opposite from insertion. FIGS. 56A through 56C illustrate a further embodiment of an implant 4700 in accordance with the present invention arranged between adjacent spinous processes 2,4. In such an embodiment, upper and lower winglets 4712,4714 can be disposed within the distraction guide 4710 and can be deployed by actuating an actuator arrangement including a shaft connected with a cam 4707, the shaft having an engageable head 4706, or alternatively including some other mechanism such as a gear. As can be seen in FIG. 56A the implant 4700 can be disposed between adjacent spinous processes 2,4 as described above in reference to FIG. 50. The distraction guide 4710 of the implant 4700 can be employed to pierce and/or distract an interspinous ligament 6 connected between the adjacent spinous process 2,4. The implant 4700 can then be urged between the spinous processes 2,4 so that the distraction guide 4710 further distracts the interspinous ligament 6 to form a space within which a spacer 4220 can be disposed. In the embodiment shown, the spacer 4220 can pivot about a central body extending from the first wing 4230 of the implant 4700. The first wing 4230 limits and/or blocks movement along a longitudinal axis 4725 of the implant 4700 in the direction of insertion.

Once the implant 4700 is arranged as desired, the actuator arrangement can be actuated to deploy the upper and lower winglets, 4712,4714, thereby forming a second wing 4760 as shown in FIG. 56C. The second wing 4760 limits and/or blocks movement along the longitudinal axis 4725 in a direction opposite the direction of insertion. With the second wing 4760 deployed, the adjacent spinous processes 2,4 are at least partially disposed between the wings 4730,4760, preventing the implant 4800 from becoming undesirably dislodged from the space between the adjacent spinous processes 2,4. As shown in FIG. 56C, the first wing 4730 and the second wing 4760 can be arranged sufficiently far apart that the adjacent spinous processes 2,4 can move relative to one another slightly (e.g., laterally—such as during a twisting motion), allowing the patient greater flexibility of movement.

FIGS. 56B and 56C are partial cross-sectional posterior views of the implant 4700 shown in FIG. 56A. m an embodiment, the deployable winglets 4712,4714 can be extended from the distraction guide 4710 using an actuator arrangement comprising a shaft 4707 and cam 4716. The cam 4716 can be rotated to force the winglets 4712,4714 to pivot outward from the distraction guide 4710. As shown, the winglets 4712,4714 are at least partially disposed within a cavity of the distraction guide 4710.

FIGS. 56A through 57E illustrate a still further embodiment of an implant 4800 in accordance with the present invention arranged between adjacent spinous processes 2,4. In such an embodiment, upper and lower winglets 4812,4814 can be disposed within the distraction guide 4810 and can be deployed by actuating an actuator arrangement including a screw 4807 having an engageable head 4806, or alternatively including some other mechanism such as a gear. As can be seen in FIG. 57A the implant 4800 can be disposed between adjacent spinous processes 2,4 as described above in reference to FIG. 50. The distraction guide 4810 of the implant 4800 can be employed to pierce and/or distract an interspinous ligament 6 connected between the adjacent spinous process 2,4. The implant 4800 can then be urged between the spinous processes 2,4 so that the distraction guide 4810 further distracts the interspinous ligament 6 to form a space within which a spacer 4220 can be disposed. In the embodiment shown, the spacer 4220 can pivot about a central body extending from the first wing 4230 of the implant 4800. The first wing 4230 limits and/or blocks movement along a longitudinal axis 4825 of the implant 4800 in the direction of insertion.

Once the implant 4800 is arranged as desired, the actuator arrangement can be actuated to deploy the upper and lower winglets, 4812,4814, thereby forming a second wing 4860 as shown in FIG. 56B. The second wing 4860 limits and/or blocks movement along the longitudinal axis 4825 in a direction opposite the direction of insertion. With the second wing 4860 deployed, the adjacent spinous processes 2,4 are at least partially disposed between the wings 4830,4860, preventing the implant 4800 from becoming undesirably dislodged from the space between the adjacent spinous processes 2,4. As shown in FIG. 56B, the first wing 4830 and the second wing 4860 can be arranged sufficiently far apart that the adjacent spinous processes 2,4 can move relative to one another slightly (e.g., laterally—such as during a twisting motion), allowing the patient greater flexibility of movement.

Figure 57A:
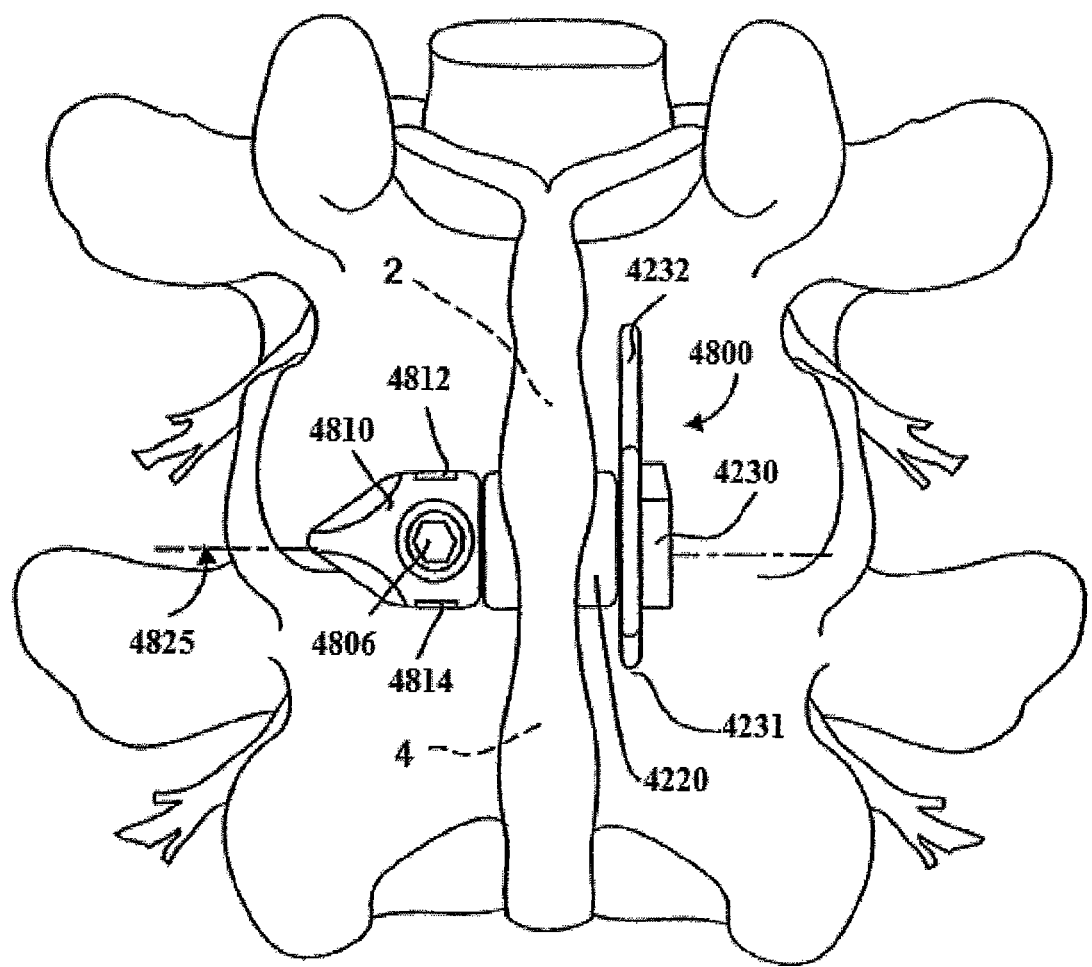
FIG. 57A is a side view of an alternative embodiment of the implant positioned between adjacent spinous processes.
Figure 57B:
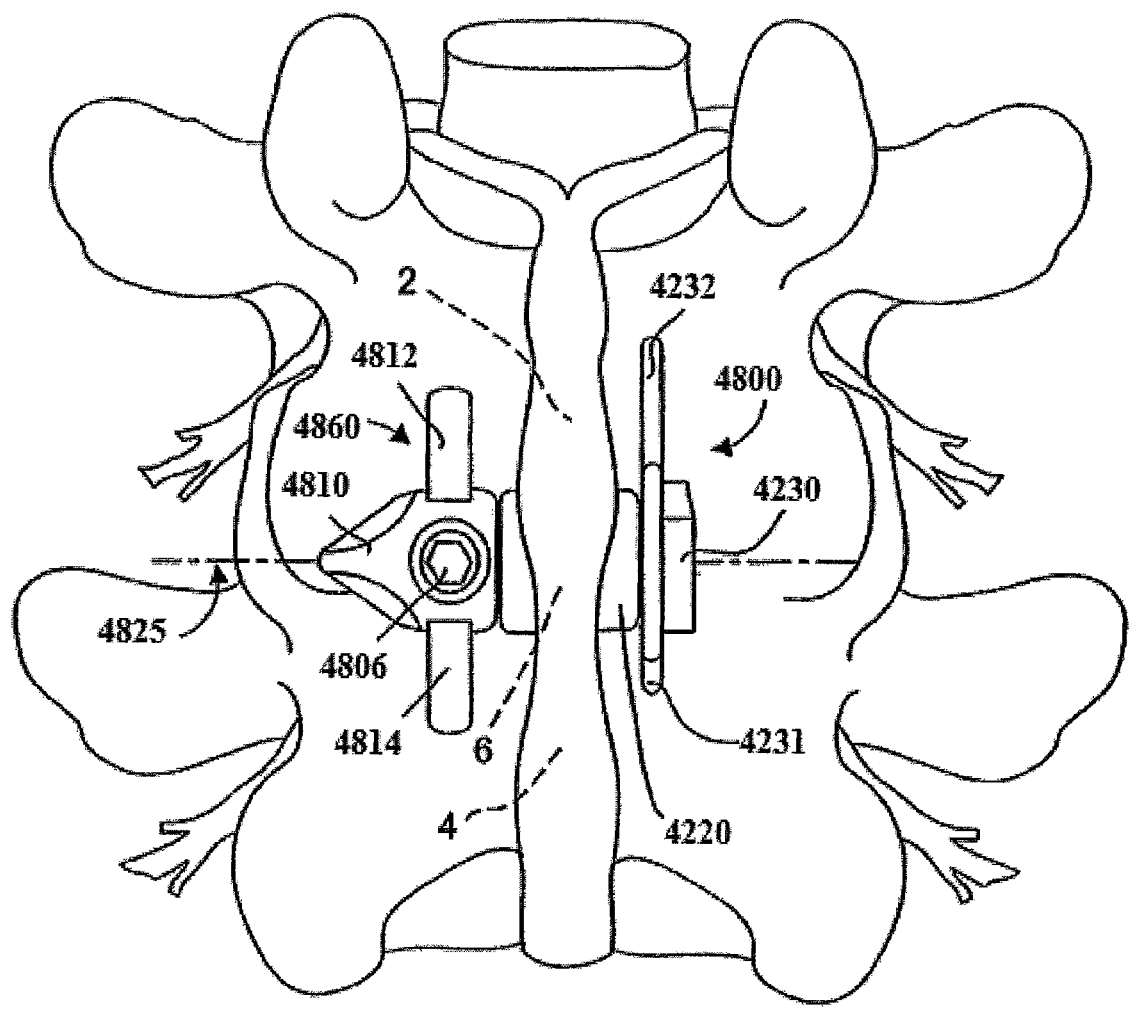
FIG. 57B is a side view of the implant of FIG. 57A positioned between adjacent spinous processes wherein the winglets deployed.
Figure 57C:
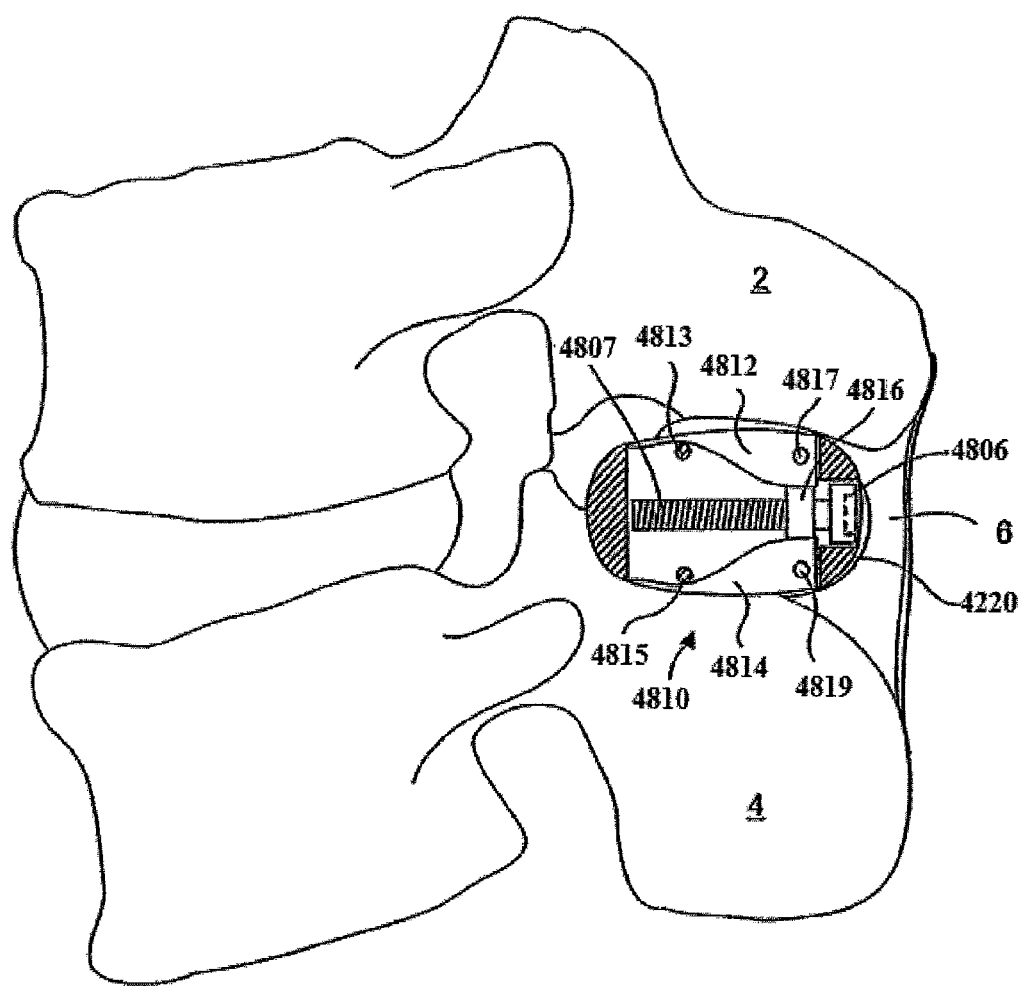
FIG. 57C is a partial cross-sectional end view of the implant of FIG. 57A showing deployable winglets disposed within a distraction guide of the implant.
Figure 57D:
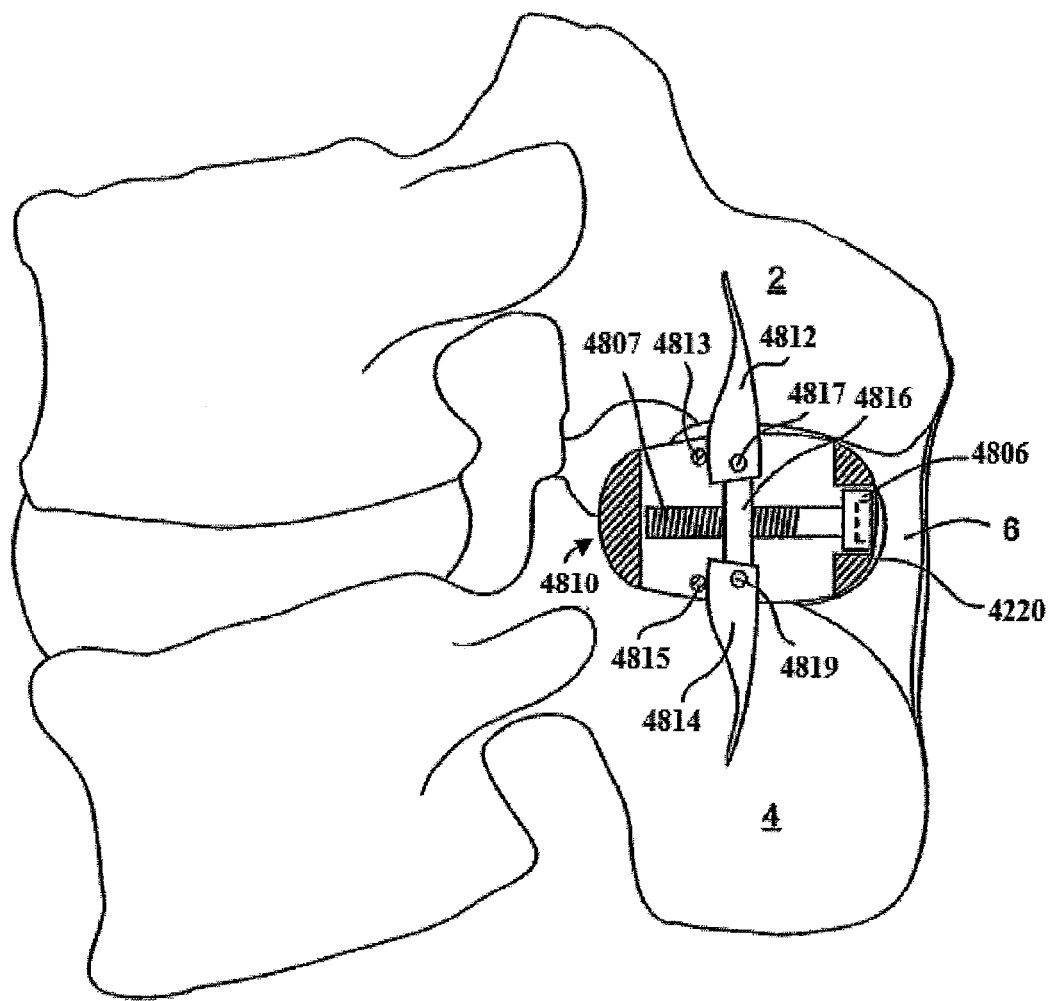
FIG. 57D is a partial cross-sectional end view of the implant of FIGS. 57A-57C showing the winglets deployed so that the winglets extend from the distraction guide of the implant.

FIGS. 57C and 57D are partial cross-sectional end views of the implant 4800 shown in FIGS. 57A and 57B. In an embodiment, the deployable winglets 4812,4814 can be extended from the distraction guide 4810 using an actuator arrangement comprising a screw 4806 and threaded collar 4816. The threaded collar 4816 can be driven along the screw 4806 to force the winglets 4812,4814 to pivot outward from the distraction guide 4810. As shown, the winglets 4812,4814 are at least partially disposed within a cavity of the distraction guide 4810. The winglets 4812,4814 are pivotably connected with the threaded collar 4816 at an upper pivot point 4817 and a lower pivot point 4819. Pins 4813,4815 or other obstruction devices can be disposed within the cavity and arranged so that the pins 4813,4815 do not interfere with the arrangement of the winglets 4812,4814 in a nested, or undeployed, position. However, as the threaded collar 4816 travels along the screw 4806 in a posterior-to-anterior direction, the inner surface of the winglets 4812,4814 contact the pins 4813,4815 and the winglets 4812,4814 pivot away from the distraction guide 4810. If desired the winglets 4812,4814 can be spring biased against the posts 4813,4815 such that in the nested positions and in any deployed position the winglets 4812,4814 are held against the posts 4813,4815.

Figure 57E:
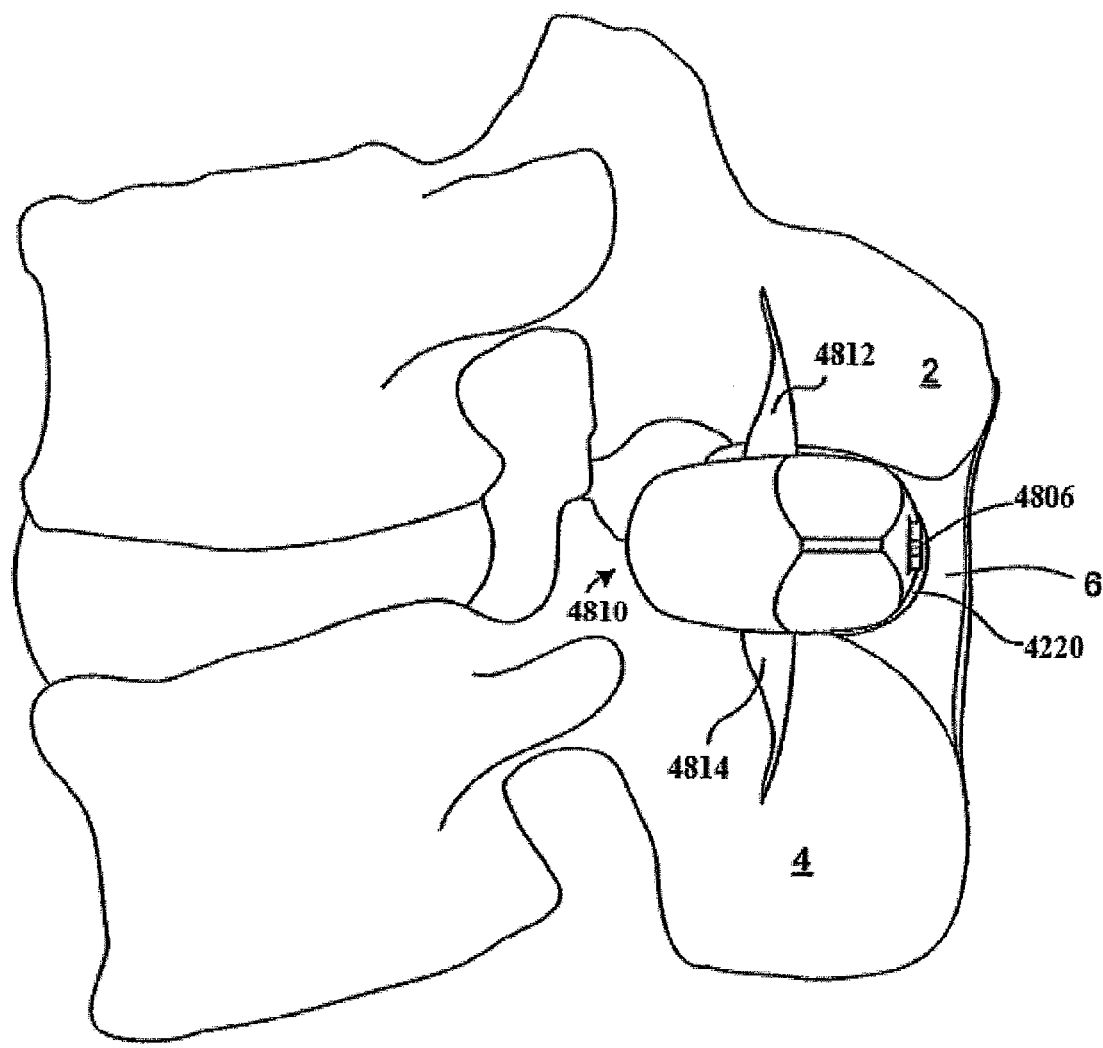
FIG. 57E is an end view of the implant of FIGS. 57A-57D showing the distraction guide and the deployed winglets relative to the distraction guide.

As shown in FIGS. 57D and 57E, when the threaded collar 4816 has traveled a distance along the screw 4806, the winglets 4812,4814 are deployed to form a second wing 4860. The winglets 4812,4814 extend along a significant portion of the outer surface of the spinous processes 2,4. When urged along the longitudinal axis 4825 in a direction opposite the direction of insertion, the winglets 4812,4814 contact the adjacent spinous processes 2,4 and resist further movement in said direction. FIG. 57E is an end view of the implant 4800 with the second wing 4860 deployed. As shown, the screw head 4806 extends from the distraction guide 4810; however, when implemented, it is preferable for the screw head 4806 to be either flush with the surface of the distraction guide 4810 or slightly receded from the surface of the distraction guide 4810 so that movement of the implant 4800 is not obstructed during distraction of the interspinous ligament 6 and/or the spinous processes 2,4. The screw head 4806 is shown extending from the distraction guide 4810 to demonstrate possible arrangement relative to the proximal end of the distraction guide 4810.

Figure 58A:
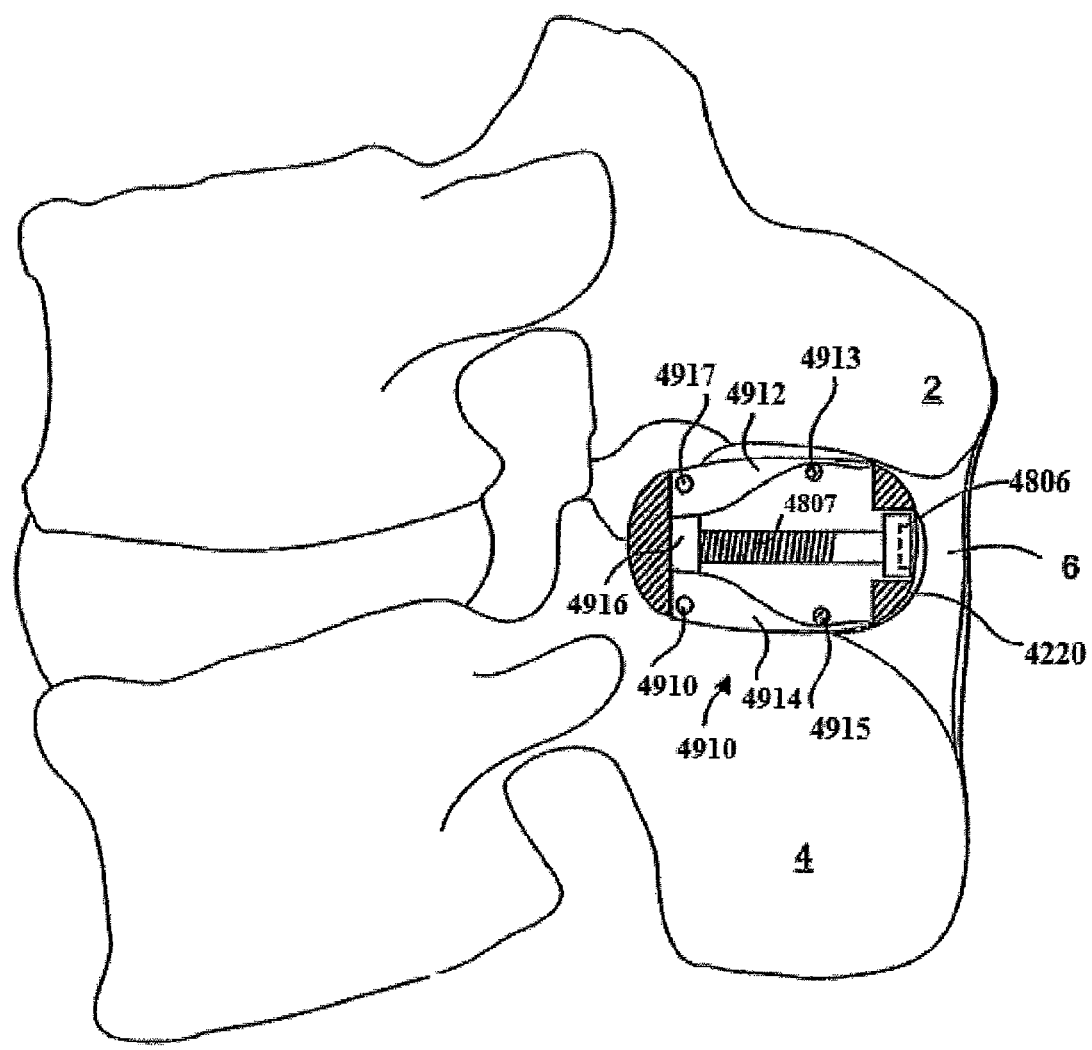
FIG. 58A is a partial cross-sectional end view of an alternative embodiment of an implant in accordance with the present invention including an alternative actuator arrangement.
Figure 58B:
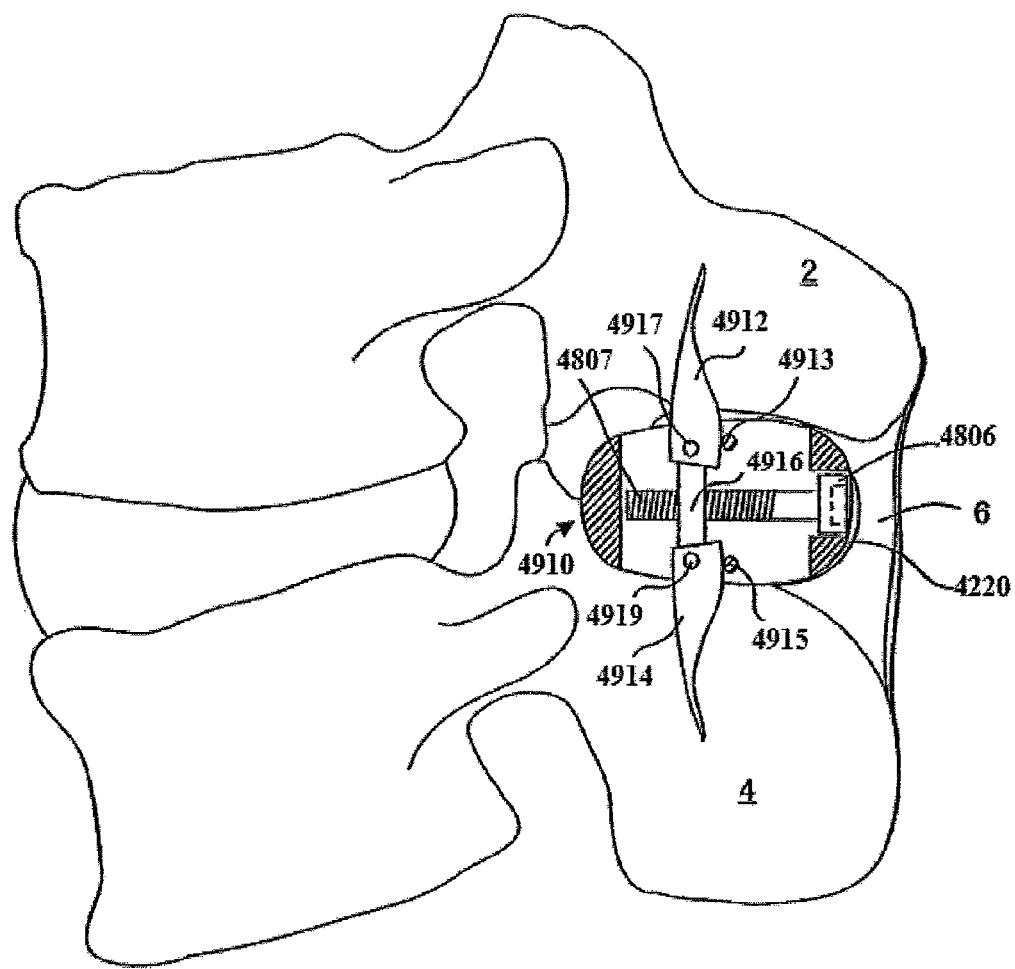
FIG. 58B is an partial cross-sectional end view of the implant of FIG. 58A showing the winglets deployed so that the winglets extend from the distraction guide of the implant.
Figure 59A:
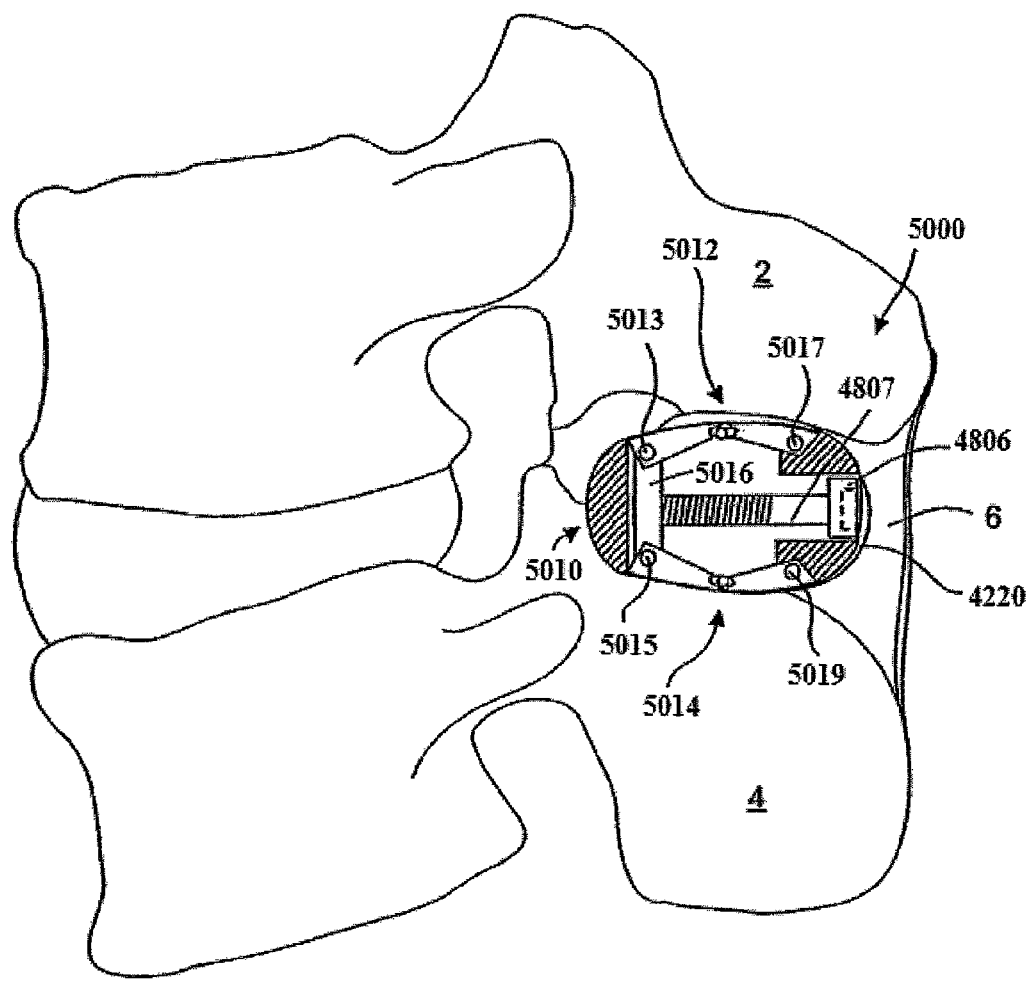
FIG. 59A is a partial cross-sectional end view of still another embodiment of an implant in accordance with the present invention having an alternative actuator arrangement wherein the winglets comprise two hinged portions.
Figure 59B:
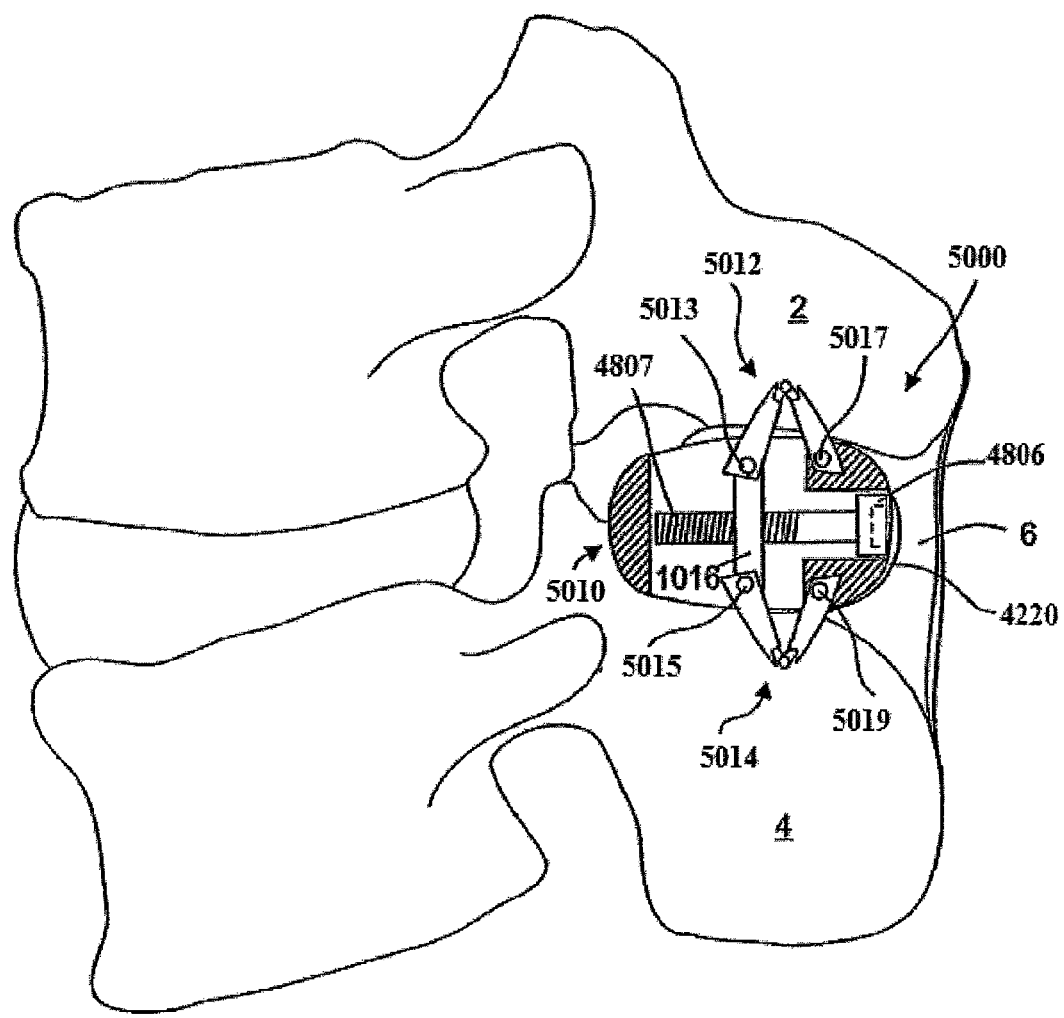
FIG. 59B is a partial cross-sectional end view of the implant of FIG. 59A showing the winglets deployed so that the winglets extend from the distraction guide of the implant.

FIGS. 58A and 58B illustrate yet another embodiment of the implant 4900 having an alternative actuation arrangement. In such an embodiment, the winglets 4912,4914 can be reversed in arrangement so that the winglets 4912,4914 are deployed by urging the threaded collar 4916 toward the screw head 4806. FIGS. 59A and 59B illustrate a still further embodiment of the implant 5000 having an alternative actuation arrangement. In such embodiments, the winglets 5012, 5014 include two hinged portions, each winglet 5012,5014 folding outward to form a portion of a second wing 5060. The second wing 5060 does not extend as far along the axis of the spine, i.e. the total height of the second wing 5060 along the spine is smaller than previous embodiments. A reduced second wing height can be advantageous where implants are positioned at adjacent motion segments, thereby preventing undesired contact of adjacent implants.

Figure 60:
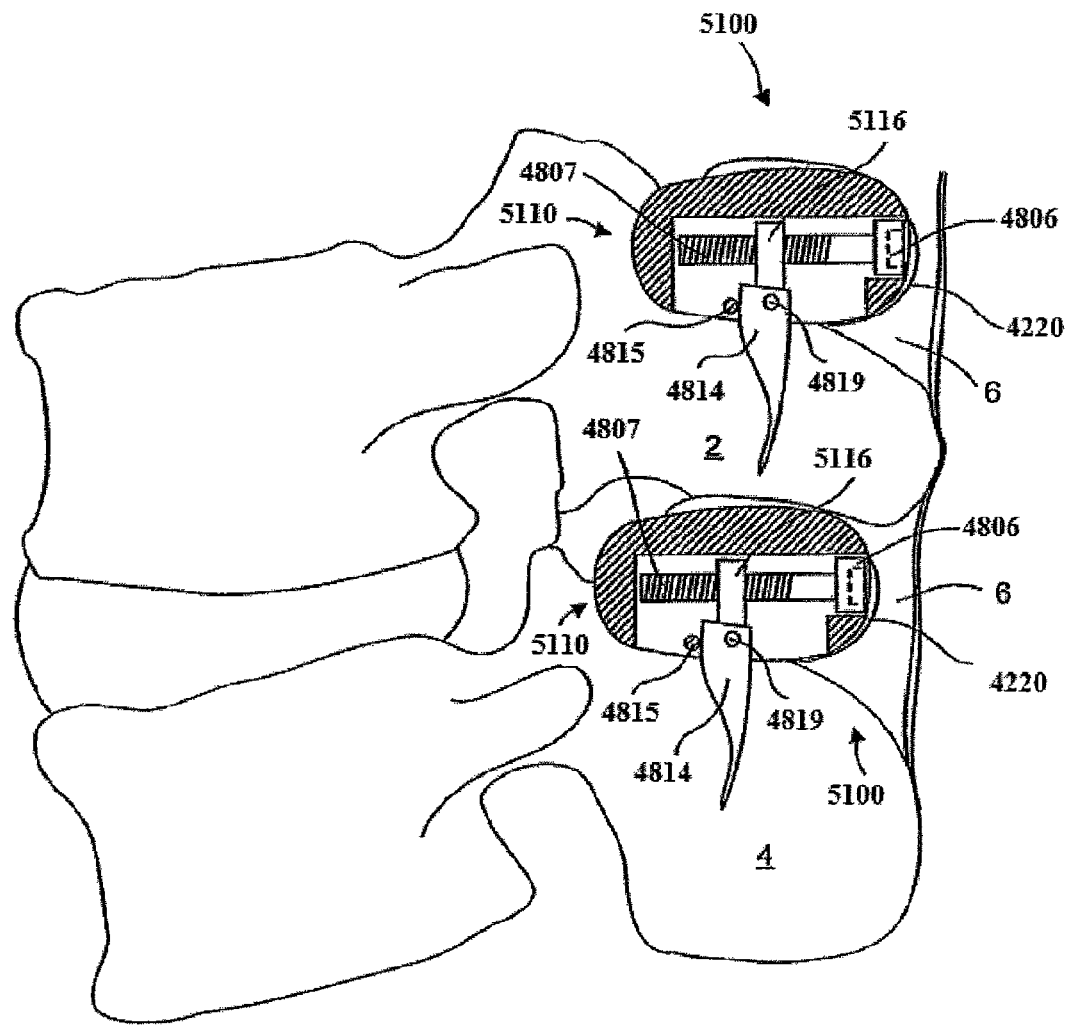
FIG. 60 is a partial cross-sectional end view of a still further embodiment of an implant in accordance with the present invention wherein implants are arranged at adjacent motion segments.

As mentioned above, in other embodiments in accordance with the present invention, the winglets can be deployed from the distraction guide using a mechanism other than a screw and threaded collar. For example, one or more gears can be employed. Further, in still other embodiments the upper and lower winglets can have a shape along other than those shapes shown in FIGS. 57A through 57B. The invention is not intended to be limited to winglets having shapes such as shown. In still further embodiments, such as shown in FIG. 60, the implant 5100 can include only one of the upper and lower winglets. For example, where implants are positioned at adjacent motion segments it can be advantageous to have a lower winglet 4814, thereby preventing undesired contact of adjacent implants 5100. As will be obvious to one of ordinary skill in the art, myriad different actuation arrangements can be employed to form a second wing. Implants in accordance with the present invention are not intended to be limited to those described in detail herein.

Materials for Use in Implants of the Present Invention

In some embodiments, the implant, and components of the implant (i.e., the spacer, the distraction guide, etc.) can be fabricated from medical grade metals such as titanium, stainless steel, cobalt chrome, and alloys thereof, or other suitable implant material having similar high strength and biocompatible properties. Additionally, the implant can be at least partially fabricated from a shape memory metal, for example Nitinol, which is a combination of titanium and nickel. Such materials are typically radiopaque, and appear during x-ray imaging, and other types of imaging. Implants in accordance with the present invention, and/or portions thereof can also be fabricated from somewhat flexible and/or deflectable material. In these embodiments, the implant and/or portions thereof can be fabricated in whole or in part from medical grade biocompatible polymers, copolymers, blends, and composites of polymers. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer. Many polymers, copolymers, blends, and composites of polymers are radiolucent and do not appear during x-ray or other types of imaging. Implants comprising such materials can provide a physician with a less obstructed view of the spine under imaging, than with an implant comprising radiopaque materials entirely. However, the implant need not comprise any radiolucent materials.

One group of biocompatible polymers is the polyaryletherketone group which has several members including polyetheretherketone (PEEK), and polyetherketoneketone (PEKK). PEEK is proven as a durable material for implants, and meets the criterion of biocompatibility. Medical grade PEEK is available from Victrex Corporation of Lancashire, Great Britain under the product name PEEK-OPTIMA. Medical grade PEKK is available from Oxford Performance Materials under the name OXPEKK, and also from CoorsTek under the name BioPEKK. These medical grade materials are also available as reinforced polymer resins, such reinforced resins displaying even greater material strength. In an embodiment, the implant can be fabricated from PEEK 450G, which is an unfilled PEEK approved for medical implantation available from Victrex. Other sources of this material include Gharda located in Panoli, India. PEEK 450G has the following approximate properties:

| Property | Value |
| --- | --- |
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

PEEK 450G has appropriate physical and mechanical properties and is suitable for carrying and spreading a physical load between the adjacent spinous processes. The implant and/or portions thereof can be formed by extrusion, injection, compression molding and/or machining techniques. It should be noted that the material selected can also be filled. Fillers can be added to a polymer, copolymer, polymer blend, or polymer composite to reinforce a polymeric material. Fillers are added to modify properties such as mechanical, optical, and thermal properties. For example, carbon fibers can be added to reinforce polymers mechanically to enhance strength for certain uses, such as for load bearing devices. In some embodiments, other grades of PEEK are available and contemplated for use in implants in accordance with the present invention, such as 30% glass-filled or 30% carbon-filled grades, provided such materials are cleared for use in implantable devices by the FDA, or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to have enhanced compressive strength and stiffness, and a lower expansion rate relative to unfilled PEEK. Carbon-filled PEEK also offers wear resistance and load carrying capability.

As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. As mentioned, the implant can be comprised of polyetherketoneketone (PEKK). Other material that can be used include polyetherketone (PEK), polyetherketoneetherketoneketone (PEKEKK), polyetheretherketoneketone (PEEKK)5 and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A13 dated Jan. 3, 2002, entitled "Bio-Compatible Polymeric Materials." Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

Methods for Implanting Interspinous Implants

Figure 61:
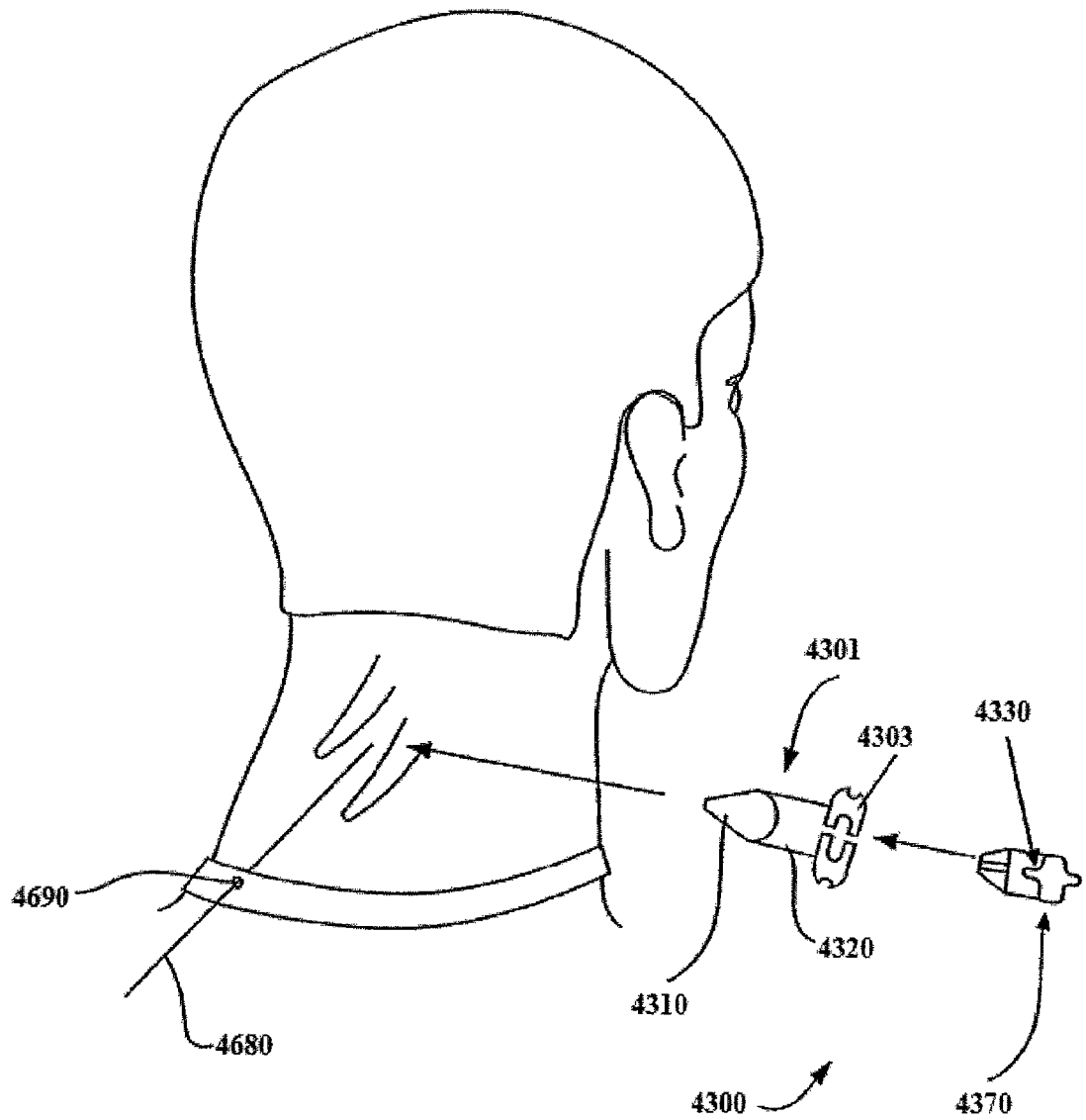
FIG. 61 illustrates an embodiment of a method for implanting the implant of FIGS. 49A-55 between adjacent spinous processes in accordance with the present invention.

A minimally invasive surgical method for implanting an implant 4300 as shown in FIGS. 49A-55 in the cervical spine is disclosed and taught herein. In this method, as shown in FIG. 61, preferably a guide wire 4780 is inserted through a placement network 4790 into the neck of the implant recipient. The guide wire 4780 is used to locate where the implant 4300 is to be placed relative to the cervical spine, including the spinous processes. Once the guide wire 4780 is positioned with the aid of imaging techniques, an incision is made on the side of the neck so that an implant 4300 in accordance with an embodiment of the present invention, can be positioned in the neck thorough an incision and along a line that is about perpendicular to the guide wire 4780 and directed at the end of the guide wire 4780. The main body 4301 of the implant 4300 is inserted into the neck of the patient. Preferably during insertion, the distraction guide 4310 pierces or separates the tissue without severing the tissue. Once the main body 4301 is satisfactorily positioned, an insert 4370 can be positioned within a cavity of the main body 4301, causing the distraction guide 4310 of the main body 4301 to be arranged in a second configuration so that at least a portion of the distraction guide 4310 forms a second wing. The insert 4370 can be inserted along a line that is generally collinear with the line over which the main body 4301 is inserted. The anatomy of the neck is such that it is most convenient and minimally invasive to enter the neck from the side with respect to the main body 4301 and the insert 4370.

Figure 62:
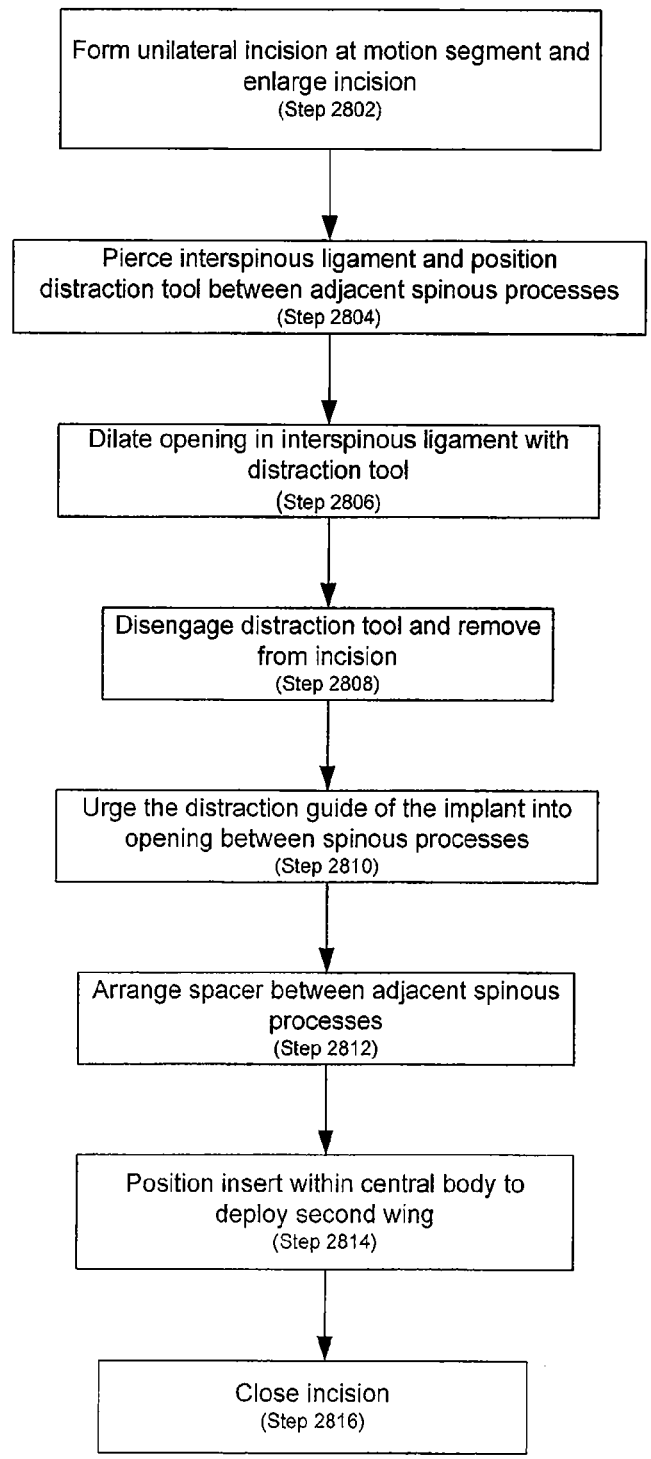
FIG. 62 illustrates an embodiment of a method for implanting the interspinous implant of FIGS. 49A-55 between adjacent spinous processes in accordance with the present invention.

Further, a minimally invasive surgical method for implanting an implant as described in FIGS. 49A-55 in the lumbar spine is disclosed and taught herein. In this method, as shown in the flowchart of FIG. 62, preferably a unilateral incision or opening can be made using a posterior-anterior approach (Step 2802). The unilateral incision can be made, for example, at a location some distance to the left of an axis along the spinous process. The incision or opening can be enlarged, and a distraction tool can be positioned within the incision so that the proximal end of the distraction tool (Step 2804) can access an exposed side of the interspinous ligament. The distraction tool can be urged through the interspinous ligament, thereby distracting the interspinous ligament so as to receive the implant (Step 2806). Once the interspinous ligament is sufficiently distracted, the distraction tool can be disengaged and removed from the incision (Step 2808).

Figure 63:
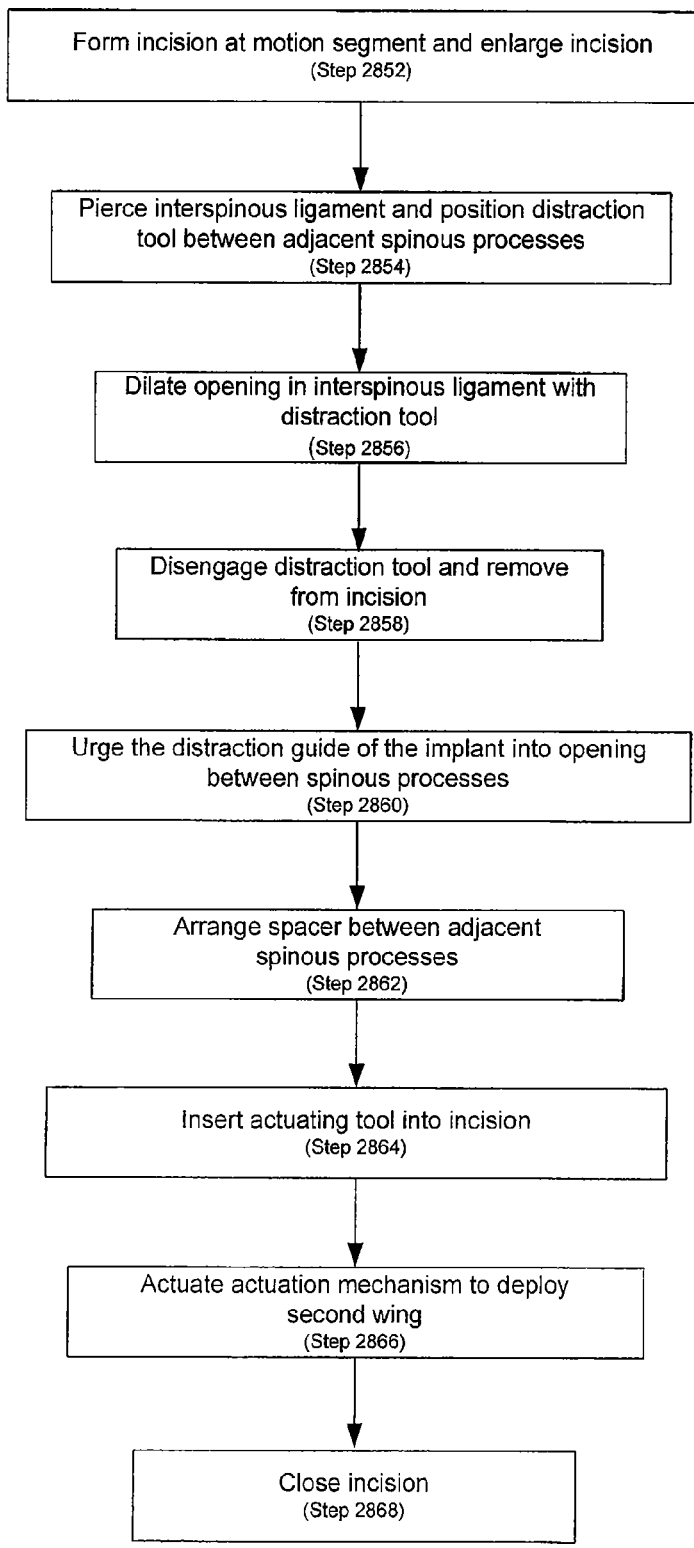
FIG. 63 illustrates an embodiment of a method for implanting the interspinous implant of FIGS. 56A-60 between adjacent spinous processes in accordance with the present invention.

Once the distraction tool has been removed from the incision, the implant can be positioned at the dilated opening, and the distraction guide of the implant can be urged through the dilated opening (Step 2810). The implant can be further urged through the opening until the spacer is positioned as desired between the adjacent spinous processes of the targeted motion segment (Step 2812). The spacer is free to rotate so that the load is distributed more evenly over the surface of the spinous processes. Optionally, the implant can be urged through the dilated opening until the first wing contacts the adjacent spinous processes, thereby blocking further movement in the direction of insertion. Once the implant is properly arranged, the insert can be positioned at the distal end of the implant so that the insert can be urged into and through the hollow cavity of the hollow central body (Step 2814). As the insert is seated inside of the cavity, the distraction guide splits, and the upper winglet and the lower winglet deploy as a second wing. The remaining tools can be removed from the incision, and the incision can be closed (Step 2816). Preferably during insertion, the distraction end pierces or separates the tissue without severing the tissue. Further, a minimally invasive surgical method for implanting an implant as shown in FIGS. 56A-60 in the lumbar spine is disclosed and taught herein. In this method, as shown in the flowchart of FIG. 63, an incision or opening can be made using a posterior-anterior approach (Step 2852). The incision or opening can be enlarged, and a distraction tool can be positioned within the incision so that the proximal end of the distraction tool (Step 2854) can access an exposed side of the interspinous ligament. The distraction guide can be urged through the interspinous ligament and distracted, thereby distracting the interspinous ligament so as to receive the implant (Step 2856). Once the interspinous ligament is sufficiently distracted, the distraction tool can be disengaged and removed from the incision (Step 2858).

Once the distraction guide has been removed from the incision, the implant can be positioned at the dilated opening, and the distraction guide of the implant can be urged through the dilated opening (Step 2860). The implant can be further urged through the opening until the spacer is positioned as desired between the adjacent spinous processes of the targeted motion segment (Step 2862). The spacer is free to rotate so that the load is distributed more evenly over the surface of the spinous processes. Optionally, the implant can be urged through the dilated opening until the first wing contacts the adjacent spinous processes, thereby blocking further movement in the direction of insertion. Once the implant is properly arranged, an actuation tool can be inserted within the incision at an opposite side of the adjacent spinous processes from the point of insertion (Step 2864). The actuation tool can engage the actuation arrangement, and can actuate the actuation arrangement so that the upper winglet and the lower winglet deploy as a second wing, as described above (Step 2866). The remaining tools can be removed from the incision, and the incision can be closed (Step 2868). Preferably during insertion, the distraction end pierces or separates the tissue without severing the tissue.

The foregoing description of the present invention have been presented for purposes of illustration and description. It is not intended to be exhaustive or to limit the invention to the precise forms disclosed. Many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

Implants Having Deployable Wings

Figure 64A:
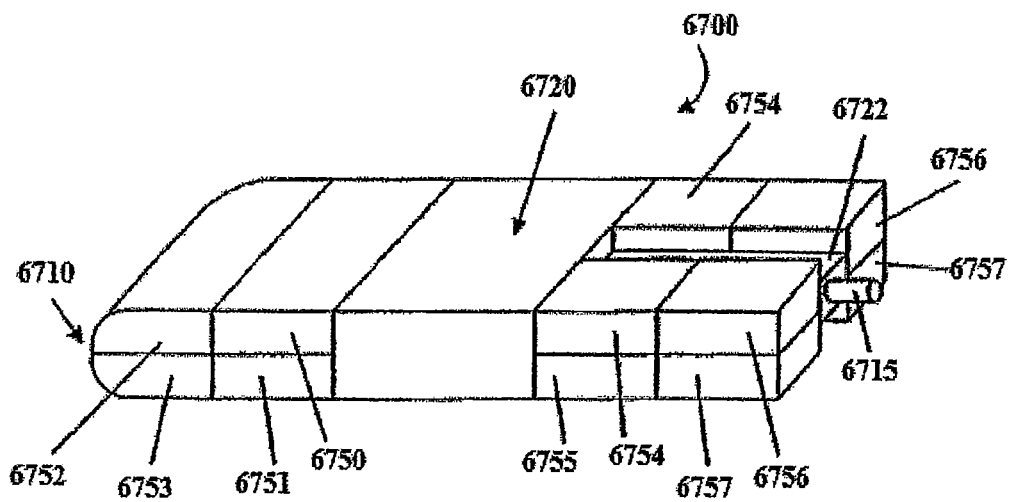
FIG. 64A is a perspective view of an alternative embodiment of an implant in accordance with the present invention having a first wing and a second wing that can be deployed after arranging the implant between adjacent spinous processes.
Figure 64B:
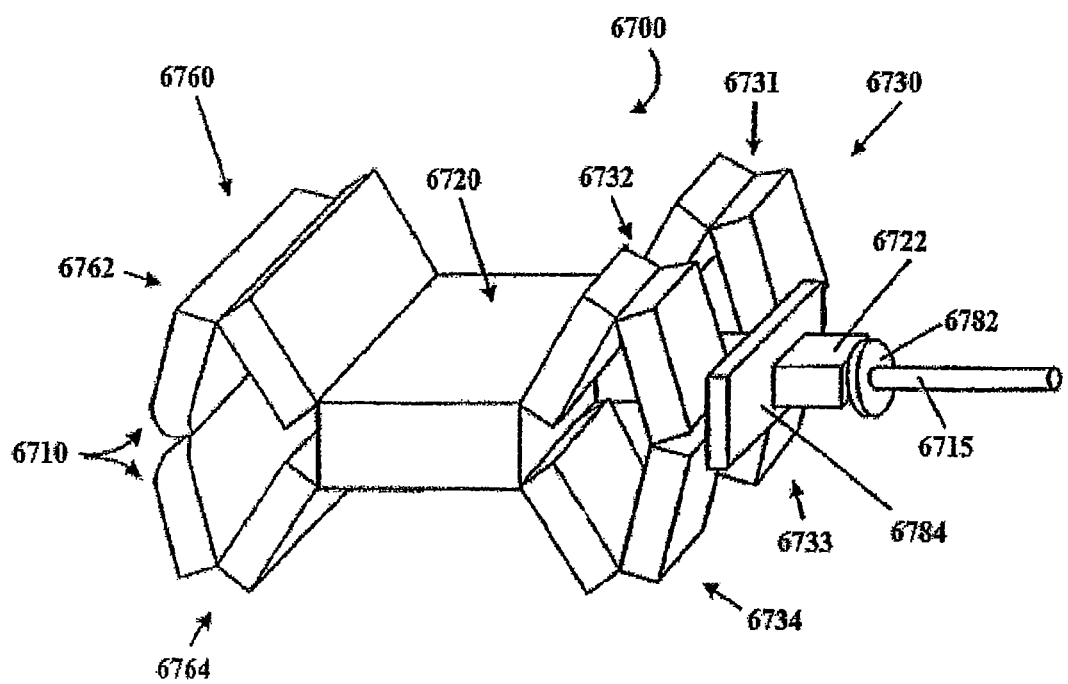
FIG. 64B is a perspective view of the implant of FIG. 64A in a deployed configuration.

In other embodiments, implants in accordance with the present invention can comprise a "matchbox"—like structure having a first configuration (as shown in FIG. 64A) and a second, deployed configuration (as shown in FIG. 64B). Arranged in the first configuration, such implants 6700 can have a substantially flat profile having an approximately uniform thickness.

The uniform thickness approximates the thickness of a spacer 6720 of the implant 6700. The implant 6700 can comprise a distraction guide 6710 at a proximal end of the implant, the distraction guide 6710 having a slightly rounded or tapered shape to pierce and/or distract a space between adjacent spinous processes. The implant 6700 can further comprise a plurality of hinged structures 6750-6757, the hinged structures 6750-6757 being collapsed so as to facilitate the substantially flat profile. The hinged structures 6750-6757 are pivotally connected with the spacer 6720 and extend from both sides of the spacer 6720. As shown in FIG. 64A, a support structure 6722 extends from the spacer 6720 toward the distal end of the implant 6700. A rod 6715 (or alternatively some other mechanism such as a tab) can be connected with the proximal end of the implant 6700 and can extend through the hinged structures 6750-6753, through the spacer 66720, and through the support structure 6722 so that the rod 6715 is accessible.

Referring to FIG. 64B, once the implant 6700 is positioned as desired between adjacent spinous processes, the rod 6715 can be drawn in a direction opposite the direction of insertion along the longitudinal axis 6725 so that the hinged structures 6750-6757 fold outward to form a first wing 6730 and a second wing 6760 between which is arranged the spacer 6720 and a portion of the spinous processes. As the hinged structures 6750-6757 fold outward, the height of the first and second wings 6730,6760 increases from approximately the same as the thickness of the spacer 6720 to a height such that the first and second wing 6730,6760 can limit or block movement of the implant 6700 along the longitudinal axis 6725 when positioned between adjacent spinous processes. As can be seen, the second wing 6760 includes four hinged structures 6750-6753: an upper first structure 6750 connected by a hinge to an upper second structure 6752, and a lower first structure 6751 connected by a hinge to a lower second structure 6753. The hinged structures 6750-6753 pivot outward to form an upper end 6762 of the second wing and a lower end 6764 of the second wing. Likewise, the first wing 6730 includes four hinged structures 6754-6757: an upper first structure 6754 connected by a hinge to an upper second structure 6756, and a lower first structure 6755 connected by a hinge to a lower second structure 6757. However, unlike the second wing 6760, the first wing 6730 is (effectively) bisected by the support structure 6722 so that the first wing 6730 comprises four winglets 6731-6734. The hinged structures 6754-6757 pivot outward to form upper winglets 6731,6732 of the first wing and lower winglets 6733,6734 of the first wing.

As mentioned above, the support structure 6722 extends from the spacer 6720 toward the distal end of the implant 6700. The spacer 6720 and the support structure 6722 include a bore or other cavity through which the rod 6715 can travel. Applying resistive force to the support structure 6722 can fix the spacer 6720 in place between spinous processes when drawing the rod 6715 through the bore. As the rod 6715 is drawn through the bore, the hinged structures 6752,6753 with which the proximal end of the rod 6715 is connected are drawn with the rod 6715. As the rod 6715 is drawn through the spacer 6720, the hinged structures 6752,6753 are drawn toward the spacer 6720. The hinged structures 6750-6753 pivot outward to accommodate the relative movement between the rod 6715 and the spacer 66720. Accordingly, the second wing 6760 has been satisfactorily deployed.

The hinged structures 6756,6757 of the first wing 6730 can cause deployment of the first wing 6730 by applying resistive force to the hinged structures 6756,6757 while drawing the spacer 6720 (via the support structure 6722), or by urging the hinged structures 6756,6757 toward the spacer 6720. The resistive force or urging can be applied by a second stop 6784 that can fit around the support structure 6722 and can be interference fit or otherwise selectively fixed with the support structure 6722. As the second stop 6784 is pushed along the longitudinal axis 6725, along the support structure 6722, the hinged structures 6754-6757 pivot outward to accommodate the relative movement between the second stop 6784 and the spacer 6720. Accordingly, the first wing 6730 has been satisfactorily deployed.

Figure 65A:
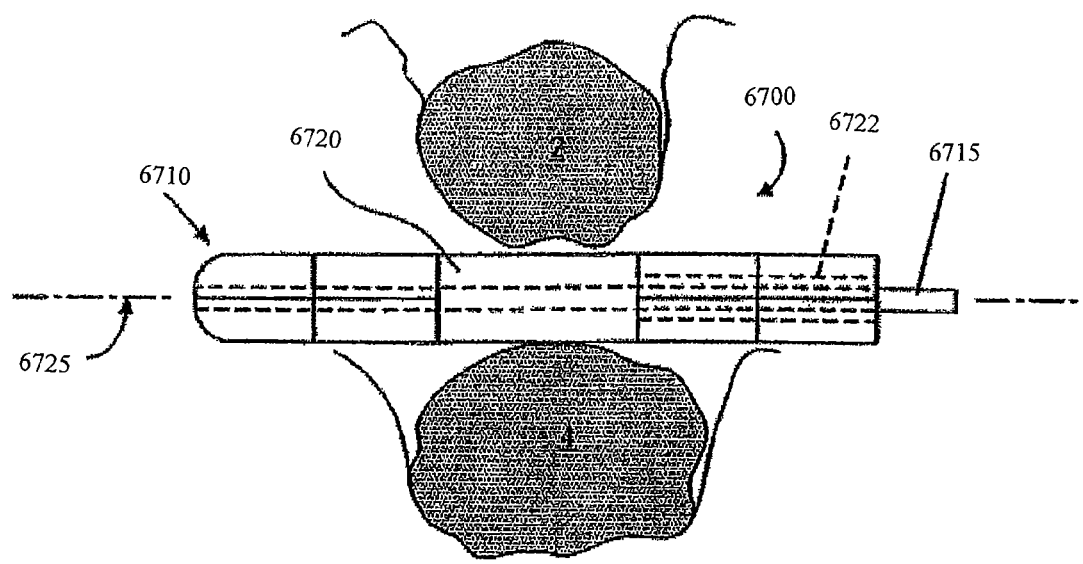
FIG. 65A is a posterior view of the implant of FIGS. 64A and 64B positioned between adjacent spinous processes in an undeployed configuration.
Figure 65B:
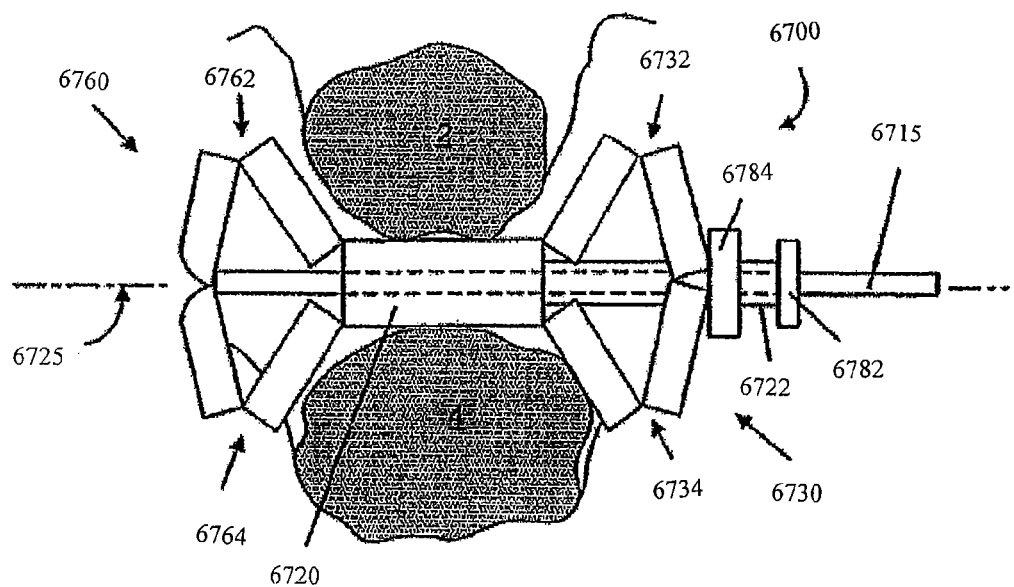
FIG. 65B is a posterior view of the implant of FIGS. 64A and 64B positioned between adjacent spinous processes in a deployed configuration.

FIGS. 65A and 65B are posterior views of the implant 6700 positioned between adjacent spinous processes 2,4 demonstrating an embodiment of a method for deploying the implant 6700 between the spinous processes 2,4. The implant 6700 can be positioned so that a distraction guide 6710 of the implant 6700 is arranged at a space between the spinous processes 2,4. The implant 6700 can then be urged between the spinous processes 2,4 so that the spacer 6720 is positioned as desired. The substantially flat profile of the implant 6700 can ease positioning of the spacer 6720 by reducing potential obstructing surfaces that can resist movement of the implant 6700 during implantation. The second wing 6760 and the first wing 6730 can then be deployed to limit movement of the implant 6700. To deploy the second wing 6760 the rod 6715 is drawn in a direction opposite the direction of insertion along the longitudinal axis 6725. The upper end 6762 and lower end 6764 of the second wing extend outward as described above. Once the second wing 6760 is deployed, the rod 6715 can be fixed in position relative to the spacer 6720. This can be accomplished using myriad different mechanisms. For example, as shown a first stop 6782 can be interference fit to the rod 6715 and positioned against the support structure 6722 along the rod 6715. The first stop 6782 can grip the rod 6715, as with a friction fit between the first stop 6782 and the rod 6715, so that the rod 6715 is prevented from moving through the bore of the support structure 6722 by interference between the first stop 6782 and the support structure 6722. In other embodiments, some other mechanism can be used, such as a pin (e.g., a cotter pin), a latch system, etc. One of ordinary skill in the art will appreciate the myriad different mechanisms for fixing a rod 6715 in position relative to the spacer 6720. The upper second structure 6756 and the lower second structure 6757 can be urged toward the spacer 6720 in the direction of insertion along the longitudinal axis 6725 using a second stop 6784 as described above, causing the upper winglets 6731,6732 and lower winglets 6733,6734 to extend outward to form the first wing 6730. Once the first wing 6730 is deployed, the hinged structures 6754-6757 can be fixed in position using the second stop 6784 or some other mechanism. The second stop 6784 can grip the support structure 6722, as with a friction fit or pin, and resist movement of the hinged structures 6754-6757, thereby preventing collapse. As above, one of ordinary skill in the art will appreciate the myriad different mechanisms for fixing the first wing 6730 in a deployed position. With the first wing 6730 and the second wing 6760 deployed, movement of the implant 6700 along the longitudinal axis 6725 can be limited or blocked, thereby resisting undesirable displacement of the implant 6700.

It should be noted that with implants as described above in reference to FIGS. 64A-67 the rod 6715 can optionally be trimmed or otherwise partially detached to decrease a space required to accommodate the implant 6700,6800 within the patient's spine. For example, the structure of the rod 6715 can be beveled or otherwise weakened near a distal end of the rod 6715 to allow the rod 6715 to be snapped off when the first and second wings 6730,6760,6830,6860 are deployed and the rod 6715 is fixed in place. In other embodiments, a tool (not shown) can be used to cut the rod 6715 after the first and second wings 6730,6760,6830,6860 are deployed and the rod 6715 is fixed in place. Still further, the rod 6715 need not comprise a rigid structure, but rather alternatively can include a tether, string, or similarly flexible structure that can be placed in tension to retain the second wing 6760,6860 and/or first wing 6730,6830 in a deployed position.

Figure 66A:
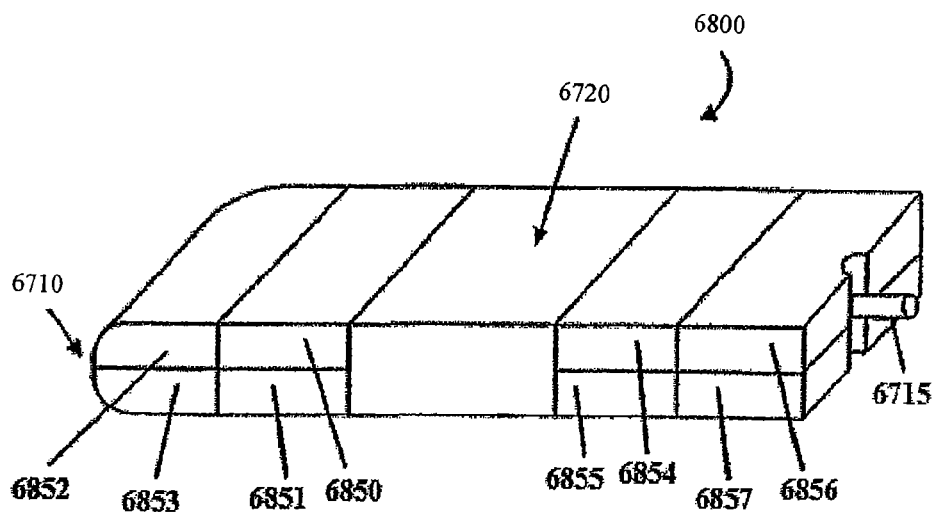
FIG. 66A is a perspective view of still another embodiment of an implant in accordance with the present invention having a first wing and a second wing that can be deployed after arranging the implant between adjacent spinous processes.
Figure 66B:
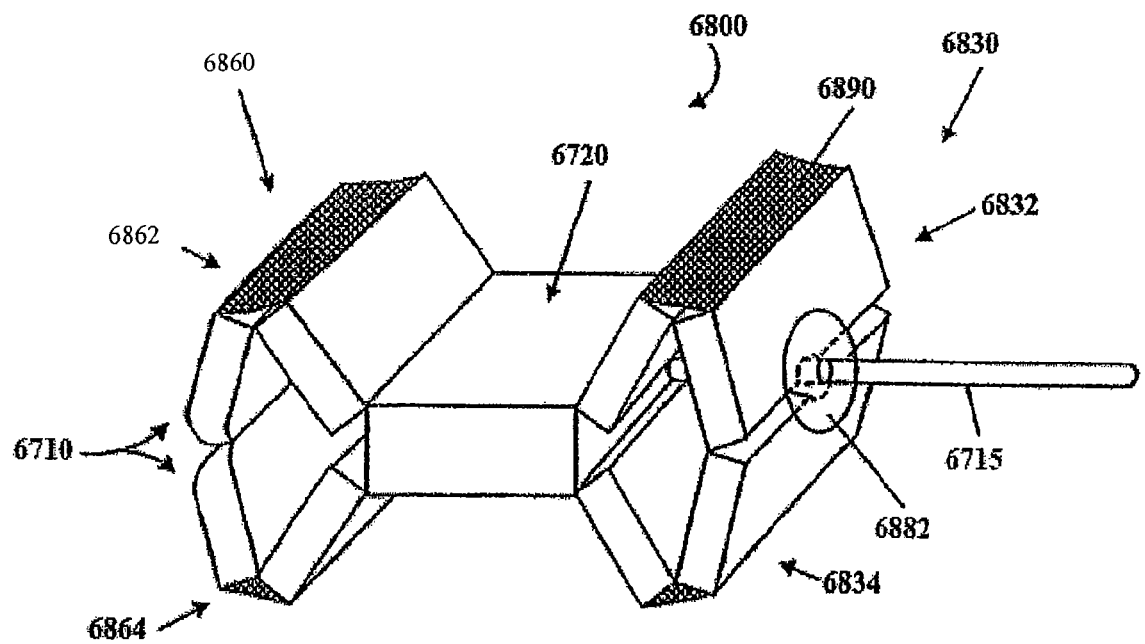
FIG. 66B is a perspective view of the implant of FIG. 66A in a deployed configuration.

Referring to FIGS. 66A and 66B, a still further embodiment of an implant 6800 in accordance with the present invention is shown. In such an embodiment, a flexible strap 6890 can be connected between pairs of hinged structures (i.e., 6850 and 6852, 6851 and 6853, 6854 and 6856, 6855 and 6857). The flexible strap 6890 can limit the relative movement of the hinged structures 6850-6857 so that first wing 6830 and second wing 6860 have increased rigidity when fully deployed. The implant 6800 need not include the support structure 6722 of the previous embodiment. A resistive force can be applied to the hinged structures 6856,6857 so that as the rod 6715 is drawn in a direction opposite the direction of insertion along the longitudinal axis 6825 the resistive force causes the hinged structures 6854-6857 to extend outward to form the first wing 6830. As the hinged structures 6854-6857 extend outward the flexible strap 6890 connected opposite the hinge unfolds. Once the hinged structures 6854-6857 reach a maximum extension, the flexible strap 6890 becomes taut and resists further extension, locking the first wing 6830 in place. The flexible straps 6890 can provide the first wing 6830 with sufficient rigidity to resist movement of the spacer 6720, so that as the rod 6715 is further drawn the rod 6715 moves through the spacer 6720 and the hinged structures 6852,6853 connected with the rod 6715 are drawn toward the spacer 6720. As the hinged structures 6852,6853 connected with the rod 6715 are drawn toward the spacer 6720, all of the hinged structures 6850-6853 extend outward to deploy the second wing 6860. The flexible strap 6890, connected opposite the hinge, unfolds. Once the hinged structures 6854-6857 reach a maximum extension the flexible strap 6890 becomes taut and resists further extension, locking the first wing 6830 in place. A stop 6882 (or alternatively some other mechanism such as a pin) can be fixed to the rod 6715 to create interference between the stop 6882 and the hinged structures 6832,6834 of the first wing 6830 that resists movement of the rod 6715. The flexible straps 6890 can be made from a biocompatible material. In an embodiment, the flexible straps 6890 can be made from a braided polyester suture material. Braided polyester suture materials include, for example, Ethibond, Ethiflex, Mersilene, and Dacron, and are non-absorbable, having high tensile strength, low tissue reactivity and improved handling. In other embodiments, the flexible straps 6890 can be made from stainless steel (i.e., surgical steel), which can be woven into a strap, for example. In still other embodiments, flexible straps 6890 can be made from some other material (or combination of materials) having similar properties.

Figure 67:
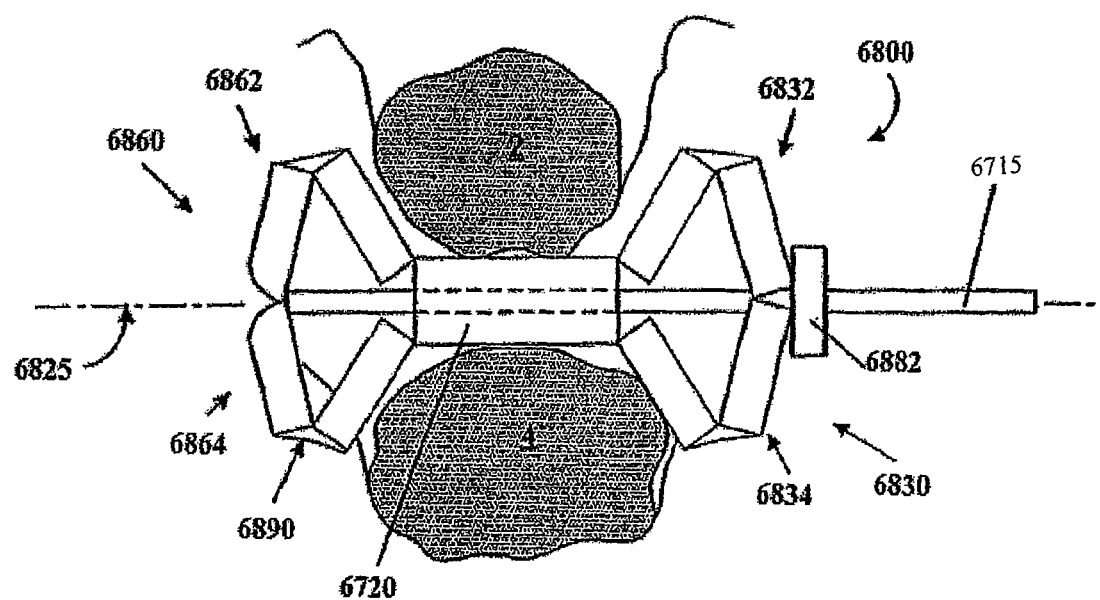
FIG. 67 is a posterior view of the implant of FIGS. 66A and 66B positioned between adjacent spinous processes in a deployed configuration.

FIG. 67 is a posterior view of the implant 6800 positioned between adjacent spinous processes 2,4 demonstrating an embodiment of a method for deploying the implant 6800 between the spinous processes 2,4. The first wing 6830 can be deployed to limit movement of the implant 6800 relative to the spinous processes 2,4. To deploy the first wing 6830 the rod 6715 can be held fixed in position or urged in a direction opposite the direction of insertion along the longitudinal axis 6825 while a force is applied to the hinged structures 6854-6857 (FIG. 66A) of the first wing 6830 to cause the upper end 6832 of the first wing and the lower end 6834 of the first wing to extend away from the rod 6715, thereby deploying the first wing 6830. The rod 6715 can be further urged in the direction opposite the direction of insertion so that the proximal end of the rod 6715 pivotably connected with the hinged structures 6852,6853 that comprise the distraction guide 6710, is drawn toward the spacer 6720, causing the upper end 6862 of the spacer, and the lower end 6864 of the spacer to extend away from the rod 6715. Once the second wing 6860 and the first wing 6830 are deployed, the rod 6715 can be fixed in position relative to the spacer 6720. As above, this can be accomplished using myriad different mechanisms. For example, as shown a first stop 6882 can be interference fit to the rod 6715 and positioned against the first wing 6830 along the rod 6715. The first stop 6882 can grip the rod 6715 so that the rod 6715 is prevented from moving by a friction fit between the first stop 6882 and the rod 6715. In other embodiments, some other mechanism can be used, such as a pin (e.g., a cotter pin), a latch system, etc. One of ordinary skill in the art will appreciate the myriad different mechanisms for fixing a rod 6715 in position relative to the spacer 6720. With the first wing 6830 and the second wing 6860 deployed, movement of the implant 6800 along the longitudinal axis 6825 can be limited or blocked, thereby resisting undesirable displacement of the implant 6800.

Figure 68A:
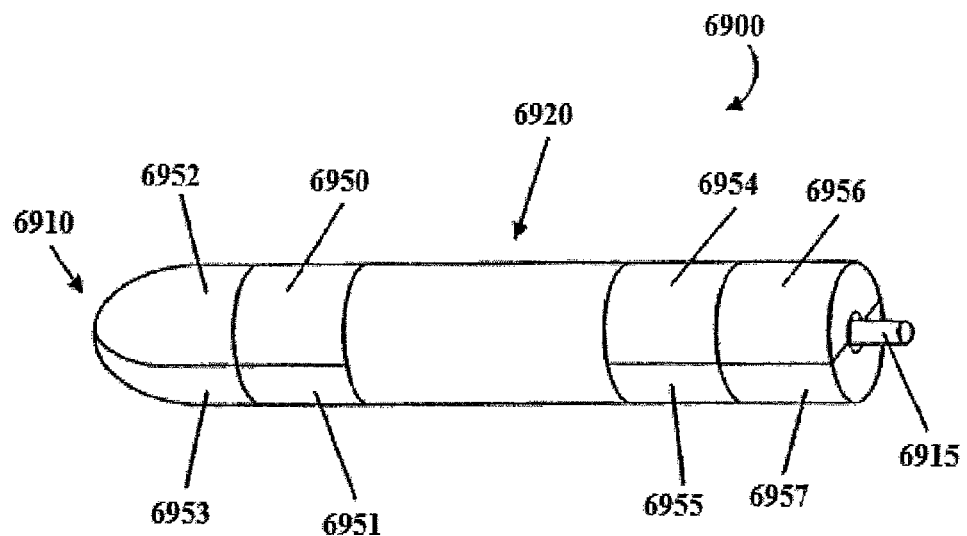
FIG. 68A is a perspective view of an alternative embodiment of an implant in accordance with the present invention having a first wing and a second wing that can be deployed after arranging the implant between adjacent spinous processes.
Figure 68B:
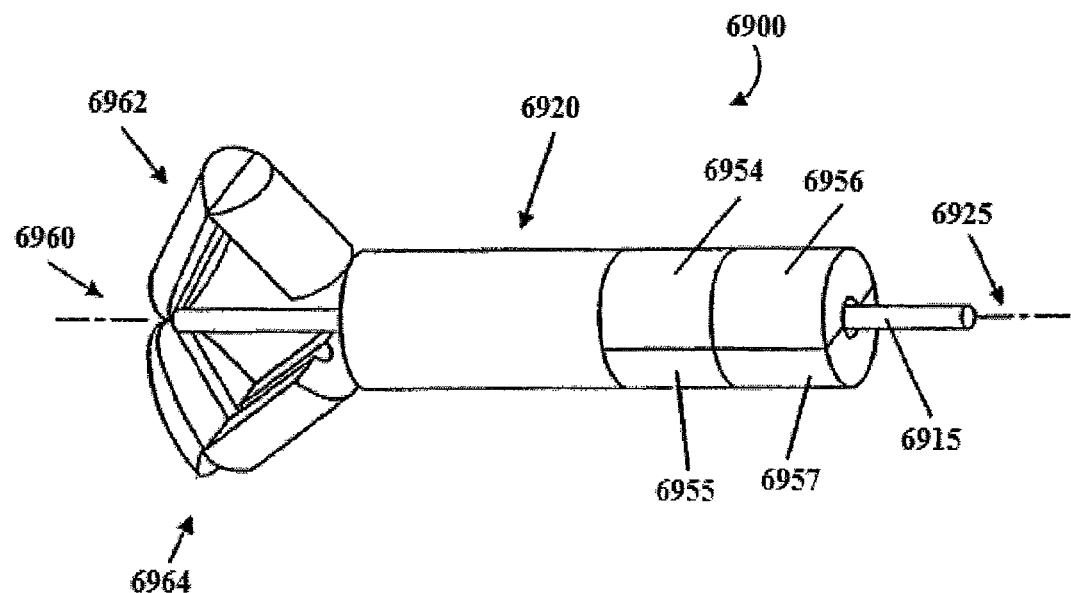
FIG. 68B is a perspective view of the implant of FIG. 68A in a partially deployed configuration.

Referring to FIGS. 68A and 68B, in still other embodiments, implants in accordance with the present invention can comprise a "matchbox"-like structure having a rounded, collapsed first configuration and a second, deployed configuration. Arranged in the first configuration, such implants 6900 can have a shape allowing the implant 6900 to be more naturally inserted through a cannula. As shown, such a shape includes a substantially circular cross-section, though in other embodiments the implant can have an ovoid or elliptical cross-section, thereby allowing a spacer shape to be employed that generally accommodates a space between adjacent spinous processes. However, it will be appreciated that an implant 6900 having a circular cross-section can most efficiently use the space of a cannula, where the cannula includes a circular cross-section; therefore, it may be preferable to employ an implant 6900 having a circular cross-section where a physician desired to minify the diameter of the cannula inserted into the surgical site.

The cross-section of the implant 6900 in a first configuration is generally consistent along the implant's length, having a diameter generally the thickness of a spacer 6920 of the implant 6900. The implant 6900 can comprise a distraction guide 6910 at a proximal end of the implant 6900, the distraction guide 6910 having a rounded (as shown) or tapered shape to pierce and/or distract a space between adjacent spinous processes. However, where a cannula is employed to deliver an implant to a surgical site, the implant 6900 can optionally include a distraction guide 6910 at the proximal end. The surgical site, and associated tissues and structures can be distracted and repositioned by the cannula, allowing substantially unobstructed access to the surgical site by the implant 6900. In such circumstance a distraction guide 6910 may not be necessary.

Figure 68C:
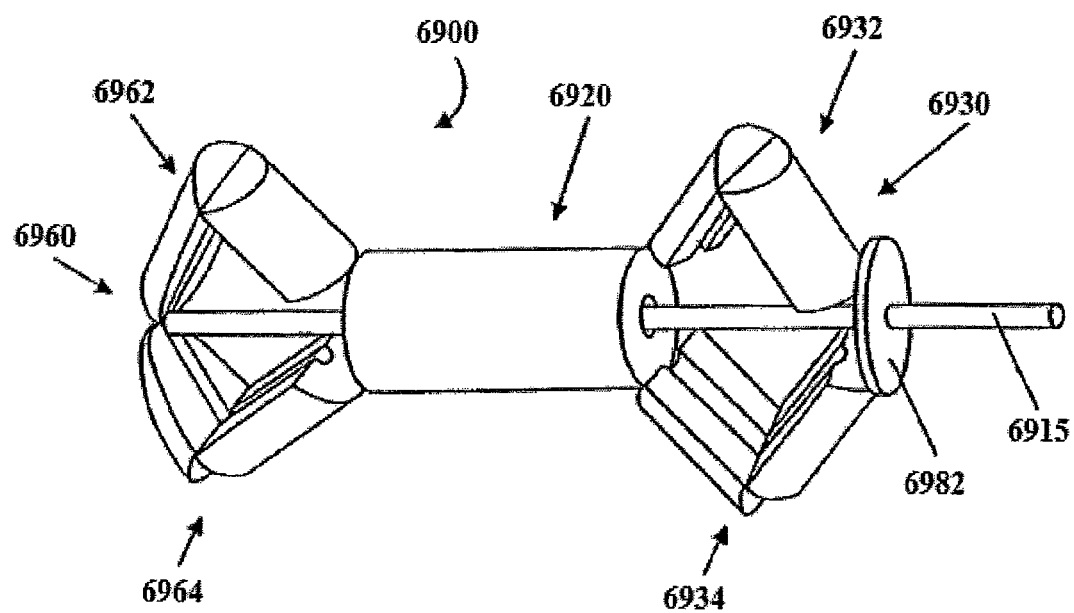
FIG. 68C is a perspective view of the implant of FIG. 68A in a fully deployed configuration.

The implant 6900 can further comprise a plurality of hinged structures 6950-6957, the hinged structures 6950-6957 being collapsed so as to facilitate the substantially collapsed profile. The hinged structures 6950-6957 are pivotally connected with the spacer 6920 and extend from both sides of the spacer 6920. A rod 6915 (or alternatively some other mechanism such as a tab) can be connected with the proximal end of the implant 900 and can extend through the hinged structures 6950-6953, and through the spacer 6920 so that the rod 6915 is accessible to a physician. Referring to FIGS. 68B and 68C, once the implant 6900 is positioned as desired between adjacent spinous processes, the rod 6915 can be drawn in a direction opposite the direction of insertion along the longitudinal axis 6925 so that the hinged structures 6950-6957 fold outward to form a first wing 6930 and a second wing 6960 between which is arranged the spacer 6920 and a portion of the spinous processes. As the hinged structures 6950-6957 fold outward, the height of the first and second wings 6930,6960 increases from approximately the same as the thickness of the spacer 6920 to a height such that the first and second wing 6930,6960 can limit or block movement of the implant 6900 along the longitudinal axis 6925 when positioned between adjacent spinous processes. As can be seen, the second wing 6960 includes four hinged structures 6950-6953: an upper first structure 6950 connected by a hinge to an upper second structure 6952, and a lower first structure 6951 connected by a hinge to a lower second structure 6953. The hinged structures 6950-6953 pivot outward to form an upper end 6962 of the second wing and a lower end 6964 of the second wing. Likewise, the first wing 6930 includes four hinged structures 6954-6957: an upper first structure 6954 connected by a hinge to an upper second structure 6956, and a lower first structure 6955 connected by a hinge to a lower second structure 6957.

Figure 69A:
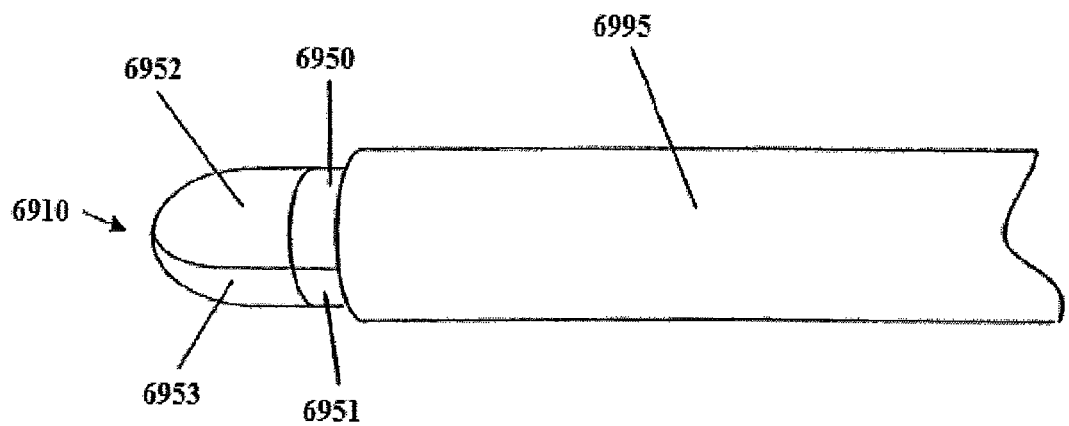
Figure 69B:
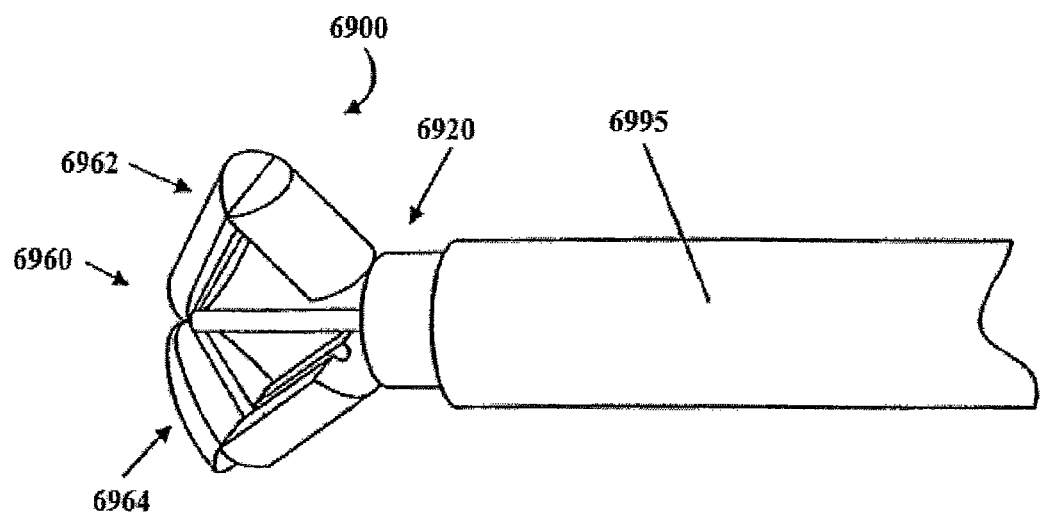
Figure 69C:
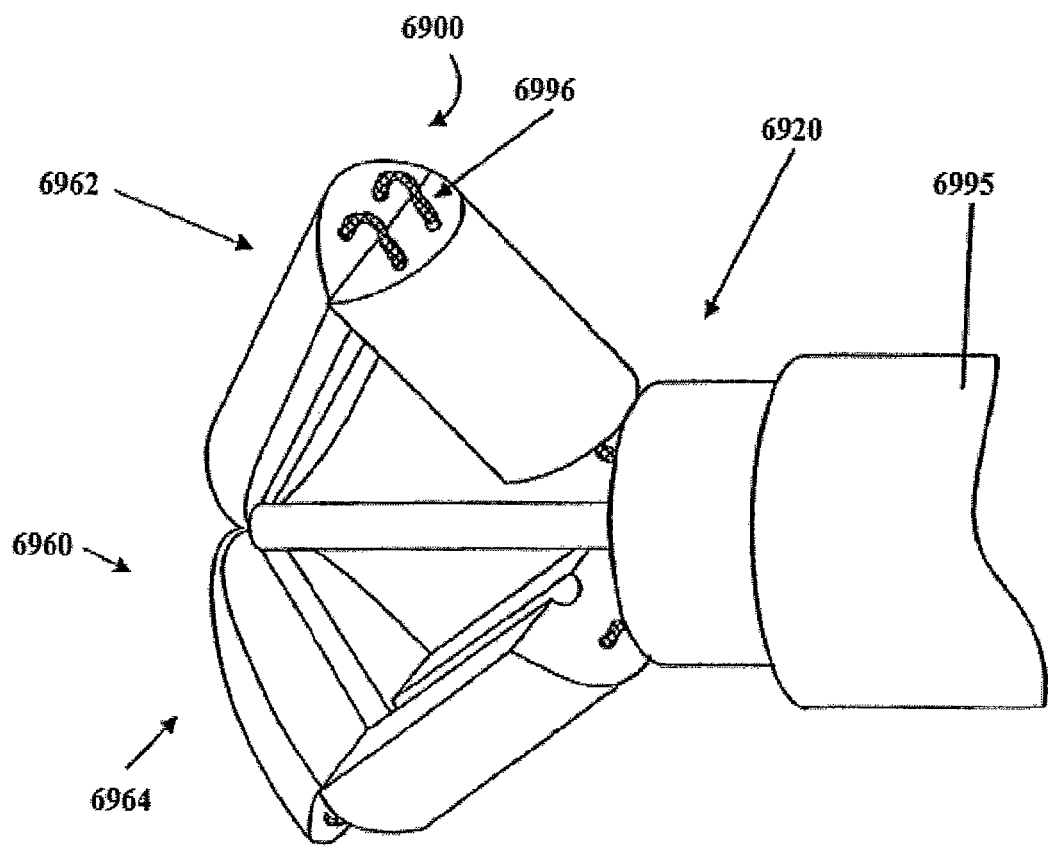

Embodiments as described above in reference to FIGS. 64A and 64B included a support structure 6722 extending from the spacer 6720. Likewise, a support structure can optionally extend from the spacer 6920 of the cannula delivered implant 6900. However, such a structure need not be necessary where the first wing 6930 is prevented from deploying during deployment of the second wing 6960 by the cannula 6995 itself (see FIG. 69B). Referring to FIGS. 69A and 69B, once the cannula is positioned at the surgical site, the implant 6900 can be urged through the cannula so that the hinged structures 6950-6953 are clear of the cannula. The rod 6915 can then be urged in an opposite direction (relative to insertion) along the longitudinal axis 6925 to deploy the second wing 6960. As the rod 6915 is drawn through the spacer 6920, the hinged structures 6952,6953 are drawn toward the spacer 6920. The hinged structures 6950-6953 pivot outward to accommodate the relative movement between the rod 6915 and the spacer 6920. Accordingly, the second wing 6960 has been satisfactorily deployed.

Once the second wing 6960 is deployed, the cannula 6995 can be retracted from the surgical site, thereby allowing the hinged structures 6956,6957 of the first wing 6930 to deploy by urging the hinged structures 6956,6957 toward the spacer 6920. The urging can be applied by a stop 6982 that can fit around the rod 6915 and can be interference fit or otherwise selectively fixed with the rod 6915. As the stop 6982 is pushed along the longitudinal axis 6925, along the rod 6915, the hinged structures 6954-6957 pivot outward to accommodate the relative movement between the stop 6982 and the spacer 6920. Accordingly, the first wing 6930 has been satisfactorily deployed.

Once the second wing 6960 and the first wing 6930 are deployed, the rod 6915 can be fixed in position relative to the spacer 6920. As above, this can be accomplished using myriad different mechanisms. For example, as shown a stop 6982 can be interference fit to the rod 6915 and positioned against the first wing 6930 along the rod 6915. The stop 6982 can grip the rod 6915 so that the rod 6915 is prevented from moving by a friction fit between the stop 6982 and the rod 6915. In other embodiments, some other mechanism can be used, such as a pin (e.g., a cotter pin), a latch system, etc. One of ordinary skill in the art will appreciate the myriad different mechanisms for fixing a rod 6915 in position relative to the spacer 6920. With the first wing 6930 and the second wing 6960 deployed, movement of the implant 6900 along the longitudinal axis 6925 can be limited or blocked, thereby resisting undesirable displacement of the implant 6900.

It should be noted that with implants as described above in reference to FIGS. 68A-69B the rod 6915 can optionally be trimmed or otherwise partially detached to decrease a space required to accommodate the implant 6900 within the patient's spine. For example, the structure of the rod 6915 can be beveled or otherwise weakened near a distal end of the rod 6915 to allow the rod 6915 to be snapped off when the first and second wings 6930,6960 are deployed and the rod 6915 is fixed in place. In other embodiments, a tool (not shown) can be used to cut the rod 6915 after the first and second wings 6930,6960 are deployed and the rod 6915 is fixed in place. Still further, the rod 6915 need not comprise a rigid structure, but rather alternatively can include a tether, string, or similarly flexible structure that can be placed in tension to retain the second wing 6960 and/or first wing 6930 in a deployed position.

Referring to FIGS. 68B, 68C and 69B, the implant 6900 is shown having operably connected "hinged" structures 6950-6957. Such structures can be hinged in any way that permits relative movement. For example, the structures may be hinged by way of flexible straps, for example as described above in reference to FIG. 66B. Alternatively, the structures can be hinged using some other technique. For example, referring to FIG. 70C, one or a pair of cords 6996 can connect pairs of hinged structures so that relative movement is restricted, thereby permitting hinging motion, while resisting separation of the structures. In still other embodiments, some other mechanism can be employed to define a range of movement of the hinged structures 6950-6957. One of ordinary skill in the art will appreciate the myriad different techniques for defining a range of motion of two mechanical parts.

As with the flexible straps 6890 above, the cord 6996 can be made from a biocompatible material. In an embodiment, the cord 996 can be made from a braided polyester suture material. Braided polyester suture materials include, for example, Ethibond, Ethiflex, Mersilene, and Dacron, and are non-absorbable, having high tensile strength, low tissue reactivity and improved handling. In other embodiments, the cords 6996 can be made from stainless steel (i.e., surgical steel), which can be woven into a strap, for example. In still other embodiments, the cords 6996 can be made from some other material (or combination of materials) having similar properties.

Materials for Use in Implants of the Present Invention

In some embodiments, the implant can be fabricated from medical grade metals such as titanium, stainless steel, cobalt chrome, and alloys thereof, or other suitable implant material having similar high strength and biocompatible properties.

Additionally, the implant can be at least partially fabricated from a shape memory metal, for example Nitinol, which is a combination of titanium and nickel. Such materials are typically radiopaque, and appear during x-ray imaging, and other types of imaging. Implants in accordance with the present invention, and/or portions thereof can also be fabricated from somewhat flexible and/or deflectable material. In these embodiments, the implant and/or portions thereof can be fabricated in whole or in part from medical grade biocompatible polymers, copolymers, blends, and composites of polymers. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer. Many polymers, copolymers, blends, and composites of polymers are radiolucent and do not appear during x-ray or other types of imaging. Implants comprising such materials can provide a physician with a less obstructed view of the spine under imaging, than with an implant comprising radiopaque materials entirely. However, the implant need not comprise any radiolucent materials.

One group of biocompatible polymers are the polyaryl ester ketones which has several members including polyetheretherketone (PEEK), and polyetherketoneketone (PEKK). PEEK is proven as a durable material for implants, and meets the criterion of biocompatibility. Medical grade PEEK is available from Victrex Corporation of Lancashire, Great Britain under the product name PEEK-OPTIMA. Medical grade PEKK is available from Oxford Performance Materials under the name OXPEKK, and also from CoorsTek under the name BioPEKK. These medical grade materials are also available as reinforced polymer resins, such reinforced resins displaying even greater material strength. In an embodiment, the implant can be fabricated from PEEK 450G, which is an unfilled PEEK approved for medical implantation available from Victrex. Other sources of this material include Gharda located in Panoli, India. PEEK 450G has the following approximate properties:

| Property | Value |
| --- | --- |
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

PEEK 450G has appropriate physical and mechanical properties and is suitable for carrying and spreading a physical load between the adjacent spinous processes. The implant and/or portions thereof can be formed by extrusion, injection, compression molding and/or machining techniques.

It should be noted that the material selected can also be filled. Fillers can be added to a polymer, copolymer, polymer blend, or polymer composite to reinforce a polymeric material. Fillers are added to modify properties such as mechanical, optical, and thermal properties. For example, carbon fibers can be added to reinforce polymers mechanically to enhance strength for certain uses, such as for load bearing devices. In some embodiments, other grades of PEEK are available and contemplated for use in implants in accordance with the present invention, such as 30% glass-filled or 30% carbon-filled grades, provided such materials are cleared for use in implantable devices by the FDA, or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to have enhanced compressive strength and stiffness, and a lower expansion rate relative to unfilled PEEK. Carbon-filled PEEK also offers wear resistance and load carrying capability.

As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. As mentioned, the implant can be comprised of polyetherketoneketone (PEKK). Other material that can be used include polyetherketone (PEK), polyetherketoneetherketoneketone (PEKEKK), polyetheretherketoneketone (PEEKK), and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02155 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials." Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

As described above, the binder can be made from a biocompatible material. In an embodiment, the binder can be made from a braided polyester suture material. Braided polyester suture materials include, for example, Ethibond, Ethiflex, Mersilene, and Dacron, and are nonabsorbable, having high tensile strength, low tissue reactivity and improved handling. In other embodiments, the binder can be made from stainless steel (i.e., surgical steel), which can be braided into a tether or woven into a strap, for example. In still other embodiments, the binder can be made from some other material (or combination of materials) having similar properties. It is to be understood that embodiments in accordance with the present invention can be constructed without a pliant material. It is also to be understood that the embodiments in accordance with the present invention can have other dimensions.

Methods for Implanting Interspinous Implants

Figure 70:
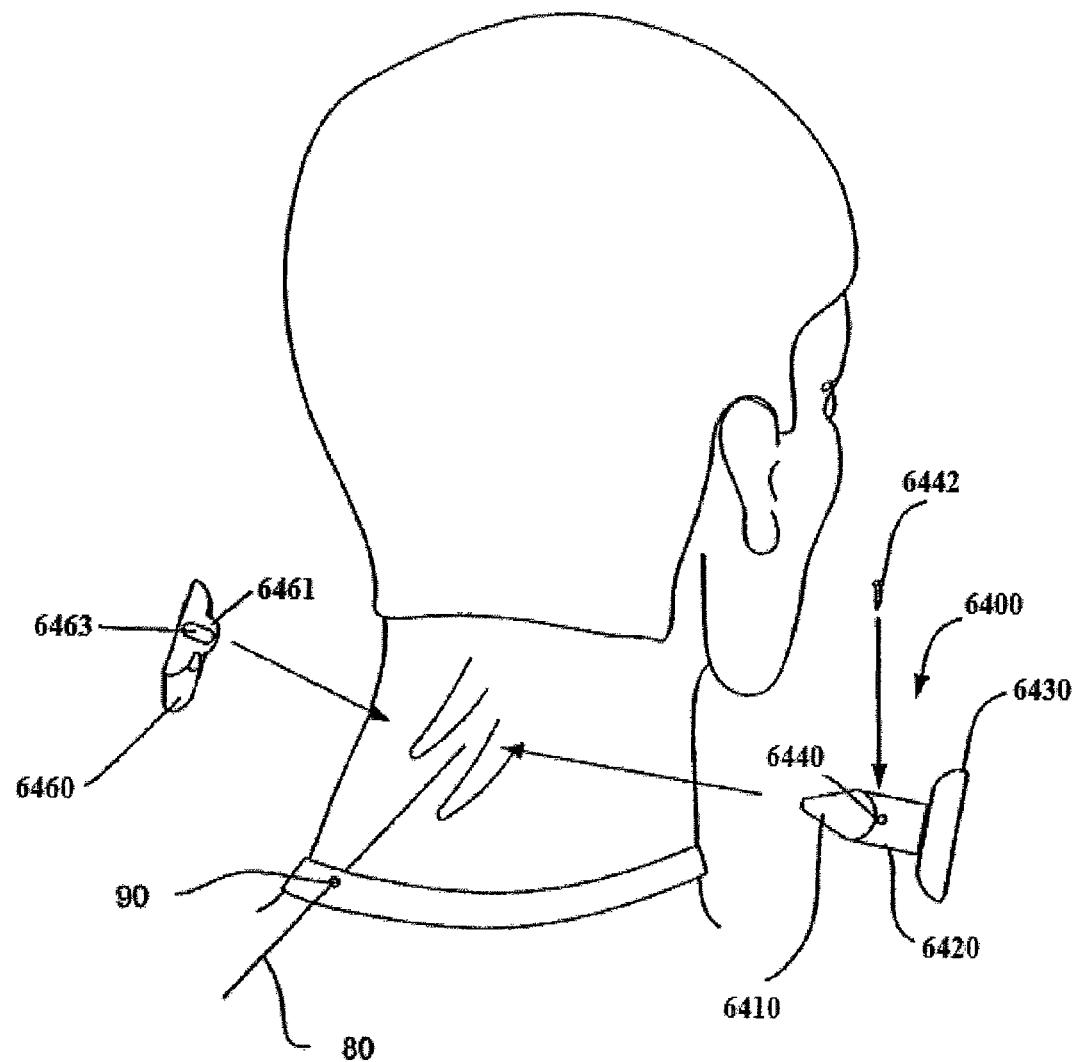
Figure 71:
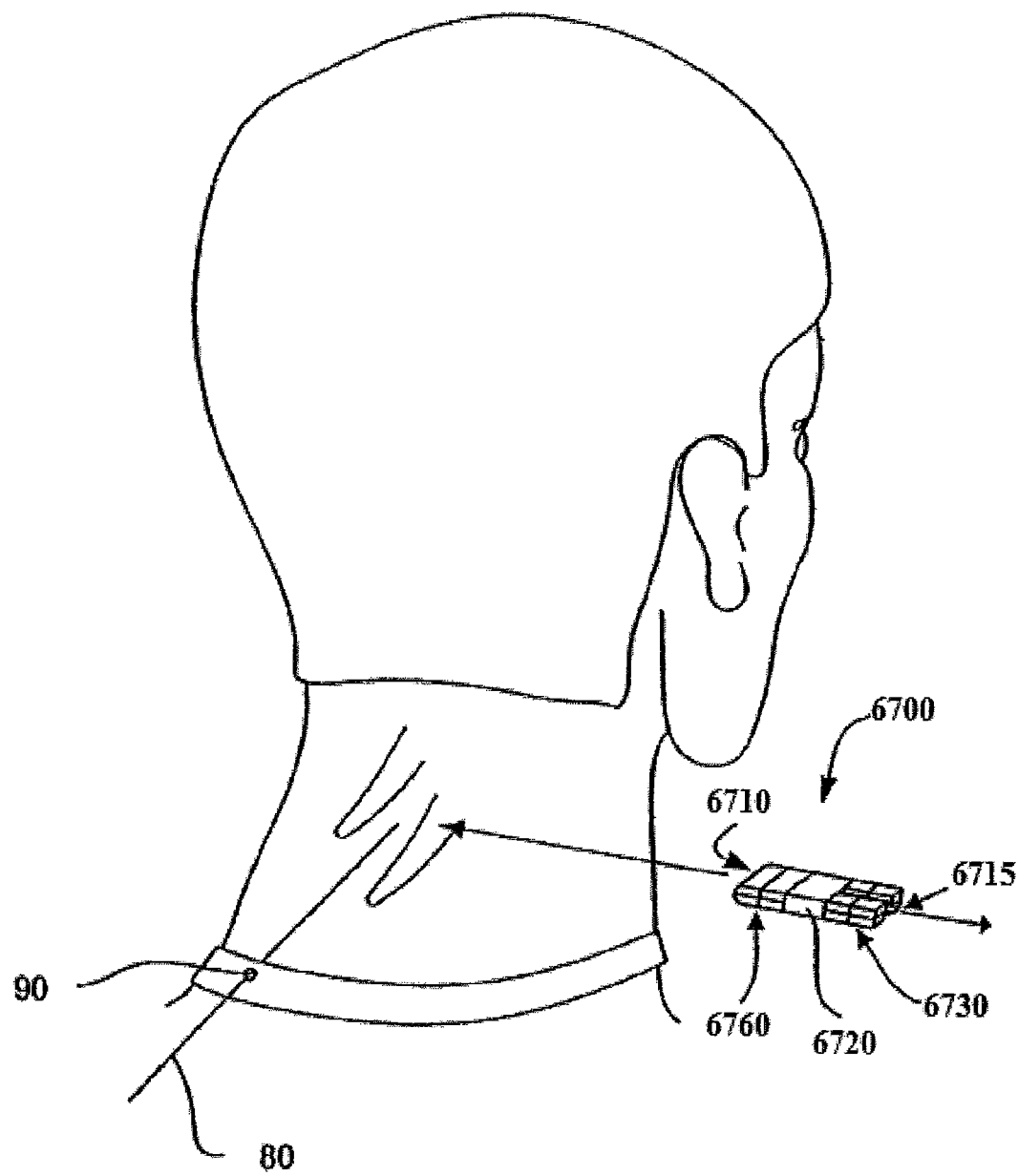

A minimally invasive surgical method for implanting an implant 6400 in the cervical spine is disclosed and taught herein. In this method, as shown in FIG. 70, preferably a guide wire 80 is inserted through a placement network or guide 90 into the neck of the implant recipient. The guide wire 80 is used to locate where the implant is to be placed relative to the cervical spine, including the spinous processes. Once the guide wire 80 is positioned with the aid of imaging techniques, an incision is made on the side of the neck so that an implant in accordance with an embodiment of the present invention, can be positioned in the neck thorough an incision and along a line that is about perpendicular to the guide wire 80 and directed at the end of the guide wire 80. In one embodiment, the implant can be a sized implant 400 (i.e., having a body that is not distractible), such as described above in FIGS. 7-23 and including a distraction guide 6410, a spacer 6420, and a first wing 6430. The implant 6400 is inserted into the neck of the patient. Preferably during insertion, the distraction guide 6410 pierces or separates the tissue without severing the tissue.

Once the implant 6400 is satisfactorily positioned, a second wing 6460 can be optionally inserted along a line that is generally collinear with the line over which the implant 6400 is inserted but from the opposite side of the neck. The anatomy of the neck is such that it is most convenient and minimally invasive to enter the neck from the side with respect to the implant 6400 and the second wing 6460. The second wing 6460 is mated to the implant and in this particular embodiment, the second wing 6460 is attached to the implant 6400 by the use of a fastener, for example by a screw 6442. Where a screw is used, the screw 6442 can be positioned using a screw driving mechanism that is directed along a posterior to anterior line somewhat parallel to the guide wire 80. This posterior to anterior line aids the physician in viewing and securing the second wing 6460 to the implant. The second wing 6460 is positioned so that a bore 6463 formed in a lip 6461 of the second wing 6460 is aligned with a bore 6440 of the implant 6400, as described above. The screw 6442 is positioned within both bores and secured, at least, to the bore 6440 of the implant 6400. In other embodiments, the second wing can be interference fit with the implant, as described above, or fastened using some other mechanism, such as a flexible hinge and protrusion.

A minimally invasive surgical method for implanting an alternative embodiment of an implant 6700 in the cervical spine is disclosed and taught herein. In this method, as shown in FIG. 25, preferably a guide wire 80 is inserted through a placement network or guide 90 into the neck of the implant recipient. The guide wire 80 is used to locate where the implant 6700 is to be placed relative to the cervical spine, including the spinous processes. Once the guide wire 80 is positioned with the aid of imaging techniques, an incision is made on the side of the neck so that an implant 700 in accordance with an embodiment of the present invention, can be positioned in the neck thorough an incision and along a line that is about perpendicular to the guide wire 80 and directed at the end of the guide wire 80. In an embodiment, the implant 6700 can include a distraction guide 6710, a spacer 6720, a rod 6715 extending through the spacer 6720, and deployable first and second wings 6730,6760. The implant 6700 can have a substantially flat profile to ease implantation, as described above. The implant 6700 is inserted into the neck of the patient. Preferably during insertion, the distraction guide 6710 pierces or separates the tissue without severing the tissue.

Figure 72:
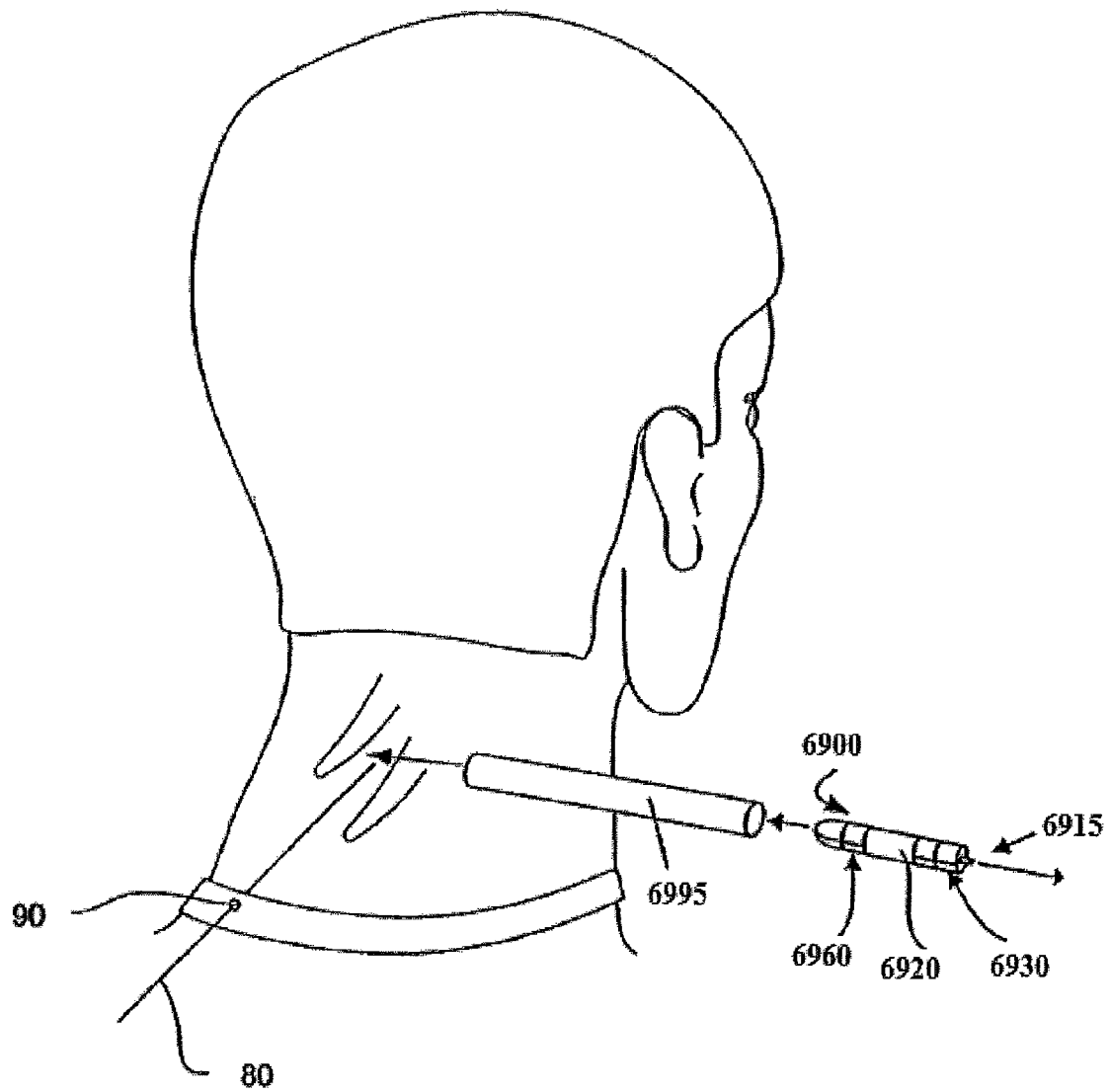

Once the implant 6700 is satisfactorily positioned, the first wing 6730 and the second wing 6760 can be deployed. As described above, the second wing 6760 can be deployed by urging the rod 6715 in a direction opposite the direction of insertion along the longitudinal axis 6725. As the rod 6715 travels through the spacer 6720, hinged structures 6750-6753 contact the spacer 66720, buckle and extend away from the rod 6715 two form an upper end 6762 of the second wing and a lower end 6764 of the second wing. When second wing 6760 is satisfactorily deployed, the rod 6715 can be fixed in place relative to the spacer 6720 using a first stop 6782, a pin, or some other mechanism. The first wing 6730 can be deployed by urging the hinged structures 6754-6757 toward the spacer 6720, causing the hinged structures 6754-6757 to buckle and extend away from one another to form an upper end 6732 of the second wing and a lower end 6734 of the second wing. The anatomy of the neck is such that it is most convenient and minimally invasive to enter the neck from the side with respect to the implant 6700. A minimally invasive surgical method for implanting an alternative embodiment of an implant 6900 in the cervical spine is disclosed and taught herein. In this method, as shown in FIG. 72, preferably a guide wire 80 is inserted through a placement network or guide 90 into the neck of the implant recipient. The guide wire 80 is used to locate where the implant 6900 is to be placed relative to the cervical spine, including the spinous processes. Once the guide wire 80 is positioned with the aid of imaging techniques, an incision is made on the side of the neck along a line that is about perpendicular to the guide wire 80 and directed at the end of the guide wire 80. The cannula 6995 is fed through the incision and positioned between the targeted adjacent spinous processes. In an embodiment, the implant 6900 can include a distraction guide 6910, a spacer 6920, a rod 6915 extending through the spacer 6920, and deployable first and second wings 6930,6960. The implant 6900 can have a substantially circular cross-section to roughly conform with an inside surface of the cannula 6995. The implant 6900 is urged through the cannula 6995 and into position between the adjacent spinous processes so that the second wing 6960 hinge structures are clear of the cannula 6995, as described above in reference to FIG. 68B. The second wing 6960 is then deployed by urging the rod 6915 in a direction opposite the direction of insertion along the longitudinal axis 6925. As the rod 6915 travels through the spacer 6920, hinged structures 6950-6953 contact the spacer 6920, buckle and extend away from the rod 6915 two form an upper end 6962 of the second wing and a lower end 6964 of the second wing. When second wing 6960 is satisfactorily deployed, the cannula 6995 can be retracted to expose the hinged structures 6954-6957 of the first wing 6930. The first wing 6930 can be deployed by urging the hinged structures 6954-6957 toward the spacer 6920, causing the hinged structures 6954-6957 to buckle and extend away from one another to form an upper end 6932 of the second wing and a lower end 6934 of the second wing. Once the first wing 6930 is deployed, the rod 6915 can optionally be shortened, and the cannula 6995 can be withdrawn from the incision. The incision can then be closed.

The foregoing description of the present invention have been presented for purposes of illustration and description. It is not intended to be exhaustive or to limit the invention to the precise forms disclosed. Many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

Interspinous Implants

Figure 73A:
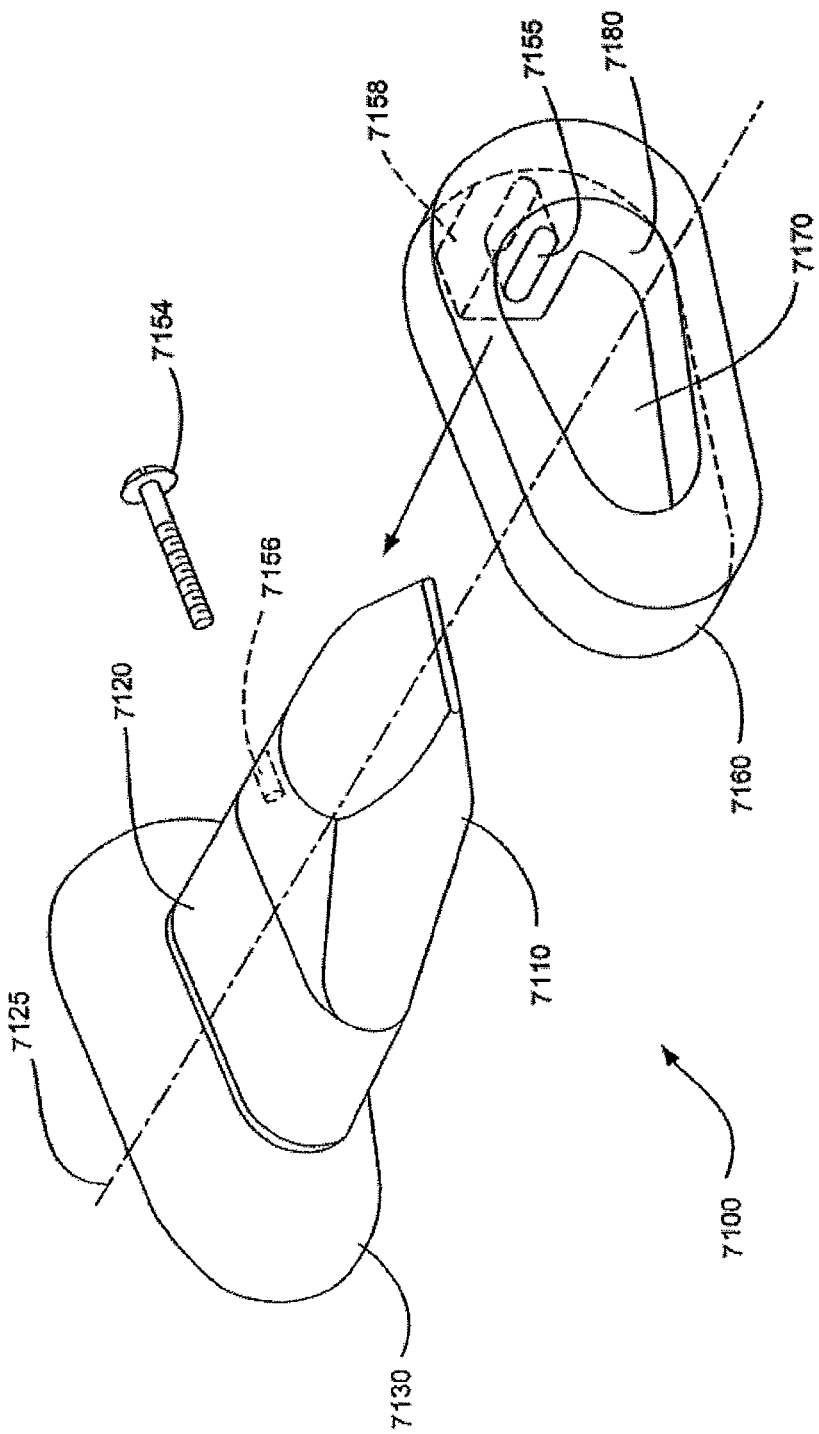

FIG. 73A is a perspective view of an implant as described in U.S. patent application Ser. No. 10/850,267, filed May 20, 2004, incorporated herein by reference. The implant 7100 comprises a first wing 7130, a spacer 7120, and a lead-in tissue expander (also referred to herein as a distraction guide) 7110. The distraction guide 7110 in this particular embodiment is wedge-shaped, i.e., the implant has an expanding cross-section from a proximal end of the implant 7100 to a region 7150 where the guide 7110 joins with the spacer 7120 (referencing for the figures is based on the point of insertion of the implant between spinous processes). As such, the distraction guide 7110 functions to initiate distraction of the soft tissue and the spinous processes when the implant 7100 is surgically inserted between the spinous processes. It is to be understood that the distraction guide 7110 can be pointed and the like, in order to facilitate insertion of the implant 7100 between the spinous processes of adjacent cervical vertebrae. It is advantageous that the insertion technique disturb as little of the bone and surrounding tissue or ligaments as possible in order to reduce trauma to the site and promote early healing, and prevent destabilization of the normal anatomy. For embodiments such as those of FIGS. 73A and 73B, there is no requirement to remove any of the bone of the spinous processes and no requirement to sever, or remove from the body, ligaments and tissues immediately associated with the spinous processes. For example, it is unnecessary to sever the supraspinal ligament of the lower vertebrae or the ligamentum nuchae (which corresponds to the supraspinal ligament) which partially cushions the spinous processes of the upper cervical vertebrae. As can be seen, the spacer 7120 can be teardrop-shaped in cross-section perpendicular to a longitudinal axis 7125 of the implant 7100. In this way, the shape of the spacer 7120 can roughly conform to a wedge-shaped space, or a portion of the space, between adjacent spinous processes within which the implant 7100 is to be positioned. As shown in FIG. 1A, the spacer 7120 (and the first wing 7108) is shaped to accommodate the anatomical form or contour of spinous processes (and/or laminae) of the C6 and C7 vertebra for placement between such spinous processes (i.e., the C6-C7 motion segment). The same shape or variations of this shape can be used to accommodate other motion segments, for example in the thoracic or lumbar regions. In other embodiments the spacer 7120 can have alternative shapes such as circular, wedge, oval, ovoid, football, and rectangular with rounded corners, and other shapes. The shape of the spacer 7120 can be selected for a particular patient so that the physician can position the implant 7100 as close as possible to the anterior portion of the surface of the spinous process. The shape selected for the spacer 7120 can affect the contact surface area of the implant 7100 and the spinous processes that are to be subject to distraction. Increasing the contact surface area between the implant 7100 and the spinous processes can distribute a load force between the spinous frame and the implant 7100. The first wing 7130 is likewise teardrop-shaped in cross-section perpendicular to a longitudinal axis 7125 of the spacer 7120 and distraction guide 7110. The dimensions of the first wing 7130 can be larger than that of the spacer 7120, particularly along the axis of the spine, and can limit or block lateral displacement of the implant 7100 in the direction of insertion along the longitudinal axis 7125. As with the spacer 7120, the first wing 7130 can have other cross-sectional shapes, such as elliptical, wedge, circular, oval, ovoid, football, and rectangular with rounded corners and other shapes.

The implant 7100 of FIG. 73A further includes an adjustable wing 7160 (also referred to herein as a second wing) separate from the distraction guide 7110, the spacer 7120 and the first wing 7130. The second wing 7160 is connectable with the distraction guide 7110 (and/or the spacer 7120) once the implant 7100 is positioned between adjacent spinous processes. The second wing 7160, similar to the first wing 7130, can limit or block lateral displacement of the implant 7100, however displacement is limited or blocked in the direction opposite insertion. When both the first wing 7130 and the second wing 7160 are connected with the implant 7100 and the implant 7100 is positioned between adjacent spinous processes, a portion of the spinous processes can be sandwiched between the first wing 7130 and the second wing 7160, limiting displacement along the longitudinal axis 7125. As can be seen, the second wing 7160 can be teardrop-shaped in cross-section. A lip 7180 defining a space 7170 through the second wing 7160 allows the second wing 7160 to pass over the distraction guide 7110 to meet and connect with the distraction guide 7110 and/or the spacer 7120. The second wing 7160 is then secured to the distraction guide 7110 and/or the spacer 7120. The second wing 7160, can be designed to be interference-fit onto the spacer 7120 or a portion of the distraction guide 7110 adjacent to the spacer 7120. Where the second wing 7160 is interference-fit, there is no additional attachment device to fasten the second wing 7160 relative to the remainder of the implant 7100.

Alternatively, various fasteners can be used to secure the second wing 7160 relative to the remainder of the implant 7100. For example, FIG. 73A illustrates an embodiment of an implant 7100 including a teardrop-shaped second wing 7160 having a tongue 7158 at the posterior end of the second wing 7160. A bore 7155 is disposed through the tongue 7158, and is aligned with a corresponding bore 7156 on the spacer 7120 when the second wing 7160 is brought into position by surgical insertion relative to the rest of the implant 7100. A threaded screw 7154 can be inserted through the aligned bores 7155,7156 in a posterior-anterior direction to secure the second wing 7160 to the spacer 7120. The direction of insertion from a posterior to an anterior direction has the screw 7154 engaging the bores 7155,7156 and the rest of the implant 7100 along a direction that is generally perpendicular to the longitudinal axis 7125. This orientation is most convenient when the physician is required to use a screw 7154 to secure the second wing 7160 to the rest of the implant 7100. The second wing 7160 can further be secured to the spacer 7120 by some other mechanism, for example such as a flexible hinge (not shown) with a protrusion that engages an indentation of one of the distraction guide 7110 and the spacer 7120. Alternatively, the second wing 7160 can be secured to one of the distraction guide 7110 and the spacer 7120 by still some other mechanism.

Figure 73B:
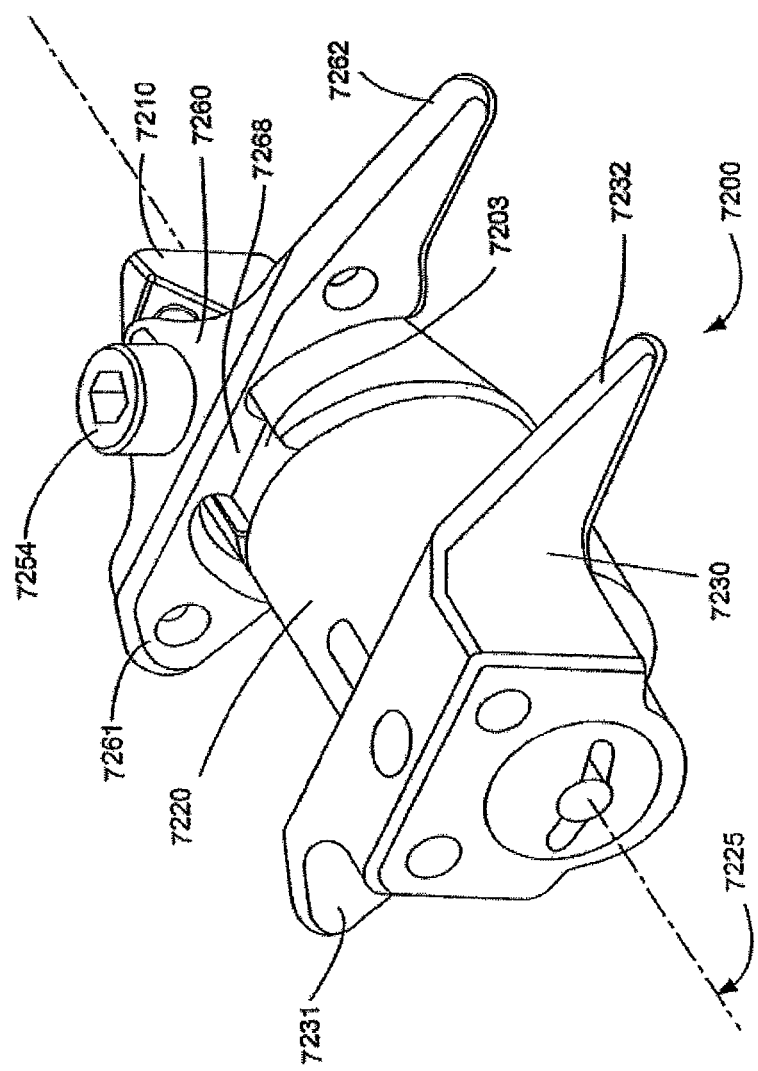

FIG. 73B is a perspective view of an implant as described in U.S. Pat. No. 6,695,842 to Zucherman, et at, incorporated herein by reference. The implant 7200 has a main body that includes a spacer 7220, a first wing 7230, a lead-in tissue expander 7210 (also referred to herein as a distraction guide) and an alignment track 7203. The main body of the implant 7200 is inserted between adjacent spinous processes and remains in place (where desired) without attachment to the bone or ligaments.

The distraction guide 7210 includes a tip from which the distraction guide 7210 expands, the tip having a diameter sufficiently small such that the tip can pierce an opening in an interspinous ligament and/or can be inserted into a small initial dilated opening. The diameter and/or cross-sectional area of the distraction guide 7210 gradually increases until it is substantially similar to the diameter of the spacer 7220. The tapered front end eases the ability of a physician to urge the implant 7200 between adjacent spinous processes. When urging the main body of the implant 7200 between adjacent spinous processes, the front end of the distraction guide 7210 distracts the adjacent spinous processes and dilates the interspinous ligament so that a space between the adjacent spinous processes is approximately the diameter of the spacer 7220.

As shown in FIG. 73B, the spacer 7220 is elliptically shaped in cross-section, and can swivel so that the spacer 7220 can self-align relative to the uneven surfaces of the spinous processes. Self-alignment can ensure that compressive loads are distributed across the surface of the bone. As contemplated in Zucherman '842, the spacer 7220 can have, for example, a diameter of six millimeters, eight millimeters, ten millimeters, twelve millimeters and fourteen millimeters. These diameters refer to the height by which the spacer 7220 distracts and maintains apart the spinous process. For an elliptically shaped spacer 7220, the selected height (i.e., diameter) is the minor dimension measurement across the ellipse. The major dimension is transverse to the alignment of the spinous process, one above the other.

The first wing 7230 has a lower portion 7231 and an upper portion 7232. The upper portion 7232 is shaped to accommodate the anatomical form or contour of spinous processes (and/or laminae) of the L4 (for an L4-L5 placement) or L5 (for an L5-S1 placement) vertebra. The same shape or variations of this shape can be used to accommodate other motion segments, such as motion segments in the cervical and thoracic regions. The lower portion 7231 can also be rounded to accommodate the spinous processes. The lower portion 7231 and upper portion 7232 of the first wing 7230 act as a stop mechanism when the implant 7200 is inserted between adjacent spinous processes. The implant 7200 cannot be inserted beyond the surfaces of the first wing 7230. Additionally, once the implant 7200 is inserted, the first wing 7230 can prevent some side-to-side, or posterior-to-anterior movement of the implant 7200. As with the implant 7100 of FIG. 73A, the implant 7200 of FIG. 73B further includes a second wing 7260. Similar to the first wing 7230, the second wing 7260 includes a lower portion 7261 and an upper portion 7262 sized and/or shaped to accommodate the anatomical form or contour of the spinous processes and/or lamina. The second wing 7260 can be secured to the main body of the implant 7200 with a fastener 7254. The second wing 7260 also has an alignment tab 7268. When the second wing 7260 is initially placed on the main body of the implant 7200, the alignment tab 7268 engages the alignment track 7203. The alignment tab 7268 slides within the alignment track 7203 and helps to maintain the adjustable wing 7260 substantially parallel with the first wing 7230. When the main body of the implant 7200 is inserted into the patient and the second wing 7260 has been attached, displacement along the longitudinal axis 7225 in either the direction of insertion or the direction opposite insertion can be limited or blocked.

Further, the second wing 7260 also can prevent some side-to-side, or posterior-to-anterior movement.

For both the implant 7100 of FIG. 73A and the implant 7200 of FIG. 73B, where a second wing 7160,7260 is connected with the implant 7100,7200 after the implant 7100, 7200 is positioned between the spinous processes, a procedure for positioning such an implant 7100,7200 and subsequently connecting the second wing 7160,7260 with the implant 7100,7200 can require a bilateral approach wherein a physician must access both sides of the interspinous ligament, a first side to pierce and/or distract the interspinous ligament and position the implant 7100,7200 so that the movement in the direction of insertion is satisfactorily limited by the first wing 7130,7230, and a second side to attach the second wing 7160,7260 such that movement in the direction opposite insertion is satisfactorily limited by the second wing 7160, 7260.

Implants Having a Lead-in Screw

Referring to FIGS. 74A through 75C, implants 7300 and methods for positioning such implants in accordance with the present invention can include, in an embodiment, a frame 7302 having a central body 7304 extending along a longitudinal axis 7325 of the implant 7300. The central body 7304 can include a distraction guide 7306 at a proximal end of the central body 7304. The distraction guide 7306 can have a tapered shape so that the distraction guide 7306 can pierce and/or distract an interspinous ligament associated with the targeted motion segment. A first wing 7330 extends from a distal end of the central body 7304 and acts to limit or block movement of the implant 7300 along the longitudinal axis 7325 in the direction of insertion.

A substantially thread-shaped lead-in screw (also referred to herein as a second wing) 7360 extends from the periphery of the central body 7304 distally located relative to the distraction guide 7306. For example, the second wing can be helical shaped, wherein a helical shape is generally a three-dimensional curve that lies on a cylinder or a cone, so that its angle to a plane perpendicular to the axis is constant. Helical shapes as described herein need not lie along a constant angle, but rather can lie along an angle that varies. A helical shape need only include a curve that has a gap 7361 (also referred to herein as a groove) between overlapping surfaces such that structures related to the adjacent spinous processes and the spinous processes can pass within the groove 7361. It is to be understood that a lead-in screw shape other than helical is within the spirit and scope of the invention. For example, a shape with a constant diameter thread, or with different or constant thread pitches can be used. Generally and preferably the second wing 7360 can have an outer diameter that steadily increases from near the proximal end of the central body 7304 distally toward the first wing 7330. The second wing 7360 terminates so that a spacer 7320 (FIG. 74B) can be arranged between the second wing 7360 and the first wing 7330. The helical shape of the second wing 7360 can facilitate implantation between adjacent spinous processes 2,4 (shown in FIGS. 75A-75E) from one or more incisions formed on one side of an interspinous ligament 6 extending between the adjacent spinous processes 2,4.

Implantation can be accomplished in such embodiments as described above by initially piercing or distracting the interspinous ligament 6 with the distraction guide 7306, and subsequently rotating the central body 7304. One or both of the interspinous ligament 6 and the adjacent spinous processes 2,4 slip within the groove 7361 of the helically shaped second wing 7360 as the central body 7304 is rotated and the central body 7304 is drawn or urged along the longitudinal axis 7325 in the direction of insertion. The interspinous ligament 6 and/or associated spinous processes 2,4 travels along the groove 7361 and therefore along the central body 7304, causing the second wing 7360 to be positioned, when the implant 7300 is seated, at an opposite side of the interspinous ligament 6 from the first wing 7330 such that the interspinous ligament 6 is disposed between the first wing 7330 and the second wing 7360 along the longitudinal axis 7325. Arranging the interspinous ligament 6, and/or the associated spinous processes 2,4 between the first wing 7330 and the second wing 7360 limits or blocks movement along the longitudinal axis 7325. In some embodiments, the distraction guide 7306 can have a generally conical shape, rather than a wedge-shape as described above in reference to FIGS. 73A and 73B. Where the distraction guide 7306 includes a wedge-shape, rotation of the central body 7304 can cause the distraction guide 7306 to distract the adjacent spinous processes 2,4 and/or interspinous ligament 6 a distance according to the major dimension of the distraction guide 7306. Referring to FIG. 74A, as with the distraction guide 7306, the first wing 7330 has a rounded shape, having substantially the same minor and major dimension. The first wing 7330 is shaped so that the first wing 7330 can rotate along with the central body 7304 while minifying interference from surrounding structures. Further, the rounded shape of the first wing 7330 can accommodate slots as described below, while providing a surface to contact the adjacent spinous processes 2,4 during implantation, thereby limiting movement along the longitudinal axis 7325 in the direction of insertion. However, in other embodiments, the first wing 7330 need not have a rounded shape.

The first wing 7330 can include one or more slots to receive a spacer 7320 so that the spacer 7320 can be arranged over the central body 7304 between the second wing 7360 and the first wing 7330. As shown, the first wing 7330 includes two slots 7332,7334 having a substantially arced shape, and arranged in opposition to one another. The maximum distance between the peripheries of the slots 7332,7334 can substantially define a minor (or alternatively a major) dimension of the spacer 7320. The slots 7332,7334 preferably have inner surfaces that transition to the outer surface of the central body 7304, so that when a spacer 7320 is urged through the slots 7332,7334, the spacer 7320 abuts the central body 7304, thereby allowing a portion of a load to be transferred to the central body 7304. In other embodiments, one or more slots can be disposed through the first wing 7330 and can be shaped as desired, such that the one or more slots having the same or different geometries.

FIG. 74B is a perspective view of the spacer 7320 having a geometry adapted to be received over the frame 7302 described above. The spacer 7320 includes a top portion 7322 and a bottom portion 7324. (It should be noted that some components of the implant are referred to herein as "top" and "bottom" components; however, positional modifiers are attached merely to distinguish between similar components and are not meant to limit use of the invention.) The top portion 7322 and the bottom portion 7324 have outer surfaces that support a respective adjacent spinous process 2,4 and inner surfaces that abut the central body 7304. As shown, a portion of the inner surfaces of the top portion 7322 and the bottom portion 7324 are grooved so as to approximately conform with a shape of the central body 7304, thereby spreading a load across the outer surface of the central body 7304. The outer surfaces are arced, and generally shaped to resemble the outer periphery of the slots 7332,7334 of the first wing 7330. In other embodiments, for example where the central body is trapezoidal, or otherwise shaped, the top portion 7322, bottom portion 7324, and corresponding slots 7332,7334 can be similarly shaped to accommodate the central body 7304. Alternatively, the central body 7304 can have an irregular or non-symmetrical shape to prevent incorrect mating of the spacer 7320 with the frame 7302. One of ordinary skill in the art will appreciate the myriad variations with which the structures can be shaped.

As can be seen, the top portion 7322 and the bottom portion 7324 include respective lead-in tissue expanders 7321,7323 (also referred to herein as a distraction guides). The distraction guide 7321,7323 for the top portion 7322 and the bottom portion 7324 can taper at the proximal end of the spacer 7320, thereby allowing the distraction guide 7306 to distract one or both of the adjacent spinous processes 2,4 and/or interspinous ligament 6.

As can be seen, the top portion 7322 and the bottom portion 7324, taken together in cross-section perpendicular to a longitudinal axis 7325, can have a split teardrop shape, similar to a cross-section of the spacer 7120 of FIG. 73A. In this way, the shape of the spacer 7320 can roughly conform to a wedge-shaped space, or a portion of the space, between adjacent spinous processes within which the implant 7300 is to be positioned. The same shape or variations of this shape can be used to accommodate different motion segments and/or different patients, as described above. In other embodiments the spacer 7320 can have alternative shapes such as circular, elliptical, wedge, oval, ovoid, football, and rectangular with rounded corners, and other shapes. The shape of the spacer 7320 can be selected for a particular patient so that the physician can position the implant 7300 as close as possible to the anterior portion of the surface of the spinous process. The shape selected for the spacer 7320 can affect the contact surface area of the implant 7300 and the spinous processes that are to be subject to distraction. Increasing the contact surface area between the implant 7300 and the spinous processes can distribute a load force between the spinous frame and the implant 7300.

The top portion 7322 and the bottom portion 7324 extend from a base 7326 and are fixed in relative position by the base 7326. As can be seen, the bottom portion 7324 extends farther than the top portion 7322. As will be described in further detail below, the top portion 7322 is truncated in length along the longitudinal axis 7325 relative to the bottom portion 7324 to avoid contacting the second wing 7360 which in the embodiment shown in FIG. 74A spirals to a termination point at the upper surface of the central body 7304. An additional advantage with the truncated top portion 7322 is that the spinous processes are distracted more gradually, first with the bottom portion 7324 and then with the top portion 7322 as the spacer 7320 is inserted into the frame 7302. The base 7326 can have a length along the longitudinal axis 7325 as desired, and preferably having a length sufficient to support the top portion 7322 and the bottom portion 7324 in an at least semi-rigid position relative to one another. The base 7326 can include a cavity 7329 for receiving one or both of an insertion tool and a fastener (not shown). The cavity 7329 can correspond to a threaded cavity 7309 disposed in the central body 7304 so that, for example, the frame 7302 and the spacer 7320 can be fixedly attached, with by way of example only a screw, once the spacer 7320 is seated.

FIG. 74C is a perspective view of the implant 7300 wherein the spacer 7320 is seated within the frame 7302 and arranged over the central body 7304. As can be seen, the bottom portion 7324 of the spacer 7320 extends further than the top portion 7322, and is unobstructed by the second wing 7360, which spirals partially above the bottom portion 7324. The first wing 7330 and the second wing 7360 have major dimensions approximately along the axis of the spine that are larger than the major dimension of the spacer 7320, thereby blocking or limiting movement of the implant 7300 along the longitudinal axis 7325.

FIGS. 75A through 75E are partial cross-sectional posterior views illustrating the implant 7300 being positioned between adjacent spinous processes. FIG. 75A illustrates the distraction guide of the frame 7302 positioned adjacent to the interspinous ligament 6 of the targeted motion segment. The frame 7302 can be urged against the interspinous ligament 6 to pierce and/or distract the interspinous ligament 6. The frame 7302 can further be urged into the interspinous ligament 6 along the longitudinal axis 7325 until the second wing 7360 contacts the interspinous ligament 6. Referring to FIG. 75B, the frame 7302 can then be rotated and urged toward the interspinous ligament 6 so that the second wing 7360 passes through the interspinous ligament 6, which is thereby positioned between a portion of the second wing 7360 and the first wing 7330 along the longitudinal axis 7325. The interspinous ligament 6 and the adjacent spinous processes 2,4 are substantially disposed within a groove 7361 between the surfaces of the second wing 7360 that overlap along the longitudinal axis 7325. Referring to FIG. 75C, the frame 7302 can be further rotated and urged into the interspinous ligament 6 until the entire second wing 7360 is substantially arranged so that the interspinous ligament 6 is disposed between the first wing 7330 and the second wing 7360. The frame 7302 can be further rotated so that the slots 7332,7334 are arranged to receive the spacer 7320 such that a load applied to the spacer 7320 is sufficiently distributed across the surface of the spacer 7320 (i.e., the spacer 7320 approximately conforms to a space between the contact surfaces of adjacent spinous processes 2,4 of the targeted motion segment). Referring to FIGS. 75D and 75E, once the frame 7304 is arranged as desired, the top portion 7322 and the bottom portion 7324 can be positioned within the corresponding slots 7332,7334 and urged over the central body 7304 so that the top portion 7322 and bottom portion 7324 further distract the interspinous ligament 6 and/or the adjacent spinous processes 2,4. The spacer 7320 can be urged in the direction of insertion until the base 7326 is seated against the first wing 7330. In a preferred embodiment, the top portion 7322 and the bottom portion 7324 can be arranged so that the top portion 7322 and bottom portion 7324 are approximately in contact or near-contact with the second wing 7360, so that the spacer 7320 fully supports a load applied by the adjacent spinous processes 2,4, without slippage.

FIG. 76A is an end view of the implant 7300 positioned between the adjacent spinous processes 2,4 of the targeted motion segment. As can be seen, the base 7326 is arranged at a slight angle relative to the axis of the spine. As can be seen, the upper spinous process 2 includes a lower contact surface that arcs slightly downward, and the lower spinous process 4 includes an upper contact surface that also arcs slightly downward. Arranging the implant 7300 as shown can increase the overall contact surface between the adjacent spinous processes 2,4 and the spacer 7320 over, for example, inserting the implant 7300 so that the base 7326 is aligned perpendicular to the axis of the spine. Increasing overall contact surface can reduce the stress applied from the motion segment to the spacer 7320, and from the spacer to the adjacent spinous processes 2,4.

As can further be seen, the base 7326 can include a cavity 7329 that in an embodiment is a bore having a diameter larger than a diameter of a corresponding cavity 7309 of the first wing 7330. Such a feature can be receive an insertion tool (not shown) for assisting in implantation, or such a feature can receive a fastener (not shown), such as a screw or bolt to secure the spacer 7320 to the frame 7302. A bore 7329 having a larger diameter than the cavity 7309 of the frame 7302 can allow a head of the fastener to be received so that the head does not extend beyond a distal face of the base 7326. In other embodiments, the base 7326 can include one or more additional cavities for receiving lock pins, or other features of an insertion tool (not shown), for example as described in U.S. Pat. No. 6,712,819, entitled "Mating Insertion Instruments for Spinal Implants and Methods of Use," issued Mar. 30, 2004 to Zucherman, et al.

FIG. 76B is a front view of the implant 7300 positioned between the adjacent spinous processes 2,4 of the targeted motion segment. As can be seen, the second wing 7360 is helical in shape and can limit or block motion in a direction opposite insertion by contacting the upper spinous process 2.

Further, a portion of the second wing 7360 can contact the lower spinous process 4. Although the second wing 7360 as shown includes a helical shape somewhat similar to that of a conch shell, in other embodiments the second wing 7360 can have a shape that varies from the shape shown. For example, the distal end of the second wing 7360 can overlap the proximal end of the second wing 7360 more or less than as shown. Alternatively, the second wing 7360 can be formed in two or more broken sections, rather than an unbroken spiral. Still further, the second wing 7360 can include slots for receiving a proximal piece of the upper and lower portions 7322,7324 of the spacer 7320. Myriad different variations of the shape shown in FIGS. 75A-76B will be readily apparent to one of skill in the art upon understanding the structure shown. Implants in accordance with the present invention are not intended to be limited to those described and shown herein, but rather apply to all such implants that utilize a wing having a major dimension larger than a major dimension of a space between spinous processes, wherein the wing can be appropriately positioned by rotating the implant while urging the implant in a direction of insertion.

Referring now to FIGS. 77A through 77C, an alternative embodiment of an implant 7400 in accordance with an embodiment of the present invention is shown. FIG. 77A is a perspective view of the frame 7402 including a central body 7404 having a distraction guide 7406 at a proximal end, and an alignment protrusion 7408 at a distal end. As can be seen, the second wing 7460 is similar to the second wing 7460 described above. The alignment protrusion 7408 extends from the central body 7404 to align a spacer 7420 as the spacer 7420 is arranged over the central body 7404, and to prevent the spacer 7420 from subsequently rotating relative to the frame 7402 once implanted. Thus, the alignment protrusion 7408 corresponds to a notch 7427 within the spacer 7420 within which the central body 7404 is partially disposed.

FIG. 77B is a perspective view of the spacer 7420. The spacer 7420 includes a bore 7428 disposed at least partially through the spacer 7420, and including a notch 7427 along the length of the bore 7428 to receive the alignment protrusion 7408 of the frame 7402. The proximal end of the spacer 7420 can be tapered to form a distraction guide 7426 to distract the interspinous ligament 6 and/or the adjacent spinous processes 2,4 of the motion segment. Similarly to the rotatable spacer 7220 of FIG. 73B, and the implant 7300 of FIGS. 74A-74C, the implant 7400 can be further rotated or adjusted to distribute a load once the spacer 7420 is positioned over the frame 7404 and between the spinous processes 2,4. As above, the spacer 7420 can have a cross-section perpendicular to the longitudinal axis 7425 that is teardrop-shaped, similar to a cross-section of the spacer 7120,7320 of FIGS. 73A and 74A. In this way, the shape of the spacer 7420 can roughly conform to a wedge-shaped space, or a portion of the space, between adjacent spinous processes 2,4 within which the implant 7400 is to be positioned. The same shape or variations of this shape can be used to accommodate different motion segments and/or different patients, as described above. In other embodiments the spacer 7420 can have alternative shapes such as circular, elliptical, wedge, oval, ovoid, football, and rectangular with rounded corners, and other shapes. The shape of the spacer 7420 can be selected for a particular patient so that the physician can position the implant 7400 as close as possible to the anterior portion of the surface of the spinous process 2,4. The shape selected for the spacer 7420 can affect the contact surface area of the implant 7400 and the spinous processes 2,4 that are to be subject to distraction. Increasing the contact surface area between the implant 7400 and the spinous processes 2,4 can distribute a load force between the spinous frame and the implant 7400.

The spacer 7420 of FIG. 77B extends from a first wing 7430 integrally formed or connected with the spacer 7420. As can be seen, a proximal end of the spacer 7420 varies in length, extending farther near the bottom section of the spacer 7420 to correspond roughly with the helical shape of the second wing 7460, thereby avoiding contacting the second wing 7460 which in the embodiment shown in FIG. 77A spirals to a termination point at the upper surface of the central body 7404. As above, once the frame 7404 is arranged as desired, the spacer 7420 can be positioned over the central body 404 and urged over the central body 7404 so that the spacer 7420 further distracts the interspinous ligament and/or the adjacent spinous processes. The spacer 7320 can be urged in the direction of insertion until the central body 7404 is seated within the bore 7428. In a preferred embodiment, the shape of the proximal end of the spacer 7420 is shaped such that when seated, the proximal end is approximately in contact or near-contact with the second wing 7460, so that the spacer 7420 fully supports a load applied by the adjacent spinous processes, without slippage.

The first wing 7430 can have a depth along the longitudinal axis 7425 as desired, and a width such that the first wing 7430 can contact one or both of the adjacent spinous processes 2,4, thereby limiting or blocking moving of the implant 7400 in the direction of insertion along the longitudinal axis 7425. As shown, the first wing 7430 has a rounded shape, having substantially the same minor and major dimension. Unlike the embodiment of the implant 7300 of FIGS. 74A-74C, the first wing 7430 need not rotate to properly arrange the second wing 7460, therefore the first wing 7430 need not have a round shape, where it is desired that the second wing 7460 have some other shape. For example, the first wing 7430 can include a shape similar to that shown in FIG. 73B. The first wing 7430 can include a cavity 7429 for receiving one or both of an insertion tool (not shown). Further, the central body 7404 can optionally include a cavity 7409 so that, for example, the frame 7402, the spacer 7420, and the first wing 7430 can be fixedly attached once the spacer 7420 is seated.

FIG. 77C is a perspective view of the implant 7400 wherein the spacer 7420 is positioned to be seated on the frame 7402 and arranged over the central body 7404. The first wing 7430 and the second wing 7460 have major dimensions approximately along the axis of the spine that are larger than the major dimension of the spacer 7420, thereby blocking or limiting movement of the implant 7400 along the longitudinal axis 7425. FIG. 78 is a posterior view of an implant 7400 as described in FIGS. 77A-77C disposed between the adjacent spinous processes.

In some embodiments of systems including implants 7300, 7400 similar to those shown in FIGS. 74A-77C, multiple different spacers 7320,7420 can be selectively associated with a single frame 7302,7402 so that a physician can choose an appropriately sized and shaped spacer 7320,7420 to accommodate a patient's anatomy. In embodiments including a central body 7304 extending from a first wing 7330, the distance between the outer peripheries of the two slots 7332, 7334 can correspond to a maximum spacer size (e.g., 14 mm). In embodiments including a central body 7404 having an alignment protrusion 7408, a series of spacer 7420 can have varying dimensions and/or shapes, and can have similarly sized cavities 7428 to receive the central body 7404. As can be readily understood from this description, a system in accordance with embodiments of the present invention can include a frame 7302,7402 and a plurality of spacers 7320,7420 having varying sizes and/or shapes.

As mentioned above, implants, and systems and methods for positioning such implants between spinous processes in accordance with the present invention are not meant to be limited to embodiments as described above and otherwise herein, but rather are meant to include all such implants that utilize a wing having a major dimension larger than a major dimension of a space between spinous processes, wherein the wing can be appropriately positioned by rotating the implant while urging the implant in a direction of insertion. Myriad different variations may be readily apparent to one of ordinary skill in the art. For example, as shown in FIGS. 79A through 79C, in still another embodiment of an implant 7500 in accordance with the present invention, the frame 7502 can include an inner central body 7504 disposed within an outer central body 7505, with a proximal portion of a second wing 7560 being connected with, or extending from the inner central body 7504, and the distal portion of the second wing 7560 being connected with, or extending from the outer central body 7505. Once the frame 7502 is arranged as desired, such that the interspinous ligament is disposed between a first wing 7330 and the second wing 7560, the inner central body 7504 can be shifted to a position more fully received in the outer central body 7505 so that the second wing 7560 collapses, reducing the space occupied by the second wing 7560.

In such embodiments as shown in FIGS. 79A through 79C, the second wing 7560 can be made from a more ductile material so that the second wing 7560 can be readily collapsed. Alternatively, the second wing 7560 can be made from a shape memory material, for example such as Nitinol, so that once the frame is positioned the second wing 7560 collapses, urging the inner central body 7504 to shift within the outer central body 7505. Additionally the second wing 7560 can be made in two parts, one part fastened to the inner central body 7504, and one part fastened to the outer central body 7505. When the inner central body 7504 is more fully received into the outer central body 7505, the portion of the second wing 7560 secure to the inner central body 7504 becomes nested in the portion of the second wing 7560 connected to the outer central body 7505.

As shown in FIG. 80, in a still further embodiment an implant 7600 in accordance with the present invention can include a distraction guide 7606 that tapers more gradually, so that the adjacent spinous processes and/or related tissues are distracted as the lead-in screw 7660 is rotated and urged toward a direction of insertion, as described above.

In still further embodiments, the spacer need not be fixed, but rather can be rotatably disposed over the central body. For example, the spacer can include an alignment notch, as described above with reference to FIG. 73B, so that when the central body is rotated, thereby threading the adjacent spinous processes and related structures within the groove of the thread-shaped wing and positioning the thread-shaped wing on an opposite side of the adjacent spinous processes, the spacer can be held in a fixed positioned. By fixing the spacer is position, the spacer can be arranged as desired between the adjacent spinous processes. Once the implant is positioned between adjacent spinous processes, the rotatable spacer can be released to conform within the space between spinous processes. These and other variations are within the scope of the invention as contemplated.

Materials for Use in Implants of the Present Invention

In some embodiments, the implant, and components of the implant (i.e., the spacer, the frame) can be fabricated from medical grade metals such as titanium, stainless steel, cobalt chrome, and alloys thereof, or other suitable implant material having similar high strength and biocompatible properties. Additionally, the implant can be at least partially fabricated from a shape memory metal, for example Nitinol, which is a combination of titanium and nickel. Such materials are typically radiopaque, and appear during x-ray imaging, and other types of imaging. Implants in accordance with the present invention, and/or portions thereof can also be fabricated from somewhat flexible and/or deflectable material. In these embodiments, the implant and/or portions thereof can be fabricated in whole or in part from medical grade biocompatible polymers, copolymers, blends, and composites of polymers. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer. Many polymers, copolymers, blends, and composites of polymers are radiolucent and do not appear during x-ray or other types of imaging. Implants comprising such materials can provide a physician with a less obstructed view of the spine under imaging, than with an implant comprising radiopaque materials entirely. However, the implant need not comprise any radiolucent materials.

One group of biocompatible polymers is the polyaryletherketone group which has several members including polyetheretherketone (PEEK), and polyetherketoneketone (PEKK). PEEK is proven as a durable material for implants, and meets the criterion of biocompatibility. Medical grade PEEK is available from Victrex Corporation of Lancashire, Great Britain under the product name PEEK-OPTIMA. Medical grade PEKK is available from Oxford Performance Materials under the name OXPEKK, and also from CoorsTek under the name Bio-PEKK. These medical grade materials are also available as reinforced polymer resins, such reinforced resins displaying even greater material strength.

In an embodiment, the implant can be fabricated from PEEK 450G, which is an unfilled PEEK approved for medical implantation available from Victrex. Other sources of this material include Gharda located in Panoli, India. PEEK 450G has the following approximate properties:

| Property | Value |
|---|---|
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

PEEK 450G has appropriate physical and mechanical properties and is suitable for carrying and spreading a physical load between the adjacent spinous processes. The implant and/or portions thereof can be formed by extrusion, injection, compression molding and/or machining techniques.

It should be noted that the material selected can also be filled. Fillers can be added to a polymer, copolymer, polymer blend, or polymer composite to reinforce a polymeric material. Fillers are added to modify properties such as mechanical, optical, and thermal properties. For example, carbon fibers can be added to reinforce polymers mechanically to enhance strength for certain uses, such as for load bearing devices. In some embodiments, other grades of PEEK are available and contemplated for use in implants in accordance with the present invention, such as 30% glass-filled or 30% carbon-filled grades, provided such materials are cleared for use in implantable devices by the FDA, or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to have enhanced compressive strength and stiffness, and a lower expansion rate relative to unfilled PEEK. Carbon-filled PEEK also offers wear resistance and load carrying capability.

As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. As mentioned, the implant can be comprised of polyetherketoneketone (PEKK). Other material that can be used include polyetherketone (PEK), polyetherketoneetherketoneketone (PEKEKK), polyetheretherketoneketone (PEEKK), and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials." Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

Methods for Implanting Interspinous Implants

A minimally invasive surgical method for implanting an implant 7300 in the cervical spine is disclosed and taught herein. In this method, as shown in FIG. 81, preferably a guide wire 7680 is inserted through a placement network 7690 into the neck of the implant recipient. The guide wire 7680 is used to locate where the implant 7300 is to be placed relative to the cervical spine, including the spinous processes. Once the guide wire 7680 is positioned with the aid of imaging techniques, an incision is made on the side of the neck so that an implant 7300 in accordance with an embodiment of the present invention, can be positioned in the neck thorough an incision and along a line that is about perpendicular to the guide wire 7680 and directed at the end of the guide wire 7680. A frame 7302 of the implant 7300 is inserted into the neck of the patient. The frame 7302 includes a distraction guide 7306 extending from the proximal end of a central body 7304 and a first wing 7330 extending from the distal end of the central body 7304. The frame 7302 further includes a helical-shaped second wing 7360 extending distally from the distraction guide 7306 some distance along the central body 7304. Preferably during insertion, the distraction guide 7306 pierces or separates the tissue without severing the tissue. The frame 7302 can be arranged so that the second wing 7360 extending from the central body 7304 is in contact or near contact with the interspinous ligament. The frame 7302 is then rotated in a direction so that the spiraling extension of the second wing 7360 "grows" and the frame 7302 is urged forward such that the adjacent spinous processes fit within a groove between spiraled surfaces of the second wing 7360. The frame 7302 is continuously rotated until the second wing 7360 has passed the adjacent spinous processes 2,4.

The frame 7302 can be further rotated until slots 7332,7334 of the first wing 7330 are arranged as desired between the adjacent spinous processes 2,4 of the targeted motion segment. Once the frame 7302 is satisfactorily positioned, a spacer 7320 can be mated with the frame 7302 so that an upper portion 7322 and a lower portion 7324 of the spacer 7320 is received through the respective slot 7332,7334 of the first wing 7330 (or simply received over the central body 7304 for example where the first wing 7330 extends from the spacer 7320 rather than extending form the central body 7304). The spacer 7320 can be inserted along a line that is generally collinear with the line over which the frame 7302 is inserted. The anatomy of the neck is such that it is most convenient and minimally invasive to enter the neck from the side with respect to the frame 7302 and the spacer 7320.

Further, a minimally invasive surgical method for implanting an implant 7300 in the lumbar spine is disclosed and taught herein. In this method, as shown in the flowchart of FIG. 82, preferably a unilateral incision can be made using a posterior-anterior approach. The unilateral incision can be made, for example, at a location some distance to the right of an axis along the spinous process 2,4 (Step 7702). The incision can be enlarged, and a distraction tool can be positioned within the incision so that the proximal end of the distraction tool can access an exposed side of the interspinous ligament 6. The distraction tool can be urged through the interspinous ligament 6 and distracted, thereby distracting the interspinous ligament 6 so as to receive the implant 7300 (Step 7704). Once the interspinous ligament 6 is sufficiently distracted, the distraction tool can be disengaged and removed from the incision.

Once the distraction tool has been removed from the incision, the frame 7302 can be positioned at the dilated opening, and the distraction guide 7306 of the frame 7302 can be urged through the dilated opening (Step 7706). As above, the frame 7302 can be arranged so that the second wing 7360 extending from the central body 7304 is in near contact with the interspinous ligament 6. The frame 7302 is then rotated in direction so that the spiraling extension of the second wing 7360 "grows", and the frame 7302 urged forward such that the adjacent spinous processes 2,4 fit within a groove between surface of the second wing 7360 (Step 7708). The frame 7302 is continuously rotated until the second wing 7360 has passed the adjacent spinous processes 2,4. The frame 7300 can be further rotated until the slots 7332,7334 are arranged as desired between the adjacent spinous processes of the targeted motion segment. The frame 7302 is free to rotate so that the load can be distributed more evenly over the surface of the spinous processes. Once the frame 7302 is satisfactorily positioned, a spacer 7320 can be inserted with slots 7322,7324 of a first wing 7330 extending from the distal end of the central body 7304 (or simply received over the central body for example where the first wing extends from the spacer). The spacer 7320 can be inserted along a line that is generally collinear with the line over which the frame 7302 is inserted (Step 7710). The remaining tools can be removed from the incision, and the incision can be closed. Preferably during insertion, the distraction end pierces or separates the tissue without severing the tissue (Step 7712). The foregoing description of the present invention have been presented for purposes of illustration and description. It is not intended to be exhaustive or to limit the invention to the precise forms disclosed. Many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

Interspinous Implant Having Slide-in Distraction Piece

FIG. 83 is a perspective end view of an alternative embodiment of an implant 8700 in accordance with the present invention. The implant 8700 can include an initiating piece 8704 and a slide-in distraction piece 8702 adapted to be slidably coupled with the initiating piece 8704.

The initiating piece 8704 and the slide-in distraction piece 8702, when positioned between adjacent spinous processes and coupled together, can resemble implants 7100 as described above with reference to FIGS. 7-23. For example, the implant 8700 of FIG. 83 includes a first wing 8730 at a distal end of the implant 8700, a fixed spacer 8720 extending from the first wing 8730, a second wing 8760 extending from the spacer 8720 so that the spacer 8720 is disposed between the first wing 8730 and the second wing 8760, and a distraction guide 8710 at a proximal end 8716 of the implant 8700. FIG. 84A is a perspective view of the initiating piece 8704. The initiating piece 8704 includes a slot 8784 within a lower sliding surface 8794 that extends through a substantial portion of the length of the initiating piece 8704, the slot 8784 being adapted to receive a rail 8782 of the slide-in distraction piece 8702. The slot 8784 extends a length at least as long as the rail 8782 and preferably does not extend through the entire initiating piece 8704 so that the distraction piece 8702 is prevented from sliding out of position in the direction of insertion. As shown, the slot 8784 includes a flange 8785 along the periphery of the slot 8784 to retain the rail 8782 within the slot 8784. The slot 8784 is thus shaped to substantially conform with a "T" shaped cross-section of the rail 8782 so that when the slide-in distraction piece 8702 is mated with the initiating piece 8704 and the rail 8782 is seated within the slot 8784, relative movement between the distraction piece 8702 and the initiating piece 8704 is limited or substantially blocked, except along the longitudinal axis 8725 in a direction opposite the direction of insertion. To limit or block movement along the longitudinal axis 8725 in a direction opposite the direction of insertion, the slot 8784 can include a recess 8787 adapted to receive a catch 8781 of the rail 8782 so that when the catch 8781 passes over the recess 8787, the catch 8781 is extended, locking the distraction piece 8702 in place, and limiting or blocking movement in a direction opposite insertion. Alternatively, the catch 8781 can be extendably associated with the slot 8784, while the recess 8787 is formed within the rail 8782 for receiving the catch 8781.

The initiating piece 8704 includes a lower distraction element 8714 having a contact surface that tapers to the proximal end 8716 from above as well as below the proximal end 8716 so that the lower distraction element 8714 has a "V" shape in cross-section along an axis of the spine. Such a geometry can ease implantation when compared with a distraction element 8714 that tapers to the proximal end only from below (or above) the proximal end 8716 by more evenly distributing a load force applied to the lower distraction element 8714 by the interspinous ligament 6 during initial piercing and/or distraction of the interspinous ligament 6. The initiating piece 8704 further includes a lower portion 8734 of the first wing, a lower portion 8764 of the second wing., and a lower portion 8724 of the spacer. In an embodiment, the lower portions 8734,8764,8724 can be integrally formed as the lower distraction element 8714, thereby avoiding discontinuities in a lower sliding surface 8794 of the initiation piece 8704. The lower sliding surface 8794 of the initiating piece 8704 is substantially flat and preferably smooth to ease receipt of the rail 8782 within the slot 8784. The lower sliding surface 8794 slopes upward relative to the longitudinal axis 8725 from the distal end of the initiating piece 8704 to the proximal end of the initiating piece 8704. The slope of the lower sliding surface 8794 causes variation in thickness of the lower portion 8724 of the spacer from the distal end of the spacer to the proximal end of the spacer. This slope aids in the distraction of the spinous processes upon insertion of the distraction piece 8702. Referring again to FIG. 83, the contact surfaces of the implant 8700 include relatively smooth transitions from the distraction guide 8710 to the second wing 8760, and from the second wing 8760 to the spacer 8720. As described in greater detail below, during implantation the initiating piece 8704 and the distraction piece 8702 are positioned as separate, single pieces. A relatively continuous surface with smooth transitions improves ease of implantation and minifies obstruction of the initiating piece 8704 and the distraction piece 8702 by the adjacent spinous processes and/or related tissues. In contrast to implants as described with reference to FIGS. 7-23, it is preferable that the distraction piece 8702 and the initiating piece 8704 have smoother transitions between the distraction guide 8710, the second wing 8760, and the spacer 8720, as such transitions even further lessen the obstruction to the movement of the implant during implantation.

The lower portion 8734 of the first wing can further optionally include one or more cavities 8770 for receiving prongs of an insertion tool. As shown in FIGS. 84A through 84C, the initiating piece 8704 includes two cavities 8770 extending from the distal end of the initiating piece 8704 toward the proximal end 8716, with one cavity 8770 being arranged on each side of the lower portion 8734 of the first wing. Each cavity 8770 can be sized to receive a prong of the insertion tool. The cavity 8770 can further include a groove 8772 extending perpendicular to the cavity 8770. Referring to FIGS. 84B and 84C, a prong 8795 of an insertion tool 8794 can include, in an embodiment, a protrusion 8796 that fits within the groove 8772. When the prong is inserted into the cavity 8770 and rotated approximately 90 degrees (FIG. 84C) so that the protrusion is rotated into the groove 8772, the prong is "locked" within the cavity 8770. Once the prongs of the insertion tool are arranged in a locked configuration, the implant 8700 can be releasably guided into position between the adjacent spinous processes.

Figure 85C:
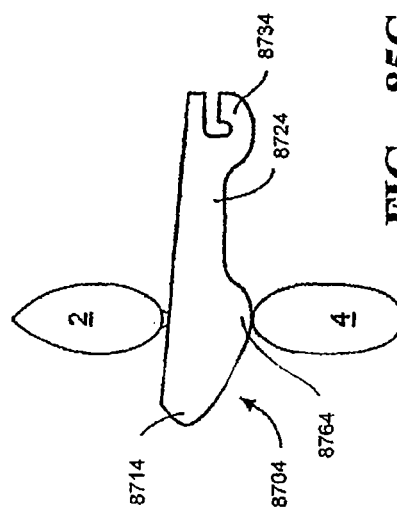

FIG. 85A is a posterior view of the initiating piece 8704 positioned adjacent to the interspinous ligament 6. As can be seen, the initiating piece 8704 has a maximum thickness T from the lower sliding surface 8794 to the lower portion 8764 of the second wing. In a preferred embodiment, the maximum thickness T of the initiating piece 8704 is approximately the same as, or less than the thickness of the spacer 8720 when the initiating piece 8704 and the distraction piece 8702 are mated and the implant 8700 is positioned between the adjacent spinous processes 2,4. Referring to FIG. 85B, as the initiating piece 8704 is urged into the interspinous ligament 6, the lower distraction element 8714 pierces and/or distracts the fibers of the interspinous ligament 6. As shown in FIG. 85C, the initiating piece 8704 is further urged through the interspinous ligament 6 so that the lower portion 8764 of the second wing passes between the adjacent spinous processes 2,4 but preferably does not distract the space between the adjacent spinous processes 2,4 beyond the maximum distraction height of the spacer 8720. As shown in FIG. 85D, the initiating piece 8704 is further urged through the interspinous ligament 6 so that the lower portion 8724 of the spacer is approximately positioned between the adjacent spinous processes 2,4. Note that in other embodiments, the maximum thickness T from the lower sliding surface 8794 to the lower portion 8764 of the second wing can be greater than the ultimate thickness of the spacer 8720 so that when the initiating piece 8704 is positioned between adjacent spinous processes 2,4, the space between the spinous processes 2,4 is distracted to a height greater than the distraction height of the spacer 8720. In such embodiments, the second wing 8760 can potentially provide greater range of flexion motion (wherein the space between adjacent spinous processes increases) while assuring that the movement of the implant 8700 will be limited or blocked in a direction opposite insertion by the second wing 8760.

FIG. 86 is a flipped perspective end view of the slide-in distraction piece 8702. The distraction piece 8702 includes a rail 8782 extending over a substantial portion of the length of the distraction piece 8702, roughly corresponding to a length of the slot 8784 of the initiating piece 8704, within which the rail 8782 is adapted to be received. The height of the rail 8782 from the upper sliding surface 8792 to the flange 8783 of the rail 8782 approximately corresponds to the depth of the slot 8784 from the lower sliding surface 8794 to the bottom of the flange 8785 of the slot, so that when the rail 8782 is received within the slot 8784, the upper sliding surface 8792 of the distraction piece 8702 is substantially flush with the lower sliding surface 8794. In other embodiments, a gap can exist between the upper sliding surface 8792 and the lower sliding surface 8794. As described above, the surface of the rail 8782 includes a catch 8781 arranged along the length of the rail 8782 so that the catch 8781 roughly corresponds to the recess 8787 disposed within the slot 8784. The catch 8781 can have a sloped leading edge (from the proximal end to a distal end of the catch 8781) and can be spring loaded, or otherwise biased so that the catch 8781 collapses when the distraction piece 8702 slides along the lower sliding surface 8794 of the initiating piece 8704 and extends when passing over the recess 8787. The catch 8781 can have a trailing edge substantially perpendicular to the slot 8784 so that the catch 8781 resists movement of the distraction piece 8702 in a direction opposite insertion. In other embodiments, the catch 8781 can be some other mechanism. For example, in an alternative embodiment, the catch 8781 can be a flexible hinge and protrusion similar in operation to that described in FIGS. 19A-20B. Still further the pieces 8702,8704 can be flexible enough that the catch 8781 is molded into the piece 8702, 8704 and can snap into the recess 8787 in the other piece 8702,8704. The distraction piece 8702 includes an upper distraction element 8712 having a contact surface that tapers so that the upper distraction element 712 has a ramp shape. The distraction piece 8702 further includes an upper portion 8732 of the first wing, an upper portion 8762 of the second wing, and an upper portion 8722 of the spacer. In an embodiment, the upper portions 8732,8762,8722 can be integrally formed with the upper distraction element 8712, thereby avoiding discontinuities in an upper sliding surface 8792 of the distraction piece 8702. As with the lower sliding surface 8790, the upper sliding surface 8792 of the distraction piece 8702 is substantially flat and preferably smooth to ease positioning of the rail 8782 within the slot 8784. The upper sliding surface 8792 slopes upward relative to the longitudinal axis 8725 from the distal end of the distracting piece 8702 to the proximal end of the distraction piece 8702, the slope of the upper sliding surface 8792 being substantially similar to the slope of the lower sliding surface 8794 so that the two surfaces 8792,8794 are substantially parallel, and mate when the rail 8782 is positioned within the slot 8784. The slope of the upper sliding surface 8792 causes variation in thickness of the upper portion 8722 of the spacer from the distal end of the spacer to the proximal end of the spacer so that the upper portion 8722 of the spacer is thicker at the distal end. When the distraction piece 8702 is mated with the initiating piece 8704 so that the rail 8782 is seated within the slot 8784, the thickness of the spacer 8720 is approximately the same across the length of the spacer 8720.

FIGS. 87A through 87D are a series of posterior views of the distraction piece 8702 mating with the initiating piece 8704 so that the implant 8700 is positioned between adjacent spinous processes 2,4 to support a load applied by the adjacent spinous processes 2,4 during an extension motion. As can be seen, the distraction piece 8702 is positioned so that the proximal end of the rail flange 8783 fits within the slot 8784. The distraction piece 8702 can then be urged toward the interspinous ligament 6 so that the rail 8782 is further received within the slot 8784. The thickness of the implant 8700 increases as the initiating piece 8704 is mated with the distraction piece 8702. FIG. 87B illustrates the distraction piece 8702 arranged so that the upper distraction element 8782 is adjacent to the interspinous ligament 6. As the distraction piece 8702 is urged further toward the interspinous ligament 6, the upper distraction element 8782 wedges between the lower sliding surface 8794 and the interspinous ligament 6 and/or the adjacent spinous processes 2,4, gradually distracting the interspinous ligament 6 and the adjacent spinous processes 2,4 as the distraction piece 8702 is further urged in the direction of insertion. As shown in FIG. 87C, as the upper portion 8762 of the second wing passes between the adjacent spinous processes 2,4, the space between the adjacent spinous processes 2,4 is distracted beyond the maximum distraction height of the spacer 8720. The distraction piece 8702 is further urged in the direction of insertion until the rail 8782 is seated within the slot 8784 and the upper portion 8762 of the second wing is arranged so that the interspinous ligament 6 and/or adjacent spinous processes 2,4 are disposed between the upper portion 8762 of the second wing and the upper portion 8732 of the first wing (see FIG. 87D). As the catch 8781 passes over the recess 8787, the catch 8781 extends into the recess 8787, locking the distraction piece 8702 in position, mated with the initiation piece 8704.

Interspinous Implant Having Slide-in Distraction Piece

FIGS. 88A and 88B are perspective end views of an alternative embodiment of an implant 8800 in accordance with the present invention. The implant 8800 can include an initiating piece 8804 and a slide-in distraction piece 8802 that can be slidably coupled with the initiating piece 8804. The initiating piece 8804 and the slide-in distraction piece 8802, when positioned between adjacent spinous processes and coupled together as shown in FIG. 88B, has a saddle shape including a first wing 8830 and a second wing 8860 that straddle one of the adjacent spinous processes. The implant 8800 approximates implants as shown above in FIGS. 7-23. For example, the implant 8800 includes the first wing 8830 at a distal end of the implant 8800, a fixed spacer 8820 extending from the first wing 8830, the second wing 8860 extending from the spacer 8820 so that the spacer 8820 is disposed between the first wing 8830 and the second wing 8860, and a distraction guide 8810 at a proximal end 8816 of the implant 8800.

The initiating piece 8804 includes a slot 8884 within a lower sliding surface 8886 that extends through a substantial portion of the length of the initiating piece 8804, the slot 8884 being adapted to receive a rail 8882 of the slide-in distraction piece 8802. The slot 8884 can optionally include a flange or some other structure to retain the rail 8882 within the slot 8884. One of the slot 8884 and the rail 8882 can further optionally include a recess (not shown) adapted to receive a catch (not shown) of the other of the slot 8884 and the rail 8882 so that when the catch passes over the recess, the catch is extended, locking the distraction piece 8802 in place, and limiting or blocking movement along the longitudinal axis 8825.

As shown, the initiating piece 8804 includes a first tab 8894 extending from the first wing 8834, the first tab 8894 including a first perforation 8893. The distraction piece 8802 likewise includes a second tab 8892 including a second perforation 8891 adapted to be aligned with the first perforation 8893 so that when the slide-in distraction piece 8802 is mated with the initiating piece 8804 and the rail 8882 is seated within the slot 8884, the first perforation 8893 and the second perforation 8891 are aligned and can be pegged together so that relative movement between the distraction piece 8802 and the initiating piece 8804 is limited or substantially blocked, hi other embodiments, the initiating piece 8804 and distraction piece 8802 need not include tabs 8892,8894, for example where a catch and recess of the slot and rail is employed. Further, where a first tab 8894 or other structure protrudes from the initiating piece 8804, the distraction piece 8802 can include a slot for receiving the tab 8894, rather than a second tab 8892 abutting the first tab 8894. As will be obvious to one of ordinary skill in the art, tabs having myriad different shapes and sizes can extend from one or both of the initiating piece 8804 and the distraction piece 8802, and perforations having myriad different shapes and sizes can be formed within such tabs to limit relative movement between the initiating piece 8804 and the distraction piece 8802. Further, myriad different locking mechanisms (e.g., a tab and slot arrangement) can be employed with one or both of the initiating pieces 8804 and the distraction piece 8802 to limit relative movement. Embodiments of implants 8800 in accordance with the present invention are not intended to be limited to those arrangements shown in FIGS. 88A-89E.

The initiating piece 8804 includes a lower distraction element 8814 having a contact surface that tapers to the proximal end 8816 from above as well as below the proximal end 8816 so that the lower distraction element 8814 has a "V" shape in cross-section along an axis of the spine. The initiating piece 8804 further includes a first portion 8834 of the first wing, the second wing 8860, and a lower portion 8824 of the spacer. In an embodiment, the lower portions 8824,8834 and the second wing 8860 can be integrally formed with the lower distraction element 8814, thereby avoiding discontinuities in a lower sliding surface 8888 of the initiating piece 8804.

A relatively continuous sliding surface 8888 with smooth transitions improves ease of implantation and minifies obstruction of the initiating piece 8804 by the adjacent spinous processes and/or related tissues. It is preferable that the initiating piece 8804 include smooth transitions between the lower distraction element 8814, the second wing 8860, and the lower portion 8824 of the spacer, as such transitions can increase obstruction of implant movement during implantation. The lower sliding surface 8888 of the initiating piece 8804 is substantially flat and preferably smooth to ease receipt of the rail 8882 within the slot 8884.

As described above, the slide-in distraction piece 8802 includes the rail 8882 extending over a substantial portion of the length of the distraction piece 8802, roughly corresponding to a length of the slot 8884 of the initiating piece 8804 within which the rail 8882 is adapted to be received. The height of the rail 8882 from the upper sliding surface 8886 approximately corresponds to the depth of the slot 8884 so that when the rail 8882 is received within the slot 8884, the upper sliding surface 8886 of the distraction piece 8802 is substantially flush with the lower sliding surface 8888. In other embodiments, a gap can exist between the upper sliding surface 8886 and the lower sliding surface 8888. As described above, the surface of the rail 8882 can include a catch (or a recess) arranged along the length of the rail 8882 so that the catch (or recess) roughly corresponds to the recess (or catch) disposed within the slot 8884. In other embodiments, the rail 8882 and slot 8884 need not include a catch and recess arrangement, but rather the initiating piece 8804 and the distraction piece 8802 can be held in relative position along the longitudinal axis 8825 when the first and second holes 8891,8893 are pegged together. In still other embodiments, some other mechanism can be used to limit or block relative movement of the initiating piece 8804 and the distraction piece 8802.

The distraction piece 8802 further includes an upper distraction element 8812, a second portion 8832 of the first wing and an upper portion 8822 of the spacer. The upper distraction element 8812 has a contact surface that tapers at a proximal end of the distraction piece 8802 so that the upper distraction element 8812 has a ramp shape. The second portion 8832 of the first wing can have a shape that roughly conforms to the shape of the first portion 8834 of the first wing so that when the distraction piece 8802 is coupled to the initiating piece 8804, the first and second portions 8832,8834 form a first wing 8830, as shown in FIG. 88B. The upper portion 8822 of the spacer can have a thickness greater or less than that of the lower portion 8824 of the spacer. As shown, the upper portion 8822 is thicker than the lower portion 8824. By minifying the thickness of the lower portion 8824, distraction of the adjacent spinous processes during implantation of the initiation piece 8804 can be minified to cause less distraction at the surgical site by the second wing 8860 as the second wing 8860 is urged between the adjacent spinous processes. Alternatively, a plurality of distraction pieces 8802 can be provided each having an upper portion 8822 of the spacer having a different thickness. Thus the doctor can select the appropriate distraction piece 8802 for the amount of distraction desired. As with the lower sliding surface 8888, the upper sliding surface 8886 of the distraction piece 8802 is substantially flat and preferably smooth to ease positioning of the rail 8882 within the slot 8884. Embodiments of systems in accordance with the present invention can include a initiating piece 8804 and a plurality of distraction pieces 8802, the distraction pieces 8802 having a variety of thicknesses. In such a system, a distraction piece 8802 can be chosen so that the overall spacer 8820 thickness is suitable for the patient and the motion segment targeted.

FIG. 89A is a posterior view of the initiating piece 8804 positioned adjacent to the interspinous ligament 6. As can be seen, the initiating piece 8804 has a maximum thickness from the lower sliding surface 8888 to the second wing 8860. As the initiating piece 8804 is urged into the interspinous ligament 6, the lower distraction element 8814 pierces and/or distracts the fibers of the interspinous ligament 6. As shown in FIG. 89B, the initiating piece 8804 is further urged through the interspinous ligament 6 so that the second wing 8860 passes between the adjacent spinous processes 2,4 and can distract the space between the adjacent spinous processes 2,4 to accommodate the second wing 8860. The distraction of the space between the adjacent spinous processes is reduced by positioning the initiating piece 8804 prior to coupling the distraction piece 8802 to the initiating piece 8804. Referring to FIG. 89C, the initiating piece 8804 is further urged through the interspinous ligament 6 so that the lower portion 8824 of the spacer is positioned between the adjacent spinous processes 2,4. The second wing 8860 and the first portion 8834 of the first wing straddle the lower spinous process 4. Once the initiating piece 8804 is properly positioned, the rail 8882 of the distracting piece 8802 can be positioned within the distal end of the slot 8884, as shown in FIG. 89D. The distraction piece 8804 can then be urged along the lower sliding surface 8888 so that the upper distraction element 8812 distracts the space between the adjacent spinous processes. As shown in FIG. 89E, the initiating piece 8804 is further urged along the lower sliding surface 8888 until the distraction piece 8802 is mated with the initiating piece 8804.

Materials for Use in Implants of the Present Invention

In some embodiments, the implant can be fabricated from medical grade metals such as titanium, stainless steel, cobalt chrome, and alloys thereof, or other suitable implant material having similar high strength and biocompatible properties. Additionally, the implant can be at least partially fabricated from a shape memory metal, for example Nitinol, which is a combination of titanium and nickel. Such materials are typically radiopaque, and appear during x-ray imaging, and other types of imaging. Implants in accordance with the present invention, and/or portions thereof can also be fabricated from somewhat flexible and/or deflectable material. In these embodiments, the implant and/or portions thereof can be fabricated in whole or in part from medical grade biocompatible polymers, copolymers, blends, and composites of polymers. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer. Many polymers, copolymers, blends, and composites of polymers are radiolucent and do not appear during x-ray or other types of imaging. Implants comprising such materials can provide a physician with a less obstructed view of the spine under imaging, than with an implant comprising radiopaque materials entirely. However, the implant need not comprise any radiolucent materials.

One group of biocompatible polymers are the polyaryletherketone group which has several members including polyetheretherketone (PEEK), and polyetherketoneketone (PEKK). PEEK is proven as a durable material for implants, and meets the criterion of biocompatibility. Medical grade PEEK is available from Victrex Corporation of Lancashire, Great Britain under the product name PEEK-OPTIMA. Medical grade PEKK is available from Oxford Performance Materials under the name OXPEKK, and also from CoorsTek under the name BioPEKK. These medical grade materials are also available as reinforced polymer resins, such reinforced resins displaying even greater material strength. In an embodiment, the implant can be fabricated from PEEK 450G, which is an unfilled PEEK approved for medical implantation available from Victrex. Other sources of this material include Gharda located in Panoli, India. PEEK 450G has the following approximate properties:

| Property | Value |
| --- | --- |
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

PEEK 450G has appropriate physical and mechanical properties and is suitable for carrying and spreading a physical load between the adjacent spinous processes. The implant and/or portions thereof can be formed by extrusion, injection, compression molding and/or machining techniques. It should be noted that the material selected can also be filled. Fillers can be added to a polymer, copolymer, polymer blend, or polymer composite to reinforce a polymeric material. Fillers are added to modify properties such as mechanical, optical, and thermal properties. For example, carbon fibers can be added to reinforce polymers mechanically to enhance strength for certain uses, such as for load bearing devices, hi some embodiments, other grades of PEEK are available and contemplated for use in implants in accordance with the present invention, such as 30% glass-filled or 30% carbon-filled grades, provided such materials are cleared for use in implantable devices by the FDA, or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to have enhanced compressive strength and stiffness, and a lower expansion rate relative to unfilled PEEK. Carbon-filled PEEK also offers wear resistance and load carrying capability.

As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. As mentioned, the implant can be comprised of polyetherketoneketone (PEKK). Other material that can be used include polyetherketone (PEK), polyetherketoneetherketoneketone (PEKEKK), polyetheretherketoneketone (PEEKK), and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials." Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

It is to be understood that embodiments in accordance with the present invention can be constructed without a pliant material. It is also to be understood that the embodiments in accordance with the present invention can have other dimensions Methods for Implanting Interspinous Implants In other embodiments of methods in accordance with the present invention, the implant can include an initiating piece 8704 and a distraction piece 8702, such as described above in FIGS. 83-87D. In such embodiments, as shown in FIG. 90, preferably a guide wire 80 is inserted through a placement network or guide 90 into the neck of the implant recipient (as shown and described above). Once the guide wire 80 is positioned with the aid of imaging techniques, an incision is made on the side of the neck so that an initiating piece 8704 of the implant 8700 can be positioned in the neck thorough an incision and along a line that is about perpendicular to the guide wire 80 and directed at the end of the guide wire. The initiating piece 8704 can include a lower distraction element 8714, a lower portion 8764 of the second wing, a lower portion 8724 of the spacer, and a lower portion 8734 of the first wing. The implant 8700 is inserted into the neck of the patient, between adjacent spinous processes. Preferably during insertion, the lower distraction element 8714 pierces or separates the tissue without severing the tissue, and the implant 8700 is positioned so that the upper portion 8724 of the spacer is disposed between the adjacent spinous processes.

Once the initiating piece 8704 is satisfactorily positioned, a distracting piece 8702 can be inserted along a line that is approximately collinear with the line over which the initiating piece 8704 is inserted, but positioned so that a rail 8782 of the distracting piece 8702 mates with a slot 8784 of the initiating piece 8704. The anatomy of the neck is such that it is most convenient and minimally invasive to enter the neck from the side with respect to the implant 8700. The distracting piece 8702 can be mated to the initiating piece 8704 through an interference fit, or using a catch 8781 and recess 8787 as described above, alternatively by connecting the distracting piece 8704 with the initiating piece 8702 using a fastener, or by some other device, as described above. It is to be understood that the embodiment described herein can be used between any of the spinous processes of the spine.

In other embodiments of methods in accordance with the present invention, the implant can include an initiating piece 8804 and a distraction piece 8802, such as described above in FIGS. 88A-89E. In such embodiments, as shown in FIG. 91, preferably a guide wire 80 is inserted through a placement network or guide 90 into the neck of the implant recipient (as shown and described above). Once the guide wire 80 is positioned with the aid of imaging techniques, an incision is made on the side of the neck so that an initiating piece 8804 of the implant 8800 can be positioned in the neck thorough an incision and along a line that is about perpendicular to the guide wire 80 and directed at the end of the guide wire. The initiating piece 8804 can include a lower distraction element 8814, the second wing 8860, a lower portion 8824 of the spacer, and a lower portion 8834 of the first wing. The implant 8800 is inserted into the neck of the patient, between adjacent spinous processes. Preferably during insertion, the lower distraction element 8814 pierces or separates the tissue without severing the tissue, and the implant 8800 is positioned so that the upper portion 8824 of the spacer is disposed between the adjacent spinous processes. Once the initiating piece 8804 is satisfactorily positioned, a distracting piece 8802 can be inserted along a line that is approximately collinear with the line over which the initiating piece 8804 is inserted, but positioned so that a rail 8882 of the distracting piece 8802 mates with a slot 8884 of the initiating piece 8804. The anatomy of the neck is such that it is most convenient and minimally invasive to enter the neck from the side with respect to the implant 8800. The distracting piece 8802 can be mated to the initiating piece 8804, by pegging the first and second perforations 8891,8893, through an interference fit, or using a catch 8881 and recess 8887 as described above, or, alternatively by connecting the distracting piece 8804 with the initiating piece 8802 using a fastener, or by some other device, as described above.

The foregoing description of the present invention have been presented for purposes of illustration and description. It is not intended to be exhaustive or to limit the invention to the precise forms disclosed. Many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. An apparatus, comprising:
   a first implant member having a central portion, a proximal end and a distal end, wherein the central portion is configured to be disposed between a first spinous process and a second spinous process, the proximal end comprising a proximal end portion extending outwardly from the central portion, the central portion comprising a spiral portion that extends outwardly from a periphery of the central portion and is spaced apart from the proximal end portion; and
   a second implant member having a first portion and a second portion having inner surfaces that abut an outer surface of the first implant member and conform with a shape of the first implant member, the second portion having a maximum length that is greater than that of the first portion, the second implant member being coupled to the first implant member after the central portion is disposed between the first spinous process and the second spinous process, the first portion being configured to be disposed between the central portion and the first spinous process, the second portion being configured to be disposed between the central portion and the second spinous process, the second implant member being received over the first implant member in a direction substantially parallel to a longitudinal axis of the first implant member so as to be coupled to the first implant member after at least a portion of the first implant member is disposed between a pair of adjacent spinous processes;

wherein when the second implant member is coupled to the first implant member, the first and second portions each extend through slots in the proximal end portion and end surfaces of the first and second portions each engage an outer surface of the spiraled portion.

2. The apparatus of claim 1 wherein the the outer surface of the spiral portion comprises spaced apart first and second arcuate surfaces, the first arcuate surface being positioned closer to the proximal end portion than the second arcuate surface, the end surface of the first portion engaging the first arcuate surface and the end surface of the second portion engaging the second arcuate surface.

3. The apparatus of claim 1 wherein at least one of the first portion of the second implant member or the second portion of the second implant member movably mates with the central portion of the first implant member.

4. The apparatus of claim 1 wherein the first and second portions each include a concave inner surface that engages a convex outer surface of the central portion.

5. The apparatus of claim 1, wherein the second implant member is coupled to the first implant member such that rotational movement of the first implant member relative to the second implant member is limited.

6. The apparatus of claim 1, wherein the first implant member has a rounded distraction portion and the second implant member has a distraction portion, the distraction portion of the first implant member being spaced apart from the spiral portion.

7. The apparatus of claim 6 wherein the distraction portion of the first implant member is distal relative to the distraction portion of the second implant member when the second implant member is coupled to the first implant member.

8. The apparatus of claim 1, wherein the first implant member has a distal end portion configured to limit lateral movement of the first implant member relative to the first spinous process and the second spinous process when the portion of the first implant member is disposed between the first spinous process and the second spinous process.

9. The apparatus of claim 1 wherein the proximal end portion of the first implant member is configured to limit lateral movement of the first implant member relative to the first spinous process and the second spinous process when the central portion of the first implant member is disposed between the first spinous process and the second spinous process.

10. The apparatus of claim 1, wherein the second implant member has a proximal end portion configured to limit lateral movement of the first implant member and the second implant member relative to the first spinous process and the second spinous process when the second implant member is coupled to the first implant member.

11. The apparatus of claim 1, wherein at least one of the first portion of the second implant member or the second portion of the second implant member is curved.

12. The apparatus of claim 1 wherein the spiraled portion is positioned distal to the central portion and is configured to move the central portion relative to the first spinous process and the second spinous process when at least a portion of the spiraled portion is disposed between the first spinous process and the second spinous process and when the spiraled portion is rotated about an axis that is substantially lateral relative to the first spinous process and the second spinous process.

13. The apparatus of claim 1, wherein at least one of the first portion of the second implant member or the second portion of the second implant member is configured to limit extension of a spinal column including the first spinous process and the second spinous process when the second implant member is coupled to the first implant member.

14. An apparatus, comprising:
an implant extending along a longitudinal axis and having first and second wings that are spaced apart from one another along the longitudinal axis, the first wing having two slots extending therethrough that are spaced apart from one another; and
a spacer having a central portion having a top portion and a bottom portion that are spaced apart from one another by a gap, the bottom portion having a maximum length that is greater than that of the to portion, the top and bottom portions having inner surfaces that abut an outer surface of the implant and conform with a shape of the implant, the central portion of the spacer being received over the implant such that the top portion extends through one of the slots, the bottom portion extends through the other slot in a direction substantially parallel to the longitudinal axis and end surfaces of the to and bottom portions engage an outer surface of the second wing so as to couple the spacer to the implant after at least a portion of the implant is disposed between a pair of adjacent spinous processes;
wherein when the central portion of the spacer extends through the slot, the central portion of the spacer is disposed outside of the portion of the implant;
the central portion of the spacer configured to define a space between the pair of adjacent spinous processes.

15. The apparatus of claim 14, wherein the inner surfaces of the top and bottom portions are free of threads and are configured to be slidably moved over the portion of the implant.

16. The apparatus of claim 14, wherein the spacer has a first distraction portion configured to distract a space between a spinous process from the pair of adjacent spinous processes and the implant, the spacer has a second distraction portion configured to distract a space between a second spinous process from the pair of adjacent spinous processes and the implant, the first distraction portion being distinct from the second distraction portion.

17. The apparatus of claim 14, wherein the spacer has a first distraction portion having a tip and a second distraction portion having a tip distal from the tip of the first distraction portion along a longitudinal axis of the spacer.

18. The apparatus of claim 14, wherein the spacer has a proximal end portion configured to limit lateral movement of the spacer and the implant relative to the pair of adjacent spinous processes when the spacer is coupled to the implant.

19. The apparatus of claim 14, wherein the central portion of the spacer defines an interior configured to receive the portion of the implant.

20. The apparatus of claim 14, wherein the spacer is lockably coupled to the implant.

21. The apparatus of claim 14, wherein a proximal end portion of the spacer has a cavity configured to receive an insertion tool.

22. The apparatus of claim 14, wherein the implant has a proximal end portion configured to limit lateral movement of the implant relative to the pair of adjacent spinous processes, the spacer has a proximal end portion configured to be coupled to the proximal end portion of the implant.

23. The apparatus of claim 14, wherein the spacer is configured to be inserted into a body percutaneously via a lateral incision.

24. The apparatus of claim 14, wherein the central portion of the implant is moved from a first position outside of a space between the pair of adjacent spinous processes to a second position within the space when the implant is rotated via an axis that is lateral relative to the pair of adjacent spinous processes.

25. An apparatus, comprising:
a first implant member defining a first longitudinal axis and having a distal retention member configured to limit lateral movement of the first implant member relative to a pair of adjacent spinous processes and a proximal retention member, an outer surface of the first implant member being free of threads between the distal and proximal retention members, the distal retention member includes two slots that are spaced apart from one another and extend parallel to the first longitudinal axis; and
a second implant member defining a second longitudinal axis and having a top portion and a bottom portion, the bottom portion has a maximum length that is greater than that of the to portion, the top and bottom portions having unthreaded inner surfaces that abut the outer surface of the first implant member and conform with a shape of the first implant member, the second implant member includes having a distraction portion configured to be disposed between the spinous processes and proximally to at least a portion of the distal retention member of the first implant member when the second implant member is coupled to the first implant member such that the top portion extends through one of the slots, the bottom portion extends through the other slot and the first implant member is disposed between the pair of adjacent spinous processes, the distraction portion being configured to distract a space between the pair of adjacent spinous processes, the second implant member being received over the first implant member in a direction substantially parallel to the first longitudinal axis such that end surfaces of the top and bottom portions engage the proximal retention member so as to couple the second implant member to the first implant member after at least a portion of the first implant member is disposed between a pair of adjacent spinous processes;
the first and second axes being substantially parallel;
wherein, when the second implant member is coupled to the first implant member;
the second implant member overlies the outer surface of the first implant member; and
a height of the apparatus, where the second implant member overlies the first implant member, is increased in a direction transverse to the longitudinal axes.

26. The apparatus of claim 25, wherein the second implant member has a central portion configured to define the space between the pair of adjacent spinous processes when the central portion of the second implant member is disposed between the pair of adjacent spinous processes.

27. The apparatus of claim 25, wherein a central portion of the first implant member is configured to be disposed inside a central portion of the second implant member when the central portion of the second implant member is disposed between the pair of adjacent spinous processes.

28. The apparatus of claim 25, wherein the first implant member is monolithic and has a distal end portion configured to dilate a bodily tissue.

29. The apparatus of claim 25, wherein the second implant member has a cavity configured to receive an insertion tool.

30. The apparatus of claim 25, wherein the proximal retention member defines a spiral portion extending outwardly from a central portion of the first implant member.

31. The apparatus of claim 25, wherein the inner surfaces of the top and bottom portions are concavely curved.

32. The apparatus of claim 25, wherein the second implant member has a proximal retention portion configured to limit lateral movement of the first implant member and the second implant member relative to the pair of adjacent spinous processes when the second implant member is coupled to the first implant member.

* * * * *